(12) United States Patent
Roberts et al.

(10) Patent No.: US 8,980,613 B2
(45) Date of Patent: *Mar. 17, 2015

(54) MODIFIED PHOTOSYNTHETIC MICROORGANISMS FOR PRODUCING LIPIDS

(75) Inventors: James Roberts, Seattle, WA (US); Fred Cross, Seattle, WA (US); Paul Warrener, Seattle, WA (US); Ernesto Javier Munoz, Seatte, WA (US); Jason W. Hickman, Seattle, WA (US)

(73) Assignee: Matrix Genetics, LLC, Seattle, WA (US)

(*) Notice: Subject to any disclaimer, the term of this patent is extended or adjusted under 35 U.S.C. 154(b) by 190 days.

This patent is subject to a terminal disclaimer.

(21) Appl. No.: 13/080,496

(22) Filed: Apr. 5, 2011

(65) Prior Publication Data

US 2011/0250659 A1    Oct. 13, 2011

Related U.S. Application Data

(60) Provisional application No. 61/425,176, filed on Dec. 20, 2010, provisional application No. 61/321,337, filed on Apr. 6, 2010.

(51) Int. Cl.
| | |
|---|---|
| *C12N 1/20* | (2006.01) |
| *C12N 15/00* | (2006.01) |
| *C12N 9/16* | (2006.01) |
| *C12N 9/10* | (2006.01) |
| *C07H 21/04* | (2006.01) |
| *C12N 9/20* | (2006.01) |
| *C12N 15/74* | (2006.01) |
| *C12P 7/64* | (2006.01) |

(52) U.S. Cl.
CPC .............. *C12N 9/20* (2013.01); *C12N 9/1051* (2013.01); *C12N 15/00* (2013.01); *C12N 9/16* (2013.01); *C12N 15/74* (2013.01); *C12P 7/6409* (2013.01); *C12P 7/6463* (2013.01); *C12P 7/649* (2013.01); *Y02E 50/13* (2013.01)
USPC ........ 435/252.3; 435/196; 435/440; 435/193; 435/320.1; 536/23.2

(58) Field of Classification Search
CPC ......... C12N 9/16; C12N 9/1051; C12N 15/74
See application file for complete search history.

(56) References Cited

U.S. PATENT DOCUMENTS

| | | | |
|---|---|---|---|
| 6,306,639 | B1 | 10/2001 | Woods et al. ............... 435/252.3 |
| 7,118,896 | B2 | 10/2006 | Kalscheuer et al. .......... 435/134 |
| 7,157,619 | B1 | 1/2007 | Lassner et al. ................ 800/281 |
| 7,427,593 | B1 | 9/2008 | Dahlqvist et al. ............... 514/12 |
| 7,498,026 | B2 | 3/2009 | Dahlqvist et al. ............. 424/94.5 |
| 7,794,969 | B1 | 9/2010 | Reppas et al. .................. 435/41 |
| 8,110,670 | B2 * | 2/2012 | Hu et al. ....................... 536/23.2 |
| 2003/0233675 | A1 | 12/2003 | Cao et al. ....................... 800/279 |
| 2006/0137043 | A1 | 6/2006 | Puzio et al. ..................... 800/289 |
| 2007/0269859 | A1 | 11/2007 | Lassner et al. ................ 435/69.1 |
| 2008/0160592 | A1 | 7/2008 | Dahlqvist et al. ............. 435/134 |
| 2009/0035832 | A1 | 2/2009 | Koshland, Jr. ................ 435/167 |
| 2009/0155864 | A1 | 6/2009 | Bauer et al. ................... 435/134 |
| 2009/0215179 | A1 | 8/2009 | Gressel et al. ................ 435/471 |
| 2009/0298143 | A1 | 12/2009 | Roessler et al. .............. 435/134 |
| 2010/0081178 | A1 | 4/2010 | Roberts et al. ................ 435/134 |
| 2010/0184169 | A1 | 7/2010 | Roberts et al. ................ 435/134 |
| 2010/0251601 | A1 | 10/2010 | Hu et al. .......................... 44/313 |
| 2010/0255551 | A1 | 10/2010 | Roberts et al. ................ 435/134 |

FOREIGN PATENT DOCUMENTS

| | | |
|---|---|---|
| WO | WO 98/39457 | 9/1998 |
| WO | WO 2007/136762 A2 | 11/2007 |
| WO | WO 2008/119082 A2 | 10/2008 |
| WO | WO 2008/130437 A2 | 10/2008 |
| WO | WO 2009/009391 A2 | 1/2009 |
| WO | WO 2009/036095 A1 | 3/2009 |
| WO | WO 2009/042950 A1 | 4/2009 |
| WO | WO 2009/062190 A2 | 5/2009 |
| WO | WO 2009/076559 A1 | 6/2009 |
| WO | WO 2009/089185 A1 | 7/2009 |
| WO | WO 2009/111513 A1 | 9/2009 |
| WO | WO 2010/006312 A2 | 1/2010 |
| WO | WO 2010/017245 A1 | 2/2010 |

(Continued)

OTHER PUBLICATIONS

A935Y7—UniProtKB Database—2008.*
Acreman, "Algae and cyanobacteria: isolation, culture and long-term maintenance," *Journal of Industrial Microbiology* 13:193-194, 1994.
Alvarez et al., "Triacylglycerols in prokaryotic microorganisms," *Appl. Microbiol. Biotechnol.* 60:367-376, 2002.
Bagchi et al., "A *Synechococcus elongates* PCC 7942 mutant with a higher tolerance toward the herbicide bentazone also confers resistance to sodium chloride stress," *Photosynth. Res.* 92:87-101, 2007.
Christensen et al., "Lipid domains of mycobacteria studied with fluorescent molecular probes," *Molecular Microbiology* 31(5):1561-1572, 1999.

(Continued)

*Primary Examiner* — Yong Pak
(74) *Attorney, Agent, or Firm* — Lee & Hayes, PLLC

(57) ABSTRACT

This disclosure describes genetically modified photosynthetic microorganisms, e.g., Cyanobacteria, that contain one or more exogenous genes encoding a phospholipase and/or thioesterase, which are capable of producing an increased amount of lipids and/or fatty acids. This disclosure also describes genetically modified photosynthetic microorganisms that contain one or more exogenous genes encoding a diacyglycerol acyltransferase, a phosphatidate phosphatase, and/or an acetyl-CoA carboxylase, which are capable of producing increased amounts of fatty acids and/or synthesizing triglycerides, as well as photosynthetic microorganism comprising mutations or deletions in a glycogen biosynthesis or storage pathway, which accumulate a reduced amount of glycogen under reduced nitrogen conditions as compared to a wild type photosynthetic microorganism.

4 Claims, 14 Drawing Sheets

(56) References Cited

FOREIGN PATENT DOCUMENTS

| | | |
|---|---|---|
| WO | WO 2010/019813 A2 | 2/2010 |
| WO | WO 2010/021711 A1 | 2/2010 |
| WO | WO 2010/022090 A1 | 2/2010 |
| WO | WO 2010/027516 A2 | 3/2010 |
| WO | WO 2010/033921 A2 | 3/2010 |
| WO | WO 2010/036951 A2 | 4/2010 |
| WO | WO 2010/042664 A2 | 4/2010 |
| WO | WO 2010/044960 A1 | 4/2010 |
| WO | WO 2010/048568 A1 | 4/2010 |
| WO | WO 2010/062480 A2 | 6/2010 |
| WO | WO 2010/062707 A1 | 6/2010 |
| WO | WO 2010/075440 A1 | 7/2010 |
| WO | WO 2010/075483 A2 | 7/2010 |
| WO | WO 2010/078584 A1 | 7/2010 |
| WO | WO 2010/104763 A1 | 9/2010 |
| WO | WO 2010/118410 A1 | 10/2010 |
| WO | WO 2010/126891 A1 | 11/2010 |
| WO | WO 2011/008535 A1 | 1/2011 |
| WO | WO 2011/008565 A1 | 1/2011 |
| WO | WO 2011/011568 A2 | 1/2011 |
| WO | WO 2011/029013 A2 | 3/2011 |
| WO | WO 2011/038132 A1 | 3/2011 |
| WO | WO 2011/038134 A1 | 3/2011 |
| WO | WO 2011/059745 A1 | 5/2011 |

OTHER PUBLICATIONS

Chungjatupornchai et al., "Isolation and Characterization of *Synechococcus* PCC7942 Promoters: tRNA$^{pro}$ Gene Functions as a Promoter," *Current Microbiology* 38:210-216, 1999.

Coleman et al., "Physiological and Nutritional Regulation of Enzymes of Triacylglycerol Synthesis," *Annu. Rev. Nutr.* 20:77-103, 2000.

Dahlqvist et al., "Phospholipid: diacylglycerol acyltransferase: An enzyme that catalyzes the acyl-CoA-independent formation of triacylglycerol in yeast and plants," *Proc. Natl. Acad. Sci.* 97(12):6487-6492, 2000.

Daniel et al., "Induction of a Novel Class of Diacylglycerol Acyltransferases and Triacylglycerol Accumulation in *Mycobacterium tuberculosis* as It Goes into a Dormancy-Like State in Culture," *Journal of Bacteriology* 186(15):5017-5030, 2004.

Daum et al., "Biochemistry, Cell Biology and Molecular Biology of Lipids of *Saccharomyces cerevisiae*," *Yeast* 14:1471-1510, 1998.

Davis et al., "Overproduction of Acetyl-CoA Carboxylase Activity Increases the Rate of Fatty Acid Biosynthesis in *Escherichia coli*," *The Journal of Biological Chemistry* 275(37):28593-28598, 2000.

Han et al., "The Cellular Functions of the Yeast Lipin Homolog Pah1p Are Dependent on Its Phosphatidate Phosphatase Activity," *The Journal of Biological Chemistry* 282(51):37026-37035, 2007.

Han et al., "The *Saccharomyces cerevisiae* Lipin Homolog Is a Mg$^{2+}$-dependent Phosphatidate Phosphatase Enzyme," *The Journal of Biological Chemistry* 281(14):9210-9218, 2006.

Harwood, "Recent advances in the biosynthesis of plant fatty acids," *Biochimica et Biophysica Ata* 1301:7-56, 1996.

Hu et al., "Microalgal triaglycerols as feedstocks for biofuel production: perspectives and advances," *The Plant Journal* 54:621-639, 2008.

Imashimizu et al., "Thymine at −5 Is Crucial for *cpc* Promoter Activity of *Synechocystis* sp. Strain PCC 6714," *Journal of Bacteriology* 185(21):6477-6480, 2003.

Kalscheuer et al., "A Novel Bifunctional Wax Ester Synthase/Acyl-CoA:Diacylglycerol Acyltransferase Mediates Wax Ester and Triacylglycerol Biosynthesis in *Acinetobacter calcoaceticus* ADP1," *The Journal of Biological Chemistry* 278(10):8075-8082, 2003.

Kalscheuer et al., "Neutral Lipid Biosynthesis in Engineered *Escherichia coli*: Jojoba Oil-Like Wax Esters and Fatty Acid Butyl Esters," *Applied and Environmental Microbiology* 72(2):1373-1379, 2006.

Koksharova et al., "Genetic tools for cyanobacteria," *Appl. Micrbiol. Biotechnol.* 58:123-137, 2002.

Maeda et al., "*cis*-Acting Sequences Required for NtcB-Dependent, Nitrite-Responsive Positive Regulation of the Nitrate Assimilation Operon in the Cynabacterium *Synechococcus* sp. Strain PCC-7942," *Journal of Bacteriology* 180(16):4080-4088, 1998.

Mermet-Bouvier et al., "Transfer and Replication of RSF1010-Derived Plasmids in Several Cyanobacteria of the Genera *Synechocystis* and *Synechococcus*," *Current Microbiology* 27:323-327, 1993.

Mermet-Bouvier et al., "A Conditional Expression Vector for the Cyanobacteria *Synechocystis* sp. Strains PCC6803 and PCC6714 or *Synechococcus* sp. Strains PCC7942 and PCC6301," *Current Microbiology* 28:145-148, 1994.

Nakamura et al., "Plastidic Phosphatidic Acid Phosphatases Identified in a Distinct Subfamily of Lipid Phosphate Phosphatases with Prokaryotic Origin," *The Journal of Biological Chemistry* 282(39):29013-29021, 2007.

Nedbal et al., "A Photobioreactor System for Precision Cultivation of Photoautotrophic Microorganisms and for High-Content Analysis of Suspension Dynamics," *Biotechnology and Bioengineering* 100(5):902-910, 2008.

Nishizuka, "Intracellular Signaling by Hydrolysis of Phospholipids and Activation of Protein Kinase C," *Science* 258:607-614, 1992.

Office Action mailed Sep. 17, 2010, U.S. Appl. No. 12/605,204, filed Oct. 23, 2009.

Qi et al., "Application of the *Synechoccous nirA* Promoter to Establish an Inducible Expression System for Engineering the *Synechocystis* Tocopherol Pathway," *Applied and Environmental Microbiology* 71(10):5678-5684, 2005.

Ronen-Tarazi et al., "The Genomic Region of *rbcLS* in *Synechococcus* sp. PCC 7942 Contains Genes Involved in the Ability to Grow under Low $CO_2$ Concentration and in Chlorophyll Biosynthesis," *Plant Physiol.* 108:1461-1469, 1995.

Saha et al., "Cytosolic Triacylglycerol Biosynthetic Pathway in Oilseeds. Molecular Cloning and Expression of Peanut Cytosolic Diacylglycerol Acyltransferase," *Plant Physiology* 141:1533-1543, 2006.

Singh et al., "Bioactive Compounds from Cyanobacteria and Microalgae: An Overview," *Critical Reviews in Biotechnology* 25:73-95, 2005.

Van Heeke et al., "The N-terminal Cysteine of Human Asparagine Synthetase Is Essential for Glutamine-dependent Activity," *The Journal of Biological Chemistry* 264(33):19475-19477, 1989.

Waditee et al., "Overexpression of a $Na^+/H^+$ antiporter confers salt tolerance on a freshwater cyanobacterium, making it capable of growth in sea water," *Proc. Natl. Acad. Sci.* 99(6):4109-4114, 2002.

Waltermann et al., "Mechanism of lipid-body formation in prokaryotes: how bacteria fatten up," *Molecular Microbiology* 55(3):750-763, 2005.

Waltermann et al., "Neutral Lipid Bodies in Prokaryotes: Recent Insights into Structure, Formation, and Relationship to Eukaryotic Lipid Depots," *Journal of Bacteriology* 187(11):3607-3619, 2005.

Wirth et al., "Transformation of various species of gram-negative bacteria belonging to 11 different genera by electroporation," *Mol. Gen. Genet.* 216:175-177, 1989.

Yu et al., "Production of Eicosapentaenoic Acid by a Recombinant Marine Cyanobacterium, *Synechococcus* sp.," *Lipids* 35(10):1061-1064, 2000.

Zhang et al., "Crystal Structure of the Carboxyltransferase Domain of Acetyl-Coenzyme A Carboxylase," *Science* 299:2064-2067, 2003.

Jiang et al, "Inhibition of Fatty Acid Synthesis in *Escherichia coli* in the Absence of Phospholipid Synthesis and Release of Inhibition by Thioesterase Action," *Journal of Bacteriology* 176(10):2814-2821, 1994.

Kalscheuer et al., "Microdiesel: *Escherichia coli* engineered for fuel production," *Microbiology* 152:2529-2536, 2006.

Liu et al., "$CO_2$-limitation-inducible Green Recovery of fatty acids from cyanobacterial biomass," *PNAS Early Edition*, www.pnas.org/cgi/doi/10.1073/pnas.1103016108, 2011. (4 pages).

Liu et al., "Fatty acid production in genetically modified cyanobacteria," *PNAS Early Edition*, www.pnas.org/cgi/doi/10.1073/pnas.1103014108, 2011. (6 pages).

Lykidis et al., "Genomic prospecting for microbial biodiesel production," U.S. Department of Energy Office of Science, Biological and

(56) References Cited

OTHER PUBLICATIONS

Environmental Research Program and The University of California, Lawrence Berkeley National Laboratory, 2008. (39 pages).

Morgan-Kiss et al., "The *Escherichia coli fadK (ydiD)* Gene Encodes an Anerobically Regulated Short Chain Acyl-CoA Synthetase," *The Journal of Biological Chemistry* 279(36):37324-37333, 2004.

Qiu et al., "Metabolic engineering of *Aeromonas hydrophila* for the enhanced production of poly(3-hydroxybutyrate-*co*-3-hydroxyhexanoate)," *Appl. Mircobiol. Biotechnol.* 69:537-542, 2006.

Roberts et al., "Modified Photosynthetic Microorganisms for Producing Lipids," International application No. PCT/US2011/031273, filed Apr. 5, 2011, 306 pages.

Voelker et al., "Alteration of the Specificity and Regulation of Fatty Acid Synthesis of *Escherichia coli* by Expression of a Plant Medium-Chain Acyl-Acyl Carrier Protein Thioesterase," *Journal of Bacteriology* 176(23):7320-7327, 1994.

Zhang et al., "Molecular effect of FadD on the regulation and metabolism of fatty acid in *Escherichia coli*," *FEMS Microbiol. Lett.* 259:249-253, 2006.

NCBI Gene ID 951909 "glgc glucose-1-phosphate adenylytransferase {*Synechocystis* sp. PCC 6803]" Aug. 2003 dowloaded from http://www.ncbi.nlm.nih.gov/gene on Jun. 2, 2011.

GenBank Accession No. CP000100. *Synechococcus* elongates PCC 7942, complete genome (Dec. 2007).

* cited by examiner

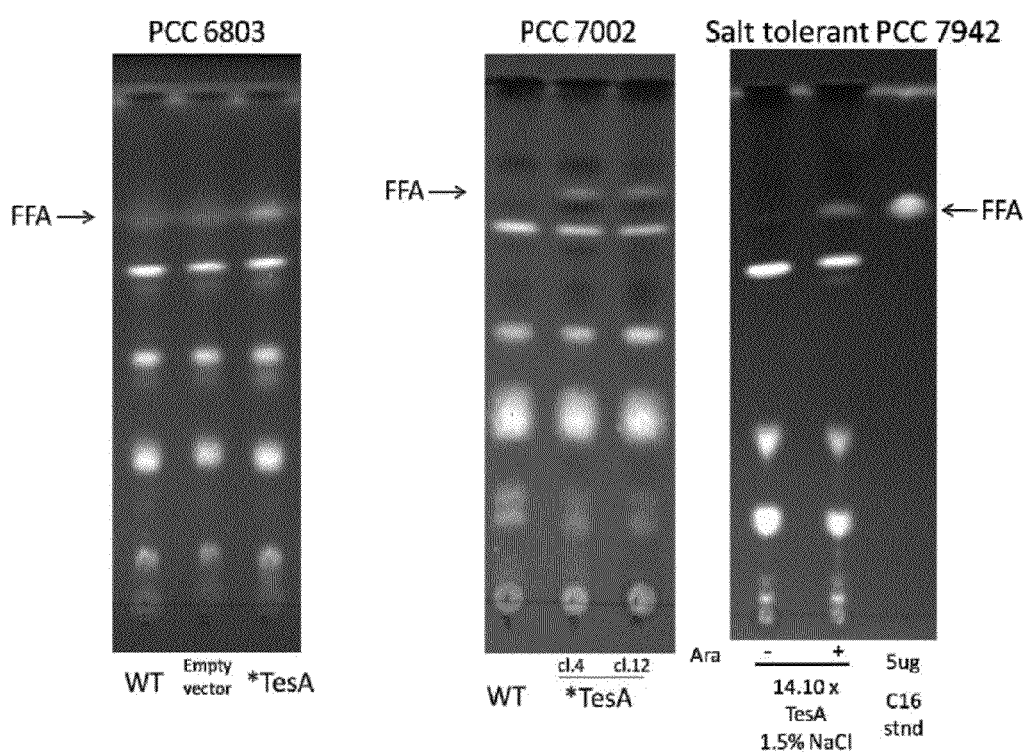
*FIG. 7A*  *FIG. 7B*  *FIG. 7C*

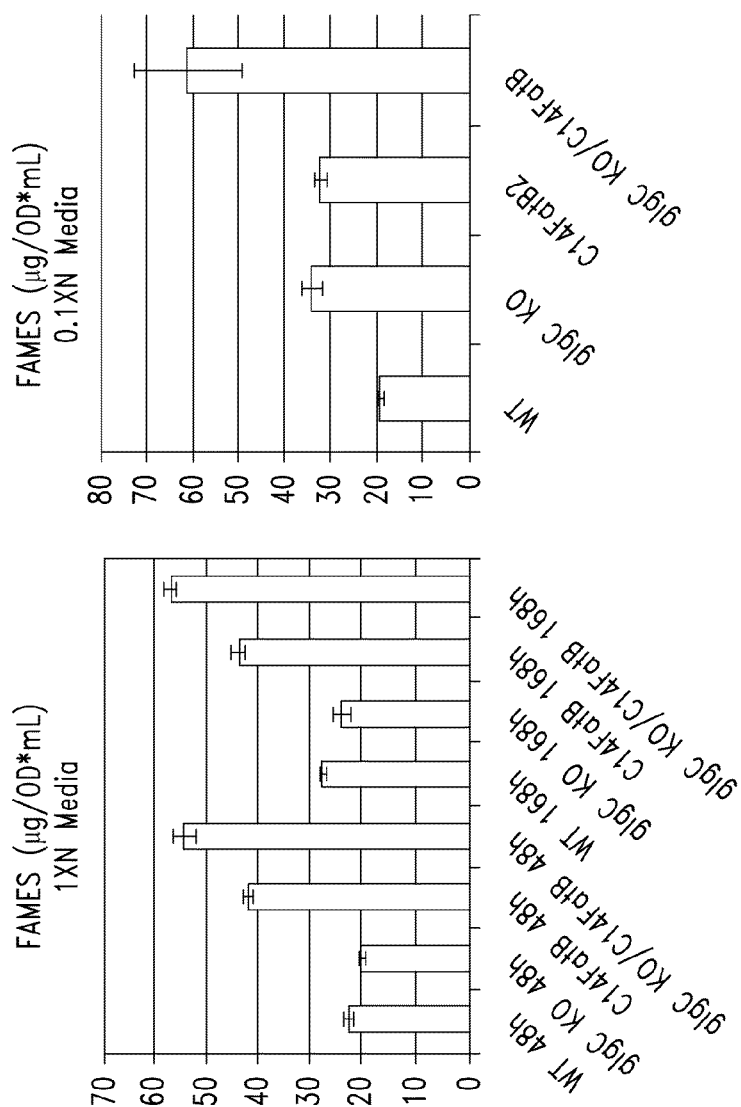
*FIG. 10C*
*FIG. 10B*
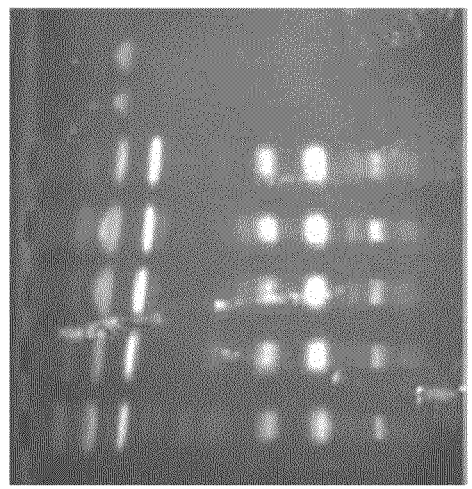
*FIG. 10A*

MODIFIED PHOTOSYNTHETIC MICROORGANISMS FOR PRODUCING LIPIDS

CROSS-REFERENCE(S) TO RELATED APPLICATION(S)

This application claims the benefit under 35 U.S.C. §119 (e) of U.S. Provisional Patent Application No. 61/321,337, filed Apr. 6, 2010; and U.S. Provisional Patent Application No. 61/425,176, filed Dec. 20, 2010, where these (two) provisional applications are incorporated herein by reference in their entireties.

SEQUENCE LISTING

The Sequence Listing associated with this application is provided in text format in lieu of a paper copy, and is hereby incorporated by reference into the specification. The name of the text file containing the Sequence Listing is 890071_403_SEQUENCE_LISTING.txt. The text file is about 331 KB, was created on Apr. 5, 2011, and is being submitted electronically via EFS-Web.

BACKGROUND

1. Technical Field

The present invention relates generally to genetically modified photosynthetic microorganisms, e.g., Cyanobacteria, that overexpress one or more lipases, e.g., phospholipases, lysophospholipases, thioesterases, including enzymes having one or all of these activities, and synthesize high levels of lipids, as well as related methods of using these genetically modified photosynthetic microorganisms as a feedstock, e.g., for producing biofuels and other specialty chemicals.

2. Description of the Related Art

Triglycerides are neutral polar molecules consisting of glycerol esterified with three fatty acid molecules. Triglycerides are utilized as carbon and energy storage molecules by most eukaryotic organisms, including plants and algae, and by certain prokaryotic organisms, including certain species of actinomycetes and members of the genus *Acinetobacter*.

Triglycerides may also be utilized as a feedstock in the production of biofuels and/or various specialty chemicals. For example, triglycerides may be subject to a transesterification reaction, in which an alcohol reacts with triglyceride oils, such as those contained in vegetable oils, animal fats, recycled greases, to produce biodiesels such as fatty acid alkyl esters. Such reactions also produce glycerin as a by-product, which can be purified for use in the pharmaceutical and cosmetic industries Certain organisms can be utilized as a source of triglycerides in the production of biofuels. For example, algae naturally produce triglycerides as energy storage molecules, and certain biofuel-related technologies are presently focused on the use of algae as a feedstock for biofuels. Algae are photosynthetic organisms, and the use of triglyceride-producing organisms such as algae provides the ability to produce biodiesel from sunlight, water, $CO_2$, macronutrients, and micronutrients. Algae, however, cannot be readily genetically manipulated, and produce much less oil (i.e., triglycerides) under culture conditions than in the wild.

Like algae, Cyanobacteria obtain energy from photosynthesis, utilizing chlorophyll A and water to reduce $CO_2$. Certain Cyanobacteria can produce metabolites, such as carbohydrates, proteins, and fatty acids, from just sunlight, water, $CO_2$, water, and inorganic salts. Unlike algae, Cyanobacteria can be genetically manipulated. For example, *Synechococcus* is a genetically manipulable, oligotrophic Cyanobacterium that thrives in low nutrient level conditions, and in the wild accumulates fatty acids in the form of lipid membranes to about 10% by dry weight. Cyanobacteria such as *Synechococcus*, however, produce no triglyceride energy storage molecules, since Cyanobacteria typically lack the essential enzymes involved in triglyceride synthesis. Instead, *Synechococcus* in the wild typically accumulates glycogen as its primary carbon storage form.

Clearly, therefore, there is a need in the art for modified photosynthetic microorganisms, including Cyanobacteria, capable of producing increased amounts of lipids such as triglycerides and fatty acids, e.g., to be used as feed stock in the production of biofuels and/or various specialty chemicals.

BRIEF SUMMARY

In various embodiments, the present invention provides modified photosynthetic microorganisms, as well as methods of producing and using the same.

In one embodiment, the present invention includes a modified photosynthetic microorganism comprising an introduced polynucleotide encoding a lipase (e.g., a phospholipase, lysophospholipase, thioesterase), or a fragment or variant thereof, wherein said modified microorganism produces an increased amount of fatty acid and/or lipid as compared to the unmodified photosynthetic microorganism. In particular embodiments, the lipase is a lysophospholipase. In certain embodiments, the lysophospholipase comprises both lysophospholipase and thioesterase activities.

In one embodiment, the present invention includes a modified photosynthetic microorganism comprising an introduced polynucleotide encoding a thioesterase, or a fragment or variant thereof, wherein said modified microorganism produces an increased amount of fatty acid and/or lipid as compared to the unmodified photosynthetic microorganism.

In another embodiment, the present invention provides a method of producing a modified photosynthetic microorganism that accumulates an increased amount of fatty acid and/or lipid as compared to a corresponding wild-type photosynthetic microorganism, comprising introducing a polynucleotide encoding a lipase, e.g., a phospholipase, lysophospholipase, thioesterase, or a fragment or variant thereof, into a photosynthetic microorganism. In particular embodiments, the lipase is a lysophospholipase. In certain embodiments, the lipase comprises both phospholipase (e.g., lysophospholipase) and thioesterase activities. In other embodiments, the lipase has only one activity selected from lysophospholipase and thioesterase activities.

In another embodiment, the present invention provides a method of producing a modified photosynthetic microorganism that accumulates an increased amount of fatty acid and/or lipid as compared to a corresponding wild-type photosynthetic microorganism, comprising introducing a polynucleotide encoding a thioesterase, or a fragment or variant thereof, into a photosynthetic microorganism. In particular embodiments, the lipase is a phospholipase, such as a lysophospholipase. In certain embodiments, the phospholipase comprises both phospholipase and thioesterase activities. In other embodiments, the lipase has only one activity selected from phospholipase and thioesterase activities.

In one embodiment of any of the above methods for producing a modified photosynthetic microorganism, the method further comprises one or more of the following: (i) introducing one or more polynucleotides encoding one or more enzymes associated with fatty acid, lipid and/or triglyceride biosynthesis into said photosynthetic microorganism (e.g., a diacylglycerol acyltransferase (DGAT), phosphatidate phosphatase, or ACCase), or a fragment or variant thereof; (ii) mutating one or more genes of a glycogen biosynthesis or storage pathway in said photosynthetic microorganism (e.g., a glucose-1-phosphate adenyltransferase (glgC) and/or a phosphoglucomutase (pgm) gene); and/or (iii) introducing one or more polynucleotides encoding proteins of a glycogen breakdown pathway, or a fragment or variant thereof, into said photosynthetic microorganism.

In another embodiment, the present invention provides a method for the production of fatty acid and/or lipid, comprising culturing a modified photosynthetic microorganism comprising an introduced polynucleotide encoding a lipase (e.g., a phospholipase, lysophospholipase, thioesterase), or a fragment or variant thereof, wherein said modified photosynthetic microorganism accumulates an increased amount of fatty acid or lipid as compared to a corresponding wild-type photosynthetic microorganism. In particular embodiments, the lipase is a lysophospholipase. In certain embodiments, the phospholipase comprises both phospholipase (e.g., lysophospholipase) and thioesterase activities. In other embodiments, the lipase has only one activity selected from phospholipase (e.g., lysophospholipase) and thioesterase activities. In particular embodiments, the method further comprises inducing expression of the lipase. In certain embodiments, the method comprises culturing the modified photosynthetic microorganism under static growth conditions, e.g., prior to inducing expression and/or while inducing expression of the lipase.

In another embodiment, the present invention provides a method for the production of fatty acid and/or lipid, comprising culturing a modified photosynthetic microorganism comprising an introduced polynucleotide encoding a thioesterase, or a fragment or variant thereof, wherein said modified photosynthetic microorganism accumulates an increased amount of fatty acid or lipid as compared to a corresponding wild-type photosynthetic microorganism. In certain embodiments, the thioesterase comprises both phospholipase (e.g., lysophospholipase) and thioesterase activities. In other embodiments, the thioesterase has only thioesterase activity. In particular embodiments, the method further comprises inducing expression of the thioesterase. In certain embodiments, the method comprises culturing the modified photosynthetic microorganism under static growth conditions, e.g., prior to inducing expression and/or while inducing expression of the thioesterase.

In particular embodiments of the present invention, expression of the lipase is optimized by using endogenous or exogenous promoters of varying strengths and/or one or more copies of the lipase such that continuous high level FFA production without microorganism lethality is achieved. In certain embodiments, the modified photosynthetic microorganism expresses an amount of lipase optimized for continuous, high level fatty acid production without substantial toxicity to the modified photosynthetic microorganism, wherein expression of said amount is regulated by a promoter operably linked to said introduced polynucleotide and/or copy number of said introduced polynucleotide.

In particular embodiments of the present invention, the modified photosynthetic microorganism is a Cyanobacterium. In various embodiments, the Cyanobacterium is a *Synechococcus elongatus*, a *Synechococcus elongatus* PCC 7942, a salt tolerant variant of *Synechococcus elongatus* PCC 7942, a *Synechococcus* sp. PCC 7002, a *Synechocystis* sp. PCC 6803, or an *Anabaena* 7120.

In particular embodiments, the lipase is a phospholipase, a lysophospholipase, or a thioesterase. Certain thioesterases, such as TesA, can hydrolyze both acyl-ACP and acyl-CoA, i.e., acyl-ACP/acyl-CoA thioesterases. Other thioesterases, such as FatB, can hydrolyze acyl-ACP but not acyl-CoA. Certain thioesterase preferentially hydrolyze either acyl-ACP or acyl-CoA. Hence, in certain embodiments, a thioesterase has only one or both of acyl-ACP and/or acyl-CoA hydrolyzing activity, or a has a significantly higher amount of one of either of these activities. In certain embodiments, the lipase is an *E. coli* TesB, which is a thioesterase that preferentially hydrolyzes acyl-CoA. In one embodiment, the *E. coli* TesB comprises a deletion or substitution of one or more amino acids required for transport of TesB from the cytoplasm to the periplasm. In one embodiment, the *E. coli* TesB has the amino acid sequence of SEQ ID NO:92.

In particular embodiments, lipases used according to the present invention have broad substrate specificity. In related embodiments, they have both thioesterase activity and lysophospholipase activity. In other embodiments, the lipase has only one activity selected from thioesterase activity and lysophospholipase activity. For instance, certain lipases have only thioesterase activity, e.g., acyl-ACP thioesterase activity and/or acyl-CoA thioesterase activity, and certain lipases have only lysophospholipase activity.

In related embodiments, the lipase, phospholipase, thioesterase, or lysophospholipase is derived from a bacterium. In certain embodiments, the lysophospholipase is a cytoplasmic-localized *E. coli* Lysophospholipase L1. In one embodiment, the *E. coli* Lysophospholipase L1 comprises a deletion or substitution of one or more amino acids required for transport of Lysophospholipase L1 from the cytoplasm to the periplasm. In one embodiment, the cytoplasmic-localized *E. coli* Lysophospholipase L1 has the amino acid sequence of SEQ ID NO:94. In other embodiments, the lysophospholipase is a periplasmic-localized *E. coli* Lysophospholipase L1. In one embodiment, the *E. coli* Lysophospholipase L1 has the amino acid sequence of SEQ ID NO:86. In further embodiments, the lysophospholipase is a Lysophospholipase L2. In particular embodiments, the Lysophospholipase L2 has the sequence of SEQ ID NO:88. In further embodiments, the lipase is Vu Patatin 1 protein. In particular embodiments, the Vu Patatin 1 protein has the sequence of SEQ ID NO:90.

In certain embodiments, as noted above, the lipase is a thioesterase, having only thioesterase activity and no measurable lysophospholipase activity. In particular embodiments, the thioesterase is derived from a plant. In certain of these and related embodiments, the thioesterase is an acyl-ACP thioesterase but not an acyl-CoA thioesterase, which hydrolyzes acyl-ACP but not acyl-CoA. In other embodiments, the thioesterase is an acyl-CoA thioesterase but not an acyl-ACP thioesterase, which hydrolyzes acyl-CoA but not acyl-ACP. In particular embodiments, the thioesterase is a C8/C10, C12, C14, and/or a C16 FatB acyl-ACP thioesterase, which hydrolyzes acyl-ACP but not acyl-CoA. In some embodiments, the acyl-ACP thioesterase is a *Cuphea hookeriana* C8/C10 FatB2, comprising the amino acid sequence of SEQ ID NO:98 (full-length protein) or SEQ ID NO:99 (mature protein without signal sequence), or a variant thereof. In other embodiments, the acyl-ACP thioesterase is a *Umbellularia californica* C12 FatB1, comprising the amino acid sequence of SEQ ID NO:102 (full-length protein) or SEQ ID NO:103 (mature protein without signal sequence), or a variant thereof. In some embodiments, the acyl-ACP thioesterase is a *Cinnamomum camphora* C14 FatB1, comprising the amino acid sequence of SEQ ID NO:106 (full-length protein) or SEQ ID NO:107 (mature protein without signal sequence), or a variant thereof. In particular embodiments, the acyl-ACP thioesterase is a *Cuphea hookeriana* C16 FatB1, comprising the amino acid sequence of SEQ ID NO:110 (full-length protein) or SEQ ID NO:111 (mature protein without signal sequence), or a variant thereof.

In related embodiments, modified photosynthetic microorganisms of the present invention, which comprise an introduced polynucleotide encoding a lipase (e.g., a phospholipase, lysophosphoholipase, thioesterase), or a fragment or variant thereof, may further comprise one or more additional genetic modifications, e.g., one or more additional introduced polynucleotides and/or one or more partial of full gene deletions.

In one particular embodiment, modified photosynthetic microorganisms of the present invention further comprise one or more introduced polynucleotides encoding one or more enzymes associated with fatty acid, lipid, and/or triglyceride biosynthesis, e.g., a diacylglycerol acyltransferase (DGAT) or a phosphatidate phosphatase, or a fragment or variant thereof. In one embodiment, the DGAT is an *Acinetobacter* DGAT, a *Streptomyces coelicolor* DGAT, or an *Alcanivorax* DGAT. In one embodiment, the phosphatidate phosphatase is a yeast phosphatidate phosphatase.

In another particular embodiment, modified photosynthetic microorganisms of the present invention have reduced expression of one or more genes of a glycogen biosynthesis or storage pathway as compared to the wild type photosynthetic microorganism. In one embodiment, the modified photosynthetic microorganism further comprises a full or partial deletion of one or more genes of a glycogen biosynthesis or storage pathway, e.g., a glucose-1-phosphate adenyltransferase (glgC) gene and/or a phosphoglucomutase (pgm) gene.

In another particular embodiment, modified photosynthetic microorganisms of the present invention further comprise one or more introduced polynucleotides encoding a protein of a glycogen breakdown pathway, or a functional fragment or variant thereof.

In particular embodiments, the modified photosynthetic microorganism accumulates a reduced amount of glycogen under one or more stress conditions as compared to said wild type photosynthetic microorganism. In particular embodiments, the modified photosynthetic microorganism accumulates an increased amount of fatty acid and/or lipid as compared to said wild type photosynthetic microorganism.

In particular embodiments, one or more introduced polynucleotide is present in one or more expression construct, which may optionally be stably integrated into the genome of said modified photosynthetic microorganism. In particular embodiments, the expression construct comprises an inducible promoter. In certain embodiments, the introduced polynucleotide encoding the lipase (e.g., phospholipase) or thioesterase, or fragment or variant thereof, is present in an expression construct and/or is stably integrated into the genome of the modified photosynthetic microorganism, e.g., Cyanobacterium. In certain embodiments, all introduced polynucleotides are present in one or more expression construct and/or stably integrated into the genome of the modified photosynthetic microorganism. In certain embodiments, the introduced polynucleotide encoding said lipase is present in an expression construct comprising a weak promoter under non-induced conditions, such as the pBAD vector.

In certain embodiments, one or more introduced polynucleotide is codon-optimized for expression in a Cyanobacterium, e.g., a *Synechococcus elongatus*. In particular embodiments, the introduced polynucleotide encoding a lipase (e.g., phospholipase, lysophospholipase, thioesterase), or fragment or variant thereof, is codon-optimized for expression in a Cyanobacterium, e.g., a *Synechococcus elongatus*.

BRIEF DESCRIPTION OF THE SEVERAL VIEWS OF THE DRAWINGS

FIG. 2A depicts the results from cells overexpressing periplasmic PldC (TesA), and FIG. 2B depicts the results from cells overexpressing TesB. 5 and 10 μg of a palmitic acid were loaded as a reference for free fatty acids. Cells were grown under shaking (FIG. 2A) or static (FIG. 2B) conditions and induced with the indicated concentrations of arabinose. For FIG. 2A, PldC (*TesA) samples are from cells harvested at 24, 48 or 120 hours post-induction. 1 OD equivalent was loaded per lane for all samples in FIG. 2A. For FIG. 2B, TesB (clones 1 or 2) samples were harvested at 120 h from cultures grown statically and induced with the indicated amounts of arabinose at hour 0 and re-induced at 96 h later. PldC/*tesA samples are from 24 hours post induction. 1 OD equivalent was loaded per lane for TesB clones, and 0.5 OD equivalent was loaded per lane for PldC/*TesA in FIG. 2B. Free fatty acids (FFA) are indicated by arrows to the right of the figures.

FIGS. 7A and 7B show that overexpression of PldC(*tesA) in phylogenetically diverse strains of Cyanobacteria (see FIG. 7A for PCC 6803 and FIG. 7B for PCC 7002) results in increased production of free fatty acids (FFA) relative to wildtype (WT) and empty vector controls. FIG. 7C shows that overexpression of PldC(*tesA) in a salt tolerant variant of *Synechococcus elongatus* of PCC 7942 results in production of free fatty acids.

FIG. 10 shows that overexpression of C14FatB in a glgC knock out mutant which lacks the ability to synthesize glycogen, produces increased amounts of free fatty acis as shown by thin layer chromatography (FIG. 10A, 7 days post induction of C14FatB) or GC analysis of total FAMES μg/OD*ml (FIG. 10B, at indicated time points) when grown in complete media (1× nitrogen, N), as well as when grown in nitrogen depleted conditions-media containing 10% the amount of normal nitrogen found in the media used to grow cyanobacteria (0.1× nitrogen, N)—8 days post induction (FIG. 10O).

DETAILED DESCRIPTION

Figure 1:
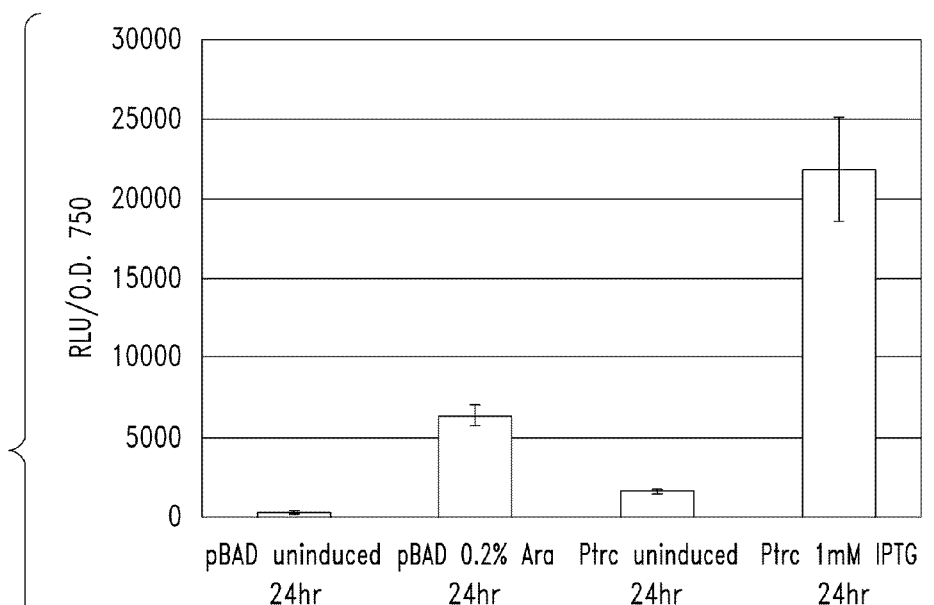
FIG. 1 provides a graph of luciferase activity produced using different promoters and a table indicating whether colonies were produced using these promoters, which demonstrates that expression of *E. coli* lysophospholipase L1 in cyanobacteria requires the use of a low strength promoter. Strains were grown in BG11 media to mid logarithmic phase. The pTrc-luxAB construct was then induced with 1 mM IPTG for 24 h, while the pBAD-luxAB contruct was induced with 0.2% (w/v) arabinose for 24 h. Luciferase activity was detected using a Spectramax M5 spectrophotometer to measure relative luminescence with an integration of 1000 ms. Total luminescence was normalized to the optical density of the cultures at 750 nm.

The present invention is based upon the discovery that photosynthetic microorganisms, e.g., Cyanobacteria, modified to overexpress a lipase (e.g., a lysophospholipase), or a fragment or variant thereof, produce increased amounts of lipids, e.g., triglycerides, free fatty acids, and/or wax esters, and demonstrate an increase in total cellular lipid content, which is advantageous for the production of carbon-based products, including biofuels.

As described in the accompanying Examples, a modified Cyanobacterium overexpressing a mutant form of the lysophospholipase *E. coli* Lysophospholipase L1 (PldC/*TesA), which localizes to the cytoplasm (but retains lipase and thioesterase activities), produced an increased amount of fatty acids and had a net two-fold increase in lipid content, thus doubling lipid content from 10% to 20% of biomass. A further increase in lipid content was generated by co-expressing the mutant Lysophospholipase L1 (PldC/*TesA) with a diacylglycerol acyltransferase (DGAT), resulting in an increase in lipid content from 20% to 30% of biomass, thus yielding strains attractive for biofuel production. Without wishing to be bound by theory, it is understood that overexpression of the phospholipase deregulates and increases de novo lipid synthesis, while overexpression of DGAT provides a metabolic sink for the additional fatty acid generated by the phospholipase.

The present invention, therefore, relates generally to modified photosynthetic microorganisms, including modified Cyanobacteria, that overexpress one or more lipases (e.g., phospholipase, lysophospholipase, thioesterase), or a fragment or variant thereof, including enzymes having one or all of these lipase activities, as well as methods of producing such modified photosynthetic microorganisms and methods of using them for the production of fatty acids and lipid, e.g., for use in the production of carbon-based products. In particular embodiments, the modified photosynthetic microorganism comprises one or more introduced polynucleotides encoding a phospholipase, e.g., a lysophospholipase, or a fragment or variant thereof. In particular embodiments, the phospholipase, e.g., a lysophospholipase, is modified such that it localizes preferentially to the cytoplasm or periplasm.

In particular embodiments, expression of the lipase by the modified photosynthetic microorganism is optimized using endogenous or exogenous promoters of varying strengths and/or one or more copies of the lipase such that continuous high level FFA production without substantial microorganism lethality or toxicity is achieved. In certain embodiments, a modified photosynthetic microorganism of the present invention produces FFA and retains 50% or more of its photosynthetic activity as compared to a corresponding wild type or unmodified phtoosynthetic microorgansism, e.g., the same microorganism prior to modification. Photosynthetic activity may be measured by the rate of light-dependent oxygen evolution.

In particular embodiments, lipases, e.g., phospholipasess, lysophospholipases, thioesterases, used according to the present invention have broad substrate specificity. In some embodiments, they have both thioesterase activity and lysophospholipase activity. In other embodiments, they have only thioesterase activity. Certain thioesterases can hydrolyze both acyl-CoA and acyl-ACP, and are referred to as acyl-CoA/acyl-ACP thioesterases. In some embodiments, thioesterases can hydrolyze acyl-ACP but not acyl-CoA, and are referred to as acyl-ACP thioesterases. Hence, in various embodiments, the lipases used according to the present invention include acyl-CoA/acyl-ACP thioesterases and acyl-ACP thioesterases.

As described above, embodiments of the present invention are also useful in combination with the related discovery that photosynthetic microorganisms, including Cyanobacteria, such as *Synechococcus*, which do not naturally produce triglycerides, can be genetically modified to synthesize triglycerides, as described herein and in International Patent Application US2009/061936 and U.S. patent application Ser. No. 12/605,204, filed Oct. 23, 2009, titled Modified Photosynthetic Microorganisms for Producing Triglycerides. For instance, the addition of one or more polynucleotide sequences that encode one or more enzymes associated with triglyceride synthesis renders Cyanobacteria capable of converting their naturally-occurring fatty acids into triglyceride energy storage molecules. Examples of enzymes associated with triglyceride synthesis include enzymes having a phosphatidate phosphatase activity and enzymes having a diacylglycerol acyltransferase activity (DGAT). Specifically, phosphatidate phosphatase enzymes catalyze the production of diacylglycerol molecules, an immediate pre-cursor to triglycerides, and DGAT enzymes catalyze the final step of triglyceride synthesis by converting the diacylglycerol precursors to triglycerides.

Aspects of the present invention can also be combined with the discovery that photosynthetic microorganisms such as Cyanobacteria can be genetically modified in other ways to increase the production of fatty acids, as described herein and in International Patent Application US2009/061936 and U.S. patent application Ser. No. 12/605,204. Since fatty acids provide the starting material for triglycerides, increasing the production of fatty acids in genetically modified photosynthetic microorganisms may be utilized to increase the production of triglycerides, as described herein and in International Patent Application PCT/US2009/061936. In addition to diverting carbon usage away from glycogen synthesis and towards lipid production, photosynthetic microorganisms of the present invention can also be modified to increase the production of fatty acids by introducing one or more exogenous polynucleotide sequences that encode one or more enzymes associated with fatty acid synthesis. In certain aspects, the exogenous polynucleotide sequence encodes an enzyme that comprises an acyl-CoA carboxylase (ACCase) activity, typically allowing increased ACCase expression, and, thus, increased intracellular ACCase activity. Increased intracellular ACCase activity contributes to the increased production of fatty acids because this enzyme catalyzes the "commitment step" of fatty acid synthesis. Specifically, ACCase catalyzes the production of a fatty acid synthesis precursor molecule, malonyl-CoA. In certain embodiments, the polynucleotide sequence encoding the ACCase is not native the photosynthetic microorganisms's genome.

Aspects of the present invention may also be combined with the discovery that the functional removal of certain genes involved in glycogen synthesis, such as by mutation or deletion, leads to reduced glycogen accumulation and/or storage in photosynthetic microorganisms, such as Cyanobacteria, as described in PCT Application No. US2009/069285 and U.S. patent application Ser. No. 12/645,228. For instance, Cyanobacteria, such as *Synechococcus*, which contain deletions of the glucose-1-phosphate adenylyltransferase gene (glgC), the phosphoglucomutase gene (pgm), and/or the glycogen synthase gene (glgA), individually or in various combinations, may produce and accumulate significantly reduced levels of glycogen as compared to wild-type Cyanobacteria. The reduction of glycogen accumulation may be especially pronounced under stress conditions, including the reduction of nitrogen. Aspects of the present invention may be further combined with the discovery that overexpression of genes or proteins involved in glycogen breakdown in photosynthetic microorganisms, such as Cyanobacteria, also leads to reduced glycogen and/or storage.

A. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. The term "reference sequence" refers generally to a nucleic acid coding sequence, or amino acid sequence, to which another sequence is being compared.

Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 500, 600 or more contiguous nucleotides or amino acid residues in length, including all integers in between, which comprise or encode a polypeptide having an activity of a reference polynucleotide or polypeptide. Representative biologically active fragments generally participate in an interaction, e.g., an intra-molecular or an inter-molecular interaction. An inter-molecular interaction can be a specific binding interaction or an enzymatic interaction. Examples of enzymatic interactions or activities include phospholipase activity, lysophospholipase activity, thioesterase activity, diacylglycerol acyltransferase activity, phosphatidate phosphatase activity, and/or acetyl-CoA carboxylase activity, as described herein.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

By "enzyme reactive conditions" it is meant that any necessary conditions are available in an environment (i.e., such factors as temperature, pH, lack of inhibiting substances) which will permit the enzyme to function. Enzyme reactive conditions can be either in vitro, such as in a test tube, or in vivo, such as within a cell.

As used herein, a "fatty acyl-ACP thioesterase" is an enzyme that catalyzes the cleavage of a fatty acid from an acyl carrier protein (ACP) during lipid synthesis.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

By "increased" or "increasing" is meant the ability of one or more modified photosynthetic microorganisms, e.g., Cyanobacteria, to produce or store a greater amount of a given fatty acid, lipid molecule, or triglyceride as compared to a control photosynthetic microorganism, such as an unmodified Cyanobacteria or a differently modified Cyanobacteria, typically of the same species. Also included are increases in total lipids, total fatty acids, total free fatty acids, total intracellular fatty acids, and/or total secreted fatty acids, separately or together. For instance, in certain embodiments, total lipids may increase, with either corresponding increases in all types of lipids, or relative increases in one or more specific types of lipid (e.g., fatty acids, free fatty acids, secreted fatty acids, triglycerides). In certain embodiments, total lipids may increase or they may stay the same (i.e., total lipids are not significantly increased compared to an unmodified microorganism of the same type), and the production or storage of fatty acids (e.g., free fatty acids, secreted fatty acids) may increase relative to other lipids. In particular embodiments, the production or storage of one or more selected types of fatty acids (e.g., secreted fatty acids, free fatty acids, intracellular fatty acids) may increase relative to other types of fatty acids (e.g., secreted fatty acids, free fatty acids, intracellular fatty acids).

An "increased" or "enhanced" amount is typically a "statistically significant" amount, and may include an increase that is about 1.1, 1.2, 1.5, 1.7, 2, 2.5, 3, 3.5, 4, 4.5, 5, 6, 7, 8, 9, 10, 15, 20, 30 or more times (e.g., 100, 500, 1000 times) (including all integers and decimal points in between and above 1, e.g., 1.5, 1.6, 1.7. 1.8, etc.) the amount produced by an unmodified microorganism or a differently modified microorganism, e.g., of the same species or strain. In particular embodiments, production or storage of total lipids, total triglycerides, total fatty acids, total free fatty acids, total intracellular fatty acids, and/or total secreted fatty acids is increased relative to an unmodified or differently modified microorganism (e.g., for triglycerides, a DGAT-only expressing strain, or a DGAT-expressing strain that does not overexpress an acyl-ACP reductase), as described above, or by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%. In certain embodiments, production or storage of total lipids, total triglycerides, total fatty acids, total free fatty acids, total intracellular fatty acids, and/or total secreted fatty acids is increased by 50% to 200%. The production of "high levels" of total lipids, total triglycerides, total fatty acids, total free fatty acids, total intracellular fatty acids, and/or total secreted fatty acids by a modified photosynthetic microorganism of the present invention refers to levels of at least 120%, at least 150%, at least 200%, at least 300%, at least 400%, at least 500%, at least 1000%, at least 2000%, at least 5000% as compared to a corresponding unmodified photosynthetic microorganism, e.g., the same strain of photosynthetic microorgansim before the modification. "Continuous" high level production of total lipids, total triglycerides, total fatty acids, total free fatty acids, total intracellular fatty acids, and/or total secreted fatty acids by a modified photosynthetic microorganism refers to production of high levels of total lipids, total triglycerides, total fatty acids, total free fatty acids, total intracellular fatty acids, and/or total secreted fatty acids during the time period that the modified photosynthetic microorganism expresses the introduced lipase. Thus, for introduced lipases encoded by polynucleotides operatively linked to a constitutive promoter, continuous, high level production of total lipids, total triglycerides, total fatty acids, total free fatty acids, total intracellular fatty acids, and/or total secreted fatty acids refers to continuous production of high levels of the total lipids, total triglycerides, total fatty acids, total free fatty acids, total intracellular fatty acids, and/or total secreted fatty acids following introduction and expression of the polynucleotide encoding the lipase, whereas for introduced lipases encoded by polynucleotides operably linked to an inducible promoter, continuous, high level production of total lipids, total triglycerides, total fatty acids, total free fatty acids, total intracellular fatty acids, and/or total secreted fatty acids refers to continuous production of high levels of the total lipids, total triglycerides, total fatty acids, total free fatty acids, total intracellular fatty acids, and/or total secreted fatty acids following induction of the promoter and while the promoter is induced.

Production of lipids such as fatty acids can be measured according to techniques known in the art, such as Nile Red staining, thin layer chromatography and gas chromatography. Production of triglycerides can be measured, for example, using commercially available enzymatic tests, including colorimetric enzymatic tests using glycerol-3-phosphate-oxidase. Production of free fatty acids can be measured in absolute units such as overall accumulation of FAMES (e.g., OD/ml, µg/ml) or in units that reflect the production of FAMES over time, i.e., the rate of FAMES production (e.g., OD/ml/day, µg/ml/day). For example, certain modified microorganisms described herein may produce at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 ug/mL/day; and/or in the range of at least about 20-30, 20-35, 20-40, 20-45, 20-50, 25-30, 25-35, 25-40, 25-45, 25-50, 30-35, 30-40, 30-45, 30-50, 35-40, 35-45, 35-50, 40-45, or 40-50 ug/mL/day Production of TAGs can be measured similarly.

In certain instances, by "decreased" or "reduced" is meant the ability of one or more modified photosynthetic microorganisms, e.g., Cyanobacteria, to produce or accumulate a lesser amount (e.g., a statistically significant amount) of a given carbon-based product, such as glycogen, as compared to a control photosynthetic microorganism, such as an unmodified Cyanobacteria or a differently modified Cyanobacteria. Production of glycogen and related molecules can be measured according to techniques known in the art, as exemplified herein (see Example 6; and Suzuki et al., *Biochimica et Biophysica Acta* 1770:763-773, 2007). In certain instances, by "decreased" or "reduced" is meant a lesser level of expression (e.g., a statistically significant amount), by a modified photosynthetic microorganism, e.g., Cyanobacteria, of one or more genes associated with a glycogen biosynthesis or storage pathway, as compared to the level of expression in a control photosynthetic microorganism, such as an unmodified Cyanobacteria or a differently modified Cyanobacteria. In particular embodiments, production or accumulation of a carbon-based product, or expression of one or more genes associated with glycogen biosynthesis or storage is reduced by at least 10%, at least 20%, at least 30%, at least 40%, at least 50%, at least 60%, at least 70%, at least 80%, at least 90%, or 100%. In particular embodiments, production or accumulation of a carbon-based product, or expression of one or more genes associated with glycogen biosynthesis or storage is reduced by 50-100%.

"Stress conditions" refers to any condition that imposes stress upon the Cyanobacteria, including both environmental and physical stresses. Examples of stresses include but not limited to: reduced or increased temperature as compared to standard; nutrient deprivation; reduced or increased light exposure, e.g., intensity or duration, as compared to standard; exposure to reduced or increased nitrogen, iron, sulfur, phosphorus, and/or copper as compared to standard; altered pH, e.g., more or less acidic or basic, as compared to standard; altered salt conditions as compared to standard; exposure to an agent that causes DNA synthesis inhibitor or protein synthesis inhibition; and increased or decreased culture density as compared to standard. Standard growth and culture conditions for various Cyanobacteria are known in the art.

"Reduced nitrogen conditions," or conditions of "nitrogen limitation," refer generally to culture conditions in which a certain fraction or percentage of a standard nitrogen concentration is present in the culture media. Such fractions typically include, but are not limited to, about 1/50, 1/40, 1/30, 1/10, 1/5, 1/4, or about 1/2 the standard nitrogen conditions. Such percentages typically include, but are not limited to, less than about 1%, 2%, 3%, 4%, 5%, 6%, 7%, 8%, 9%, 10%, 15%, 20%, 30%, 40%, or 50% the standard nitrogen conditions. "Standard" nitrogen conditions can be estimated, for example, by the amount of nitrogen present in BG11 media, as exemplified herein and known in the art. For instance, BG11 media usually contains nitrogen in the form of $NaNO_3$ at a concentration of about 1.5 grams/liter (see, e.g., Rippka et al., *J. Gen Microbiol.* 111:1-61, 1979).

As used herein, the term "not substantially toxic" indicates that a modification to a photosynthetic mcroorganism did not cause substantial lethality or toxicity to the microorganism, such that the photosynthetic activity of the modified photosynthetic microorganism is 50% or greater as compared to the photosynthetic activity of a corresponding wild type or unmodified phtoosynthetic microorgansism, e.g., the same microorganism prior to modification. Photosynthetic activity may be measured by the rate of light-dependent oxygen evolution.

By "obtained from" is meant that a sample such as, for example, a polynucleotide or polypeptide is isolated from, or derived from, a particular source, such as a desired organism or a specific tissue within a desired organism. "Obtained from" can also refer to the situation in which a polynucleotide or polypeptide sequence is isolated from, or derived from, a particular organism or tissue within an organism. For example, a polynucleotide sequence encoding a diacylglycerol acyltransferase, phosphatidate phosphatase, and/or acetyl-CoA carboxylase enzyme may be isolated from a variety of prokaryotic or eukaryotic organisms, or from particular tissues or cells within certain eukaryotic organism.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the gene from which it is derived. "Constitutive promoters" are typically active, i.e., promote transcription, under most conditions. "Inducible promoters" are typically active only under certain conditions, such as in the presence of a given molecule factor (e.g., IPTG) or a given environmental condition (e.g., particular $CO_2$ concentration, nutrient levels, light, heat). In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence that encodes a lipase, a phospholipase, a lysophospholipase, a thioesterase, a diacylglycerol acyltransferase, a phosphatidate phosphatase, and/or an acetyl-CoA carboxylase enzyme, among other enzymes described herein. The terms "polynucleotide variant" and "variant" also include naturally-occurring allelic variants and orthologs that encode these enzymes.

With regard to polynucleotides, the term "exogenous" refers to a polynucleotide sequence that does not naturally occur in a wild type cell or organism, but is typically introduced into the cell by molecular biological techniques. Examples of exogenous polynucleotides include vectors, plasmids, and/or man-made nucleic acid constructs encoding a desired protein. With regard to polynucleotides, the term "endogenous" or "native" refers to naturally occurring polynucleotide sequences that may be found in a given wild type cell or organism. For example, certain Cyanobacterial species do not typically contain a DGAT gene, and, therefore, do not comprise an "endogenous" polynucleotide sequence that encodes a DGAT polypeptide. Also, a particular polynucleotide sequence that is isolated from a first organism and transferred to second organism by molecular biological techniques is typically considered an "exogenous" polynucleotide with respect to the second organism.

The recitations "mutation" or "deletion," in relation to the genes of a "glycogen biosynthesis or storage pathway," refer generally to those changes or alterations in a photosynthetic microorganism, e.g., a Cyanobacterium, that render the product of that gene non-functional or having reduced function with respect to the synthesis and/or storage of glycogen. Examples of such changes or alterations include nucleotide substitutions, deletions, or additions to the coding or regulatory sequences of a targeted gene (e.g., glgA, glgC, and pgm), in whole or in part, which disrupt, eliminate, down-regulate, or significantly reduce the expression of the polypeptide encoded by that gene, whether at the level of transcription or translation. Techniques for producing such alterations or changes, such as by recombination with a vector having a selectable marker, are exemplified herein and known in the molecular biological art. In particular embodiments, one or more alleles of a gene, e.g., two or all alleles, may be mutated or deleted within a photosynthetic microorganism. In particular embodiments, modified photosynthetic microorganisms, e.g., Cyanobacteria, of the present invention are merodiploids or partial diploids.

The "deletion" of a targeted gene may also be accomplished by targeting the mRNA of that gene, such as by using various antisense technologies (e.g., antisense oligonucleotides and siRNA) known in the art. Accordingly, targeted genes may be considered "non-functional" when the polypeptide or enzyme encoded by that gene is not expressed by the modified photosynthetic microorganism, or is expressed in negligible amounts, such that the modified photosynthetic microorganism produces or accumulates less glycogen than an unmodified or differently modified photosynthetic microorganism.

In certain aspects, a targeted gene may be rendered "non-functional" by changes or mutations at the nucleotide level that alter the amino acid sequence of the encoded polypeptide, such that a modified polypeptide is expressed, but which has reduced function or activity with respect to glycogen biosynthesis or storage, whether by modifying that polypeptide's active site, its cellular localization, its stability, or other functional features apparent to a person skilled in the art. Such modifications to the coding sequence of a polypeptide involved in glycogen biosynthesis or storage may be accomplished according to known techniques in the art, such as site directed mutagenesis at the genomic level and/or natural selection (i.e., directed evolution) of a given photosynthetic microorganism.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use in the methods described herein of variants of full-length enzymes having lipase activity, phospholipase activity, lysophospholipase activity, thioesterase activity, lysophospholipase and thioesterase activities, diacylglycerol acyltransferase activity, phosphatidate phosphatase activity, and/or acetyl-CoA carboxylase activity, polypeptides associated with a glycogen breakdown pathway, truncated fragments of these full-length enzymes and polypeptides, variants of truncated fragments, as well as their related biologically active fragments. Typically, biologically active fragments of a polypeptide may participate in an interaction, for example, an intra-molecular or an inter-molecular interaction. An inter-molecular interaction can be a specific binding interaction or an enzymatic interaction (e.g., the interaction can be transient and a covalent bond is formed or broken). Biologically active fragments of a polypeptide/enzyme having a lipase activity, a phospholipase activity, a lysophospholipase activity, a thioesterase activity, lysophospholipase and thioesterase activities, a diacylglycerol acyltransferase activity, a phosphatidate phosphatase activity, and/or acetyl-CoA carboxylase activity, or polypeptides associated with a glycogen breakdown pathway, include peptides comprising amino acid sequences sufficiently similar to, or derived from, the amino acid sequences of a (putative) full-length reference polypeptide sequence. Typically, biologically active fragments comprise a domain or motif with at least one activity of a lipase polypeptide, phospholipase polypeptide, lysophospholipase polypeptide, thioesterase polypeptide, diacylglycerol acyltransferase polypeptide, phosphatidate phosphatase polypeptide, acetyl-CoA carboxylase polypeptide, or polypeptide associated with a glycogen breakdown pathway, and may include one or more (and in some cases all) of the various active domains. A biologically active fragment of a lipase, phospholipase, lysophospholipase, thioesterase, diacylglycerol acyltransferase, phosphatidate phosphatase, acetyl-CoA carboxylase polypeptide, or a polypeptide associated with a glycogen breakdown pathway can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 600 or more contiguous amino acids, including all integers in between, of a reference polypeptide sequence. In certain embodiments, a biologically active fragment comprises a conserved enzymatic sequence, domain, or motif, as described elsewhere herein and known in the art. Suitably, the biologically-active fragment has no less than about 1%, 10%, 25%, 50% of an activity of the wild-type polypeptide from which it is derived.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, the term "triglyceride" (triacylglycerol or neutral fat; TAG) refers to a fatty acid triester of glycerol. Triglycerides are typically non-polar and water-insoluble. Phosphoglycerides (or glycerophospholipids) are major lipid components of biological membranes, and include, for example, any derivative of sn-glycero-3-phosphoric acid that contains at least one O-acyl, or O-alkyl or O-alk-1'-enyl residue attached to the glycerol moiety and a polar head made of a nitrogenous base, a glycerol, or an inositol unit. Phosphoglycerides can also be characterized as amphipathic lipids formed by esters of acylglycerols with phosphate and another hydroxylated compound.

"Transformation" refers to the permanent, heritable alteration in a cell resulting from the uptake and incorporation of foreign DNA into the host-cell genome; also, the transfer of an exogenous gene from one organism into the genome of another organism.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a photosynthetic microorganism cell, such as a Cyanobacterial cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The terms "wild type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild type" form of the gene.

B. Modified Photosynthetic Microorganisms

Certain embodiments of the present invention relate to modified photosynthetic microorganisms, including Cyanobacteria, and methods of use thereof, wherein the modified photosynthetic microorganisms comprise one or more exogenous or introduced polynucleotides encoding a lipase (e.g., a phospholipase, a lysophospholipase, a thioesterase), or a fragment or variant thereof. In particular embodiments, the fragment or variant thereof retains at least 50% of one or more activities of the wild type lipases. In certain embodiments, the lipase has both phospholipase (e.g., lysophospholipase) and thioesterase activities. In particular embodiments, the fragment or variant retains at least 50% of both the phospholipase and thioesterase activities of a lipase.

Lipases (e.g., phospholipase, lysophospholipases, thioesterases), and fragments and variants thereof, which may be used according to the compositions and methods of the present invention are described in further detail infra. In particular embodiments, the phospholipase is modified to direct its subcellular localization. Accordingly, in particular embodiments, wild type or modified phospholipases used according to the invention localize predominantly to the cytoplasm or the periplasm. For example, the wild type Lysophospholipase L1 is a periplasmically-localized enzyme, while a modified Lysophospholipase L1 having a deletion of its N-terminal amino acid sequence required for transport of Lysophospholipase L1 from the cytoplasm to the periplasm is predominantly localized to the cytoplasm. One of skill in the art could construct similar modified forms of other phospholipases in order to modulate their sub-cellular localization, e.g., to direct localization to the cytoplasm.

In certain embodiments of the various aspects of the present invention described herein, the introduced lipase has both thioesterase activity and phospholipase, e.g., lysophospholipase, activity. In other embodiments, the lipases have only thioesterase activity, i.e., they have little or no lysophospholipase activity. In certain embodiments, thioesterases such as TesA are capable of hydrolyzing both acyl-ACP and acyl-CoA, i.e., they can cleave fatty acids from both ACP and CoA. In other embodiments, thioesterases such as FatB thioesterases have only acyl-ACP thioesterase activity, e.g., they are capable of hydrolyzing acyl-ACP but not acyl-CoA.

In certain embodiments, the introduced phospholipase is derived from a bacteria, e.g., *E. coli*. In particular embodiments the lysophospholipase is selected from *E. coli* Lysophospholipase L1, *E. coli* TesB, *E. coli* Lysophospholipase L2, Vu Patatin 1 protein, or a variant or fragment thereof, i.e., a mutant form that preferentially remains localized in the cytoplasm.

In particular embodiments, the introduced lipase is a FatB thioesterase derived from a plant. In particular embodiments, the thioesterase is a C8/C10, C12, C14, and/or a C16 FatB acyl-ACP thioesterase. In specific embodiments, the thioesterase is a *Cuphea hookeriana* C8/C10 FatB thioesterase, a *Umbellularia californica* C12 FatB1 thioesterase, a *Cinnamomum camphora* C14 FatB1 thioesterase, or a *Cuphea hookeriana* C16 FatB1 thioesterase. In certain embodiments, the FatB thioesterase is capable of hydrolyzing acyl-ACP but not acyl-CoA, i.e., it does not have significant acyl-CoA thioesterase activity.

In addition, modified photosynthetic microorganisms, e.g., Cyanobacteria, of the present invention may comprise two or more introduced polynucleotides encoding a lipase (e.g., a phospholipase, a lysophospholipase, a thioesterase), or a fragment or variant thereof. Any of the encoded polypeptides may be the same or different. For example, one introduced polynucleotide may encode a Lysophospholipase L1 that localizes to the periplasm, while a second introduced polynucleotide may encode a Lysophospholipase L2 that localizes to the cytoplasm. Another introduced polynucleotide may encode, for example, a FatB thioesterase.

Certain embodiments of the present invention also relate to modified photosynthetic microorganisms, e.g., Cyanobacteria, and methods of use thereof, wherein the modified photosynthetic microorganisms comprise both: (1) one or more introduced polynucleotides encoding a lipase (e.g., a phospholipase, a lysophospholipase, a thioesterase), or a fragment or variant thereof; and (2) one or more introduced polynucleotides encoding one or more enzymes associated with triglyceride biosynthesis, such as wherein the enzymes comprise a diacylglycerol acyltransferase (DGAT) activity and/or a phosphatidate phosphatase activity.

In one embodiment, a modified photosynthetic microorganism of the present invention comprises both: (1) an introduced polynucleotide encoding a phospholipase, e.g., a lysophospholipase, or a fragment or variant thereof; and (2) an introduced polynucleotide encoding a DGAT, or a fragment or variant thereof. Without wishing to be bound by theory, it is understood that overexpression of a phospholipase increases de novo fatty acid synthesis, while expression of a DGAT provides a metabolic sink for the additional fatty acid generated by the phospholipase.

In various embodiments, fragments and variants of polypeptides utilized according to the present invention are functional fragments or functional variants that retain at least 50% of a biological or enzymatic activity of the wild type protein. For example, lysophospholipase fragments or variants may retain thioesterase and/or lysophospholipase activity, and DGAT variants may retain DGAT activity.

The present invention contemplates the use of naturally-occurring and non-naturally-occurring variants of these DGAT and phosphatidate phosphatase enzymes, as well as variants of their encoding polynucleotides. In certain aspects, the DGAT encoding polynucleotide sequence is derived from *Acinetobacter baylii* (ADP1-DGAT) and the phosphatidate phosphatase encoding polynucleotide sequence is from *Saccharomyces cerevisiae* (yPah1). These enzyme encoding sequences, however, may be derived from any organism having a suitable DGAT or phosphatidate phosphatase enzyme, and may also include any man-made variants thereof, such as any optimized coding sequences (i.e., codon-optimized polynucleotides) or optimized polypeptide sequences. Thus, in certain embodiments, modified Cyanobacterium that comprise one or more mutations or deletions in one or more genes of a glycogen biosynthesis or storage pathway may also comprise one or more polynucleotides encoding one or more enzymes associated with triglyceride biosynthesis.

In certain embodiments, the modified photosynthetic microorganisms of the present invention may comprise two or more polynucleotides that encode DGAT or a variant or fragment thereof. In particular embodiments, the two or more polynucleotides are identical or express the same DGAT. In certain embodiments, these two or more polynucleotides may be different or may encode two different DGAT polypeptides. For example, in one embodiment, one of the polynucleotides may encode ADGATd, while another polynucleotide may encode ScoDGAT. In particular embodiments, the following DGATs are coexpressed in modified photosynthetic microorganisms, e.g., Cyanobacteria, using one of the following double DGAT strains: ADGATd(NS1)::ADGATd(NS2); ADGATn(NS1)::ADGATn(NS2); ADGATn(NS1)::SDGAT (NS2); SDGAT(NS1)::ADGATn(NS2); SDGAT(NS1)::SDGAT(NS2). For the NS1 vector, pAM2291, EcoRI follows ATG and is part of the open reading frame (ORF). For the NS2 vector, pAM1579, EcoRI follows ATG and is part of the ORF. A DGAT having EcoRI nucleotides following ATG may be cloned in either pAM2291 or pAM1579; such a DGAT is referred to as ADGATd. Other embodiments utilize the vector, pAM2314FTrc3, which is an NS1 vector with Nde/BglIII sites, or the vector, pAM1579FTrc3, which is the NS2 vector with Nde/BglIII sites. A DGAT without EcoRI nucleotides may be cloned into either of these last two vectors. Such a DGAT is referred to as ADGATn. As shown in the accompanying Examples, modified photosynthetic microorganisms expressing different DGATs express TAGs having different fatty acid compositions. Accordingly, certain embodiments of the present invention contemplate expressing two or more different DGATs, in order to produce TAGs having varied fatty acid compositions.

Certain embodiments of the present invention also relate to modified photosynthetic microorganisms, e.g., Cyanobacteria, and methods of use thereof, wherein the modified photosynthetic microorganisms comprise both: (1) one or more introduced polynucleotides encoding a lipase (e.g., phospholipase, a lysophospholipase, a thioesterase), or a fragment or variant thereof; and (2) one or more introduced polynucleotides encoding one or more enzymes associated with fatty acid synthesis, or a fragment or variant thereof.

In certain aspects, the enzymes associated with fatty acid synthesis comprise an acetyl-CoA carboxylase (ACCase) activity, including naturally-occurring and non-naturally-occurring functional variants of such enzymes and their encoding polynucleotides. In certain embodiments, the polynucleotide sequences encoding the ACCase enzyme is derived from *Synechococcus* sp. PCC 7002 (7002-ACCase). As above, however, these ACCase enzyme encoding sequences may be derived from any organism having a suitable ACCase enzyme, and may also include any man-made variants thereof, such as any optimized coding sequences (i.e., codon-optimized polynucleotides) or optimized polypeptide sequences.

Since fatty acids provide the starting material for triglyceride production, genetically modified photosynthetic microorganisms, e.g., Cyanobacteria, having increased fatty acid production may by utilized to improve the overall production of triglycerides. Accordingly, certain embodiments relate to further modified photosynthetic microorganisms, and methods of use thereof, wherein the modified photosynthetic microorganisms comprise one or more introduced polynucleotides encoding a lipase (e.g., phospholipase, a lysophospholipase, a thioesterase), or a fragment or variant thereof, including enzymes having one or all of these activities, and one or more polynucleotides encoding an enzyme associated with fatty acid synthesis and/or triglyceride synthesis. As such, in certain embodiments, the modified photosynthetic microorganisms of the present invention comprise one or more polynucleotides encoding enzymes that comprise a phospholipase, e.g., a lysophospholipase, activity, in combination with one or more of a DGAT activity, a phosphatidate phosphatase activity, and/or an ACCase activity.

Certain embodiments of modified photosynthetic microorganisms of the present invention comprise both: (1) one or more introduced polynucleotides encoding a lipase (e.g., a phospholipase, a lysophospholipase, a thioesterase), or a fragment or variant thereof; and (2) a further modification such that the modified photosynthetic microorganisms have a reduced level of expression of one or more genes of a glycogen biosynthesis or storage pathway, as compared to the level of expression of the one or more genes in a control photosynthetic microorganism. In certain embodiments, the modified photosynthetic microorganism comprises one or more mutations or deletions in one or more genes of a glycogen biosynthesis or storage pathway. In particular embodiments, said one or more genes include a glucose-1-phosphate adenyltransferase (glgC), a phosphoglucomutase (pgm), and/or a glycogen synthase (glgA) gene. The present invention contemplates the use of any method to reduce expression of the one or more genes in the modified photosynthetic microorganism, including the use of any type of mutation or deletion in the one or more genes associated with glycogen biosynthesis or storage, as long as the modified photosynthetic microorganism, e.g., Cyanobacteria, accumulates a reduced amount of glycogen as compared to a wild type photosynthetic microorganism, e.g., Cyanobacteria (e.g., under reduced nitrogen conditions).

Certain embodiments of modified photosynthetic microorganisms of the present invention comprise both: (1) one or more introduced polynucleotides encoding a lipase (e.g., a phospholipase, a lysophospholipase, a thioesterase), or a fragment or variant thereof; and (2) a further modification such that the modified photosynthetic microorganisms have an increased level of expression of one or more polynucleotides encoding one or more enzymes or proteins associated with glycogen breakdown, removal, and/or elimination (e.g., due to the presence of one or more introduced polynucleotides encoding one or more enzymes or proteins associated with glycogen breakdown, removal, and/or elimination, or a functional fragment or variant thereof). In particular embodiments, said one or more polynucleotides encode a glycogen phosphorylase (GlgP), a glycogen debranching enzyme (GlgX), an amylomaltase (MalQ), a phosphoglucomutase (Pgm), a glucokinase (Glk), and/or a phosphoglucose isomerase (Pgi), or a functional fragment or variant thereof. Pgm, Glk, and Pgi are bidirectional enzymes that can promote glycogen synthesis or breakdown depending on conditions. The present invention contemplates the use of any type of polynucleotide encoding a protein or enzyme associated with glycogen breakdown, removal, and/or elimination, as long as the modified photosynthetic microorganism accumulates a reduced amount of glycogen as compared to the wild type photosynthetic microorganism (e.g., under stress conditions).

Certain embodiments of the present invention also relate to modified photosynthetic microorganisms, e.g., Cyanobacteria, that comprise an introduced polynucleotide encoding a lipase (e.g., a phospholipase, a lysophospholipase, a thioesterase), or a fragment or variant thereof; and any combination of one or more of the additional modifications described above.

Modified photosynthetic microorganisms of the present invention may be produced using any type of photosynthetic microorganism. These include, but are not limited to photosynthetic bacteria, green algae, and cyanobacteria. The photosynthetic microorganism can be, for example, a naturally photosynthetic microorganism, such as a Cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; eukaryotes, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella sp., Scenedesmus obliquus, Anabaenopsis, Aulosira, Cylindrospermum, Synechococcus sp., Synechocystis sp., Gloeothece sp. (e.g. Gloeothece sp. PCC 6909), Cyanothece sp. (e.g., Cyanothece sp. 51142 and/or Tolypothrix.* In particular embodiments, the photosynthetic microorganisms is a nitrogen fixer.

A modified Cyanobacteria of the present invention may be from any genera or species of Cyanobacteria that is genetically manipulable, i.e., permissible to the introduction and expression of exogenous genetic material. Examples of Cyanobacteria that can be engineered according to the methods of the present invention include, but are not limited to, the genus *Synechocystis, Synechococcus, Thermosynechococcus, Nostoc, Prochlorococci, Microcystis, Anabaena, Spirulina,* and *Gloeobacter.*

Cyanobacteria, also known as blue-green algae, blue-green bacteria, or Cyanophyta, is a phylum of bacteria that obtain their energy through photosynthesis. Cyanobacteria can produce metabolites, such as carbohydrates, proteins, lipids and nucleic acids, from $CO_2$, water, inorganic salts and light. Any Cyanobacteria may be used according to the present invention.

Cyanobacteria include both unicellular and colonial species. Colonies may form filaments, sheets or even hollow balls. Some filamentous colonies show the ability to differentiate into several different cell types, such as vegetative cells, the normal, photosynthetic cells that are formed under favorable growing conditions; akinetes, the climate-resistant spores that may form when environmental conditions become harsh; and thick-walled heterocysts, which contain the enzyme nitrogenase, vital for nitrogen fixation.

Heterocysts may also form under the appropriate environmental conditions (e.g., anoxic) whenever nitrogen is necessary. Heterocyst-forming species are specialized for nitrogen fixation and are able to fix nitrogen gas, which cannot be used by plants, into ammonia ($NH_3$), nitrites ($NO_2^-$), or nitrates ($NO_3^-$), which can be absorbed by plants and converted to protein and nucleic acids.

Many Cyanobacteria also form motile filaments, called hormogonia, which travel away from the main biomass to bud and form new colonies elsewhere. The cells in a hormogonium are often thinner than in the vegetative state, and the cells on either end of the motile chain may be tapered. In order to break away from the parent colony, a hormogonium often must tear apart a weaker cell in a filament, called a necridium.

Each individual Cyanobacterial cell typically has a thick, gelatinous cell wall. Cyanobacteria differ from other gram-negative bacteria in that the quorum sensing molecules autoinducer-2 and acyl-homoserine lactones are absent. They lack flagella, but hormogonia and some unicellular species may move about by gliding along surfaces. In water columns some Cyanobacteria float by forming gas vesicles, like in archaea.

Cyanobacteria have an elaborate and highly organized system of internal membranes that function in photosynthesis. Photosynthesis in Cyanobacteria generally uses water as an electron donor and produces oxygen as a by-product, though some Cyanobacteria may also use hydrogen sulfide, similar to other photosynthetic bacteria. Carbon dioxide is reduced to form carbohydrates via the Calvin cycle. In most forms the photosynthetic machinery is embedded into folds of the cell membrane, called thylakoids. Due to their ability to fix nitrogen in aerobic conditions, Cyanobacteria are often found as symbionts with a number of other groups of organisms such as fungi (e.g., lichens), corals, pteridophytes (e.g., Azolla), and angiosperms (e.g., *Gunnera*), among others.

Cyanobacteria are the only group of organisms that are able to reduce nitrogen and carbon in aerobic conditions. The water-oxidizing photosynthesis is accomplished by coupling the activity of photosystem (PS) II and I (Z-scheme). In anaerobic conditions, Cyanobacteria are also able to use only PS I (i.e., cyclic photophosphorylation) with electron donors other than water (e.g., hydrogen sulfide, thiosulphate, or molecular hydrogen), similar to purple photosynthetic bacteria. Furthermore, Cyanobacteria share an archaeal property; the ability to reduce elemental sulfur by anaerobic respiration in the dark. The Cyanobacterial photosynthetic electron transport system shares the same compartment as the components of respiratory electron transport. Typically, the plasma membrane contains only components of the respiratory chain, while the thylakoid membrane hosts both respiratory and photosynthetic electron transport.

Phycobilisomes, attached to the thylakoid membrane, act as light harvesting antennae for the photosystems of Cyanobacteria. The phycobilisome components (phycobiliproteins) are responsible for the blue-green pigmentation of most Cyanobacteria. Color variations are mainly due to carotenoids and phycoerythrins, which may provide the cells with a red-brownish coloration. In some Cyanobacteria, the color of light influences the composition of phycobilisomes. In green light, the cells accumulate more phycoerythrin, whereas in red light they produce more phycocyanin. Thus, the bacteria appear green in red light and red in green light. This process is known as complementary chromatic adaptation and represents a way for the cells to maximize the use of available light for photosynthesis.

In particular embodiments, the Cyanobacteria may be, e.g., a marine form of Cyanobacteria or a fresh water form of Cyanobacteria. Examples of marine forms of Cyanobacteria include, but are not limited to *Synechococcus* WH8102, *Synechococcus* RCC307, *Synechococcus* NKBG 15041c, and *Trichodesmium*. Examples of fresh water forms of Cyanobacteria include, but are not limited to, *S. elongatus* PCC 7942, *Synechocystis* PCC 6803, *Plectonema boryanum*, and *Anabaena* sp. Exogenous genetic material encoding the desired enzymes may be introduced either transiently, such as in certain self-replicating vectors, or stably, such as by integration (e.g., recombination) into the Cyanobacterium's native genome.

In other embodiments, a genetically modified Cyanobacteria of the present invention may be capable of growing in brackish or salt water. When using a fresh water form of Cyanobacteria, the overall net cost for production of triglycerides will depend on both the nutrients required to grow the culture and the price for freshwater. One can foresee freshwater being a limited resource in the future, and in that case it would be more cost effective to find an alternative to freshwater. Two such alternatives include: (1) the use of waste water from treatment plants; and (2) the use of salt or brackish water.

Salt water in the oceans can range in salinity between 3.1% and 3.8%, the average being 3.5%, and this is mostly, but not entirely, made up of sodium chloride (NaCl) ions. Brackish water, on the other hand, has more salinity than freshwater, but not as much as seawater. Brackish water contains between 0.5% and 3% salinity, and thus includes a large range of salinity regimes and is therefore not precisely defined. Waste water is any water that has undergone human influence. It consists of liquid waste released from domestic and commercial properties, industry, and/or agriculture and can encompass a wide range of possible contaminants at varying concentrations.

There is a broad distribution of Cyanobacteria in the oceans, with *Synechococcus* filling just one niche. Specifically, *Synechococcus* sp. PCC 7002 (formerly known as *Agmenellum quadruplicatum* strain PR-6) grows in brackish water, is unicellular and has an optimal growing temperature of 38° C. While this strain is well suited to grow in conditions of high salt, it will grow slowly in freshwater. In particular embodiments, the present invention contemplates the use of a Cyanobacteria *S. elongatus* PCC 7942, altered in a way that allows for growth in either waste water or salt/brackish water. A *S. elongatus* PCC 7942 mutant resistant to sodium chloride stress has been described (Bagchi, S. N. et al., Photosynth Res. 2007, 92:87-101), and a genetically modified *S. elongatus* PCC 7942 tolerant of growth in salt water has been described (Waditee, R. et al., PNAS 2002, 99:4109-4114). Salt water tolerant Cyanobacteria may also be prepared as described in the accompanying Examples. According to the present invention a salt water tolerant strain is capable of growing in water or media having a salinity in the range of 0.5% to 4.0% salinity, although it is not necessarily capable of growing in all salinities encompassed by this range. In one embodiment, a salt tolerant strain is capable of growth in water or media having a salinity in the range of 1.0% to 2.0% salinity. In another embodiment, a salt water tolerant strain is capable of growth in water or media having a salinity in the range of 2.0% to 3.0% salinity.

Examples of Cyanobacteria that may be utilized and/or genetically modified according to the methods described herein include, but are not limited to, *Chroococcales* Cyanobacteria from the genera *Aphanocapsa, Aphanothece, Chamaesiphon, Chroococcus, Chroogloeocystis, Coelosphaerium, Crocosphaera, Cyanobacterium, Cyanobium, Cyanodictyon, Cyanosarcina, Cyanothece, Dactylococcopsis, Gloeocapsa, Gloeothece, Merismopedia, Microcystis, Radiocystis, Rhabdoderma, Snowella, Synechococcus, Synechocystis, Thermosenechococcus*, and *Woronichinia; Nostacales* Cyanobacteria from the genera *Anabaena, Anabaenopsis, Aphanizomenon, Aulosira, Calothrix, Coleodesmium, Cyanospira, Cylindrospermosis, Cylindrospermum, Fremyella, Gleotrichia, Microchaete, Nodularia, Nostoc, Rexia, Richelia, Scytonema, Sprirestis, and Toypothrix; Oscillatoriales* Cyanobacteria from the genera *Arthrospira, Geitlerinema, Halomicronema, Halospirulina, Katagnymene, Leptolyngbya, Limnothrix, Lyngbya, Microcoleus, Oscillatoria, Phormidium, Planktothricoides, Planktothrix, Plectonema, Pseudoanabaena/Limnothrix, Schizothrix, Spirulina, Symploca, Trichodesmium, Tychonema; Pleurocapsales* cyanobacterium from the genera *Chroococcidiopsis, Dermocarpa, Dermocarpella, Myxosarcina, Pleurocapsa, Stanieria, Xenococcus; Prochlorophytes* Cyanobacterium from the genera *Prochloron, Prochlorococcus, Prochlorothrix;* and *Stigonematales* cyanobacterium from the genera *Capsosira, Chlorogeoepsis, Fischerella, Hapalosiphon, Mastigocladopsis, Nostochopsis, Stigonema, Symphyonema, Symphonemopsis, Umezakia,* and *Westiellopsis*. In certain embodiments, the Cyanobacterium is from the genus *Synechococcus*, including, but not limited to *Synechococcus bigranulatus, Synechococcus elongatus, Synechococcus leopoliensis, Synechococcus lividus, Synechococcus nidulans,* and *Synechococcus rubescens*.

In certain embodiments, the Cyanobacterium is *Anabaena* sp. strain PCC 7120, *Synechocystis* sp. strain PCC 6803, *Nostoc muscorum, Nostoc ellipsosporum,* or *Nostoc* sp. strain PCC 7120. In certain preferred embodiments, the Cyanobacterium is *S. elongatus* sp. strain PCC 7942.

Additional examples of Cyanobacteria that may be utilized in the methods provided herein include, but are not limited to, *Synechococcus* sp. strains WH7803, WH8102, WH8103 (typically genetically modified by conjugation), Baeocyte-forming *Chroococcidiopsis* spp. (typically modified by conjugation/electroporation), non-heterocyst-forming filamentous strains *Planktothrix* sp., *Plectonema boryanum* M101 (typically modified by electroporation), and Heterocyst-forming strains *Anabaena* sp. strains ATCC 29413 (typically modified by conjugation), *Tolypothrix* sp. strain PCC 7601 (typically modified by conjugation/electroporation), *Nostoc punctiforme* strain ATCC 29133 (typically modified by conjugation/electroporation), *Gloeothece* sp. PCC 6909, and *Cyanothece* sp. 51142.

In certain preferred embodiments, the Cyanobacterium may be *S. elongatus* sp. strain PCC 7942 or *Synechococcus* sp. PCC 7002 (originally known as *Agmenellum quadruplicatum*).

In particular embodiments, the genetically modified, photosynthetic microorganism, e.g., Cyanobacteria, of the present invention may be used to produce triglycerides and/or other carbon-based products from just sunlight, water, air, and minimal nutrients, using routine culture techniques of any reasonably desired scale. In particular embodiments, the present invention contemplates using spontaneous mutants of photosynthetic microorganisms that demonstrate a growth advantage under a defined growth condition. Among other benefits, the ability to produce large amounts of triglycerides from minimal energy and nutrient input makes the modified photosynthetic microorganism, e.g., Cyanobacteria, of the present invention a readily manageable and efficient source of feedstock in the subsequent production of both biofuels, such as biodiesel, as well as specialty chemicals, such as glycerin.

C. Methods of Producing Modified Photosynthetic Microorganisms

Embodiments of the present invention also include methods of producing the modified photosynthetic microorganisms, e.g., a Cyanobacterium, of the present invention.

In one embodiment, the present invention comprises a method of modifying a photosynthetic microorganism to produce a modified photosynthetic microorganism that produces an increased amount of lipids, e.g., free fatty acids, triglycerides, as compared to a corresponding wild type photosynthetic microorganism, comprising introducing into said microorganism one or more polynucleotides encoding a lipase (e.g., phospholipase, lysophospholipase, thioesterase), or a fragment or variant thereof. In certain embodiments, the lipase has only one or both of phospholipase (e.g., lysophospholipase) activity and thioesterase activity. In certain embodiments, the lipase (e.g., thioesterase) is capable of hydrolyzing only one or both of acyl-ACP and acyl-CoA.

The method may further comprise a step of selecting for photosynthetic microorganisms in which the one or more desired polynucleotides were successfully introduced, where the polynucleotides were, e.g., present in a vector that expressed a selectable marker, such as an antibiotic resistance gene. As one example, selection and isolation may include the use of antibiotic resistant markers known in the art (e.g., kanamycin, spectinomycin, and streptomycin).

In certain embodiments, methods of the present invention comprise both: (1) introducing into said photosynthetic microorganism one or more polynucleotides encoding a lipase (e.g., a phospholipase, a lysophospholipase, a thioesterase), or a fragment or variant thereof; and (2) introducing into said photosynthetic microorganism one or more polynucleotides encoding one or more enzymes associated with fatty acid and/or triglyceride biosynthesis into the photosynthetic microorganism. In certain embodiments, the one or more enzymes comprise a diacylglycerol acyltransferase (DGAT) enzymatic activity and/or a phosphatidate phosphatase enzymatic activity. In certain embodiments, the one or more enzymes comprise an acyl-CoA carboxylase (ACCase) enzymatic activity. Thus, in one particular embodiment, the present invention includes a method of producing a modified photosynthetic microorganism, e.g., a Cyanobacteria, comprising: (1) introducing into said photosynthetic microorganism one or more polynucleotides encoding a lipase (e.g., a phospholipase, a lysophospholipase, a thioesterase), or a fragment or variant thereof; and (2) introducing into said photosynthetic microorganism one or more polynucleotides encoding a DGAT, or a fragment or variant thereof.

In certain embodiments, methods of the present invention comprise both: (1) introducing into said photosynthetic microorganism one or more polynucleotides encoding a lipase (e.g., a phospholipase, a lysophospholipase, a thioesterase), or a fragment or variant thereof; and (2) modifying the photosynthetic microorganism so that it expresses a reduced amount of one or more genes associated with a glycogen biosynthesis or storage pathway and/or an increased amount of one or more polynucleotides encoding a polypeptide associated with a glycogen breakdown pathway. Thus, in one particular embodiment, the present invention includes a method of producing a modified photosynthetic microorganism, e.g., a Cyanobacteria, comprising: (1) introducing into said photosynthetic microorganism one or more polynucleotides encoding a lipase (e.g., a phospholipase, a lysophospholipase, a thioesterase), or a fragment or variant thereof; and (2) modifying the photosynthetic microorganism so that it has a reduced level of expression of one or more genes of a glycogen biosynthesis or storage pathway. In particular embodiments, expression or activity is reduced by mutating or deleting a portion or all of said one or more genes. In particular embodiments, expression or activity is reduced by knocking out or knocking down one or more alleles of said one or more genes. In particular embodiments, expression or activity of the one or more genes is reduced by contacting the photosynthetic microorganism with an antisense oligonucleotide or interfering RNA, e.g., an siRNA, that targets said one or more genes. In particular embodiments, a vector that expresses a polynucleotide that hybridizes to said one or more genes, e.g., an antisense oligonucleotide or an siRNA is introduced into said photosynthetic microorganism.

In certain embodiments, methods of the present invention comprise introducing both: (1) introducing into said photosynthetic microorganism one or more polynucleotides encoding a lipase (e.g., a phospholipase, a lysophospholipase, a thioesterase), or a fragment or variant thereof; (2) introducing into said photosynthetic microorganism one or more polynucleotides encoding one or more enzymes associated with fatty acid and/or triglyceride biosynthesis into the photosynthetic microorganism; and (3) modifying the photosynthetic microorganism so that it expresses a reduced amount of one or more genes associated with a glycogen biosynthesis or storage pathway and/or an increased amount of one or more polynucleotides encoding a polypeptide associated with a glycogen breakdown pathway.

Photosynthetic microorganisms, e.g., Cyanobacteria, may be genetically modified according to techniques known in the art, e.g., to delete a portion or all of a gene or to introduce a polynucleotide that expresses a functional polypeptide. As noted above, in certain aspects, genetic manipulation in photosynthetic microorganisms, e.g., Cyanobacteria, can be performed by the introduction of non-replicating vectors which contain native photosynthetic microorganism sequences, exogenous genes of interest, and selectable markers or drug resistance genes. Upon introduction into the photosynthetic microorganism, the vectors may be integrated into the photosynthetic microorganism's genome through homologous recombination. In this way, an exogenous gene of interest and the drug resistance gene are stably integrated into the photosynthetic microorganism's genome. Such recombinants cells can then be isolated from non-recombinant cells by drug selection. Cell transformation methods and selectable markers for Cyanobacteria are also well known in the art (see, e.g., Wirth, *Mol Gen Genet* 216:175-7, 1989; and Koksharova, *Appl Microbiol Biotechnol* 58:123-37, 2002; and THE CYANOBACTERIA: MOLECULAR BIOLOGY, GENETICS, AND EVOLUTION (eds. Antonio Herrera and Enrique Flores) Caister Academic Press, 2008, each of which is incorporated by reference for their description on gene transfer into Cyanobacteria, and other information on Cyanobacteria).

Generation of deletions or mutations of any of the one or more genes associated with the biosynthesis or storage of glycogen can be accomplished according to a variety of methods known in the art, including the use of a non-replicating, selectable vector system that is targeted to the upstream and downstream flanking regions of a given gene (e.g., glgC, pgm), and which recombines with the Cyanobacterial genome at those flanking regions to replace the endogenous coding sequence with the vector sequence. Given the presence of a selectable marker in the vector sequence, such as a drug selectable marker, Cyanobacterial cells containing the gene deletion can be readily isolated, identified and characterized. Such selectable vector-based recombination methods need not be limited to targeting upstream and downstream flanking regions, but may also be targeted to internal sequences within a given gene, as long as that gene is rendered "non-functional," as described herein.

The generation of deletions or mutations can also be accomplished using antisense-based technology. For instance, Cyanobacteria have been shown to contain natural regulatory events that rely on antisense regulation, such as a 177-nt ncRNA that is transcribed in antisense to the central portion of an iron-regulated transcript and blocks its accumulation through extensive base pairing (see, e.g., Dühring, et al., *Proc. Natl. Acad. Sci. USA* 103:7054-7058, 2006), as well as a alr1690 mRNA that overlaps with, and is complementary to, the complete furA gene, which acts as an antisense RNA (α-furA RNA) interfering with furA transcript translation (see, e.g., Hernandez et al., *Journal of Molecular Biology* 355:325-334, 2006). Thus, the incorporation of antisense molecules targeted to genes involved in glycogen biosynthesis or storage would be similarly expected to negatively regulate the expression of these genes, rendering them "non-functional," as described herein.

As used herein, antisense molecules encompass both single and double-stranded polynucleotides comprising a strand having a sequence that is complementary to a target coding strand of a gene or mRNA. Thus, antisense molecules include both single-stranded antisense oligonucleotides and double-stranded siRNA molecules.

Photosynthetic microorganism may be cultured according to techniques known in the art. For example, Cyanobacteria may be cultured or cultivated according to techniques known in the art, such as those described in Acreman et al. (*Journal of Industrial Microbiology and Biotechnology* 13:193-194, 1994), in addition to photobioreactor based techniques, such as those described in Nedbal et al. (*Biotechnol Bioeng.* 100: 902-10, 2008). One example of typical laboratory culture conditions for Cyanobacterium is growth in BG-11 medium (ATCC Medium 616) at 30° C. in a vented culture flask with constant agitation and constant illumination at 30-100 μmole photons $m^{-2} sec^{-1}$.

A wide variety of mediums are available for culturing Cyanobacteria, including, for example, Aiba and Ogawa (AO) Medium, Allen and Arnon Medium plus Nitrate (ATCC Medium 1142), Antia's (ANT) Medium, Aquil Medium, Ashbey's Nitrogen-free Agar, ASN-III Medium, ASP 2 Medium, ASW Medium (Artificial Seawater and derivatives), ATCC Medium 617 (BG-11 for Marine Blue-Green Algae; Modified ATCC Medium 616 [BG-11 medium]), ATCC Medium 819 (Blue-green Nitrogen-fixing Medium; ATCC Medium 616 [BG-11 medium] without $NO_3$), ATCC Medium 854 (ATCC Medium 616 [BG-11 medium] with Vitamin $B_{12}$), ATCC Medium 1047 (ATCC Medium 957 [MN marine medium] with Vitamin $B_{12}$), ATCC Medium 1077 (Nitrogen-fixing marine medium; ATCC Medium 957 [MN marine medium] without $NO_3$), ATCC Medium 1234 (BG-11 Uracil medium; ATCC Medium 616 [BG-11 medium] with uracil), *Beggiatoa* Medium (ATCC Medium 138), *Beggiatoa* Medium 2 (ATCC Medium 1193), BG-11 Medium for Blue Green Algae (ATCC Medium 616), Blue-Green (BG) Medium, Bold's Basal (BB) Medium, Castenholtz D Medium, Castenholtz D Medium Modified (Halophilic cyanobacteria), Castenholtz DG Medium, Castenholtz DGN Medium, Castenholtz ND Medium, *Chloroflexus* Broth, *Chloroflexus* Medium (ATCC Medium 920), Chu's #10 Medium (ATCC Medium 341), Chu's #10 Medium Modified, Chu's #11 Medium Modified, DCM Medium, DYIV Medium, E27 Medium, E31 Medium and Derivatives, f/2 Medium, f/2 Medium Derivatives, Fraquil Medium (Freshwater Trace Metal-Buffered Medium), Gorham's Medium for Algae (ATCC Medium 625), h/2 Medium, Jaworski's (JM) Medium, K Medium, L1 Medium and Derivatives, MN Marine Medium (ATCC Medium 957), Plymouth Erdschreiber (PE) Medium, *Prochlorococcus* PC Medium, Proteose Peptone (PP) Medium, Prov Medium, Prov Medium Derivatives, S77 plus Vitamins Medium, S88 plus Vitamins Medium, Saltwater Nutrient Agar (SNA) Medium and Derivatives, SES Medium, SN Medium, Modified SN Medium, SNAX Medium, Soil/Water Biphasic (S/W) Medium and Derivatives, SOT Medium for *Spirulina*: ATCC Medium 1679, *Spirulina* (SP) Medium, van Rijn and Cohen (RC) Medium, Walsby's Medium, Yopp Medium, and Z8 Medium, among others.

D. Methods of Producing Lipids, Fatty Acids, and Triglycerides

The modified photosynthetic microorganisms of the present invention may be used to produce lipids, fatty acids and/or triglycerides. Accordingly, the present invention provides methods of producing lipids, fatty acids, and/or triglycerides, comprising culturing any of the modified photosynthetic microorganisms of the present invention under conditions wherein the modified photosynthetic microorganism accumulates an increased amount of cellular lipid as compared to a corresponding wild-type photosynthetic microorganism. In one embodiment, the modified photosynthetic microorganism is a Cyanobacterium.

In various embodiments, the modified photosynthetic microorganism comprises an introduced polynucleotide encoding a lipase, or a fragment or variant thereof. In particular embodiments, said lipase is a phospholipase or a lysophospholipase. In some embodiments, said lipase is a thioesterase. In some embodiments, the lipase has both lysophospholipase and thioesterase activities. In other embodiments, the lipase has thioesterase activity and little or no lysophospholipase activity. Certain thioesterases are capable of hydrolyzing both acyl-ACP and acyl-CoA (e.g., TesA), and other thioesterases are capable of hydrolyzing acyl-ACP but not acyl-CoA (e.g., FatB). Other thioesterases preferentially hydrolyze acyl-CoA as oppoed to acyl-ACP (e.g., *E. coli* TesB).). In one embodiment, said thioesterase is a cytoplasmic-localized *E. coli* TesB, e.g., the *E. coli* TesB having the amino acid sequence of SEQ ID NO:92.

In certain embodiments, the lipase or lysophospholipase is derived from a bacterium. In particular embodiments, said lysophospholipase is a cytoplasmic-localized *E. coli* lysophospholipase L1. In one embodiment, the *E. coli* Lysophospholipase L1 comprises a deletion or substitution of one or more amino acids required for transport of *E. coli* lysophospholipase L1 from the cytoplasm to the periplasm, e.g., an *E. coli* lysophospholipase L1 having the amino acid sequence of SEQ ID NO:94 (PldC(*TesA)). In other embodiments, the lysophospholipase is a periplasmic-localized *E. coli* lysophospholipase L1, e.g., an *E. coli* lysophospholipase L1 having the amino acid sequence of SEQ ID NO:86 (TesA). In a further embodiment, said lysophospholipase is a lysophospholipase L2, e.g., the lysophospholipase L2 having the amino acid sequence of SEQ ID NO:88. In another embodiment, the lipase is a Vu patatin 1 protein, e.g., the Vu patanin 1 protein having the amino acid sequence of SEQ ID NO:90.

In certain embodiments, said lipase is a thioesterase, having little or no lysophospholipase activity. In particular embodiments, the thioesterase is a FatB acyl-ACP thioesterase, which hydrolyzes acyl-ACP but not acyl-CoA. In some embodiments, the thioesterase is a C8/C10, C12, C14, and/or a C16 FatB acyl-ACP thioesterase. In specific embodiments, the thioesterase is a *Cuphea hookeriana* C8/C10 FatB, comprising the amino acid sequence of SEQ ID NO:98 (full-length protein) or SEQ ID NO:99 (mature protein without signal sequence). In particular embodiments, the thioesterase is a *Umbellularia californica* C12 FatB1, comprising the amino acid sequence of SEQ ID NO:102 (full-length protein) or SEQ ID NO:103 (mature protein without signal sequence). In certain embodiments, the thioesterase is a *Cinnamomum camphora* C14 FatB1, comprising the amino acid sequence of SEQ ID NO:106 (full-length protein) or SEQ ID NO:107 (mature protein without signal sequence). In particular embodiments, the thioesterase is a *Cuphea hookeriana* C16 FatB1, comprising the amino acid sequence of SEQ ID NO:110 (full-length protein) or SEQ ID NO:111 (mature protein without signal sequence).

In certain embodiments, the modified photosynthetic microorganism, e.g., Cyanobacteria, further comprises one or more additional modifications. For example, the modified photosynthetic microorganism may further comprises one or more introduced polynucleotides encoding one or more enzymes associated with fatty acid, lipid and/or triglyceride biosynthesis, or a fragment or variant thereof. In particular embodiments, said one or more enzymes comprise a diacylglycerol acyltransferase (DGAT), e.g., an *Acinetobacter* DGAT, a *Streptomyces coelicolor* DGAT, and an *Alcanivorax borkumensis* DGAT. In particular embodiments, said one or more enzymes comprise a phosphatidate phosphatase, e.g., a yeast phosphatidate phosphatase.

In certain embodiments, the modified photosynthetic microorganism further comprises one or more mutated genes of a glycogen biosynthesis or storage pathway; and/or one or more introduced polynucleotides encoding proteins of a glycogen breakdown pathway, or a fragment or variant thereof. Specific examples of these genes and proteins are described infra. In one embodiment, the modified photosynthetic microorganism accumulates a reduced amount of glycogen under one or more stress conditions as compared to said wild type photosynthetic microorganism. In certain embodiments, the one or more mutated genes comprise a glucose-1-phosphate adenyltransferase (glgC) or a phosphoglucomutase (pgm). In various embodiments, said mutation is a complete or partial gene deletion. In other embodiments, the one or more introduced polynucleotides are present in one or more expression constructs. In particular embodiments, the one or more expression constructs comprises one or more inducible promoters. In certain embodiments, the one or more expression constructs are stably integrated into the genome of said modified photosynthetic microorganism. In certain embodiments, the introduced polynucleotide encoding said lipase is present in an expression construct comprising a weak promoter under non-induced conditions. In certain embodiments, the one or more of introduced polynucleotides are codon-optimized for expression in a Cyanobacterium, e.g., a *Synechococcus elongatus*.

In particular embodiments, the photosynthetic microorganism is a *Synechococcus elongatus*, such as *Synechococcus elongatus* strain PCC 7942 or a salt tolerant variant of *Synechococcus elongatus* strain PCC 7942.

In particular embodiments, the photosynthetic microorganism is a *Synechococcus* sp. PCC 7002, a *Synechocystis* sp. PCC 6803 or an Anabaena 7120.

In particular embodiments, the modified photosynthetic microorganisms are cultured under conditions suitable for inducing expression of said lipase (or any other introduced polynucleotide), e.g., when said introduced polynucleotide encoding said lipase comprises an inducible promoter. Conditions and reagents suitable for inducing inducible promoters are known and available in the art.

In certain embodiments, modified photosynthetic microorganisms, e.g., Cyanobacteria, are grown under conditions favorable for producing lipids, triglycerides and/or fatty acids. In particular embodiments, light intensity is between 100 and 2000 uE/m2/s, or between 200 and 1000 uE/m2/s. In particular embodiments, the pH range of culture media is between 7.0 and 10.0. In certain embodiments, $CO_2$ is injected into the culture apparatus to a level in the range of 1% to 10%. In particular embodiments, the range of $CO_2$ is between 2.5% and 5%. In certain embodiments, nutrient supplementation is performed during the linear phase of growth. Each of these conditions is desirable for triglyceride production.

In certain embodiments, the modified photosynthetic microorganisms are cultured, at least for some time, under static growth conditions as opposed to shaking conditions. For example, the modified photosynthetic microorganisms may be cultured under static conditions prior to inducing expression of an introduced polynucleotide, e.g., the lipase, and/or the modified photosynthetic microorganism may be cultured under static conditions while expression of an introduced polynucleotide, e.g., the lipase, is being induced, or during a portion of the time period during which expression on an introduced polynucleotide is being induced. Static growth conditions may be defined as growth without shaking or growth wherein the cells are shaken at less than or equal to 30 rpm or less than or equal to 50 rpm.

In certain embodiments, the modified photosynthetic microorganisms are cultured, at least for some time, in media supplemented with varying amounts of bicarbonate. For example, the modified photosynthetic microorganisms may be cultured with bicarbonate at 5, 10, 20, 50, 75, 100, 200, 300, 400, 500, 600, 700, 800, 900, 1000 mM bicarbonate prior to inducing expression of an introduced polynucleotide (e.g., TesA, FatB, DGAT) and/or the modified photosynthetic microorganism may be cultured with aforementioned bicarbonate concentrations while expression of an introduced polynucleotide is being induced, or during a portion of the time period during which expression on an introduced polynucleotide is being induced.

In related embodiments, modified photosynthetic microorganisms and methods of the present invention may be used in the production of a biofuel and/or a specialty chemical, such as glycerin. Thus, in particular embodiments, a method of producing a biofuel comprises culturing any of the modified photosynthetic microorganisms of the present invention under conditions wherein the modified photosynthetic microorganism accumulates an increased amount of total cellular lipid, fatty acid, and/or triglyceride, as compared to a corresponding wild-type photosynthetic microorganism, obtaining cellular lipid, fatty acid, and/or triglyceride from said microorganism, and processing the obtained cellular lipid, fatty acid, and/or triglyceride to produce a biofuel. In another embodiment, a method of producing a biofuel comprises processing lipids, fatty acids, and/or triglycerides produced by a modified photosynthetic microorganism of the present invention to produce a biofuel. In a further embodiment, a method of producing a biofuel comprises obtaining lipid, fatty acid, and/or triglyceride produced by a modified photosynthetic microorganism of the present invention, and processing the obtained cellular lipid, fatty acid, and/or triglyceride to produce a biofuel.

Methods of processing lipids from microorganisms to produce a biofuel or specialty chemical, e.g., biodiesel, are known and available in the art. For example, triglycerides may be transesterified to produce biodiesel. Transesterification may be carried out by any one of the methods known in the art, such as alkali-, acid-, or lipase-catalysis (see, e.g., Singh et al. Recent Pat Biotechnol. 2008, 2(2):130-143). Various methods of transesterification utilize, for example, use of a batch reactor, a supercritical alcohol, an ultrasonic reactor, or microwave irradiation (Such methods are described, e.g., in Jeong and Park. Appl Biochem Biotechnol. 2006, 131(1-3):668-679; Fukuda et al. Journal of Bioscience and Engineering. 2001, 92(5):405-416; Shah and Gupta. Chemistry Central Journal. 2008, 2(1):1-9; and Carrillo-Munoz et al. J Org. Chem. 1996, 61(22):7746-7749). The biodiesel may be further processed or purified, e.g., by distillation, and/or a biodiesel stabilizer may be added to the biodiesel, as described in U.S. patent application publication No. 2008/0282606.

E. Nucleic Acids and Polypeptides

Modified photosynthetic microorganisms of the present invention comprise one or more exogenous or introduced nucleic acids that encode a lipase (e.g., phospholipase, lysophospholipase), a thioesterase, an enzyme having one or all of these activities, or a fragment or variant thereof. Lipases, including phospholipases, lysophospholipases, thioesterases, and enzymes having one, two, or all three of these activities, typically catalyze the hydrolysis of ester chemical bonds in lipid substrates. In addition, the modified photosynthetic microorgansims may further comprise one or more introduced polynucleotides associated with fatty acid or triglyceride biosynthesis or glycogen breakdown. Also, they may further comprise a mutation or deletion in one or more genes associated with glycogen biosynthesis or storage. In particular embodiments, modified photosynthetic microorganisms of the present invention, which comprise one or more exogenous or introduced nucleic acids that encode a lipase (e.g., a phospholipase, a lysophospholipase, a thioesterase), an enzyme having one or all of these activities, or a fragment or variant thereof, may comprise any combination of one or more of the additional modifications noted above.

1. Lipases

In various embodiments, modified photosynthetic microorganisms, e.g., Cyanobacteria, of the present invention comprise one or more exogenous or introduced nucleic acids that encode a polypeptide having a lipase activity, e.g., a phospholipase, thioesterase, or lysophospholipase, or a fragment or variant thereof. A phospholipase is an enzyme that hydrolyzes phospholipids into fatty acids and other lipophilic substances. There are four major classes, termed A, B, C and D distinguished by what type of reaction they catalyze. Phospholipase A1 cleaves the SN-1 acyl chain, while Phospholipase A2 cleaves the SN-2 acyl chain, releasing arachidonic acid. Phospholipase B cleaves both SN-1 and SN-2 acyl chains, and is also known as a lysophospholipase. Phospholipase C cleaves before the phosphate, releasing diacylglycerol and a phosphate-containing head group. Phospholipase Cs play a central role in signal transduction, releasing the second messenger, inositol triphosphate. Phospholipase D cleaves after the phosphate, releasing phosphatidic acid and an alcohol. Types C and D are considered phosphodiesterases. In various embodiments of the present invention, one or more phospholipase from any one of these classes may be used, alone or in any combination.

In particular embodiments, the present invention contemplates using a lysophospholipase. A lysophospholipase is an enzyme that catalyzes the chemical reaction:

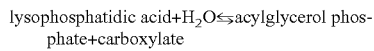

lysophosphatidic acid+$H_2O$⇌acylglycerol phosphate+carboxylate

Thus, the two substrates of this enzyme are lysophosphatidic acid and $H_2O$, whereas its two products are acyl glycerol phosphate and carboxylate.

Lysophospholipases are members of the hydrolase family, specifically those acting on carboxylic ester bonds. Lysophospholipases participate in glycerophospholipid metabolism. Examples of lysophospholipases include, but are not limited to, 2-Lysophosphatidylcholine acylhydrolase, Lecithinase B, Lysolecithinase, Phospholipase B, Lysophosphatidase, Lecitholipase, Phosphatidase B, Lysophosphatidylcholine hydrolase, Lysophospholipase A1, Lysophospholipase L1 (TesA), Lysophopholipase L2, Lysophospholipase transacylase, Neuropathy target esterase, NTE, NTE-LysoPLA, and NTE-lysophospholipase. In particular embodiments, lysophospholipases utilized according to the present invention are derived from a bacteria, e.g., E. coli, or a plant. Any of these lysophospholipases may be used according to various embodiments of the present invention.

Certain lysophospholipases, such as Lysophospholipase L1 (also referred to as PldC or TesA) are periplasmically-localized or cytoplasmically-localized enzymes that have both lysophospholipase and thioesterase activity. Thioesterases exhibit esterase activity (splitting of an ester into acid and alcohol, in the presence of water) specifically at a thiol group. Fatty acids are attached to cofactor molecules, such as coenzyme A (CoA) and acyl carrier protein (ACP), by thioester linkages during the process of de novo fatty acid synthesis. Wild type TesA, being localized to the periplasm, is normally used to hydrolyze thioester linkages of fatty acid-ACP (acyl-ACP) or fatty acid-CoA (acyl-CoA) compounds scavenged from the environment. A mutant lysophospholipase/thioesterase described in the accompanying Examples, PldC(*TesA), is not exported to the periplasm due to deletion of an N-terminal amino acid sequence required for proper transport of TesA from the cytoplasm to the periplasm. This results in a cytoplasmic-localized PldC(*TesA) protein that has access to endogenous acyl-ACP and acyl-CoA intermediates. Overexpressed PldC(*TesA) results in hydrolysis of acyl groups from endogenous acyl-ACP and acyl-CoA molecules. Cells expressing PldC(*TesA) must channel additional cellular carbon and energy to maintain production of acyl-ACP and acyl-coA molecules, which are required for membrane lipid synthesis. Thus, PldC(*TesA) expression results in a net increase in cellular lipid content. As described herein, PldC(*TesA) is expressed in Synechococcus lipid content doubles from 10% of biomass to 20% of biomass.

In certain embodiments of the present invention, lipases utilized according to the present invention have both lysophospholipase and thioesterase activities. Examples of lysophospholipases that have both activities include, e.g., Lysophospholipase L1 (TesA), such as E. coli Lysophospholipase L1, as well as fragments and variants thereof, including those described in the paragraph above. These thioesterases can typically hydrolyze both acyl-ACP and acyl-CoA.

In certain embodiments, lipases have only thioesterase activity, e.g., they have no significant lysophospholipase activity. Examples of thioesterases that have only thioesterase activity include FatB acyl-ACP thioesterases (e.g., C8, C10, C12, C14, C16 thioesterases), such as those derived from Cuphea hookeriana, Umbellularia californica, and Cinnamomum camphora. Certain of these FatB thioesterases can hydrolyze acyl-ACP but not acyl-CoA. Additional thioesterases include E. coli TesB, which preferentially hydrolyzes acyl-CoA as opposed to acyl-ACP.

In other embodiments, a lipase that may be used is Vu Patatin 1 protein, which is a galactolipase.

2. Triglyceride and Fatty Acid Biosynthesis

In various embodiments, modified photosynthetic microorganisms, e.g., Cyanobacteria, of the present invention further comprise one or more exogenous or introduced nucleic acids that encode a polypeptide having an activity associated with triglyceride or fatty acid biosynthesis, including but not limited to any of those described herein. In particular embodiments, the exogenous nucleic acid does not comprise a nucleic acid sequence that is native to the microorganism's genome. In particular embodiments, the exogenous nucleic acid comprises a nucleic acid sequence that is native to the microorganism's genome, but it has been introduced into the microorganism, e.g., in a vector or by molecular biology techniques, for example, to increase expression of the nucleic acid and/or its encoded polypeptide in the microorganism.

a. Triglyceride Biosynthesis

Triglycerides, or triacylglycerols (TAGs), consist primarily of glycerol esterified with three fatty acids, and yield more energy upon oxidation than either carbohydrates or proteins. Triglycerides provide an important mechanism of energy storage for most eukaryotic organisms. In mammals, TAGs are synthesized and stored in several cell types, including adipocytes and hepatocytes (Bell et al. Annu. Rev. Biochem. 49:459-487, 1980) (herein incorporated by reference). In plants, TAG production is mainly important for the generation of seed oils.

In contrast to eukaryotes, the observation of triglyceride production in prokaryotes has been limited to certain actinomycetes, such as members of the genera *Mycobacterium, Nocardia, Rhodococcus* and *Streptomyces*, in addition to certain members of the genus *Acinetobacter*. In certain *Actinomycetes* species, triglycerides may accumulate to nearly 80% of the dry cell weight, but accumulate to only about 15% of the dry cell weight in *Acinetobacter*. In general, triglycerides are stored in spherical lipid bodies, with quantities and diameters depending on the respective species, growth stage, and cultivation conditions. For example, cells of *Rhodococcus opacus* and *Streptomyces lividans* contain only few TAGs when cultivated in complex media with a high content of carbon and nitrogen; however, the lipid content and the number of TAG bodies increase drastically when the cells are cultivated in mineral salt medium with a low nitrogen-to-carbon ratio, yielding a maximum in the late stationary growth phase. At this stage, cells can be almost completely filled with lipid bodies exhibiting diameters ranging from 50 to 400 nm. One example is *R. opacus* PD630, in which lipids can reach more than 70% of the total cellular dry weight.

In bacteria, TAG formation typically starts with the docking of a diacylglycerol acyltransferase enzyme to the plasma membrane, followed by formation of small lipid droplets (SLDs). These SLDs are only some nanometers in diameter and remain associated with the membrane-docked enzyme. In this phase of lipid accumulation, SLDs typically form an emulsive, oleogenous layer at the plasma membrane. During prolonged lipid synthesis, SLDs leave the membrane-associated acyltransferase and conglomerate to membrane-bound lipid prebodies. These lipid prebodies reach distinct sizes, e.g., about 200 nm in *A. calcoaceticus* and about 300 nm in *R. opacus*, before they lose contact with the membrane and are released into the cytoplasm. Free and membrane-bound lipid prebodies correspond to the lipid domains occurring in the cytoplasm and at the cell wall, as observed in *M. smegmatis* during fluorescence microscopy and also confirmed in *R. opacus* PD630 and *A. calcoaceticus* ADP1 (see, e.g., Christensen et al., *Mol. Microbiol.* 31:1561-1572, 1999; and Wältermann et al., *Mol. Microbiol.* 55:750-763, 2005). Inside the lipid prebodies, SLDs coalesce with each other to form the homogenous lipid core found in mature lipid bodies, which often appear opaque in electron microscopy.

The compositions and structures of bacterial TAGs vary considerably depending on the microorganism and on the carbon source. In addition, unusual acyl moieties, such as phenyldecanoic acid and 4,8,12 trimethyl tridecanoic acid, may also contribute to the structural diversity of bacterial TAGs (see, e.g., Alvarez et al., *Appl Microbiol Biotechnol.* 60:367-76, 2002).

As with eukaryotes, the main function of TAGs in prokaryotes is to serve as a storage compound for energy and carbon. TAGs, however, may provide other functions in prokaryotes. For example, lipid bodies may act as a deposit for toxic or useless fatty acids formed during growth on recalcitrant carbon sources, which must be excluded from the plasma membrane and phospholipid (PL) biosynthesis. Furthermore, many TAG-accumulating bacteria are ubiquitous in soil, and in this habitat, water deficiency causing dehydration is a frequent environmental stress. Storage of evaporation-resistant lipids might be a strategy to maintain a basic water supply, since oxidation of the hydrocarbon chains of the lipids under conditions of dehydration would generate considerable amounts of water. Cyanobacteria such as *Synechococcus*, however, do not produce triglycerides, because these organisms lack the enzymes necessary for triglyceride biosynthesis.

Triglycerides are synthesized from fatty acids and glycerol. As one mechanism of triglyceride (TAG) synthesis, sequential acylation of glycerol-3-phosphate via the "Kennedy Pathway" leads to the formation of phosphatidate. Phosphatidate is then dephosphorylated by the enzyme phosphatidate phosphatase to yield 1,2 diacylglycerol (DAG). Using DAG as a substrate, at least three different classes of enzymes are capable of mediating TAG formation. As one example, an enzyme having diacylglycerol transferase (DGAT) activity catalyzes the acylation of DAG using acyl-CoA as a substrate. Essentially, DGAT enzymes combine acyl-CoA with 1,2 diacylglycerol molecule to form a TAG. As an alternative, Acyl-CoA-independent TAG synthesis may be mediated by a phospholipid:DAG acyltransferase found in yeast and plants, which uses phospholipids as acyl donors for DAG esterification. Third, TAG synthesis in animals and plants may be mediated by a DAG-DAG-transacylase, which uses DAG as both an acyl donor and acceptor, yielding TAG and monoacylglycerol.

Modified photosynthetic microorganisms, e.g., Cyanobacteria, of the present invention may comprise one or more exogenous polynucleotides encoding polypeptides comprising one or more of the polypeptides and enzymes described above. In particular embodiments, the one or more exogenous polynucleotides encode a diacylglycerol transferase and/or a phosphatidate phosphatase, or a variant or function fragment thereof.

Since wild type Cyanobacteria do not typically encode the enzymes necessary for triglyceride synthesis, such as the enzymes having phosphatidate phosphatase activity and diacylglycerol transferase activity, embodiments of the present invention include genetically modified Cyanobacteria that comprise polynucleotides encoding one or more enzymes having a phosphatidate phosphatase activity and/or one or more enzymes having a diacylglycerol transferase activity.

Moreover, since triglycerides are typically formed from fatty acids, the level of fatty acid biosynthesis in a cell may limit the production of triglycerides. Increasing the level of fatty acid biosynthesis may, therefore, allow increased production of triglycerides. As discussed below, Acetyl-CoA carboxylase catalyzes the commitment step to fatty acid biosynthesis. Thus, certain embodiments of the present invention include Cyanobacterium, and methods of use thereof, comprising polynucleotides that encode one or more enzymes having Acetyl-CoA carboxylase activity to increase fatty acid biosynthesis and lipid production, in addition to one or more enzymes having phosphatidate phosphatase and/or diacylglycerol transferase activity to catalyze triglyceride production.

b. Diacylglycerol Acyltransferases (DGATs)

Diacylglycerol acyltransferases (DGATs) are members of the O-acyltransferase superfamily, which esterify either sterols or diacyglycerols in an oleoyl-CoA-dependent manner. DGAT in particular esterifies diacylglycerols, which reaction represents the final enzymatic step in the production of triacylglycerols in plants, fungi and mammals. Specifically, DGAT is responsible for transferring an acyl group from acyl-coenzyme-A to the sn-3 position of 1,2-diacylglycerol (DAG) to form triacylglycerol (TAG). DGAT is an integral membrane protein that has been generally described in Harwood (*Biochem. Biophysics. Acta,* 1301:7-56, 1996), Daum et al. (*Yeast* 16:1471-1510, 1998), and Coleman et al. (*Annu. Rev. Nutr.* 20:77-103, 2000) (each of which are herein incorporated by reference).

In plants and fungi, DGAT is associated with the membrane and lipid body fractions. In catalyzing TAGs, DGAT contributes mainly to the storage of carbon used as energy reserves. In animals, however, the role of DGAT is more complex. DGAT not only plays a role in lipoprotein assembly and the regulation of plasma triacylglycerol concentration (Bell, R. M., et al.), but participates as well in the regulation of diacylglycerol levels (Brindley, *Biochemistry of Lipids, Lipoproteins and Membranes*, eds. Vance, D. E. & Vance, J. E. (Elsevier, Amsterdam), 171-203; and Nishizuka, *Science* 258:607-614 (1992) (each of which are herein incorporated by reference)).

In eukaryotes, at least three independent DGAT gene families (DGAT1, DGAT2, and PDAT) have been described that encode proteins with the capacity to form TAG. Yeast contain all three of DGAT1, DGAT2, and PDAT, but the expression levels of these gene families varies during different phases of the life cycle (Dahlqvst, A., at al. *Proc. Natl. Acad. Sci. USA* 97:6487-6492 (2000) (herein incorporated by reference).

In prokaryotes, WS/DGAT from *Acinetobacter calcoaceticus* ADP1 represents the first identified member of a widespread class of bacterial wax ester and TAG biosynthesis enzymes. This enzyme comprises a putative membrane-spanning region but shows no sequence homology to the DGAT1 and DGAT2 families from eukaryotes. Under in vitro conditions, WS/DGAT shows a broad capability of utilizing a large variety of fatty alcohols, and even thiols as acceptors of the acyl moieties of various acyl-CoA thioesters. WS/DGAT acyltransferase enzymes exhibit extraordinarily broad substrate specificity. Genes for homologous acyltransferases have been found in almost all bacteria capable of accumulating neutral lipids, including, for example, *Acinetobacter baylii, A. baumanii*, and *M. avium*, and *M. tuberculosis* CDC1551, in which about 15 functional homologues are present (see, e.g., Daniel et al., *J. Bacteriol.* 186:5017-5030, 2004; and Kalscheuer et al., *J. Biol. Chem.* 287:8075-8082, 2003).

DGAT proteins may utilize a variety of acyl substrates in a host cell, including fatty acyl-CoA and fatty acyl-ACP molecules. In addition, the acyl substrates acted upon by DGAT enzymes may have varying carbon chain lengths and degrees of saturation, although DGAT may demonstrate preferential activity towards certain molecules.

Like other members of the eukaryotic O-acyltransferase superfamily, eukaryotic DGAT polypeptides typically contain a FYxDWWN (SEQ ID NO:13) heptapeptide retention motif, as well as a histidine (or tyrosine)-serine-phenylalanine (H/YSF) tripeptide motif, as described in Zhongmin et al. (*Journal of Lipid Research*, 42:1282-1291, 2001) (herein incorporated by reference). The highly conserved FYxDWWN (SEQ ID NO:13) is believed to be involved in fatty Acyl-CoA binding.

DGAT enzymes utilized according to the present invention may be isolated from any organism, including eukaryotic and prokaryotic organisms. Eukaryotic organisms having a DGAT gene are well-known in the art, and include various animals (e.g., mammals, fruit flies, nematodes), plants, parasites, and fungi (e.g., yeast such as *S. cerevisiae* and *Schizosaccharomyces pombe*). Examples of prokaryotic organisms include certain actinomycetes, a group of Gram-positive bacteria with high G+C ratio, such as those from the representative genera *Actinomyces, Arthrobacter, Corynebacterium, Frankia, Micrococcus, Mocrimonospora, Mycobacterium, Nocardia, Propionibacterium, Rhodococcus* and *Streptomyces*. Particular examples of actinomycetes that have one or more genes encoding a DGAT activity include, for example, *Mycobacterium tuberculosis, M. avium, M. smegmatis, Micromonospora echinospora, Rhodococcus opacus, R. ruber*, and *Streptomyces lividans*. Additional examples of prokaryotic organisms that encode one or more enzymes having a DGAT activity include members of the genera *Acinetobacter*, such as *A. calcoaceticus, A. baumanii*, and *A. baylii*. In certain embodiments, a DGAT gene or enzyme is isolated from *Acinetobacter baylii* sp. ADP1, a gram-negative triglyceride forming prokaryote, which contains a well-characterized DGAT (AffA).

c. Phosphatidate Phosphatase

As used herein, a "phosphatidate phosphatase" gene of the present invention includes any polynucleotide sequence encoding amino acids, such as protein, polypeptide or peptide, obtainable from any cell source, which demonstrates the ability to catalyze the dephosphorylation of phosphatidate (PtdOH) under enzyme reactive conditions, yielding diacylglycerol (DAG) and inorganic phosphate, and further includes any naturally-occurring or non-naturally occurring variants of a phosphatidate phosphatase sequence having such ability.

Phosphatidate phosphatases (PAP, 3-sn-phosphatidate phosphohydrolase) catalyze the dephosphorylation of phosphatidate (PtdOH), yielding diacylglycerol (DAG) and inorganic phosphate. This enzyme belongs to the family of hydrolases, specifically those acting on phosphoric monoester bonds. The systematic name of this enzyme class is 3-sn-phosphatidate phosphohydrolase. Other names in common use include phosphatic acid phosphatase, acid phosphatidyl phosphatase, and phosphatic acid phosphohydrolase. This enzyme participates in at least 4 metabolic pathways: glycerolipid metabolism, glycerophospholipid metabolism, ether lipid metabolism, and sphingolipid metabolism.

PAP enzymes have roles in both the synthesis of phospholipids and triacylglycerol through its product diacylglycerol, as well as the generation or degradation of lipid-signaling molecules in eukaryotic cells. PAP enzymes are typically classified as either $Mg^{2+}$-dependent (referred to as PAP1 enzymes) or $Mg^{2+}$-independent (PAP2 or lipid phosphate phosphatase (LPP) enzymes) with respect to their cofactor requirement for catalytic activity. In both yeast and mammalian systems, PAP2 enzymes are known to be involved in lipid signaling. By contrast, PAP1 enzymes, such as those found in *Saccharomyces cerevisiae*, play a role in de novo lipid synthesis (Han, et al. *J Biol Chem.* 281:9210-9218, 2006), thereby revealing that the two types of PAP are responsible for different physiological functions.

In both yeast and higher eukaryotic cells, the PAP reaction is the committed step in the synthesis of the storage lipid triacylglycerol (TAG), which is formed from PtdOH through the intermediate DAG. The reaction product DAG is also used in the synthesis of the membrane phospholipids phosphatidylcholine (PtdCho) and phosphatidylethanolamine. The substrate PtdOH is used for the synthesis of all membrane phospholipids (and the derivative inositol-containing sphingolipids) through the intermediate CDP-DAG. Thus, regulation of PAP activity might govern whether cells make storage lipids and phospholipids through DAG or phospholipids through CDP-DAG. In addition, PAP is involved in the transcriptional regulation of phospholipid synthesis.

PAP1 enzymes have been purified and characterized from the membrane and cytosolic fractions of yeast, including a gene (Pah1, formerly known as Smp2) been identified to encode a PAP1 enzyme in *S. cerevisiae*. The Pah1-encoded PAP1 enzyme is found in the cytosolic and membrane fractions of the cell, and its association with the membrane is peripheral in nature. As expected from the multiple forms of PAP1 that have been purified from yeast, pah1Δ mutants still contain PAP1 activity, indicating the presence of an additional gene or genes encoding enzymes having PAP1 activity.

Analysis of mutants lacking the Pah1-encoded PAP1 has provided evidence that this enzyme generates the DAG used for lipid synthesis. Cells containing the pah1Δ mutation accumulate PtdOH and have reduced amounts of DAG and its acylated derivative TAG. Phospholipid synthesis predominates over the synthesis of TAG in exponentially growing yeast, whereas TAG synthesis predominates over the synthesis of phospholipids in the stationary phase of growth. The effects of the pah1Δ mutation on TAG content are most evident in the stationary phase. For example, stationary phase cells devoid of the Pah1 gene show a reduction of >90% in TAG content. Likewise, the pah1Δ mutation shows the most marked effects on phospholipid composition (e.g. the consequent reduction in PtdCho content) in the exponential phase of growth. The importance of the Pah1-encoded PAP1 enzyme to cell physiology is further emphasized because of its role in the transcriptional regulation of phospholipid synthesis.

The requirement of $Mg^{2+}$ ions as a cofactor for PAP enzymes is correlated with the catalytic motifs that govern the phosphatase reactions of these enzymes. For example, the Pah1-encoded PAP1 enzyme has a DxDxT (SEQ ID NO:30) catalytic motif within a haloacid dehalogenase (HAD)-like domain ("x" is any amino acid). This motif is found in a superfamily of $Mg^{2+}$-dependent phosphatase enzymes, and its first aspartate residue is responsible for binding the phosphate moiety in the phosphatase reaction. By contrast, the DPP1- and LPP1-encoded PAP2 enzymes contain a three-domain lipid phosphatase motif that is localized to the hydrophilic surface of the membrane. This catalytic motif, which comprises the consensus sequences KxxxxxxRP (domain 1) (SEQ ID NO:10), PSGH (domain 2) (SEQ ID NO:11), and SRxxxxxHxxxD (domain 3) (SEQ ID NO:12), is shared by a superfamily of lipid phosphatases that do not require $Mg^{2+}$ ions for activity. The conserved arginine residue in domain 1 and the conserved histidine residues in domains 2 and 3 may be essential for the catalytic activity of PAP2 enzymes. Accordingly, a phosphatidate phosphatase polypeptide may comprise one or more of the above-described catalytic motifs.

A polynucleotide encoding a polypeptide having a phosphatidate phosphatase enzymatic activity may be obtained from any organism having a suitable, endogenous phosphatidate phosphatase gene. Examples of organisms that may be used to obtain a phosphatidate phosphatase encoding polynucleotide sequence include, but are not limited to, *Homo sapiens, Mus musculus, Rattus norvegicus, Bos taurus, Drosophila melanogaster, Arabidopsis thaliana, Magnaporthe grisea, Saccharomyces cerevisiae, Schizosaccharomyces pombe, Cryptococcus neoformans,* and *Bacillus pumilus*, among others. As used herein, a "diacylglycerol acyltransferase" (DGAT) gene of the present invention includes any polynucleotide sequence encoding amino acids, such as protein, polypeptide or peptide, obtainable from any cell source, which demonstrates the ability to catalyze the production of triacylglycerol from 1,2-diacylglycerol and fatty acyl substrates under enzyme reactive conditions, in addition to any naturally-occurring (e.g., allelic variants, orthologs) or non-naturally occurring variants of a diacylglycerol acyltransferase sequence having such ability. DGAT genes of the present invention also polynucleotide sequences that encode bi-functional proteins, such as those bi-functional proteins that exhibit a DGAT activity as well as a CoA:fatty alcohol acyltransferase activity, i.e., a wax ester synthesis (WS) activity, as often found in many TAG producing bacteria.

d. Fatty Acid Biosynthesis

Fatty acids are a group of negatively charged, linear hydrocarbon chains of various length and various degrees of oxidation states. The negative charge is located at a carboxyl end group and is typically deprotonated at physiological pH values (pK~2-3). The length of the fatty acid 'tail' determines its water solubility (or rather insolubility) and amphipathic characteristics. Fatty acids are components of phospholipids and sphingolipids, which form part of biological membranes, as well as triglycerides, which are primarily used as energy storage molecules inside cells.

Fatty acids are formed from acetyl-CoA and malonyl-CoA precursors. Malonyl-CoA is a carboxylated form of acetyl-CoA, and contains a 3-carbon dicarboxylic acid, malonate, bound to Coenzyme A. Acetyl-CoA carboxylase catalyzes the 2-step reaction by which acetyl-CoA is carboxylated to form malonyl-CoA. In particular, malonate is formed from acetyl-CoA by the addition of $CO_2$ using the biotin cofactor of the enzyme acetyl-CoA carboxylase.

Fatty acid synthase (FAS) carries out the chain elongation steps of fatty acid biosynthesis. FAS is a large multienzyme complex. In mammals, FAS contains two subunits, each containing multiple enzyme activities. In bacteria and plants, individual proteins, which associate into a large complex, catalyze the individual steps of the synthesis scheme. For example, in bacteria and plants, the acyl carrier protein is a smaller, independent protein.

Fatty acid synthesis starts with acetyl-CoA, and the chain grows from the "tail end" so that carbon 1 and the alpha-carbon of the complete fatty acid are added last. The first reaction is the transfer of an acetyl group to a pantothenate group of acyl carrier protein (ACP), a region of the large mammalian fatty acid synthase (FAS) protein. In this reaction, acetyl CoA is added to a cysteine —SH group of the condensing enzyme (CE) domain: acetyl CoA+CE-cys-SH->acetyl-cys-CE+CoASH. Mechanistically, this is a two step process, in which the group is first transferred to the ACP (acyl carrier peptide), and then to the cysteine —SH group of the condensing enzyme domain.

In the second reaction, malonyl CoA is added to the ACP sulfhydryl group: malonyl CoA+ACP-SH->malonyl ACP+CoASH. This —SH group is part of a phosphopantethenic acid prosthetic group of the ACP.

In the third reaction, the acetyl group is transferred to the malonyl group with the release of carbon dioxide: malonyl ACP+acetyl-cys-CE->beta-ketobutyryl-ACP+$CO_2$.

In the fourth reaction, the keto group is reduced to a hydroxyl group by the beta-ketoacyl reductase activity: beta-ketobutyryl-ACP+NADPH+$H^+$->beta-hydroxybutyryl-ACP+$NAD^+$.

In the fifth reaction, the beta-hydroxybutyryl-ACP is dehydrated to form a trans-monounsaturated fatty acyl group by the beta-hydroxyacyl dehydratase activity: beta-hydroxybutyryl-ACP->2-butenoyl-ACP+$H_2O$.

In the sixth reaction, the double bond is reduced by NADPH, yielding a saturated fatty acyl group two carbons longer than the initial one (an acetyl group was converted to a butyryl group in this case): 2-butenoyl-ACP+NADPH+$H^+$->butyryl-ACP+$NADP^+$. The butyryl group is then transferred from the ACP sulfhydryl group to the CE sulfhydryl: butyryl-ACP+CE-cys-SH->ACP-SH+butyryl-cys-CE. This step is catalyzed by the same transferase activity utilized previously for the original acetyl group. The butyryl group is now ready to condense with a new malonyl group (third reaction above) to repeat the process. When the fatty acyl group becomes 16 carbons long, a thioesterase activity hydrolyses it, forming free palmitate: palmitoyl-ACP+$H_2O$->palmitate+ACP-SH. Fatty acid molecules can undergo further modification, such as elongation and/or desaturation.

Modified photosynthetic microorganisms, e.g., Cyanobacteria, may comprise one or more exogenous polynucleotides encoding any of the above polypeptides or enzymes involved in fatty acid synthesis. In particular embodiments, the enzyme is an acetyl-CoA carboxylase or a variant or functional fragment thereof.

As used herein, an "acetyl CoA carboxylase" gene of the present invention includes any polynucleotide sequence encoding amino acids, such as protein, polypeptide or peptide, obtainable from any cell source, which demonstrates the ability to catalyze the carboxylation of acetyl-CoA to produce malonyl-CoA under enzyme reactive conditions, and further includes any naturally-occurring or non-naturally occurring variants of an acetyl-CoA carboxylase sequence having such ability.

Acetyl-CoA carboxylase (ACCase) is a biotin-dependent enzyme that catalyses the irreversible carboxylation of acetyl-CoA to produce malonyl-CoA through its two catalytic activities, biotin carboxylase (BC) and carboxyltransferase (CT). The biotin carboxylase (BC) domain catalyzes the first step of the reaction: the carboxylation of the biotin prosthetic group that is covalently linked to the biotin carboxyl carrier protein (BCCP) domain. In the second step of the reaction, the carboxyltransferase (CT) domain catalyzes the transfer of the carboxyl group from (carboxy) biotin to acetyl-CoA. Formation of malonyl-CoA by acetyl-CoA carboxylase (ACCase) represents the commitment step for fatty acid synthesis, because malonyl-CoA has no metabolic role other than serving as a precursor to fatty acids. Because of this reason, acetyl-CoA carboxylase represents a pivotal enzyme in the synthesis of fatty acids.

In most prokaryotes, ACCase is a multi-subunit enzyme, whereas in most eukaryotes it is a large, multi-domain enzyme. In yeast, the crystal structure of the CT domain of yeast ACCase has been determined at 2.7 A resolution (Zhang et al., *Science*, 299:2064-2067 (2003). This structure contains two domains, which share the same backbone fold. This fold belongs to the crotonase/ClpP family of proteins, with a b-b-a superhelix. The CT domain contains many insertions on its surface, which are important for the dimerization of ACCase. The active site of the enzyme is located at the dimer interface.

Although Cyanobacteria, such as *Synechococcus*, express a native ACCase enzyme, these bacteria typically do not produce or accumulate significant amounts of fatty acids. For example, *Synechococcus* in the wild accumulates fatty acids in the form of lipid membranes to a total of about 4% by dry weight.

Given the role of ACCase in the commitment step of fatty acid biosynthesis, embodiments of the present invention include methods of increasing the production of fatty acid biosynthesis, and, thus, lipid production, in Cyanobacteria by introducing one or more polynucleotides that encode an ACCase enzyme that is exogenous to the Cyanobacterium's native genome. Embodiments of the present invention also include a modified Cyanobacterium, and compositions comprising said Cyanobacterium, comprising one or more polynucleotides that encode an ACCase enzyme that is exogenous to the Cyanobacterium's native genome.

A polynucleotide encoding an ACCase enzyme may be isolated or obtained from any organism, such as any prokaryotic or eukaryotic organism that contains an endogenous ACCase gene. Examples of eukaryotic organisms having an ACCase gene are well-known in the art, and include various animals (e.g., mammals, fruit flies, nematodes), plants, parasites, and fungi (e.g., yeast such as *S. cerevisiae* and *Schizosaccharomyces pombe*). In certain embodiments, the ACCase encoding polynucleotide sequences are obtained from *Synechococcus* sp. PCC7002.

Examples of prokaryotic organisms that may be utilized to obtain a polynucleotide encoding an enzyme having ACCase activity include, but are not limited to, *Escherichia coli, Legionella pneumophila, Listeria monocytogenes, Streptococcus pneumoniae, Bacillus subtilis, Ruminococcus obeum* ATCC 29174, marine gamma proteobacterium HTCC2080, *Roseovarius* sp. HTCC2601, *Oceanicola granulosus* HTCC2516, *Bacteroides caccae* ATCC 43185, *Vibrio alginolyticus* 12G01, *Pseudoalteromonas tunicata* D2, *Marinobacter* sp. ELB17, marine gamma proteobacterium HTCC2143, *Roseobacter* sp. SK209-2-6, Oceanicola batsensis HTCC2597, *Rhizobium leguminosarum* bv. *trifolii* WSM1325, *Nitrobacter* sp. Nb-311A, *Chloroflexus aggregans* DSM 9485, *Chlorobaculum parvum, Chloroherpeton thalassium, Acinetobacter baumannii, Geobacillus,* and *Stenotrophomonas maltophilia*, among others.

3. Glycogen Synthesis and Storage

In particular embodiments, a modified photosynthetic microorganism further comprises additional modifications, such that it has reduced expression of one or more genes associated with a glycogen synthesis or storage pathway and/or increased expression of one or more polynucleotides that encode a protein associated with a glycogen breakdown pathway, or a functional variant of fragment thereof.

In various embodiments, modified photosynthetic microorganisms, e.g., Cyanobacteria, of the present invention have reduced expression of one or more genes associated with glycogen synthesis and/or storage. In particular embodiments, these modified photosynthetic microorganisms have a mutated or deleted gene associated with glycogen synthesis and/or storage. In particular embodiments, these modified photosynthetic microorganisms comprise a vector that includes a portion of a mutated or deleted gene, e.g., a targeting vector used to generate a knockout or knockdown of one or more alleles of the mutated or deleted gene. In certain embodiments, these modified photosynthetic microorganisms comprise an antisense RNA or siRNA that binds to an mRNA expressed by a gene associated with glycogen synthesis and/or storage.

In certain embodiments, modified photosynthetic microorganisms, e.g., Cyanobacteria, of the present invention comprise one or more exogenous or introduced nucleic acids that encode a polypeptide having an activity associated with a glycogen breakdown or triglyceride or fatty acid biosynthesis, including but not limited to any of those described herein. In particular embodiments, the exogenous nucleic acid does not comprise a nucleic acid sequence that is native to the microorganism's genome. In particular embodiments, the exogenous nucleic acid comprises a nucleic acid sequence that is native to the microorganism's genome, but it has been introduced into the microorganism, e.g., in a vector or by molecular biology techniques, for example, to increase expression of the nucleic acid and/or its encoded polypeptide in the microorganism.

a. Glycogen Biosynthesis

Glycogen is a polysaccharide of glucose, which functions as a means of carbon and energy storage in most cells, including animal and bacterial cells. More specifically, glycogen is a very large branched glucose homopolymer containing about 90% $\alpha$-1,4-glucosidic linkages and 10% $\alpha$-1,6 linkages. For bacteria in particular, the biosynthesis and storage of glycogen in the form of $\alpha$-1,4-polyglucans represents an important strategy to cope with transient starvation conditions in the environment.

Glycogen biosynthesis involves the action of several enzymes. For instance, bacterial glycogen biosynthesis occurs generally through the following general steps: (1) formation of glucose-1-phosphate, catalyzed by phosphoglucomutase (Pgm), followed by (2) ADP-glucose synthesis from ATP and glucose 1-phosphate, catalyzed by glucose-1-phosphate adenylyltransferase (GlgC), followed by (3) transfer of the glucosyl moiety from ADP-glucose to a pre-existing α-1,4 glucan primer, catalyzed by glycogen synthase (GlgA). This latter step of glycogen synthesis typically occurs by utilizing ADP-glucose as the glucosyl donor for elongation of the α-1,4-glucosidic chain.

In bacteria, the main regulatory step in glycogen synthesis takes place at the level of ADP-glucose synthesis, or step (2) above, the reaction catalyzed by glucose-1-phosphate adenylyltransferase (GlgC), also known as ADP-glucose pyrophosphorylase (see, e.g., Ballicora et al., *Microbiology and Molecular Biology Reviews* 6:213-225, 2003). In contrast, the main regulatory step in mammalian glycogen synthesis occurs at the level of glycogen synthase. As shown herein, by altering the regulatory and/or other active components in the glycogen synthesis pathway of photosynthetic microorganisms such as Cyanobacteria, and thereby reducing the biosynthesis and storage of glycogen, the carbon that would have otherwise been stored as glycogen can be utilized by said photosynthetic microorganism to synthesize other carbon-based storage molecules, such as lipids, fatty acids, and triglycerides.

b. Glycogen Biosynthesis Genes

Therefore, certain modified photosynthetic microorganisms, e.g., Cyanobacteria, of the present invention may comprise a mutation, deletion, or any other alteration that disrupts one or more of these steps (i.e., renders the one or more steps "non-functional" with respect to glycogen biosynthesis and/or storage), or alters any one or more of the enzymes directly involved in these steps, or the genes encoding them. As noted above, such modified photosynthetic microorganisms, e.g., Cyanobacteria, are typically capable of producing and/or accumulating an increased amount of lipids, such as fatty acids, as compared to a wild type photosynthetic microorganism.

i. Phosphoglucomutase Gene (pgm)

In one embodiment, a modified photosynthetic microorganism, e.g., a Cyanobacteria, expresses a reduced amount of the phosphoglucomutase gene. In particular embodiments, it may comprise a mutation or deletion in the phosphoglucomutase gene, including any of its regulatory elements (e.g., promoters, enhancers, transcription factors, positive or negative regulatory proteins, etc.). Phosphoglucomutase (Pgm), encoded by the gene pgm, catalyzes the reversible transformation of glucose 1-phosphate into glucose 6-phosphate, typically via the enzyme-bound intermediate, glucose 1,6-biphosphate (see, e.g., Lu et al., *Journal of Bacteriology* 176:5847-5851, 1994). Although this reaction is reversible, the formation of glucose-6-phosphate is markedly favored.

However, typically when a large amount of glucose-6-phosphate is present, Pgm catalyzes the phosphorylation of the 1-carbon and the dephosphorylation of the c-carbon, resulting in glucose-1-phosphate. The resulting glucose-1-phosphate is then converted to UDP-glucose by a number of intermediate steps, including the catalytic activity of GlgC, which can then be added to a glycogen storage molecule by the activity of glycogen synthase, described below. Thus, under certain conditions, the Pgm enzyme plays an intermediary role in the biosynthesis and storage of glycogen.

The pgm gene is expressed in a wide variety of organisms, including most, if not all, Cyanobacteria. The pgm gene is also fairly conserved among Cyanobacteria, as can be appreciated upon comparison of SEQ ID NOs:37 (*S. elongatus* PCC 7942), 75 (*Synechocystis* sp. PCC 6803), and 79 (*Synechococcus* sp. WH8102), which provide the polynucleotide sequences of various pgm genes from Cyanobacteria.

Deletion of the pgm gene in Cyanobacteria, such as *Synechococcus*, has been demonstrated herein for the first time to reduce the accumulation of glycogen in said Cyanobacteria, and also to increase the production of other carbon-based products, such as lipids and fatty acids.

ii. Glucose-1-Phosphate Adenylyltransferase (glgC)

In one embodiment, a modified photosynthetic microorganism, e.g., a Cyanobacteria, expresses a reduced amount of a glucose-1-phosphate adenylyltransferase (glgC) gene. In certain embodiments, it may comprise a mutation or deletion in the glgC gene, including any of its regulatory elements. The enzyme encoded by the glgC gene (e.g., EC 2.7.7.27) participates generally in starch, glycogen and sucrose metabolism by catalyzing the following chemical reaction:

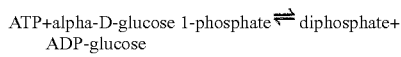

ATP+alpha-D-glucose 1-phosphate ⇌ diphosphate+ ADP-glucose

Thus, the two substrates of this enzyme are ATP and alpha-D-glucose 1-phosphate, whereas its two products are diphosphate and ADP-glucose. The glgC-encoded enzyme catalyzes the first committed and rate-limiting step in starch biosynthesis in plants and glycogen biosynthesis in bacteria. It is the enzymatic site for regulation of storage polysaccharide accumulation in plants and bacteria, being allosterically activated or inhibited by metabolites of energy flux.

The enzyme encoded by the glgC gene belongs to a family of transferases, specifically those transferases that transfer phosphorus-containing nucleotide groups (i.e., nucleotidyltransferases). The systematic name of this enzyme class is typically referred to as ATP:alpha-D-glucose-1-phosphate adenylyltransferase. Other names in common use include ADP glucose pyrophosphorylase, glucose 1-phosphate adenylyltransferase, adenosine diphosphate glucose pyrophosphorylase, adenosine diphosphoglucose pyrophosphorylase, ADP-glucose pyrophosphorylase, ADP-glucose synthase, ADP-glucose synthetase, ADPG pyrophosphorylase, and ADP:alpha-D-glucose-1-phosphate adenylyltransferase.

The glgC gene is expressed in a wide variety of plants and bacteria, including most, if not all, Cyanobacteria. The glgC gene is also fairly conserved among Cyanobacteria, as can be appreciated upon comparison of SEQ ID NOs:67 (*S. elongatus* PCC 7942), 59 (*Synechocystis* sp. PCC 6803), 73 (*Synechococcus* sp. PCC 7002), 69 (*Synechococcus* sp. WH8102), 71 (*Synechococcus* sp. RCC 307), 65 (*Trichodesmium erythraeum* IMS101), 63 (*Anabaena varibilis*), and 61 (*Nostoc* sp. PCC 7120), which describe the polynucleotide sequences of various glgC genes from Cyanobacteria.

Deletion of the glgC gene in Cyanobacteria, such as *Synechococcus*, has been demonstrated herein for the first time to reduce the accumulation of glycogen in said Cyanobacteria, and also to increase the production of other carbon-based products, such as lipids and fatty acids.

iii. Glycogen Synthase (glgA)

In one embodiment, a modified photosynthetic microorganism, e.g., a Cyanobacteria, expresses a reduced amount of a glycogen synthase gene. In particular embodiments, it may comprise a deletion or mutation in the glycogen synthase gene, including any of is regulatory elements. Glycogen synthase (GlgA), also known as UDP-glucose-glycogen glucosyltransferase, is a glycosyltransferase enzyme that catalyses the reaction of UDP-glucose and $(1,4-\alpha-D-glucosyl)_n$ to yield UDP and $(1,4-\alpha-D-glucosyl)_{n+1}$. Glycogen synthase is an α-retaining glucosyltransferase that uses ADP-glucose to incorporate additional glucose monomers onto the growing glycogen polymer. Essentially, GlgA catalyzes the final step of converting excess glucose residues one by one into a polymeric chain for storage as glycogen.

Classically, glycogen synthases, or α-1,4-glucan synthases, have been divided into two families, animal/fungal glycogen synthases and bacterial/plant starch synthases, according to differences in sequence, sugar donor specificity and regulatory mechanisms. However, detailed sequence analysis, predicted secondary structure comparisons, and threading analysis show that these two families are structurally related and that some domains of animal/fungal synthases were acquired to meet the particular regulatory requirements of those cell types.

Crystal structures have been established for certain bacterial glycogen synthases (see, e.g., Buschiazzo et al., *The EMBO Journal* 23, 3196-3205, 2004). These structures show that reported glycogen synthase folds into two Rossmann-fold domains organized as in glycogen phosphorlyase and other glycosyltransferases of the glycosyltransferases superfamily, with a deep fissure between both domains that includes the catalytic center. The core of the N-terminal domain of this glycogen synthase consists of a nine-stranded, predominantly parallel, central β-sheet flanked on both sides by seven α-helices. The C-terminal domain (residues 271-456) shows a similar fold with a six-stranded parallel β-sheet and nine α-helices. The last α-helix of this domain undergoes a kink at position 457-460, with the final 17 residues of the protein (461-477) crossing over to the N-terminal domain and continuing as α-helix, a typical feature of glycosyltransferase enzymes.

These structures also show that the overall fold and the active site architecture of glycogen synthase are remarkably similar to those of glycogen phosphorylase, the latter playing a central role in the mobilization of carbohydrate reserves, indicating a common catalytic mechanism and comparable substrate-binding properties. In contrast to glycogen phosphorylase, however, glycogen synthase has a much wider catalytic cleft, which is predicted to undergo an important interdomain 'closure' movement during the catalytic cycle.

Crystal structures have been established for certain GlgA enzymes (see, e.g., Jin et al., *EMBO J.* 24:694-704, 2005, incorporated by reference). These studies show that the N-terminal catalytic domain of GlgA resembles a dinucleotide-binding Rossmann fold and the C-terminal domain adopts a left-handed parallel beta helix that is involved in cooperative allosteric regulation and a unique oligomerization. Also, communication between the regulator-binding sites and the active site involves several distinct regions of the enzyme, including the N-terminus, the glucose-1-phosphate-binding site, and the ATP-binding site.

The glgA gene is expressed in a wide variety of cells, including animal, plant, fungal, and bacterial cells, including most, if not all, Cyanobacteria. The glgA gene is also fairly conserved among Cyanobacteria, as can be appreciated upon comparison of SEQ ID NOs:51 (*S. elongatus* PCC 7942), 43 (*Synechocystis* sp. PCC 6803), 57 (*Synechococcus* sp. PCC 7002), 53 (*Snyechococcus* sp. WH8102), 55 (*Synechococcus* sp. RCC 307), 49 (*Trichodesmium erythraeum* IMS101), 47 (*Anabaena variabilis*), and 45 (*Nostoc* sp. PCC 7120), which describe the polynucleotide sequences of various glgA genes from Cyanobacteria.

c. Glycogen Breakdown Genes

In certain embodiments, a modified photosynthetic microorganism of the present invention expresses an increased amount of one or more genes associated with a glycogen breakdown pathway. In particular embodiments, said one or more polynucleotides encode glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof. Pgm, Glk, and Pgi are bidirectional enzymes that can promote glycogen synthesis or breakdown depending on conditions.

F. Polynucleotides and Vectors

Modified photosynthetic microorganisms, e.g., Cyanobacteria, of the present invention, comprise one or more introduced polynucleotides encoding a lipase (e.g., a phospholipase, a lysophospholipase, or a thioesterase), or a fragment or variant thereof. In certain embodiments, modified photosynthetic microorganisms of the present invention further comprise one or more exogenous polynucleotides encoding a polypeptide associated with glycogen breakdown or with triglyceride or fatty acid biosynthesis, or a variant or a functional fragment thereof. Accordingly, the present invention utilizes isolated polynucleotides that encode lipases, e.g., phospholipases, lysophospholipases o thioesterases, the various glycogen breakdown pathway proteins, and triglyceride and lipid biosynthesis enzymes described herein, such as diacylglycerol acyltransferase, phosphatidate phosphatase, and acetyl-CoA carboxylase, in addition to nucleotide sequences that encode any functional naturally-occurring variants or fragments (i.e., allelic variants, orthologs, splice variants) or non-naturally occurring variants or fragments of these native enzymes (i.e., optimized by engineering), as well as compositions comprising such polynucleotides, including, e.g., cloning and expression vectors.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man. In certain embodiments, a polynucleotide sequence used according to the present invention includes only coding sequence of any of the polynucleotide sequences provided herein.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a diacylglycerol acyltransferase, a phosphatidate phosphatase, an acetyl-CoA carboxylase, or a portion thereof) or may comprise a variant, or a biological functional equivalent of such a sequence. Polynucleotide variants may contain one or more substitutions, additions, deletions and/or insertions, as further described below, preferably such that the enzymatic activity of the encoded polypeptide is not substantially diminished relative to the unmodified polypeptide. The effect on the enzymatic activity of the encoded polypeptide may generally be assessed as described herein.

In certain embodiments of the present invention, a modified photosynthetic microorganism comprises one or more polynucleotides encoding one or more lipases, phospholipases, lysophospholipases, or thioesterases, or a fragment or variant thereof. In certain embodiments, the encoded lysophospholipase is Lysophospholipase L1 (TesA), Lysophospholipase L2, or a homolog thereof. In other embodiments, the encoded lipase is TesB or Vu Patatin 1 protein.

In particular embodiments, the encoded lipase or phospholipase, e.g., a lysophospholipase, is a bacterial phospholipase, or a fragment or variant thereof, and the polynucleotide comprises a bacterial phospholipase polynucleotide sequence, e.g., a sequence derived from *Escherichia coli, Enterococcus faecalis*, or *Lactobacillus plantarum*. In particular embodiments, the encoded phospholipase is Lysophospholipase L1 (TesA), Lysophospholipase L2, or a functional fragment thereof. In other embodiments, the encoded lipase is TesB, or Vu Patatin 1 protein, In certain embodiments, a lysophospholipase is a bacterial Lysophospholipase L1 (TesA), such as an *E. coli* Lysophospholipase L1 encoded by a polynucleotide (pldC) having the wild-type sequence set forth in SEQ ID NO:85. The polypeptide sequence of *E. coli* Lysophospholipase L1 is provided in SEQ ID NO:86. In other embodiments, a lysophospholipase is a Lysophospholipase L2, such as an *E. coli* Lysophospholipase L2 encoded by a polynucleotide (pldB) having the wild-type sequence set forth in SEQ ID NO:87. The polypeptide sequence of *E. coli* Lysophospholipase L2 is provided in SEQ ID NO:88.

In certain embodiments, a lipase is a bacterial lipase, such as *E. coli* TesB encoded by a polynucleotide having the wild-type sequence set forth in SEQ ID NO:91. The polypeptide sequence of *E. coli* TesB is provided in SEQ ID NO:92. In other embodiments, the lipase is a Vu patatin 1 protein encoded by a polynucleotide having the wild-type sequence set forth in SEQ ID NO:89. The polypeptide sequence of Vu patatin 1 protein is provided in SEQ ID NO:90.

In particular embodiments, lipase is a phospholipase variant, wherein the polynucleotide encoding the phospholipase variant is modified such that it encodes a phospholipase that localizes predominantly to the cytoplasm instead of the periplasm. For example, it may encode a phospholipase having a deletion or mutation in a region associated with periplasmic localization. In particular embodiments, the encoded phospholipase variant is derived from Lysophospholipase L1 (TesA) or TesB. In certain embodiments, the Lysophospholipase L1 (TesA) or TesB variant is a bacterial TesA or TesB variant, such as an *E. coli* Lysophospholipase (TesA) variant encoded by a polynucleotide having the sequence set forth in SEQ ID NO:93. The polypeptide sequence of the Lysophospholipase L1 variant is provided in SEQ ID NO:94 (PldC (*TesA)).

In certain embodiments, the polynucleotide encodes a thioesterase, having only thioesterase activity and little or no lysophospholipase activity, such as TesB, for example. In specific embodiments, the thioesterase is a FatB acyl-ACP thioesterase, which can hydrolyze acyl-ACP but not acyl-CoA. SEQ ID NO:96 is an exemplary nucleotide sequence of a C8/C10 FatB2 thioesterase derived from *Cuphea hookeriana*, and SEQ ID NO:97 is codon-optimized for expression in Cyanobacteria. SEQ ID NO:100 is an exemplary nucleotide sequence of a C12 FatB1 acyl-ACP thioesterase derived from *Umbellularia californica*, and SEQ ID NO:101 is a codon-optimized version of SEQ ID NO:100 for optimal expression in Cyanobacteria. SEQ ID NO:104 is an exemplary nucleotide sequence of a C14 FatB1 thioesterase derived from *Cinnamomum camphora*, and SEQ:105 is a codon-optimized version of SEQ ID NO:104. SEQ ID NO:108 is an exemplary nucleotide sequence of a C16 FatB1 thioesterase derived from *Cuphea hookeriana*, and SEQ ID NO:109 is a codon-optimized version of SEQ ID NO:108. In certain embodiments, one or more FatB sequences are operably linked to a strong promoter, such as a Ptrc promoter. In other embodiments, one or more FatB sequences are operably linked to a relatively weak promoter, such as an arabinose promoter.

In certain embodiments of the present invention, a polynucleotide encodes a DGAT comprising of consisting of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd (*Acinetobacter baylii* sp.). In certain embodiments of the present invention, a DGAT polynucleotide comprises or consists of a polynucleotide sequence set forth in any one of SEQ ID NOs:4, 7, 16, 17, or 19, or a fragment or variant thereof. SEQ ID NO:4 is a codon-optimized for expression in Cyanobacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd. DGATn and DGATd correspond to *Acinetobacter baylii* DGAT and a modified form thereof, which includes two additional amino acid residues immediately following the initiator methionine.

In certain embodiments of the present invention, a polynucleotide encodes a phosphatidate phosphatase comprising or consisting of a polypeptide sequence set forth in SEQ ID NO:2, or a fragment or variant thereof. In particular embodiments, a phosphatidate phosphatase polynucleotide comprises or consists of a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPAH1), and SEQ ID NO:5 is a codon-optimized for expression in Cyanobacteria sequence that encodes yPAH1.

In certain embodiments of the present invention, a polynucleotide encodes an acetyl-CoA carboxylase (ACCase) comprising or consisting of a polypeptide sequence set forth in any of SEQ ID NOs:3, 20, 21, 22, 23, or 28, or a fragment or variant thereof. In particular embodiments, a ACCase polynucleotide comprises or consists of a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yAcc1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *Triticum aestivum* ACCase; and SEQ ID NO:29 encodes this *Triticum aestivum* ACCase.

In certain embodiments of the present invention, a modified photosynthetic microorganism comprises one or more polynucleotides encoding one or more polypeptides associated with a glycogen breakdown, or a fragment or variant thereof. In particular embodiments, the one or more polypeptides are glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof. A representative glgP polynucleotide sequence is provided in SEQ ID NO:31, and a representative GlgP polypeptide sequence is provided in SEQ ID NO:32. A representative glgX polynucleotide sequence is provided in SEQ ID NO:33, and a representative GlgX polypeptide sequence is provided in SEQ ID NO:34. A representative malQ polynucleotide sequence is provided in SEQ ID NO:35, and a representative MalQ polypeptide sequence is provide in SEQ ID NO:36. A representative phosphoglucomutase (pgm) polynucleotide sequence is provided in SEQ ID NO:37, and a representative phosphoglucomutase (Pgm) polypeptide sequence is provided in SEQ ID NO:38, with others provided infra (SEQ ID NOs:75-84). A representative glk polynucleotide sequence is provided in SEQ ID NO:39, and a representative Glk polypeptide sequence is provided in SEQ ID NO:40. A representative pgi polynucleotide sequence is provided in SEQ ID NO:41, and a representative Pgi polypeptide sequence is provided in SEQ ID NO:42. In particular embodiments of the present invention, a polynucleotide comprises one of these polynucleotide sequences, or a fragment or variant thereof, or encodes one of these polypeptide sequences, or a fragment or variant thereof.

In certain embodiments, the present invention provides isolated polynucleotides comprising various lengths of contiguous stretches of sequence identical to or complementary to a phospholipase, a lysophospholipase, a diacylglycerol acyltransferase, a phosphatidate phosphatase, or an acetyl-CoA carboxylase, wherein the isolated polynucleotides encode a biologically active, truncated enzyme.

Exemplary nucleotide sequences that encode the proteins and enzymes of the application encompass full-length lipases (e.g., a phospholipase, a lysophospholipase, a thioesterase), diacylglycerol acyltransferases, phosphatidate phosphatases, and/or acetyl-CoA carboxylases, as well as portions of the full-length or substantially full-length nucleotide sequences of these genes or their transcripts or DNA copies of these transcripts. Portions of a nucleotide sequence may encode polypeptide fragments, portions or segments that retain the biological activity of the reference polypeptide. A fragment or portion of a nucleotide sequence that encodes a biologically active fragment of an enzyme provided herein may encode at least about 20, 21, 22, 23, 24, 25, 30, 40, 50, 60, 70, 80, 90, 100, 120, 150, 200, 300, 400, 500, 600, or more contiguous amino acid residues, almost up to the total number of amino acids present in a full-length enzyme. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The invention also contemplates variants of the nucleotide sequences of the lipases (e.g., a phospholipase, a lysophospholipase, a thioesterase), diacylglycerol acyltransferases, phosphatidate phosphatases, and acetyl-CoA carboxylases utilized according to methods and compositions provided herein. Nucleic acid variants can be naturally-occurring, such as allelic variants (same locus), homologs (different locus), and orthologs (different organism) or can be non naturally-occurring. Naturally occurring variants such as these can be identified and isolated using well-known molecular biology techniques including, for example, various polymerase chain reaction (PCR) and hybridization-based techniques as known in the art. Naturally occurring variants can be isolated from any organism that encodes one or more genes having a lipase activity, phospholipase activity, a lysophospholipase activity, a thioesterase activity, a diacylglycerol acyltransferase activity, a phosphatidate phosphatase activity, and/or a acetyl-CoA carboxylase activity. Embodiments of the present invention, therefore, encompass Cyanobacteria comprising such naturally occurring polynucleotide variants.

Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. In certain aspects, non-naturally occurring variants may have been optimized for use in Cyanobacteria, such as by engineering and screening the enzymes for increased activity, stability, or any other desirable feature. The variations can produce both conservative and non-conservative amino acid substitutions (as compared to the originally encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a biologically active polypeptide, such as a polypeptide having one or more of a lipase activity, a phospholipase activity, a lysophospholipase activity, a thioesterase activity, a diacylglycerol acyltransferase activity, a phosphatidate phosphatase activity, or a acetyl-CoA carboxylase activity. Generally, variants of a particular reference nucleotide sequence will have at least about 30%, 40% 50%, 55%, 60%, 65%, 70%, generally at least about 75%, 80%, 85%, 90%, 95% or 98% or more sequence identity to that particular nucleotide sequence as determined by sequence alignment programs described elsewhere herein using default parameters.

Known lipase (e.g., phospholipase, lysophospholipase, thioesterase), glycogen breakdown polypeptide, diacylglycerol acyltransferase, phosphatidate phosphatase, and/or acetyl-CoA carboxylase nucleotide sequences can be used to isolate corresponding sequences and alleles from other organisms, particularly other microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other reference coding sequences present in a population of cloned genomic DNA fragments or cDNA fragments (i.e., genomic or cDNA libraries) from a chosen organism.

Accordingly, the present invention also contemplates polynucleotides that hybridize to reference lipases, phospholipases, lysophospholipases, thioesterases, glycogen breakdown polypeptides, diacylglycerol acyltransferase, phosphatidate phosphatase, or acetyl-CoA carboxylase nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and nonaqueous methods are described in that reference and either can be used.

Reference herein to "low stringency" conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6×sodium chloride/sodium citrate (SSC) at about 45°□C., followed by two washes in 0.2×SSC, 0.1% SDS at least at 50° C. (the temperature of the washes can be increased to 55° C. for low stringency conditions).

"Medium stringency" conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45°□C., followed by one or more washes in 0.2×SSC, 0.1% SDS at 60° C.

"High stringency" conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a lipase, phospholipase, lysophospholipase, thioesterase, glycogen breakdown polypeptide, diacylglycerol acyltransferase enzyme, phosphatidate phosphatase enzyme, or acetyl-CoA carboxylase enzyme is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6(\log_{10} M)+0.41(\% \text{ G+C})-0.63 (\% \text{ formamide})-(600/\text{length})$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m-15°$ C. for high stringency, or $T_m-30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionizer formamide, 5×SSC, 5× Reinhardt's solution (0.1% fecal, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2× SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a triglyceride or lipid biosynthesis enzyme in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such nucleotides are typically referred to as "codon-optimized."

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector that contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. In certain embodiments, the polynucleotides of the present invention may be introduced and expressed in Cyanobacterial systems. As such, the present invention contemplates the use of vector and plasmid systems having regulatory sequences (e.g., promoters and enhancers) that are suitable for use in various Cyanobacteria (see, e.g., Koksharova et al. *Applied Microbiol Biotechnol* 58:123-37, 2002). For example, the promiscuous RSF1010 plasmid provides autonomous replication in several Cyanobacteria of the genera *Synechocystis* and *Synechococcus* (see, e.g., Mermet-Bouvier et al., *Curr Microbiol* 26:323-327, 1993). As another example, the pFC1 expression vector is based on the promiscuous plasmid RSF1010. pFC1 harbors the lambda cI857 repressor-encoding gene and pR promoter, followed by the lambda cro ribosome-binding site and ATG translation initiation codon (see, e.g., Mermet-Bouvier et al., *Curr Microbiol* 28:145-148, 1994). The latter is located within the unique NdeI restriction site (CATATG) of pFC1 and can be exposed after cleavage with this enzyme for in-frame fusion with the protein-coding sequence to be expressed.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. Generally, it is well-known that strong *E. coli* promoters work well in Cyanobacteria. Also, when cloning in Cyanobacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. Other vectors containing IPTG inducible promoters, such as pAM1579 and pAM2991trc, may be utilized according to the present invention.

Certain embodiments may employ a temperature inducible system. As one example, an operon with the bacterial phage left-ward promoter ($P_L$) and a temperature sensitive repressor gene CI857 may be employed to produce a temperature inducible system for producing fatty acids and/or triglycerides in Cyanobacteria (see, e.g., U.S. Pat. No. 6,306,639, herein incorporated by reference). It is believed that at a non-permissible temperature (low temperature, 30 degrees Celsius), the repressor binds to the operator sequence, and thus prevents RNA polymerase from initiating transcription at the $P_L$ promoter. Therefore, the expression of encoded gene or genes is repressed. When the cell culture is transferred to a permissible temperature (37-42 degrees Celsius), the repressor cannot bind to the operator. Under these conditions, RNA polymerase can initiate the transcription of the encoded gene or genes.

In Cyanobacterial systems, a number of expression vectors may be selected depending upon the use intended for the expressed polypeptide. When large quantities are needed, vectors which direct high level expression of encoded proteins may be used. For example, overexpression of ACCase enzymes may be utilized to increase fatty acid biosynthesis. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST).

Certain embodiments may employ Cyanobacterial promoters or regulatory operons. In certain embodiments, a promoter may comprise an rbcLS operon of *Synechococcus*, as described, for example, in Ronen-Tarazi et al. (*Plant Physiology* 18:1461-1469, 1995), or a cpc operon of *Synechocystis* sp. strain PCC 6714, as described, for example, in Imashimizu et al. (*J. Bacteriol.* 185:6477-80, 2003). In certain embodiments, the tRNApro gene from *Synechococcus* may also be utilized as a promoter, as described in Chungjatupornchai et al. (*Curr Microbiol.* 38:210-216, 1999). Certain embodiments may employ the nirA promoter from *Synechococcus* sp. strain PCC 7942, which is repressed by ammonium and induced by nitrite (see, e.g., Maeda et al., *J. Bacteriol.* 180:4080-4088, 1998; and Qi et al., *Applied and Environmental Microbiology* 71:5678-5684, 2005). The efficiency of expression may be enhanced by the inclusion of enhancers which are appropriate for the particular Cyanobacterial cell system which is used, such as those described in the literature.

In certain embodiments, expression vectors utilized to express a lipase (e.g., a phospholipase, a lysophospholipase, a thioesterase), or fragment or variant thereof, comprise a weak promoter under non-inducible conditions, e.g., to avoid toxic effects of long-term overexpression of any of these polypeptides. One example of such a vector for use in Cyanobacteria is the pBAD vector system. Expression levels from any given promoter may be determined, e.g., by performing quantitative polymerase chain reaction (qPCR) to determine the amount of transcript or mRNA produced by a promoter, e.g., before and after induction. In certain instances, a weak promoter is defined as a promoter that has a basal level of expression of a gene or transcript of interest, in the absence of inducer, that is ≤2.0% of the expression level produced by the promoter of the mpB gene in *S. elongatus* PCC7942. In other embodiments, a weak promoter is defined as a promoter that has a basal level of expression of a gene or transcript of interest, in the absence of inducer, that is ≤5.0% of the expression level produced by the promoter of the mpB gene in *S. elongatus* PCC7942. One specific example of a weak promoter is the arabinose promoter.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed.

However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983). The presence of a desired polynucleotide, such as a diacylglycerol acyltransferase, phosphatidate phosphatase, and/or an acetyl-CoA carboxylase encoding polypeptide, may also be confirmed by PCR.

In particular embodiments, expression of the lipase is optimized using endogenous or exogenous promoters of varying strengths and/or one or more copies of the lipase such that continuous high level FFA production without significant or substantial microorganism lethality is achieved. For example, expression of the lipase may be increased by expressing two, three, or more copies of a lipase in the modified photosynthetic microorganism. The two, three, or more lipases expressed in the photosynthetic microorganism may be the same lipase, or they may be two or more different lipases. For example, in one embodiment, a modified photosynthetic microorganism of the present invention comprises one or more introduced polynucleotides, each encoding two or more lipases, which may be the same or different. In a related embodiment, a modified photosynthetic microorganisms or the present invention comprises two or more introduced polynucleotides, each encoding one or more lipases, which may be the same or different. In particular embodiments, the two or more lipases are selected from phospholipases, lysophospholipases, galactolipases, and thioesterases. In certain embodiments, the two or more lipases include one or more thioesterase. In particular embodiments, the thioesterase is TesA or TesB. In particular embodiments, the thioesterase is a C8/C10, C12, C14, and/or a C16 FatB acyl-ACP thioesterase. In some embodiments, the thioesterase is a *Cuphea hookeriana* C8/C10 FatB2. In other embodiments, the thioesterase is a *Umbellularia californica* C12 FatB1. In some embodiments, the thioesterase is a *Cinnamomum camphora* C14 FatB1. In particular embodiments, the thioesterase is a *Cuphea hookeriana* C16 FatB1. In one particular embodiment, a modified photosynthetic microorganism expresses two copies of C14 FatB acyl-ACP thioesterase (see, e.g., FIG. 8H).

In particular embodiments wherein two or more lipases are expressed in the modified photosynthetic microorganism, expression of each of the two or more lipases may be optimized by having each lipase operably linked to an endogenous or exogenous promoter that achieves a desired expression level. For example, expression of the two or more lipases may be optimized to achieve high levels of fatty acid production with minimal toxicity. In certain embodiments, an inducible promoter is used to drive expression of one or more of the two or more lipases. In particular embodiments, two or more lipases are expressed using inducible promoters, which may be the same or different inducble promoters, thereby allowing simultaneous induction of expression of two or more lipases (same inducible promoter) or separate or coordinate induction of expression of two or more lipases (different inducible promoters). According to these methods, modified photosynthetic microorganisms that produce high levels of free fatty acids without substantial toxicity may be generated.

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Cyanobacterial host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct localization of the encoded polypeptide to a desired site within the cell. Other recombinant constructions may be used to join sequences encoding a polypeptide of interest to nucleotide sequence encoding a polypeptide domain which will direct secretion of the encoded protein.

In particular embodiments of the present invention, a modified photosynthetic microorganism of the present invention has reduced expression of one or more genes selected from glucose-1-phosphate adenyltransferase (glgC), phosphoglucomutase (pgm), and/or glycogen synthase (glgA). In particular embodiments, the modified photosynthetic microorganism comprises a mutation of one or more of these genes. Specific glgC, pgm, and glgA sequences may be mutated or modified, or targeted to reduce expression.

Examples of such glgC polynucleotide sequences are provided in SEQ ID NOs:59 (*Synechocystis* sp. PCC 6803), 61 (*Nostoc* sp. PCC 7120), 63 (*Anabaena variabilis*), 65 (*Trichodesmium erythraeum* IMS101), 67 (*Synechococcus elongatus* PCC 7942), 69 (*Synechococcus* sp. WH8102), 71 (*Synechococcus* sp. RCC 307), and 73 (*Synechococcus* sp. PCC 7002), which respectively encode GlgC polypeptides having sequences set forth in SEQ ID NOs: 60, 62, 64, 66, 68, 70, 72, and 74.

Examples of such pgm polynucleotide sequences are provided in SEQ ID NOs: 75 (*Synechocystis* sp. PCC 6803), 77 (*Synechococcus elongatus* PCC 7942), 79 (*Synechococcus* sp. WH8102), 81 (*Synechococcus* RCC307), and 83 (*Synechococcus* 7002), which respectively encode Pgm polypeptides having sequences set forth in SEQ ID NOs:76, 78, 80, 82, and 84.

Examples of such glgA polynucleotide sequences are provided in SEQ ID NOs:43 (*Synechocystis* sp. PCC 6803), 45 (*Nostoc* sp. PCC 7120), 47 (*Anabaena variabilis*), 49 (*Trichodesmium erythraeum* IMS101), 51 (*Synechococcus elongatus* PCC 7942), 53 (*Synechococcus* sp. WH8102), 55 (*Synechococcus* sp. RCC 307), and 57 (*Synechococcus* sp. PCC 7002), which respectively encode GlgA polypeptides having sequences set forth in SEQ ID NOs:44, 46, 48, 50, 52, 54, 56, and 58.

G. Polypeptides

The present invention contemplates the use of modified photosynthetic microorganisms, e.g., Cyanobacteria, comprising one or more introduced polynucleotides encoding a lipase (e.g., a phospholipase, a lysophospholipase, a thioesterase), or a fragment or variant thereof. Certain embodiments of the present invention contemplate the use of modified photosynthetic microorganisms, e.g., Cyanobacteria, further comprising one or more additional introduced polypeptides, including those associated with a glycogen breakdown pathway or having a diacylglycerol acyltransferase activity, a phosphatidate phosphatase activity, and/or an acetyl-CoA carboxylase activity, including truncated, variant and/or modified polypeptides thereof, for increasing lipid production and/or producing triglycerides in said modified photosynthetic microorganism.

In particular embodiments, the phospholipase is a bacterial phospholipase, e.g., lysophospholipase, or a fragment or variant thereof, e.g., a phospholipase derived from *Escherichia coli*, *Enterococcus faecalis*, or *Lactobacillus plantarum*.

In particular embodiments, the encoded phospholipase comprises or consists of a Lysophospholipase L1 (TesA), Lysophospholipase L2, TesB, or Vu patatin 1 protein, or a homolog, fragment, or variant thereof. In certain embodiments, the Lysophospholipase L1 (TesA), Lysophospholipase L2, or TesB is a bacterial Lysophospholipase L1 (TesA), Lysophospholipase L2, or TesB, such as an *E. coli* Lysophospholipase L1 (TesA) having the wild-type sequence set forth in SEQ ID NO:86, an *E. coli* Lysophospholipase L2 having the wild-type sequence set forth in SEQ ID NO:88, or an *E. coli* TesB having the wild-type sequence set forth in SEQ ID NO:92. In particular embodiment, the Vu patatin 1 protein has the wild-type sequence set forth in SEQ ID NO:90.

In particular embodiments, the phospholipase is modified such that it localizes predominantly to the cytoplasm instead of the periplasm. For example, the phospholipase may have a deletion or mutation in a region associated with periplasmic localization. In particular embodiments, the phospholipase variant is derived from Lysophospholipase L1 (TesA) or TesB. In certain embodiments, the Lysophospholipase L1 (TesA) or TesB variant is a bacterial Lysophospholipase L1 (TesA) or TesB variant, such as a cytoplasmic *E. coli* Lysophospholipase L1 (PldC(*TesA)) variant having the sequence set forth in SEQ ID NO:94.

In certain embodiments, the encoded lipase comprises or consists of a thioesterase, such as a thioesterase having only acyl-ACP and/or acyl-CoA thioesterase activity and no measurable lysophospholipase activity. In certain of these and related embodiments, the thioesterase is a FatB acyl-ACP thioesterase, which hydrolyzes acyl-ACP but not acyl-CoA. In particular embodiments, the thioesterase is a C8/C10, C12, C14, and/or a C16 FatB acyl-ACP thioesterase, or an active fragment or variant thereof. In some embodiments, the thioesterase is a *Cuphea hookeriana* C8/C10 FatB2, comprising the amino acid sequence of SEQ ID NO:98 (full-length protein) or SEQ ID NO:99 (mature protein without the chloroplast signal sequence). In other embodiments, the thioesterase is a *Umbellularia californica* C12 FatB1, comprising the amino acid sequence of SEQ ID NO:102 (full-length protein) or SEQ ID NO:103 (mature protein without the chloroplast signal sequence). In some embodiments, the thioesterase is a *Cinnamomum camphora* C14 FatB1, comprising the amino acid sequence of SEQ ID NO:106 (full-length protein) or SEQ ID NO:107 (mature protein without the chloroplast signal sequence). In particular embodiments, the thioesterase is a *Cuphea hookeriana* C16 FatB1, comprising the amino acid sequence of SEQ ID NO:110 (full-length protein) or SEQ ID NO:111 (mature protein without the chloroplast signal sequence).

In certain embodiments of the present invention, a DGAT polypeptide comprises or consists of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd. In certain embodiments of the present invention, a DGAT polypeptide is encoded by a polynucleotide sequence set forth in any one of SEQ ID NOs:4, 7, 16, 17, or 19, or a fragment or variant thereof. SEQ ID NO:4 is a codon-optimized for expression in Cyanbacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd.

In certain embodiments of the present invention, a phosphatidate phosphatase polypeptide comprises or consists of a polypeptide sequence set forth in SEQ ID NO:2, or a fragment or variant thereof. In particular embodiments, a phosphatidate phosphatase is encoded by a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPah1), and SEQ ID NO:5 is a codon-optimized for expression in Cyanobacteria sequence that encodes yPah1.

In certain embodiments of the present invention, an acetyl-CoA carboxylase (ACCase) polypeptide comprises or consists of a polypeptide sequence set forth in any of SEQ ID NOs:3, 20, 21, 22, 23, or 28, or a fragment or variant thereof. In particular embodiments, an ACCase polypeptide is encoded by a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yAcc1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *T. aestivum* ACCase; and SEQ ID NO:29 encodes this *Triticum aestivum* ACCase.

In particular embodiments, said one or more additional polynucleotides encode glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof, including, e.g., those provided in SEQ ID NOs:32, 34, 36, 38, 40 or 41. Examples of additional Pgm polypeptide sequences useful according to the present invention are provided in SEQ ID NOs:76, 78, 80, 82, and 84.

Variant proteins encompassed by the present application are biologically active, that is, they continue to possess the enzymatic activity of a reference polypeptide. Such variants may result from, for example, genetic polymorphism or from human manipulation. Biologically active variants of a reference lipase, phospholipase, lysophospholipase, thioesterase, diacylglycerol acyltransferase, phosphatidate phosphatase, and/or acetyl-CoA carboxylase polypeptide, or other polypeptide involved in fatty acid or triglyceride biosynthesis, will have at least 40%, 50%, 60%, 70%, generally at least 75%, 80%, 85%, usually about 90% to 95% or more, and typically about 97% or 98% or more sequence similarity or identity to the amino acid sequence for a reference protein as determined by sequence alignment programs described elsewhere herein using default parameters. A biologically active variant of a reference polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a variant polypeptide differs from the reference sequences in SEQ ID NOs: 1, 2, 3, 6, 8, 10, 12, and 14 by at least one but by less than 15, 10 or 5 amino acid residues. In other embodiments, it differs from the reference sequences by at least one residue but less than 20%, 15%, 10% or 5% of the residues.

A lipase, phospholipase, lysophospholipase, thioesterase, glycogen breakdown polypeptide, diacylglycerol acyltransferase, phosphatidate phosphatase, or acetyl-CoA carboxylase polypeptide may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of lipase, phospholipase, lysophospholipase, thioesterase, diacylglycerol acyltransferase, phosphatidate phosphatase, and/or acetyl-CoA carboxylase polypeptides. Recursive ensemble mutagenesis (REM), a technique which enhances the frequency of functional mutants in the libraries, can be used in combination with the screening assays to identify polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Polypeptide variants may contain conservative amino acid substitutions at various locations along their sequence, as compared to a reference amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine, |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant polypeptide can readily be determined by assaying its enzymatic activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |

TABLE B-continued

Exemplary Amino Acid Substitutions

| Original Residue | Exemplary Substitutions | Preferred Substitutions |
|---|---|---|
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

Thus, a predicted non-essential amino acid residue in a lipase, phospholipase, lysophospholipase, thioesterase, glycogen breakdown polypeptide, diacylglycerol acyltransferase, phosphatidate phosphatase, or acetyl-CoA carboxylase polypeptide is typically replaced with another amino acid residue from the same side chain family. Alternatively, mutations can be introduced randomly along all or part of a coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of wild-type. An "essential" amino acid residue is a residue that, when altered from the wild-type sequence of a reference polypeptide, results in abolition of an activity of the parent molecule such that less than 20% of the wild-type activity is present. For example, such essential amino acid residues may include those that are conserved in lipase, phospholipase, lysophospholipase, thioesterase glycogen breakdown polypeptides, diacylglycerol acyltransferase, phosphatidate phosphatase, or acetyl-CoA carboxylase polypeptides across different species, including those sequences that are conserved in the enzymatic sites of polypeptides from various sources.

The present invention contemplates the use of fragments of naturally-occurring lipase, phospholipase, lysophospholipase, thioesterase, glycogen breakdown polypeptides, diacylglycerol acyltransferase, phosphatidate phosphatase, or acetyl-CoA carboxylase polypeptide sequences, and variants thereof. In particular embodiments, such fragments retain one or more biological or enzymatic activites of the naturally-occurring lipase, phospholipase, lysophospholipase, thioesterase, glycogen breakdown polypeptides, diacylglycerol acyltransferase, phosphatidate phosphatase, or acetyl-CoA carboxylase polypeptide sequences, and variants thereof. In particular embodiments, such fragments have at least 20%, at least 30%, at least 40%, at least 50%, at least 60%, at least 70%, at least 80%, or at least 90% of at least one biological or enzymatic activity of the corresponding wild-type polypeptide, as measured by a standard assay known in the art.

Accordingly, the present invention also contemplates variants of the naturally-occurring lipase, phospholipase, lysophospholipase, thioesterase, glycogen breakdown polypeptides, diacylglycerol acyltransferase, phosphatidate phosphatase, or acetyl-CoA carboxylase polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference polypeptide sequence. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties of a parent or reference polypeptide sequence are contemplated.

In some embodiments, variant polypeptides differ from a reference lipase, phospholipase, lysophospholipase, thioesterase, glycogen breakdown polypeptides, diacylglycerol acyltransferase, phosphatidate phosphatase, or acetyl-CoA carboxylase polypeptide sequence by at least one but by less than 50, 40, 30, 20, 15, 10, 8, 6, 5, 4, 3 or 2 amino acid residue(s). In other embodiments, variant polypeptides differ from a reference by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of a lipase, phospholipase, lysophospholipase, thioesterase, glycogen breakdown polypeptides, diacylglycerol acyltransferase, phosphatidate phosphatase, or acetyl-CoA carboxylase reference polypeptide, and retains the enzymatic activity of that reference polypeptide.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

Variants of a lipase, phospholipase, lysophospholipase, thioesterase, glycogen breakdown polypeptide, diacylglycerol acyltransferase, phosphatidate phosphatase, or acetyl-coA carboxylase reference polypeptide can be identified by screening combinatorial libraries of mutants of a reference polypeptide. Libraries or fragments e.g., N terminal, C terminal, or internal fragments, of protein coding sequence can be used to generate a variegated population of fragments for screening and subsequent selection of variants of a reference polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of polypeptides.

The present invention also contemplates the use of chimeric or fusion proteins for increasing lipid production and/or producing triglycerides. As used herein, a "chimeric protein" or "fusion protein" includes a lipase, phospholipase, lysophospholipase, thioesterase, glycogen breakdown polypeptide, diacylglycerol acyltransferase, phosphatidate phosphatase, or acetyl-CoA carboxylase reference polypeptide or polypeptide fragment linked to either another reference polypeptide (e.g., to create multiple fragments), to a non-reference polypeptide, or to both. A "non-reference polypeptide" refers to a "heterologous polypeptide" having an amino acid sequence corresponding to a protein which is different from the lipase, phospholipase, lysophospholipase, thioesterase, diacylglycerol acyltransferase, phosphatidate phosphatase, or acetyl-CoA carboxylase protein sequence, and which is derived from the same or a different organism. The reference polypeptide of the fusion protein can correspond to all or a portion of a biologically active amino acid sequence. In certain embodiments, a fusion protein includes at least one (or two) biologically active portion of a lipase, phospholipase, lysophospholipase, thioesterase, diacylglycerol acyltransferase, phosphatidate phosphatase, or acetyl-CoA carboxylase protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the enzymatic activity of the polypeptide. For example, in one embodiment, a fusion partner may comprise a sequence that assists in expressing the protein (an expression enhancer) at higher yields than the native recombinant protein. Other fusion partners may be selected so as to increase the solubility or stability of the protein or to enable the protein to be targeted to desired intracellular compartments.

The fusion protein can include a moiety which has a high affinity for a ligand. For example, the fusion protein can be a GST-fusion protein in which the lipase, phospholipase, lysophospholipase, thioesterase, diacylglycerol acyltransferase, phosphatidate phosphatase, or acetyl-CoA carboxylase sequences are fused to the C-terminus of the GST sequences. Such fusion proteins can facilitate the purification and/or identification of the resulting polypeptide. Alternatively, the fusion protein can be a lipase, phospholipase, lysophospholipase, thioesterase, glycogen breakdown polypeptide, diacylglycerol acyltransferase, phosphatidate phosphatase, or acetyl-CoA carboxylase protein containing a heterologous signal sequence at its N-terminus. In certain host cells, expression and/or secretion of such proteins can be increased through use of a heterologous signal sequence.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39 46 (1985); Murphy et al., Proc. Natl. Acad. Sci. USA 83:8258 8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences may be operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

EXAMPLES

Example 1

Generation of Cyanobacteria Expressing Phospholipases

*E. coli*, a gram-negative fatty acid degrading prokaryote, contains well-characterized lysophospholipases L1 and L2 encoded by the pldC(tesA) gene (cleaves acyl chain at the sn1 position of lysophosphatidic acid) and pldB (cleaves acyl chain at the sn2 position of lysophosphatidic acid), respectively. pldC(tesA) and pldB nucleotide sequences were synthesized, received in a plasmid, subcloned using established molecular biology techniques into an arabinose- or IPTG-inducible vectors and recombined into neutral sites 1 or 2 (NS1 or NS2) of *Synechococcus elongatus* PCC 7942. The pldB gene was codon optimized for *Synechococcus elongatus* PCC 7942 expression using DNA2.0. The sequence of the pldC(tesA) polynucleotide is shown in SEQ ID NO: 85; the sequence of the codon-optimized pldB gene is shown in SEQ ID NO: 95. Colonies were selected from BG11-spec/strep or BG11-kan, restreaked for isolation and tested by PCR for positive colonies. Inducible transcription of the genes was verified by real-time PCR

*Vigna unguiculata*, commonly known as cowpea, contains a well-characterized galactolipase enzyme that belongs to the patatin 1 family and is encoded by vupat1. The vupat1 nucleotide sequence was synthesized and codon optimized for *Synechococcus elongatus* PCC 7942 expression using DNA2.0, received in a plasmid, subcloned using established molecular biology techniques into an arabinose- or IPTG-inducible vectors and recombined into NS2 or NS1 of *Synechococcus elongatus* PCC 7942, respectively. The sequence of the vupat1 gene is shown in SEQ ID NO: 89. Colonies were selected from BG11-Kan or BG11-spec/strep plates, restreaked for isolation and tested by PCR for positive colonies.

Example 2

Generation of Cyanobacteria Expressing Acyl-CoA/ACP Thioesterases

*E. coli* contains well-characterized thioesterases which can use acyl-CoA and acyl-ACPs as substrates. These thioesterases are encoded by pldC/tesA and tesB. The TesA thioesterase (TesA) and the *E. coli* Lysophospholipase L1 (PldC) are the same polypeptide, encoded by the same gene, denoted here as pldC(tesA). The cloning of pldC(tesA) and construction of cyanobacterial strains expressing that gene were described in Example 1. An additional modified version of pldC/tesA nucleotide sequence in which the 5 prime region that targets the enzyme to the periplasm in *E. coli* is omitted, PldC(*TesA), and the tesB nucleotide sequence, were synthesized, received in a plasmid, subcloned using established molecular biology techniques into arabinose-inducible vectors, and recombined into NS2 or NS1 of *Synechococcus elongatus* PCC 7942, respectively. The pldC/*tesA polynucleotide sequence was codon-optimized for *Synechococcus elongatus* PCC 7942 expression using DNA2.0. The sequence of the codon-optimized modified pldC(*tesA) is shown in SEQ ID NO:93; The sequence of tesB is shown in SEQ ID NO: 91. Colonies were selected from BG11-Kan or -spec/strep plates, restreaked for isolation and tested by PCR for positive colonies. Inducible transcription of the gene was verified by real-time PCR.

Example 3

Expression of Phospholipases/Thioesterases Using Low Strength Promoters

The expression level of two different inducible promoter systems were tested in cyanobacteria. A reporter gene, luciferase (luxAB), was cloned under control of the IPTG-inducible pTrc promoter or the arabinose-inducible-pBAD recombination vectors for NS1 of *S. elongatus* PCC 7942 using established molecular biology techniques. The pTrc-luxAB or pBAD-luxAB containing vectors were transformed into *S. elongatus* PCC 7942 containing luxCDE genes expressed from a constitutive promoter, psbA1, recombined into NS2. The luxCDE genes produced the substrate required for the activity of luciferase enzyme encoded by luxAB. Tranformants were plated on BG11 containing Spec/Strep/Kan to select for recombinants containing the promoter-luxAB constructs in neutral site 1. Colonies that grew on BG11 spec/strep/kan were streak purified and tested for the presence of the pTrc-luxAB or pBAD-luxAB constructs in neutral site 1.

Strains containing the luciferase reporters were tested for luciferase activity in the absence and presence of inducer. Strains were grown in BG11 media, shaken at 30 C with 100 µE illumination to mid logarithmic growth. The pTrc-luxAB construct was then induced with 1 mM IPTG for 24 h, while the pBAD-luxAB construct was induced with 0.2% (w/v) arabinose for 24 h. Luciferase activity was detected using a Spectramax M5 spectrophotometer to measure relative luminescence with an integration of 1000 ms. Total luminescence was normalized to the optical density of the cultures at 750 nm. In the absence of inducer, the pTrc-luxAB strain displayed higher luciferase activity than the pBAD-luxAB strain, indicating that the pBAD promoter resulted in a lower level of expression than the pTrc promoter in the absence of inducer (FIG. 1). Likewise, the pBAD controlled luxAB strain displayed significantly lower levels of luciferase activity 24 hours post induction with arabinose than the strain containing pTrc controlled luxAB when induced with IPTG (FIG. 1).

The pldC(*tesA) gene was cloned as outlined in Examples 1 and 2 into vectors containing either pBAD (arabinose-inducible) or pTrc (IPTG-inducible) promoters. Vectors containing pBAD-pldC(*tesA) and pTrc-pldC(*tesA) were transformed into *S. elongatus* PCC 7942 and plated on BG11-Kan plates. While >200 colonies was observed from transformations with the pBAD-pldC(*tesA), no colonies were obtained from transformations with the pTrc-pldC(*tesA). This indicated that expression of pTrc-pldC(*tesA) was toxic to *S. elongatus* PCC 7942 due to the high level of expression in the absence of inducer when compared to pBAD-pldC (tesA). To further test this hypothesis, a construct containing a promoterless pldC(*tesA) gene was cloned and transformed into *S. elongatus* PCC 7942. This construct was able to be successfully transformed, similar to the pBAD-pldC(*tesA) construct.

Example 4

Increased Free Fatty Acid Production in Cyanobacteria Cyanobacteria from Examples 1 and 2 were tested for their ability to produce increased levels of fatty acids. Strains were grown in static conditions, in a T75 flask, under high light (115 uE) at 32° C. to a high cell density. Cells were subcultured to an optical density ($OD_{750}$) of 0.2 under the same conditions, and grown overnight. Induction of the transgenes was carried out by the addition of 0.02 or 0.2% arabinose or 1 mM IPTG as appropriate when cultures reached OD750=0.2-0.4. Samples were taken at 1, 2, 3, 4, 5, 6, or 7 days after induction (as indicated in figures), prepared for total lipids and separated on polar TLC plates, and/or transesterified and analyzed for lipid content by gas chromatography (GC).

Figure 2A:
FIGS. 2A-B show the result of thin layer chromatography (TLC) of crude lipid extracts (see, Bligh and Dyer, Can J Biochem Physiol 1959, 37, 911, as available on the internet at www.dot.Cyberlipid.dot.org/extract/extr0006.htm#3 on Jan. 8, 2010), separated on TLC plates using a polar solvent solution of chloroform:methanol:$H_2O$ at 70:22:3.
Figure 2B:
Figure 3:
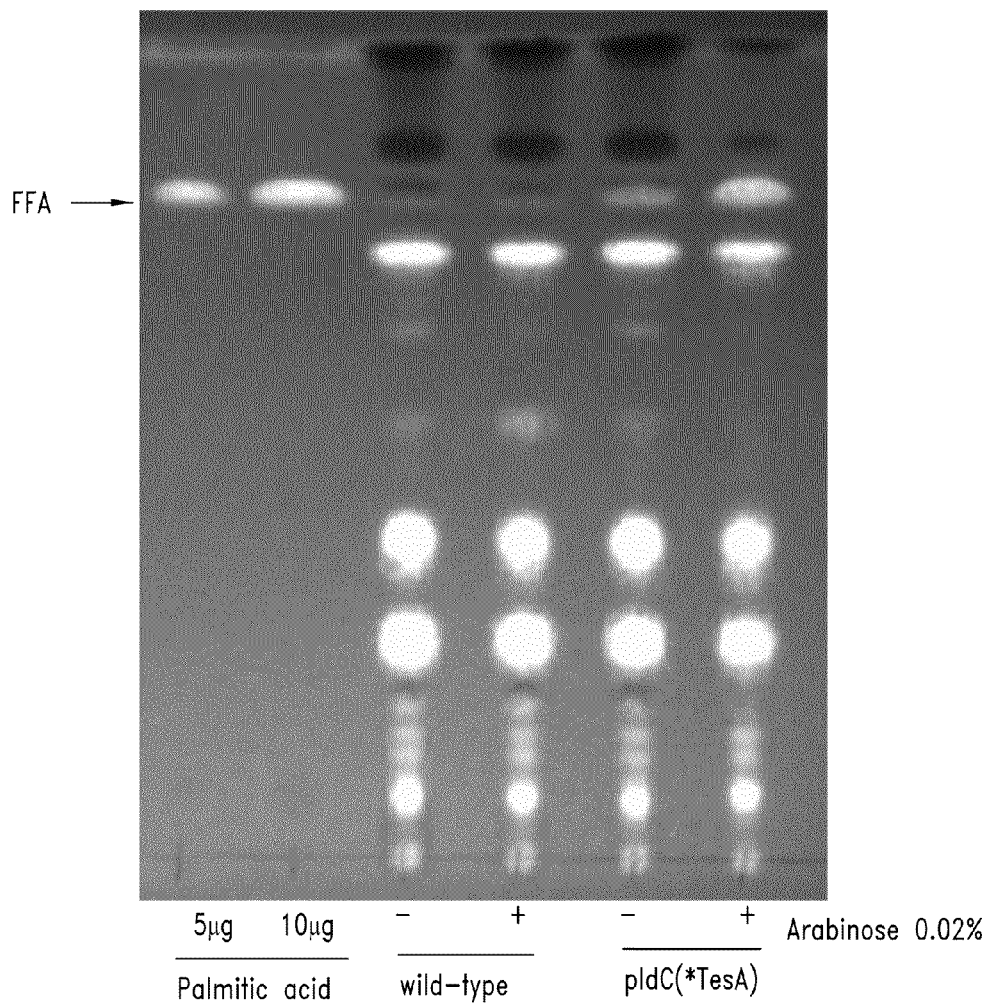
FIG. 3 shows the result of polar TLC of crude total lipid extracts obtained from wild type and PldC/*TesA cells, respectively. Bacteria were grown statically and harvested 48 h post induction with 0.02% arabinose.
Figure 4:
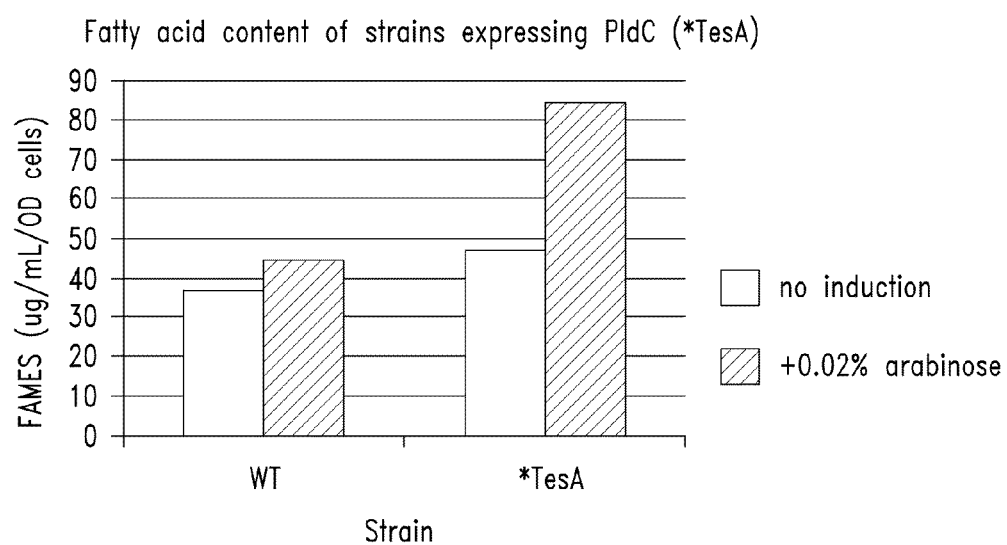
FIG. 4 is a graph depicting GC data from samples collected from WT and PldC(*TesA) cultures in the absence or presence of 0.02% arabinose. Total fatty acids are represented as μg FAMES/mL/OD cells. Bacteria were grown statically and harvested 48 h post induction with 0.2% arabinose.

As shown in FIG. 2, TLC results demonstrated that induction of lysophospholipase PldC(tesA) and TesB resulted in free fatty acid (FFA), whereas no FFAs were detected in WT PCC 7942, as determined by TLC. As seen in FIG. 2 and FIG. 3, TLC results show that induction of the modified PldC (*TesA) resulted in further increases in FFAs. In addition, GC analysis demonstrated that induced modified PldC(*TesA) strains produced increased levels of fatty acid methyl esters (FAMEs), which correlated to an increase of lipid from 10% of total biomass in WT PCC 7942 to 20% of total biomass (FIG. 4).

Example 5

Increased Free Fatty Acid and Triacylglycerol Production in Cyanobacteria

Additional strains that express both the modified PldC (*TesA) from Example 2 and diacylglycerol acyltransferases (DGATs) were produced. PldC(*TesA) was recombined into neutral site 2 in the genome of *Synechococcus* as described above. DGAT from *Acinetobacter baylii* ADP1 was ordered, codon-optimized for *Synechococcus elongatus* PCC 7942 expression using DNA 2.0 and cloned downstream of the inducible pTrc promoter in vectors pAM2991 or pAM2314trc3, and incorporated into neutral site 1 in the *Synechococcus* chromosome. The codon-optimized DGAT from *Acinetobacter baylii* ADP1 sequence is shown in SEQ ID NO:19. Furthermore, the *Streptomyces coelicolor* 0948 gene encoding a DGAT homologue was ordered, codon-optimized for *Synechococcus elongatus* PCC 7942 expression using DNA 2.0 and cloned downstream of the inducible pTrc promoter in vector pAM2314trc3, and incorporated into neutral site 1 in the *Synechococcus* chromosome. The codon-optimized DGAT from *Streptomyces coelicolor* 0948 is shown in SEQ ID NO:16.

Strains co-expressing modified lysophospholipase PldC (*TesA) and DGAT were grown as described in Example 4. Modified PldC(*TesA) expression was induced by addition of arabinose to a concentration of 0.02% (weight-to-volume) and DGAT expression was induce by addition of 1 mM IPTG. Samples were collected for analysis of lipid content by thin layer chromatography (TLC) (FIG. 4) and gas chromatography (GC) assays 24 hours post-induction.

Figure 5:
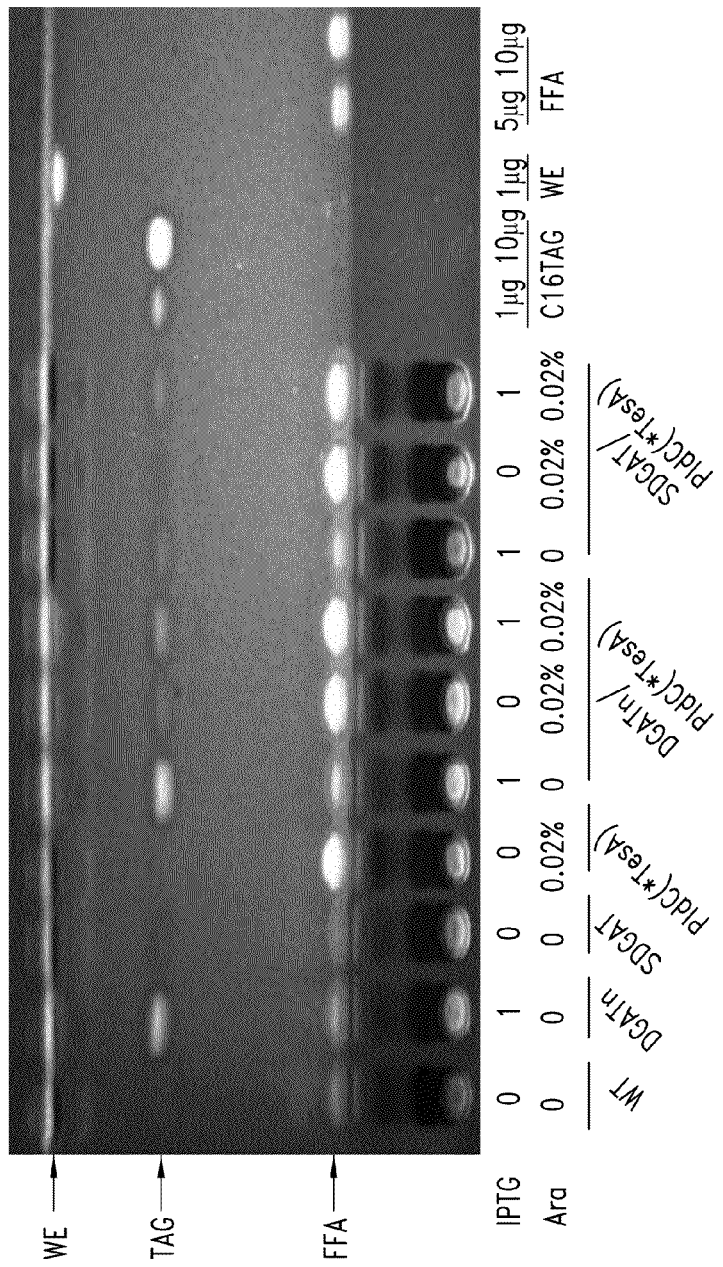
FIG. 5 shows the results of TLC of crude lipid extracts (prepared by Bligh and Dyer method, see above) from DGATn, SDGAT, PldC(*TesA), DGATn/PldC(*tesA), samples 24 hours post induction. Waxy esters (WE), triacylglycerol (TAG) and free fatty acid (FFA) are indicated on the left of the figure. Bacteria expressing *Synechococcus* codon-optimized *Acinetobacter* DGATn, *Streptomyces* DGAT, *E. coli* PldC(*tesA) or combinations thereof were inoculated at 0.1, allowed to reach 0.4 and induced by addition of 1 mM IPTG or 0.02% arabinose or both. Bacteria were grown statically in 35 mL cultures at 30° C. and ~120 microE. Cells were harvested 48 h post-induction and the equivalent of 1 OD of total lipid prep was loaded per TLC lane. Separation on TLC plates utilized a non-polar solution of hexane:diethyl ether: acetic acid at 75:24:1. As shown, addition of IPTG led to TAG formation, addition of arabinose resulted in an increase in FFAs, and addition of both IPTG and arabinose resulted in TAG formation and accumulation of FFAs. DGATn refers to *Acinetobacter* DGATn clones in pAM2314trc3 (NS1).

As shown in FIG. 5, expression of the modified PldC (*TesA) resulted in an increase in FFAs, and induction of DGATs resulted in increased formation of triacylglycerols (TAGs), while induction of both PldC(*TesA) and DGATs caused an increase in both FFA and the formation of TAGs. GC analysis demonstrated that the lipid content of cells expressing both PldC(*TesA) and DGAT correlated to 30% of total biomass. FIG. 5 further demonstrates that induction of PldC(*TesA) resulted in FFAs formation; induction of DGAT resulted in an increase in TAGs; and induction of both the modified PldC(*TesA) and DGAT resulted in TAG formation and accumulation of FFAs. SDGAT refers to *Streptomyces* DGAT cloned in pAM2314trc3, and DGATn refers to *Acinetobacter* DGAT cloned in pAM2314trc3.

It is believed that the co-expression of the modified PldC (*TesA) with DGAT generated a sink for the additional FFAs generated from PldC(*TesA) induction by allowing the synthesis of TAGs as a storage unit for lipids. Therefore, the total FAMES content of the cell increased due to the overproduction of the acyl-ACP and acyl-coA molecules required for membrane lipid synthesis.

Thioesterases, such as TesA and TesB, are enzymes that hydrolyze thioester chemical bonds. Fatty acids are attached to cofactor molecules, such as coenzyme A (CoA) and acyl carrier protein (ACP), by thioester bonds during de novo fatty acid synthesis. Wild type TesA, being localized to the periplasm, is normally used to hydrolyze thioester bonds of lysophospholipids, fatty acid-ACP or fatty acid-CoAs compounds scavenged from the environment or that leak into the periplasm from the plasma membrane where phospholipid biosynthesis occurs. A mutant thioesterase, PldC(*TesA), is not exported to the periplasm due to deletion of an N-terminal amino acid sequence required for proper transport of PldC (*TesA) from the cytoplasm to the periplasm. This results in a cytoplasmic-localized PldC(*TesA) protein that has access to endogenous acyl-ACP and acyl-CoA and cytoplasmic lysophosphatidic acid intermediates. Controlled expression of PldC(*TesA) under the relatively weak arabinose promoter was successfully used to allow hydrolysis of acyl groups from endogenous acyl-ACP, acyl-CoA and lysophosphatidic acid molecules in cyanobacteria. Cells expressing PldC(*TesA) must channel additional cellular carbon and energy to maintain production of acyl-ACP and acyl-coA and lysophosphatidic molecules, which are required for membrane lipid synthesis. Thus, PldC(*TesA) expression resulted in a net increase in cellular lipid content. When PldC/*TesA was expressed in *Synechococcus*, lipid content doubled from 10% of biomass to 20% of biomass.

Example 6

Increased Lipid Content in Cyanobacteria Under Static Growth Conditions

Figure 6:
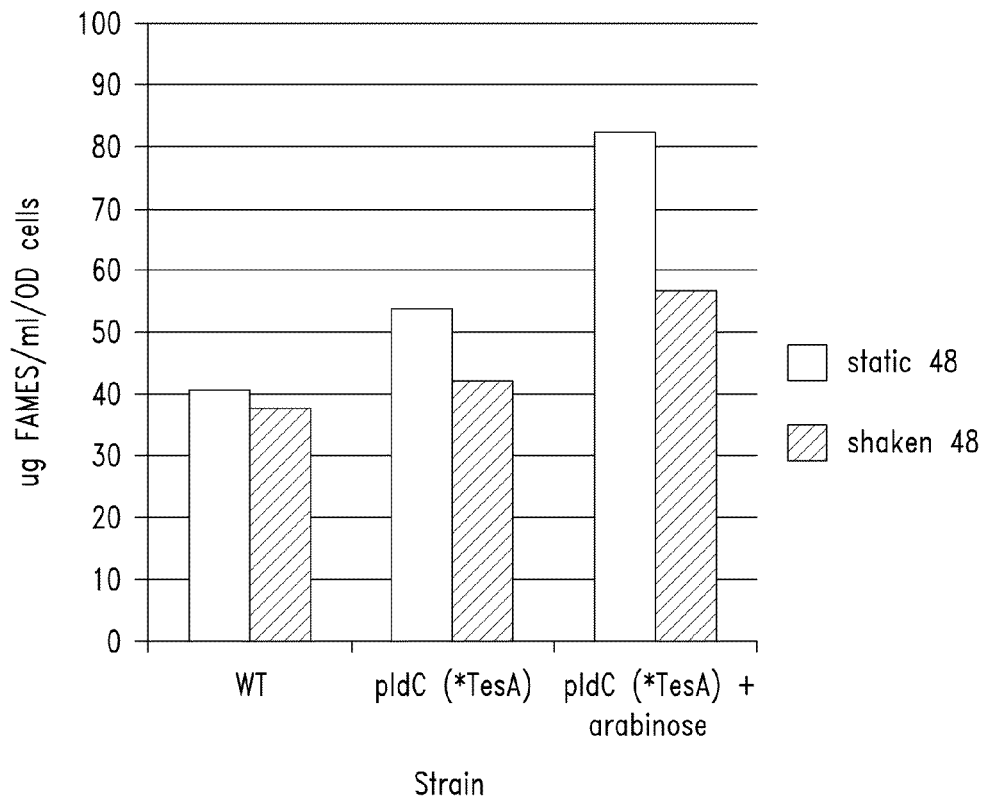
FIG. 6 is a graph depicting GC analysis of the PldC(*TesA) strain grown under static or shaken growth conditions under induced or non-induced conditions. Bacteria were grown and sampled outlined in Example 6. Data is an average of three biological replicates, and errors indicate the standard deviation among the three replicates.

Cyanobacteria from Example 2 containing PldC(*TesA) under control of the pBAD promoter were tested for their ability to produce increased levels of fatty acids under different growth conditions. Biological triplicates of the strain containing the pBAD-PldC(*TesA) construct were grown in baffled flasks shaken at 200 rpm, 115 uE at 30° C. to a high cell density. Cells were then subcultured and grown under either static or shaken growth conditions. For static growth, cells were subcultured into T75 flasks overnight without shaking, and induced with 0.02% arabinose (w/v) without shaking. Samples for quantitation of fatty acid by GC were taken 48 hours post induction. The data, an average of three biological replicates, is shown in FIG. 6. For shaken growth, cells were subcultured to an optical density ($OD_{750}$) of 0.2 in baffled flasks, and grown while shaken at 200 rpm under high light (115 uE) at 30° C. Cultures were then induced with 0.02% arabinose (w/v) while shaken at 200 rpm. Samples for quantitation of fatty acid by GC were taken 48 hours post induction. The data, an average of three biological replicates, is shown in FIG. 6.

As shown in FIG. 6, GC quantitation indicates that there is an increase in total fatty acid when PldC(*TesA) is induced during static growth. There is a smaller increase in fatty acid content when PldC (*TesA) is induced under shaken conditions. These data demonstrate that an increased amount of total fatty acid is produced by showing the PldC(*TesA) strain under static conditions.

Example 7

Increased Production of Free Fatty Acids in Phylogenetically Diverse Cyanobacteria Members of different families within the phylum Cyanobacteria were tested for their ability to produce free fatty acids after being engineered to overexpress lysophospholipase PldC(*tesA).

Cyanobacteria belonging to Family IX (*Synechocystis* sp. PCC 6803) and Family X (*Synechococcus* sp. PCC 7002) were engineered to overexpress the cytoplasmic version of lysophospholipase PldC(*tesA). For each strain, a unique vector was designed to target the lysophospholipase PldC (tesA) gene into a neutral region of the genome. Transcription of the lysophospholipase PldC(*tesA) gene was driven by the Ptrc promoter. As a control, an empty construct was made that contained the Ptrc promoter, but did not contain the PldC (*tesA) gene. Wild-type and engineered strains were grown under continuous light (~100 uE) with continuous shaking (200 rpm) at 30° C. Cells were subcultured to an optical density ($OD_{730}$) of 0.2 or 0.3 under the same conditions and grown overnight. Samples were taken 8 or 24 hours later for PCC6803 and PCC7002, respectively, prepared for total lipids and 0.2 OD equivalents separated on polar TLC plates.

As shown in FIG. 7, overexpression of PldC(*tesA) in PCC 6803 and PCC 7002 resulted in increased production of free fatty acids (FFA) compared to the wildtype (WT) or empty vector controls.

A salt tolerant PCC 7942 strain which grows indistinguishably from wildtype in BG11, but that shows a sharp increase in growth compared to wildtype PCC 7942 in media containing NaCl was previously described (PCT application publication No. WO2010/048568). A PldC(*tesA) expressing salt tolerant strain of *S. elongatus* PCC 7942 was generated by transforming this salt tolerant strain with the PldC(*tesA) arabinose construct as described in Example 3. This PldC(*tesA) salt tolerant strain showed a growth advantage over the PldC (*tesA) non-salt tolerant strain in media containing up to 1.5% salt and produced free fatty acids (FIG. 7C). This strain could be useful in production settings where it may be advantageous to use brackish water or seawater.

Example 8

Generation of Cyanobacteria Expressing FatB Acyl-ACP Thioesterases and Resulting Accumulation of Free Fatty Acids of Specific Chain Lengths Plants contain well-characterized chloroplast localized acyl-ACP thioesterases which use acyl-ACPs as substrates (see, e.g., Jones et al., *Plant Cell.* 7:359-371, 1998). FatB types prefer acyl-ACPs having saturated acyl groups of a variety of lengths. FatAs have been reported to prefer unsaturated acyl groups. These thioesterases can be acyl chain length specific.

Acyl-chain specific FatB thioesterases were overexpressed to favor the accumulation of FFA of a certain length. In particular, enzymes specific for C8/C10, C12, C14 and C16 acyl-ACP chains were overexpressed in cyanobacteria PCC 7942. In all cases, the genes expressed encoded the mature form of the proteins, predicted to lack the chloroplast signal 5' sequence based on alignments and published data. The sequences were synthesized and codon optimized for *Synechococcus elongatus* PCC 7942 expression using DNA2.0, received in a plasmid, subcloned using established molecular biology techniques into arabinose-inducible vector (pAM2314ara3(NS1)) for C16:0 acyl-ACP thioesterase or into IPTG inducible vectors (pNS3Ptrc) for C8/C10, C12 and C14 FatB acyl-ACP thioesterases and recombined into neutral sites 1 or 3 in the genome of *Synechococcus elongatus* PCC 7942, respectively. The sequence of the preprotein and the mature protein, as well as those of the polynucleotides encoding them, are shown in SEQ ID NOs:96-111. Colonies were selected from BG11-Cm (For C8/C10, C12 and C14FatBs) or -spec/strep plates for C16FatB, restreaked for isolation and tested by PCR for positive colonies.

In addition to the chain specific thioesterases expressed above, putative, uncharacterized thioesterases from bacteria, specifically *Lactobacillus plantarum* WCSF10RF LP0708 and *Enterococcus faecalis* V583 ORF EF0365 were expressed in *S. elongatus*. These ORFs were PCR amplified from genomic DNA from the respective organisms and cloned under control of an arabinose-inducible promoter in vector pAM1579ara3 and recombined into neutral site 2 (NS2). Colonies were selected from BG11 plates containing Km, restreaked for isolation, and tested by PCR for positive clones.

Figure 8A:
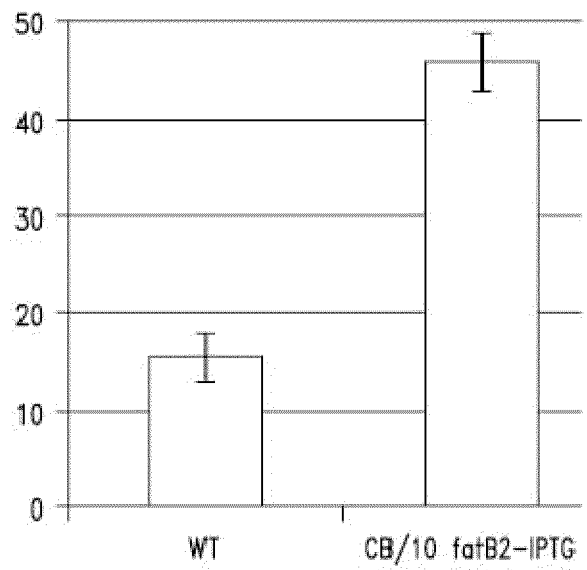
FIG. 8 shows that overexpression of FatB enzymes in Cyanobacteria increases production of fatty acid methyl esters (FAMES) (y-axis for FIGS. 8A-8F and 8H is μg FAMES/OD*ml).
FIG. 8G shows that overexpression of LP0708 or EF0365 in cyanobacteria increases production of FAMES and represents the sum of C6:0, C8:0, C10:0, C12:0 and C14:0 fatty acids produced 7 days post induction.
FIG. 8H shows that *S. elongatus* expressing two copies of C14 FatB gene has a further increase in production of FAMES relative to *S. elongatus* expressing one copy of C14 FatB gene at 48 hrs and 7 days post induction with 1 mM IPTG.
Figure 8B:
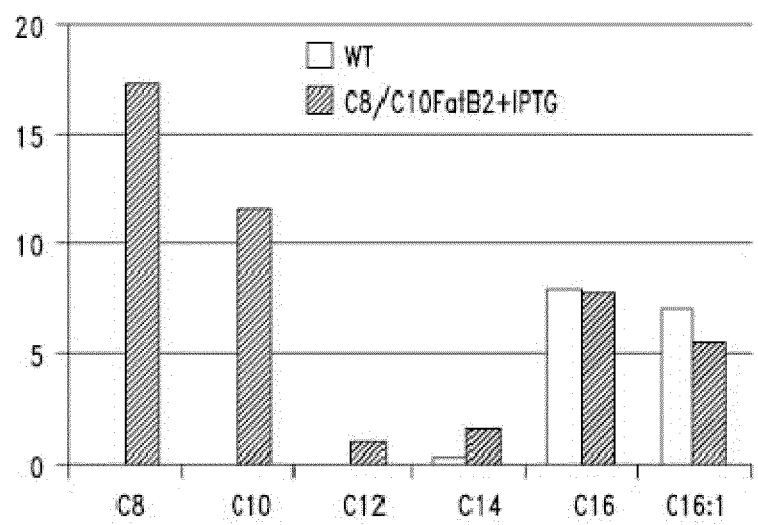
Figure 8C:
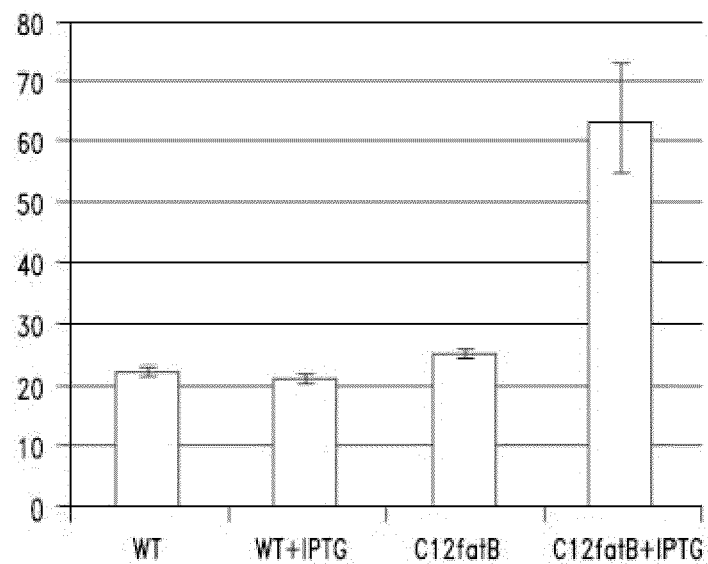
Figure 8D:
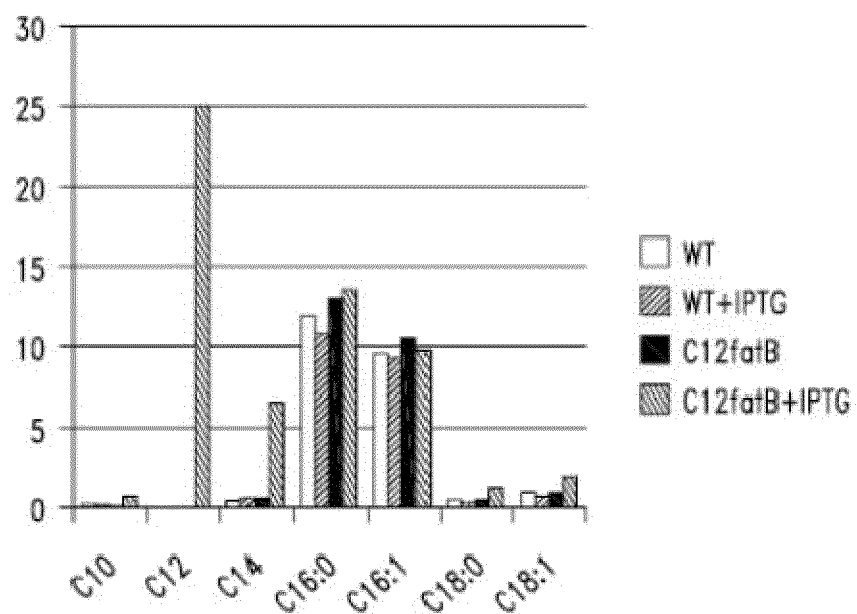
Figure 8E:
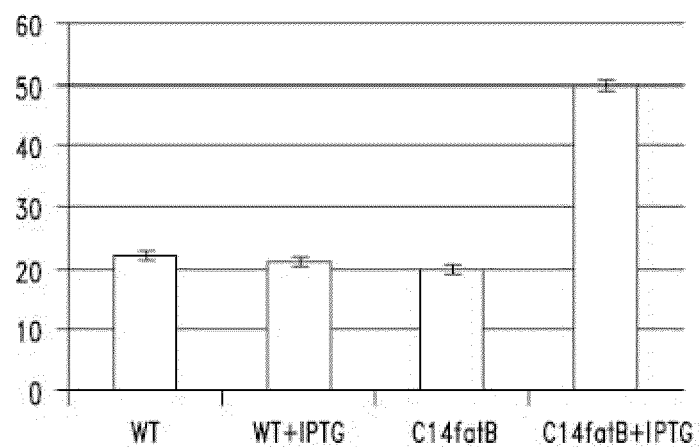
Figure 8F:
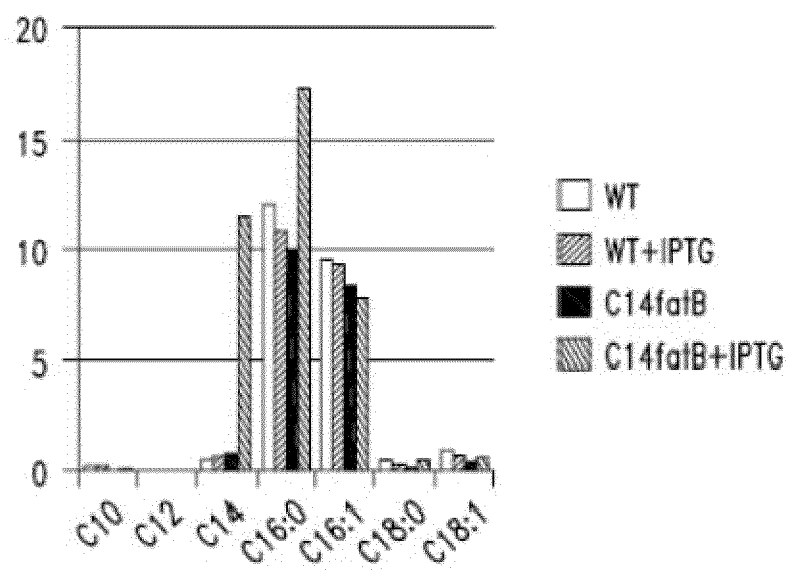
Figure 8G:
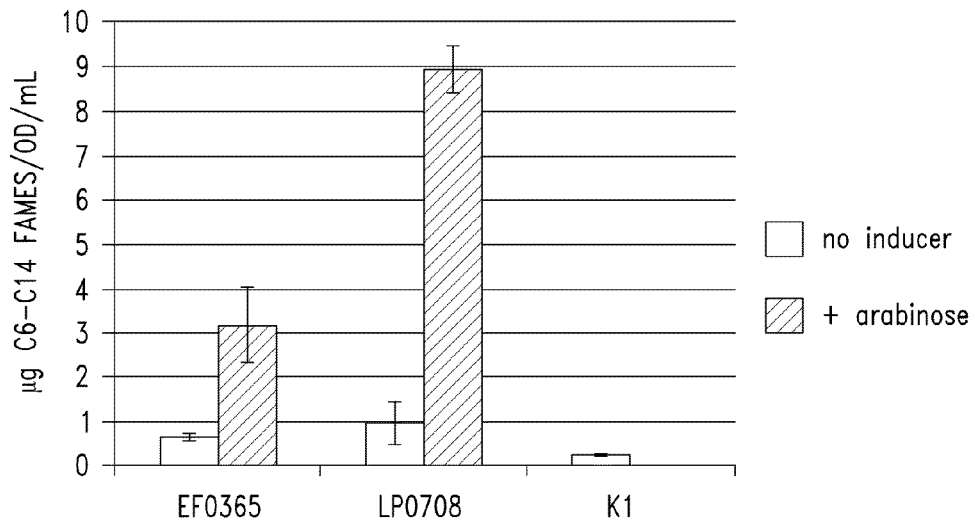

As shown in FIGS. 8A-G, overexpression of the codon-optimized mature forms of plant FatBs in PCC7942 resulted in an increase in FFAs (see, e.g., FIGS. 8A, 8C and 8D), the FFAs accumulated were C8 and C10, C12 and C14 primarily in length for strains expressing C8/C10, C12 and C14 FatB expressing strains, respectively. For strains expressing LP0708 and EF0365 increases in FFA ranging from C6:0-C14:0 were observed upon induction by addition of 0.02% arabinose (FIG. 8G).

Figure 8H:
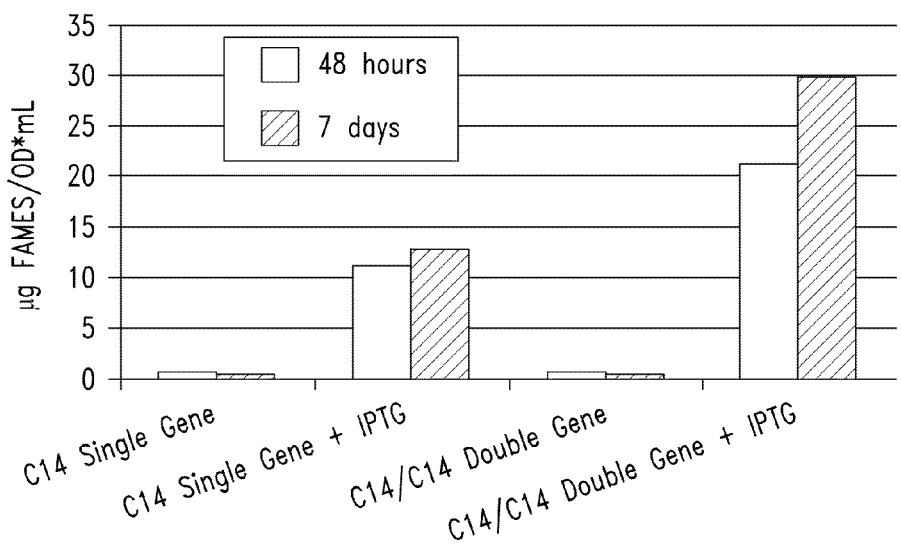
Figure 9:
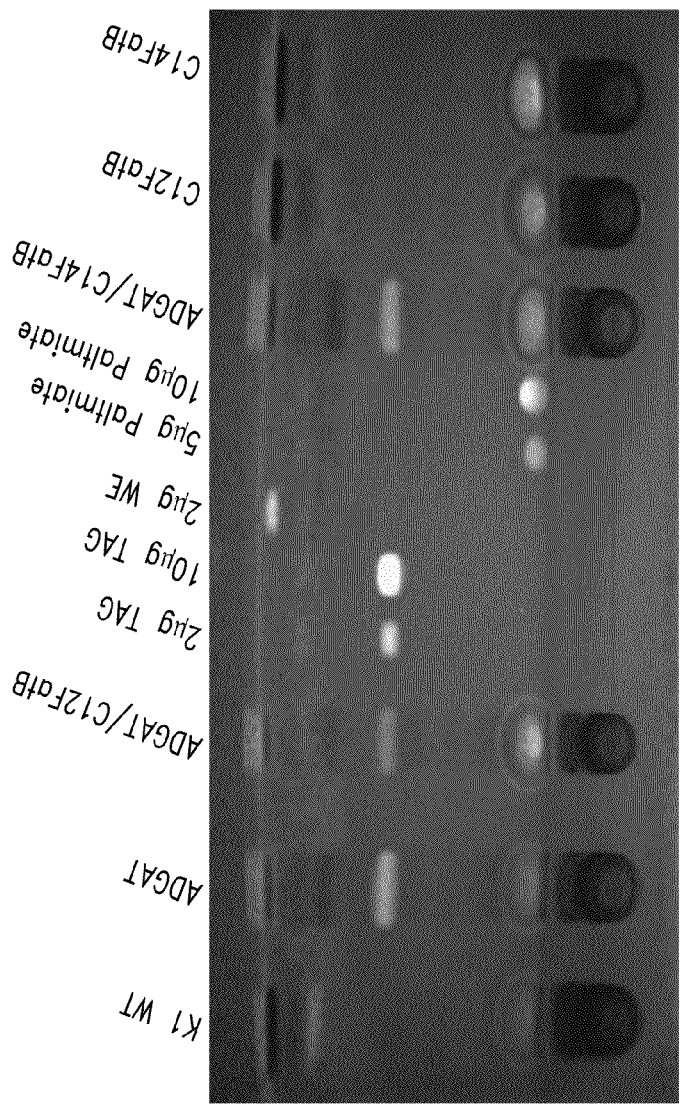
FIG. 9 shows that expression of the C12FatB and C14FatB resulted in increases in FFAs, and induction of DGATs resulted in increased formation of triacylglycerols (TAGs), while induction of both caused an increase in both FFA and the formation of TAGs. Control lanes for TAG and palmitate are shown.

To further increase FFA production an additional copy of C14 FatB was cloned into a neutral site 2 vector under control of pTrc promoter (pAM1579trc3) and recombined into neutral site 2 in a strain already containing one copy of C14 FatB in neutral site 3. Colonies were selected from BG11-Cm-Km plates and restreaked for isolation and tested by PCR for positive clones containing two copies of C14 fatB, one in neutral site 2 and one in neutral site 3. As shown in FIG. 8H expression of two copies of C14 FatB increases the amount of C14:0 fatty acid produced over that produced by a single copy of C14 FatB. In order to increase acyl-ACP availability for TAG formation, these different acyl-ACP thioesterases were then expressed in DGAT-expressing strains of Cyanobacteria. As shown in FIG. 9, expression of the C12FatB and C14FatB resulted in increases in FFAs, and induction of DGATs resulted in increased formation of triacylglycerols (TAGs), while induction of both caused an increase in both FFA and the formation of TAGs.

Example 9

Generation of Cyanobacteria Deficient in Glycogen Synthesis that Express fatB Acyl-ACP Thioesterases and Produce Increased Levels of Free Fatty Acids Cyanobacteria typically store excess carbon in the form of a polysaccharide known as glycogen. This is particularly true under stress conditions such as under nitrogen limitation when the carbon/nitrogen ratio increases. This carbon storage pathway is composed of phosphoglucomutase (pgm), glucose-1-phosphate adenyl transferase (glgC) and glycogen sythase (glgA) and results in the conversion of glucose-6-phosphate into glycogen. Previously, we have described that reduced glycogen synthesis and/or storage in modified cyanobacteria such as *Synechoccocus elongatus* which contain deletions in the glucose-1-phosphate adenylyltransferase gene (glgC) also resulted in increases in lipids under nitrogen limitation (total FAMES per OD*mL) (PCT patent application publication No. WO2010/075440), which was reflected by an increase in total lipids as separated in polar TLCs.

To determine if the carbon going into glycogen could be channeled into free fatty acid production, a glgC ko strain of *S. elongatus* PCC 7942 was transformed with a C14FatB construct where the expression of C14FatB was driven by the Ptrc-IPTG promoter as described in Example 5. A transgenic isolate was confirmed molecularly by PCR to lack glgC and to contain C14FatB in its chromosome. As seen in FIG. 10, lipid analysis by TLC and GC indicated that introduction of a FatB acyl ACP thioesterase in a glycogen deficient strain resulted in a strain that produced increased lipids as compared to a strain that either was glycogen deficient (glgC KO) or expresses C14FatB in a wild-type background when grown under nitrogen non-limiting (FIGS. 10A and B) and nitrogen limiting conditions (FIG. 10C).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A modified Cyanobacterium comprising:
   a polynucleotide encoding an acyl-ACP thioesterase, or a fragment or variant thereof, and
   reduced expression of one or more of phosphoglucomutase (pgm), glucose-1-phosphate adenyl transferase (glgC) and glycogen synthase (glgA),
   wherein said modified Cyanobacterium produces an increased amount of fatty acid as compared to a modified Cyanbacterium comprising a polynucleotide encoding an acyl-ACP thioesterase, or a fragment or variant thereof, without reduced expression of one or more of phosphoglucomutase (pgm), glucose-1-phosphate adenyl transferase (glgC) and glycogen synthase (glgA).

2. The modified photosynthetic Cyanobacterium of claim 1, wherein said acyl-ACP thioesterase is present in an expression construct.

3. The modified Cyanobacterium of claim 1, wherein said Cyanobacterium is selected from the group consisting of: a *Synechococcus elongatus*, a salt tolerant variant of *Synechococcus elongatus*, a *Synechococcus elongatus* strain PCC 7942, a *Synechococcus* sp. PCC 7002, a *Synechocystis* sp. PCC 6803 and an *Anabaena* sp. 7120.

4. The modified Cyanobacterium of claim 1, wherein said modified Cyanobacterium expresses an amount of said acyl- ACP thioesterase optimized for continuous, high level fatty acid production without substantial toxicity to the modified Cyanobacterium, and wherein expression of said amount is regulated by a promoter operably linked to said polynucleotide and/or copy number of said polynucleotide.

* * * * *

```
                        SEQUENCE LISTING

<160> NUMBER OF SEQ ID NOS: 111

<210> SEQ ID NO 1
<211> LENGTH: 458
<212> TYPE: PRT
<213> ORGANISM: Acinetobacter baylii sp.

<400> SEQUENCE: 1

Met Arg Pro Leu His Pro Ile Asp Phe Ile Phe Leu Ser Leu Glu Lys
  1               5                  10                  15

Arg Gln Gln Pro Met His Val Gly Gly Leu Phe Leu Phe Gln Ile Pro
             20                  25                  30

Asp Asn Ala Pro Asp Thr Phe Ile Gln Asp Leu Val Asn Asp Ile Arg
         35                  40                  45

Ile Ser Lys Ser Ile Pro Val Pro Pro Phe Asn Asn Lys Leu Asn Gly
     50                  55                  60

Leu Phe Trp Asp Glu Asp Glu Glu Phe Asp Leu Asp His His Phe Arg
 65                  70                  75                  80

His Ile Ala Leu Pro His Pro Gly Arg Ile Arg Glu Leu Leu Ile Tyr
                 85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
            115                 120                 125

Phe Lys Ile His His Ala Met Val Asp Gly Val Ala Gly Met Arg Leu
        130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335
```

```
Arg Met Thr Ser Asp Gln Ile Leu Asn Tyr Ser Ala Val Val Tyr Gly
                340                 345                 350

Pro Ala Gly Leu Asn Ile Ile Ser Gly Met Met Pro Lys Arg Gln Ala
            355                 360                 365

Phe Asn Leu Val Ile Ser Asn Val Pro Gly Pro Arg Glu Pro Leu Tyr
        370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Ile Gln Leu Phe Glu Gly Val Ile
        435                 440                 445

Ala Lys Gln Glu Asp Ile Lys Thr Ala Asn
            450                 455

<210> SEQ ID NO 2
<211> LENGTH: 864
<212> TYPE: PRT
<213> ORGANISM: Saccharomyces cerevisiae

<400> SEQUENCE: 2

Met Glu Phe Gln Tyr Val Gly Arg Ala Leu Gly Ser Val Ser Lys Thr
1               5                   10                  15

Trp Ser Ser Ile Asn Pro Ala Thr Leu Ser Gly Ala Ile Asp Val Ile
                20                  25                  30

Val Val Glu His Pro Asp Gly Arg Leu Ser Cys Ser Pro Phe His Val
            35                  40                  45

Arg Phe Gly Lys Phe Gln Ile Leu Lys Pro Ser Gln Lys Lys Val Gln
        50                  55                  60

Val Phe Ile Asn Glu Lys Leu Ser Asn Met Pro Met Lys Leu Ser Asp
65                  70                  75                  80

Ser Gly Glu Ala Tyr Phe Val Phe Glu Met Gly Asp Gln Val Thr Asp
                85                  90                  95

Val Pro Asp Glu Leu Leu Val Ser Pro Val Met Ser Ala Thr Ser Ser
            100                 105                 110

Pro Pro Gln Ser Pro Glu Thr Ser Ile Leu Glu Gly Gly Thr Glu Gly
        115                 120                 125

Glu Gly Glu Gly Glu Asn Glu Asn Lys Lys Lys Glu Lys Lys Val Leu
130                 135                 140

Glu Glu Pro Asp Phe Leu Asp Ile Asn Asp Thr Gly Asp Ser Gly Ser
145                 150                 155                 160

Lys Asn Ser Glu Thr Thr Gly Ser Leu Ser Pro Thr Glu Ser Ser Thr
                165                 170                 175

Thr Thr Pro Pro Asp Ser Val Glu Glu Arg Lys Leu Val Glu Gln Arg
            180                 185                 190

Thr Lys Asn Phe Gln Gln Lys Leu Asn Lys Lys Leu Thr Glu Ile His
        195                 200                 205

Ile Pro Ser Lys Leu Asp Asn Asn Gly Asp Leu Leu Leu Asp Thr Glu
    210                 215                 220

Gly Tyr Lys Pro Asn Lys Asn Met Met His Asp Thr Asp Ile Gln Leu
225                 230                 235                 240

Lys Gln Leu Leu Lys Asp Glu Phe Gly Asn Asp Ser Asp Ile Ser Ser
                245                 250                 255
```

-continued

```
Phe Ile Lys Glu Asp Lys Asn Gly Asn Ile Lys Ile Val Asn Pro Tyr
            260                 265                 270

Glu His Leu Thr Asp Leu Ser Pro Gly Thr Pro Thr Met Ala
            275                 280                 285

Thr Ser Gly Ser Val Leu Gly Leu Asp Ala Met Glu Ser Gly Ser Thr
            290                 295                 300

Leu Asn Ser Leu Ser Ser Pro Ser Gly Ser Asp Thr Glu Asp Glu
305                 310                 315                 320

Thr Ser Phe Ser Lys Glu Gln Ser Ser Lys Ser Glu Lys Thr Ser Lys
                    325                 330                 335

Lys Gly Thr Ala Gly Ser Gly Glu Thr Glu Lys Arg Tyr Ile Arg Thr
            340                 345                 350

Ile Arg Leu Thr Asn Asp Gln Leu Lys Cys Leu Asn Leu Thr Tyr Gly
            355                 360                 365

Glu Asn Asp Leu Lys Phe Ser Val Asp His Gly Lys Ala Ile Val Thr
            370                 375                 380

Ser Lys Leu Phe Val Trp Arg Trp Asp Val Pro Ile Val Ile Ser Asp
385                 390                 395                 400

Ile Asp Gly Thr Ile Thr Lys Ser Asp Ala Leu Gly His Val Leu Ala
            405                 410                 415

Met Ile Gly Lys Asp Trp Thr His Leu Gly Val Ala Lys Leu Phe Ser
            420                 425                 430

Glu Ile Ser Arg Asn Gly Tyr Asn Ile Leu Tyr Leu Thr Ala Arg Ser
            435                 440                 445

Ala Gly Gln Ala Asp Ser Thr Arg Ser Tyr Leu Arg Ser Ile Glu Gln
            450                 455                 460

Asn Gly Ser Lys Leu Pro Asn Gly Pro Val Ile Leu Ser Pro Asp Arg
465                 470                 475                 480

Thr Met Ala Ala Leu Arg Arg Glu Val Ile Leu Lys Lys Pro Glu Val
            485                 490                 495

Phe Lys Ile Ala Cys Leu Asn Asp Ile Arg Ser Leu Tyr Phe Glu Asp
            500                 505                 510

Ser Asp Asn Glu Val Asp Thr Glu Glu Lys Ser Thr Pro Phe Phe Ala
            515                 520                 525

Gly Phe Gly Asn Arg Ile Thr Asp Ala Leu Ser Tyr Arg Thr Val Gly
            530                 535                 540

Ile Pro Ser Ser Arg Ile Phe Thr Ile Asn Thr Glu Gly Glu Val His
545                 550                 555                 560

Met Glu Leu Leu Glu Leu Ala Gly Tyr Arg Ser Ser Tyr Ile His Ile
                    565                 570                 575

Asn Glu Leu Val Asp His Phe Phe Pro Pro Val Ser Leu Asp Ser Val
            580                 585                 590

Asp Leu Arg Thr Asn Thr Ser Met Val Pro Gly Ser Pro Pro Asn Arg
            595                 600                 605

Thr Leu Asp Asn Phe Asp Ser Glu Ile Thr Ser Gly Arg Lys Thr Leu
            610                 615                 620

Phe Arg Gly Asn Gln Glu Glu Lys Phe Thr Asp Val Asn Phe Trp Arg
625                 630                 635                 640

Asp Pro Leu Val Asp Ile Asp Asn Leu Ser Asp Ile Ser Asn Asp Asp
                    645                 650                 655

Ser Asp Asn Ile Asp Glu Asp Thr Asp Val Ser Gln Gln Ser Asn Ile
            660                 665                 670
```

```
Ser Arg Asn Arg Ala Asn Ser Val Lys Thr Ala Lys Val Thr Lys Ala
        675                 680                 685

Pro Gln Arg Asn Val Ser Gly Ser Thr Asn Asn Glu Val Leu Ala
690                 695                 700

Ala Ser Ser Asp Val Glu Asn Ala Ser Asp Leu Val Ser Ser His Ser
705                 710                 715                 720

Ser Ser Gly Ser Thr Pro Asn Lys Ser Thr Met Ser Lys Gly Asp Ile
                725                 730                 735

Gly Lys Gln Ile Tyr Leu Glu Leu Gly Ser Pro Leu Ala Ser Pro Lys
                740                 745                 750

Leu Arg Tyr Leu Asp Asp Met Asp Asp Glu Asp Ser Asn Tyr Asn Arg
        755                 760                 765

Thr Lys Ser Arg Arg Ala Ser Ser Ala Ala Thr Ser Ile Asp Lys
        770                 775                 780

Glu Phe Lys Lys Leu Ser Val Ser Lys Ala Gly Ala Pro Thr Arg Ile
785                 790                 795                 800

Val Ser Lys Ile Asn Val Ser Asn Asp Val His Ser Leu Gly Asn Ser
                805                 810                 815

Asp Thr Glu Ser Arg Arg Glu Gln Ser Val Asn Glu Thr Gly Arg Asn
                820                 825                 830

Gln Leu Pro His Asn Ser Met Asp Asp Lys Asp Leu Asp Ser Arg Val
        835                 840                 845

Ser Asp Glu Phe Asp Asp Glu Phe Asp Glu Asp Glu Phe Glu Asp
850                 855                 860

<210> SEQ ID NO 3
<211> LENGTH: 2235
<212> TYPE: PRT
<213> ORGANISM: Saccharomyces cerevisiae

<400> SEQUENCE: 3

Met Glu Phe Ser Glu Glu Ser Leu Phe Glu Ser Ser Pro Gln Lys Met
1               5                   10                  15

Glu Tyr Glu Ile Thr Asn Tyr Ser Glu Arg His Thr Glu Leu Pro Gly
                20                  25                  30

His Phe Ile Gly Leu Asn Thr Val Asp Lys Leu Glu Glu Ser Pro Leu
            35                  40                  45

Arg Asp Phe Val Lys Ser His Gly Gly His Thr Val Ile Ser Lys Ile
    50                  55                  60

Leu Ile Ala Asn Asn Gly Ile Ala Ala Val Lys Glu Ile Arg Ser Val
65                  70                  75                  80

Arg Lys Trp Ala Tyr Glu Thr Phe Gly Asp Asp Arg Thr Val Gln Phe
                85                  90                  95

Val Ala Met Ala Thr Pro Glu Asp Leu Glu Ala Asn Ala Glu Tyr Ile
                100                 105                 110

Arg Met Ala Asp Gln Tyr Ile Glu Val Pro Gly Gly Thr Asn Asn Asn
            115                 120                 125

Asn Tyr Ala Asn Val Asp Leu Ile Val Asp Ile Ala Glu Arg Ala Asp
    130                 135                 140

Val Asp Ala Val Trp Ala Gly Trp Gly His Ala Ser Glu Asn Pro Leu
145                 150                 155                 160

Leu Pro Glu Lys Leu Ser Gln Ser Lys Arg Lys Val Ile Phe Ile Gly
                165                 170                 175

Pro Pro Gly Asn Ala Met Arg Ser Leu Gly Asp Lys Ile Ser Ser Thr
                180                 185                 190
```

```
        Ile Val Ala Gln Ser Ala Lys Val Pro Cys Ile Pro Trp Ser Gly Thr
                    195                 200                 205

Gly Val Asp Thr Val His Val Asp Glu Lys Thr Gly Leu Val Ser Val
                    210                 215                 220

Asp Asp Asp Ile Tyr Gln Lys Gly Cys Cys Thr Ser Pro Glu Asp Gly
        225                 230                 235                 240

Leu Gln Lys Ala Lys Arg Ile Gly Phe Pro Val Met Ile Lys Ala Ser
                            245                 250                 255

Glu Gly Gly Gly Gly Lys Gly Ile Arg Gln Val Glu Arg Glu Glu Asp
                        260                 265                 270

Phe Ile Ala Leu Tyr His Gln Ala Ala Asn Glu Ile Pro Gly Ser Pro
                    275                 280                 285

Ile Phe Ile Met Lys Leu Ala Gly Arg Ala Arg His Leu Glu Val Gln
                    290                 295                 300

Leu Leu Ala Asp Gln Tyr Gly Thr Asn Ile Ser Leu Phe Gly Arg Asp
        305                 310                 315                 320

Cys Ser Val Gln Arg Arg His Gln Lys Ile Ile Glu Glu Ala Pro Val
                            325                 330                 335

Thr Ile Ala Lys Ala Glu Thr Phe His Glu Met Glu Lys Ala Ala Val
                        340                 345                 350

Arg Leu Gly Lys Leu Val Gly Tyr Val Ser Ala Gly Thr Val Glu Tyr
                    355                 360                 365

Leu Tyr Ser His Asp Asp Gly Lys Phe Tyr Phe Leu Glu Leu Asn Pro
                    370                 375                 380

Arg Leu Gln Val Glu His Pro Thr Thr Glu Met Val Ser Gly Val Asn
        385                 390                 395                 400

Leu Pro Ala Ala Gln Leu Gln Ile Ala Met Gly Ile Pro Met His Arg
                            405                 410                 415

Ile Ser Asp Ile Arg Thr Leu Tyr Gly Met Asn Pro His Ser Ala Ser
                        420                 425                 430

Glu Ile Asp Phe Glu Phe Lys Thr Gln Asp Ala Thr Lys Lys Gln Arg
                    435                 440                 445

Arg Pro Ile Pro Lys Gly His Cys Thr Ala Cys Arg Ile Thr Ser Glu
                    450                 455                 460

Asp Pro Asn Asp Gly Phe Lys Pro Ser Gly Gly Thr Leu His Glu Leu
        465                 470                 475                 480

Asn Phe Arg Ser Ser Asn Val Trp Gly Tyr Phe Ser Val Gly Asn
                            485                 490                 495

Asn Gly Asn Ile His Ser Phe Ser Asp Ser Gln Phe Gly His Ile Phe
                        500                 505                 510

Ala Phe Gly Glu Asn Arg Gln Ala Ser Arg Lys His Met Val Val Ala
                    515                 520                 525

Leu Lys Glu Leu Ser Ile Arg Gly Asp Phe Arg Thr Thr Val Glu Tyr
                    530                 535                 540

Leu Ile Lys Leu Leu Glu Thr Glu Asp Phe Glu Asp Asn Thr Ile Thr
        545                 550                 555                 560

Thr Gly Trp Leu Asp Asp Leu Ile Thr His Lys Met Thr Ala Glu Lys
                            565                 570                 575

Pro Asp Pro Thr Leu Ala Val Ile Cys Gly Ala Ala Thr Lys Ala Phe
                        580                 585                 590

Leu Ala Ser Glu Glu Ala Arg His Lys Tyr Ile Glu Ser Leu Gln Lys
                    595                 600                 605
```

```
Gly Gln Val Leu Ser Lys Asp Leu Leu Gln Thr Met Phe Pro Val Asp
610                 615                 620

Phe Ile His Glu Gly Lys Arg Tyr Lys Phe Thr Val Ala Lys Ser Gly
625                 630                 635                 640

Asn Asp Arg Tyr Thr Leu Phe Ile Asn Gly Ser Lys Cys Asp Ile Ile
                645                 650                 655

Leu Arg Gln Leu Ser Asp Gly Leu Leu Ile Ala Ile Gly Gly Lys
            660                 665                 670

Ser His Thr Ile Tyr Trp Lys Glu Val Ala Ala Thr Arg Leu Ser
        675                 680                 685

Val Asp Ser Met Thr Thr Leu Leu Glu Val Glu Asn Asp Pro Thr Gln
690                 695                 700

Leu Arg Thr Pro Ser Pro Gly Lys Leu Val Lys Phe Leu Val Glu Asn
705                 710                 715                 720

Gly Glu His Ile Ile Lys Gly Gln Pro Tyr Ala Glu Ile Glu Val Met
                725                 730                 735

Lys Met Gln Met Pro Leu Val Ser Gln Glu Asn Gly Ile Val Gln Leu
            740                 745                 750

Leu Lys Gln Pro Gly Ser Thr Ile Val Ala Gly Asp Ile Met Ala Ile
        755                 760                 765

Met Thr Leu Asp Asp Pro Ser Lys Val Lys His Ala Leu Pro Phe Glu
770                 775                 780

Gly Met Leu Pro Asp Phe Gly Ser Pro Val Ile Glu Gly Thr Lys Pro
785                 790                 795                 800

Ala Tyr Lys Phe Lys Ser Leu Val Ser Thr Leu Glu Asn Ile Leu Lys
                805                 810                 815

Gly Tyr Asp Asn Gln Val Ile Met Asn Ala Ser Leu Gln Gln Leu Ile
            820                 825                 830

Glu Val Leu Arg Asn Pro Lys Leu Pro Tyr Ser Glu Trp Lys Leu His
        835                 840                 845

Ile Ser Ala Leu His Ser Arg Leu Pro Ala Lys Leu Asp Glu Gln Met
850                 855                 860

Glu Glu Leu Val Ala Arg Ser Leu Arg Arg Gly Ala Val Phe Pro Ala
865                 870                 875                 880

Arg Gln Leu Ser Lys Leu Ile Asp Met Ala Val Lys Asn Pro Glu Tyr
                885                 890                 895

Asn Pro Asp Lys Leu Leu Gly Ala Val Val Glu Pro Leu Ala Asp Ile
            900                 905                 910

Ala His Lys Tyr Ser Asn Gly Leu Glu Ala His Glu His Ser Ile Phe
        915                 920                 925

Val His Phe Leu Glu Glu Tyr Tyr Glu Val Glu Lys Leu Phe Asn Gly
930                 935                 940

Pro Asn Val Arg Glu Glu Asn Ile Ile Leu Lys Leu Arg Asp Glu Asn
945                 950                 955                 960

Pro Lys Asp Leu Asp Lys Val Ala Leu Thr Val Leu Ser His Ser Lys
                965                 970                 975

Val Ser Ala Lys Asn Asn Leu Ile Leu Ala Ile Leu Lys His Tyr Gln
            980                 985                 990

Pro Leu Cys Lys Leu Ser Ser Lys Val Ser Ala Ile Phe Ser Thr Pro
        995                 1000                1005

Leu Gln His Ile Val Glu Leu Glu Ser Lys Ala Thr Ala Lys Val Ala
    1010                1015                1020

Leu Gln Ala Arg Glu Ile Leu Ile Gln Gly Ala Leu Pro Ser Val Lys
```

```
                1025                1030                1035                1040
Glu Arg Thr Glu Gln Ile Glu His Ile Leu Lys Ser Ser Val Val Lys
                    1045                1050                1055
Val Ala Tyr Gly Ser Ser Asn Pro Lys Arg Ser Glu Pro Asp Leu Asn
                1060                1065                1070
Ile Leu Lys Asp Leu Ile Asp Ser Asn Tyr Val Val Phe Asp Val Leu
            1075                1080                1085
Leu Gln Phe Leu Thr His Gln Asp Pro Val Val Thr Ala Ala Ala Ala
        1090                1095                1100
Gln Val Tyr Ile Arg Arg Ala Tyr Arg Ala Tyr Thr Ile Gly Asp Ile
1105                1110                1115                1120
Arg Val His Glu Gly Val Thr Val Pro Ile Val Glu Trp Lys Phe Gln
                1125                1130                1135
Leu Pro Ser Ala Ala Phe Ser Thr Phe Pro Thr Val Lys Ser Lys Met
            1140                1145                1150
Gly Met Asn Arg Ala Val Ser Val Ser Asp Leu Ser Tyr Val Ala Asn
            1155                1160                1165
Ser Gln Ser Ser Pro Leu Arg Glu Gly Ile Leu Met Ala Val Asp His
        1170                1175                1180
Leu Asp Asp Val Asp Glu Ile Leu Ser Gln Ser Leu Glu Val Ile Pro
1185                1190                1195                1200
Arg His Gln Ser Ser Ser Asn Gly Pro Ala Pro Asp Arg Ser Gly Ser
                1205                1210                1215
Ser Ala Ser Leu Ser Asn Val Ala Asn Val Cys Val Ala Ser Thr Glu
                1220                1225                1230
Gly Phe Glu Ser Glu Glu Glu Ile Leu Val Arg Leu Arg Glu Ile Leu
            1235                1240                1245
Asp Leu Asn Lys Gln Glu Leu Ile Asn Ala Ser Ile Arg Arg Ile Thr
        1250                1255                1260
Phe Met Phe Gly Phe Lys Asp Gly Ser Tyr Pro Lys Tyr Tyr Thr Phe
1265                1270                1275                1280
Asn Gly Pro Asn Tyr Asn Glu Asn Glu Thr Ile Arg His Ile Glu Pro
                1285                1290                1295
Ala Leu Ala Phe Gln Leu Glu Leu Gly Arg Leu Ser Asn Phe Asn Ile
                1300                1305                1310
Lys Pro Ile Phe Thr Asp Asn Arg Asn Ile His Val Tyr Glu Ala Val
            1315                1320                1325
Ser Lys Thr Ser Pro Leu Asp Lys Arg Phe Phe Thr Arg Gly Ile Ile
        1330                1335                1340
Arg Thr Gly His Ile Arg Asp Asp Ile Ser Ile Gln Glu Tyr Leu Thr
1345                1350                1355                1360
Ser Glu Ala Asn Arg Leu Met Ser Asp Ile Leu Asp Asn Leu Glu Val
                1365                1370                1375
Thr Asp Thr Ser Asn Ser Asp Leu Asn His Ile Phe Ile Asn Phe Ile
            1380                1385                1390
Ala Val Phe Asp Ile Ser Pro Glu Asp Val Glu Ala Ala Phe Gly Gly
        1395                1400                1405
Phe Leu Glu Arg Phe Gly Lys Arg Leu Leu Arg Leu Arg Val Ser Ser
            1410                1415                1420
Ala Glu Ile Arg Ile Ile Ile Lys Asp Pro Gln Thr Gly Ala Pro Val
1425                1430                1435                1440
Pro Leu Arg Ala Leu Ile Asn Asn Val Ser Gly Tyr Val Ile Lys Thr
            1445                1450                1455
```

```
Glu Met Tyr Thr Glu Val Lys Asn Ala Lys Gly Glu Trp Val Phe Lys
            1460                1465                1470

Ser Leu Gly Lys Pro Gly Ser Met His Leu Arg Pro Ile Ala Thr Pro
    1475                1480                1485

Tyr Pro Val Lys Glu Trp Leu Gln Pro Lys Arg Tyr Lys Ala His Leu
1490                1495                1500

Met Gly Thr Thr Tyr Val Tyr Asp Phe Pro Glu Leu Phe Arg Gln Ala
1505                1510                1515                1520

Ser Ser Ser Gln Trp Lys Asn Phe Ser Ala Asp Val Lys Leu Thr Asp
            1525                1530                1535

Asp Phe Phe Ile Ser Asn Glu Leu Ile Glu Asp Glu Asn Gly Glu Leu
        1540                1545                1550

Thr Glu Val Glu Arg Glu Pro Gly Ala Asn Ala Ile Gly Met Val Ala
            1555                1560                1565

Phe Lys Ile Thr Val Lys Thr Pro Glu Tyr Pro Arg Gly Arg Gln Phe
    1570                1575                1580

Val Val Val Ala Asn Asp Ile Thr Phe Lys Ile Gly Ser Phe Gly Pro
1585                1590                1595                1600

Gln Glu Asp Glu Phe Phe Asn Lys Val Thr Glu Tyr Ala Arg Lys Arg
            1605                1610                1615

Gly Ile Pro Arg Ile Tyr Leu Ala Ala Asn Ser Gly Ala Arg Ile Gly
        1620                1625                1630

Met Ala Glu Glu Ile Val Pro Leu Phe Gln Val Ala Trp Asn Asp Ala
            1635                1640                1645

Ala Asn Pro Asp Lys Gly Phe Gln Tyr Leu Tyr Leu Thr Ser Glu Gly
    1650                1655                1660

Met Glu Thr Leu Lys Lys Phe Asp Lys Glu Asn Ser Val Leu Thr Glu
1665                1670                1675                1680

Arg Thr Val Ile Asn Gly Glu Glu Arg Phe Val Ile Lys Thr Ile Ile
            1685                1690                1695

Gly Ser Glu Asp Gly Leu Gly Val Glu Cys Leu Arg Gly Ser Gly Leu
        1700                1705                1710

Ile Ala Gly Ala Thr Ser Arg Ala Tyr His Asp Ile Phe Thr Ile Thr
            1715                1720                1725

Leu Val Thr Cys Arg Ser Val Gly Ile Gly Ala Tyr Leu Val Arg Leu
    1730                1735                1740

Gly Gln Arg Ala Ile Gln Val Glu Gly Gln Pro Ile Ile Leu Thr Gly
1745                1750                1755                1760

Ala Pro Ala Ile Asn Lys Met Leu Gly Arg Glu Val Tyr Thr Ser Asn
            1765                1770                1775

Leu Gln Leu Gly Gly Thr Gln Ile Met Tyr Asn Asn Gly Val Ser His
        1780                1785                1790

Leu Thr Ala Val Asp Asp Leu Ala Gly Val Glu Lys Ile Val Glu Trp
    1795                1800                1805

Met Ser Tyr Val Pro Ala Lys Arg Asn Met Pro Val Pro Ile Leu Glu
1810                1815                1820

Thr Lys Asp Thr Trp Asp Arg Pro Val Asp Phe Thr Pro Thr Asn Asp
1825                1830                1835                1840

Glu Thr Tyr Asp Val Arg Trp Met Ile Glu Gly Arg Glu Thr Glu Ser
            1845                1850                1855

Gly Phe Glu Tyr Gly Leu Phe Asp Lys Gly Ser Phe Phe Glu Thr Leu
        1860                1865                1870
```

```
Ser Gly Trp Ala Lys Gly Val Val Gly Arg Ala Arg Leu Gly Gly
    1875                1880                1885

Ile Pro Leu Gly Val Ile Gly Val Glu Thr Arg Thr Val Glu Asn Leu
    1890                1895                1900

Ile Pro Ala Asp Pro Ala Asn Pro Asn Ser Ala Glu Thr Leu Ile Gln
1905                1910                1915                1920

Glu Pro Gly Gln Val Trp His Pro Asn Ser Ala Phe Lys Thr Ala Gln
                1925                1930                1935

Ala Ile Asn Asp Phe Asn Gly Glu Gln Leu Pro Met Met Ile Leu
        1940                1945                1950

Ala Asn Trp Arg Gly Phe Ser Gly Gln Arg Asp Met Phe Asn Glu
        1955                1960                1965

Val Leu Lys Tyr Gly Ser Phe Ile Val Asp Ala Leu Val Asp Tyr Lys
    1970                1975                1980

Gln Pro Ile Ile Ile Tyr Ile Pro Pro Thr Gly Glu Leu Arg Gly Gly
1985                1990                1995                2000

Ser Trp Val Val Val Asp Pro Thr Ile Asn Ala Asp Gln Met Glu Met
                2005                2010                2015

Tyr Ala Asp Val Asn Ala Arg Ala Gly Val Leu Glu Pro Gln Gly Met
        2020                2025                2030

Val Gly Ile Lys Phe Arg Arg Glu Lys Leu Leu Asp Thr Met Asn Arg
        2035                2040                2045

Leu Asp Asp Lys Tyr Arg Glu Leu Arg Ser Gln Leu Ser Asn Lys Ser
    2050                2055                2060

Leu Ala Pro Glu Val His Gln Gln Ile Ser Lys Gln Leu Ala Asp Arg
2065                2070                2075                2080

Glu Arg Glu Leu Leu Pro Ile Tyr Gly Gln Ile Ser Leu Gln Phe Ala
                2085                2090                2095

Asp Leu His Asp Arg Ser Ser Arg Met Val Ala Lys Gly Val Ile Ser
        2100                2105                2110

Lys Glu Leu Glu Trp Thr Glu Ala Arg Arg Phe Phe Phe Trp Arg Leu
        2115                2120                2125

Arg Arg Arg Leu Asn Glu Glu Tyr Leu Ile Lys Arg Leu Ser His Gln
2130                2135                2140

Val Gly Glu Ala Ser Arg Leu Glu Lys Ile Ala Arg Ile Arg Ser Trp
2145                2150                2155                2160

Tyr Pro Ala Ser Val Asp His Glu Asp Asp Arg Gln Val Ala Thr Trp
                2165                2170                2175

Ile Glu Glu Asn Tyr Lys Thr Leu Asp Asp Lys Leu Lys Gly Leu Lys
        2180                2185                2190

Leu Glu Ser Phe Ala Gln Asp Leu Ala Lys Lys Ile Arg Ser Asp His
        2195                2200                2205

Asp Asn Ala Ile Asp Gly Leu Ser Glu Val Ile Lys Met Leu Ser Thr
2210                2215                2220

Asp Asp Lys Glu Lys Leu Leu Lys Thr Leu Lys
2225                2230                2235

<210> SEQ ID NO 4
<211> LENGTH: 1377
<212> TYPE: DNA
<213> ORGANISM: Artificial Sequence
<220> FEATURE:
<223> OTHER INFORMATION: Codon-optimized Acinetobacter baylii sp. atfA

<400> SEQUENCE: 4
```

```
atgcggccct tgcaccccat tgacttcatc tttctgagtt tggagaaacg gcaacagccc     60
atgcatgtcg gtggcttgtt tctcttccaa atcccgata acgccccgga cacctttatt     120
caggatctgg tcaatgatat ccggatctcg aaatcgatcc ccgtgccgcc gtttaataat    180
aaactgaacg gcctctttg gacgaagac gaggaaatttg atctggatca ccattttcgg     240
cacatcgctt tgccccaccc gggtcggatt cgcgaactcc tgatctatat tagccaagaa    300
cacagcacgt tgttggaccg ggccaaaccg ctctggacgt gcaatatcat cgaaggcatc    360
gaaggcaacc gctttgcgat gtacttcaag attcatcacg cgatggttga cggtgtcgct    420
ggcatgcgcc tgatcgaaaa atcgctgagc catgatgtga ccgaaaagag tatcgtcccc    480
ccctggtgcg tggaaggtaa gcgcgccaag cgcctccgcg aaccgaaaac gggcaagatt    540
aagaaaatca tgagcggtat caagtcgcag ctgcaggcta ccccgaccgt gatccaggag    600
ctgtcgcaaa ccgtgtttaa ggatattggt cggaacccgg atcatgtcag tagtttccaa    660
gctccctgtt cgatcttgaa tcagcgcgtt agcagcagcc gccggttcgc tgctcaaagt    720
tttgatctcg atcggtttcg gaatattgcc aagtcgctga acgtcaccat caatgatgtg    780
gttctcgcgg tttgttcggg tgccctccgc gcgtatctga tgagccataa cagtctcccc    840
agtaagccgc tgattgctat ggttcccgcg tcgattcgga atgacgacag cgatgtgagc    900
aaccggatta ccatgatcct ggctaacctc gcgacccaca agatgatccc gttgcaacgc    960
ctggagatta tccgccgcag tgtgcagaac agtaaacagc gcttcaaacg gatgaccagt    1020
gatcaaattc tgaattacag cgctgtggtc tatggtcccg ccggcttgaa tattatcagt    1080
ggtatgatgc ccaaacgcca agcgtttaac ttggtgatca gtaatgtgcc gggtccgcgc    1140
gaacccttgt attggaacgg tgctaaactc gatgccctct accccgccag tatcgtgctc    1200
gatggccagg ctctcaatat taccatgacc agctatctcg ataaactcga ggtgggtttg    1260
attgcgtgcc gcaacgcgct gccccgcatg cagaacttgc tgacccacct ggaagaggaa    1320
atccagctct tcgagggcgt gattgcgaag caggaagata ttaaaaacggc caactag      1377
```

<210> SEQ ID NO 5
<211> LENGTH: 2595
<212> TYPE: DNA
<213> ORGANISM: Artificial Sequence
<220> FEATURE:
<223> OTHER INFORMATION: Codon-optimized S. cerevisiae phosphatidate
    phosphatase (PAH1)

<400> SEQUENCE: 5

```
atggaattcc aatatgttgg tcgggctttg ggtagtgtta gtaaaacgtg gtcgagtatc     60
aaccccgcca ccctgagcgg cgctatcgat gtcattgtcg tggaacaccc cgatggccgg    120
ctcagttgta gccccttcca tgtgcgcttt ggtaaattcc agattctgaa acccagccaa    180
aagaaagtcc aggtctttat taacgagaaa ctgtcgaata tgcccatgaa actctcggat    240
agcggcgagg cgtacttcgt ttttgagatg ggtgatcaag tgacggatgt cccggatgaa    300
ctgctcgtct cgccggtcat gagtgccacg agtagtccgc cccaatcgcc ggaaacctcg    360
attctcgaag gcggtaccga aggcgagggc gaaggtgaga atgaaaataa gaaaaaggaa    420
aagaaggtgt tggaggagcc cgactttctg gacattaatg acaccggtga cagcggcagc    480
aagaacagtg agacgacggg ttcgctctcg ccgaccgaaa gtagtacgac gacgccgccc    540
gatagcgtcg aggaacgcaa gttggtcgaa caacggacca agaattttca gcaaaagctg    600
aataagaaac tgaccgaaat ccatattccg agcaaattgg acaataacgg tgatttgctc    660
```

-continued

| | |
|---|---|
| ctggacaccg agggttataa gccgaataaa aacatgatgc acgacacgga tattcagctg | 720 |
| aagcaattgc tcaaggatga gttcggtaac gatagcgata tttcgagctt catcaaagaa | 780 |
| gacaagaatg gcaacattaa aatcgtgaac ccctatgagc atttgaccga tttgagtccc | 840 |
| ccgggtacgc ccccgaccat ggccacgagt ggcagtgtcc tgggcttgga tgcgatggag | 900 |
| agtggttcga cgctgaacag cttgagcagc agcccgagcg gcagtgacac cgaggatgag | 960 |
| acgagcttta gcaaggaaca gtcgtcgaag agtgaaaaaa cgtcgaagaa aggcaccgcg | 1020 |
| ggttcgggtg aaacggagaa acgctacatc cgcacgatcc ggctcacgaa tgatcagctg | 1080 |
| aaatgcctca acttgacgta cggtgaaaat gacttgaaat ttagtgttga ccatggcaaa | 1140 |
| gccattgtga ccagcaaatt gtttgtctgg cgctgggacg tccccatcgt tatcagcgac | 1200 |
| attgacggta cgattacgaa aagtgatgcg ctgggccacg tcctcgccat gatcggcaaa | 1260 |
| gattggaccc atctcggcgt cgctaagctg ttcagtgaga tctcgcgcaa cggttacaat | 1320 |
| atcctgtacc tgaccgcgcg ctcggccggt caggctgaca gtacccgctc gtatctccgc | 1380 |
| agtattgagc agaacggtag caagctcccg aacggccccg tcattctgag ccccgatcgg | 1440 |
| accatggctg ccctgcgccg ggaggtgatt ctgaaaaagc ccgaagtctt taaaatcgct | 1500 |
| tgcttgaacg atatccgctc gctctatttc gaagactcgg ataacgaagt ggacacggag | 1560 |
| gaaaagagca cgccgttttt cgcgggcttt ggcaatcgga tcaccgatgc gctcagctat | 1620 |
| cggacggtcg gcatcccgag tagccgcatc ttcacgatta acacggaagg cgaggtgcac | 1680 |
| atggagctgc tcgagctcgc cggttaccgg agtagctata tccatatcaa cgaactggtc | 1740 |
| gatcacttct ccccgccggt gagcctggac tcggtcgatc tgcgcacgaa cacgagcatg | 1800 |
| gtcccgggca gcccgccgaa ccgcaccctg ataactttg atagcgaaat caccagtggc | 1860 |
| cgcaagacgt tgtttcgcgg taatcaggag gaaaaattca cggacgtcaa cttttggcgc | 1920 |
| gatccgttgg tggacatcga caacctctcg gatatcagta cgatgattc ggacaatatt | 1980 |
| gatgaagaca ccgatgtgag ccaacagtcg aacatcagcc gcaaccgcgc taactcggtc | 2040 |
| aagacggcca aggtgaccaa ggctccgcag cggaatgtgt cgggcagtac gaataacaat | 2100 |
| gaagttctgg ctgcgagtag tgatgttgaa aatgccagtg acttggttag cagccactcg | 2160 |
| agtagcggct cgaccccaa caagtcgacg atgagtaagg gtgatatcgg caaacaaatc | 2220 |
| tatctggaac tgggctcgcc cttggcgagt cccaaactcc ggtatctgga cgatatggat | 2280 |
| gatgaggact cgaactataa tcgcaccaag agccgccggg ctagtagcgc cgctgctacc | 2340 |
| agcatcgaca aggagtttaa aaagctcagt gtgagtaaag ctggcgctcc caccccgcatc | 2400 |
| gttagcaaga tcaacgtgtc gaatgatgtg cacagtttgg gcaacagtga taccgaaagc | 2460 |
| cggcgggaac agagcgtcaa tgaaaccggt cgcaatcagt tgccgcacaa tagtatggat | 2520 |
| gataaggatt tggattcgcg ggtgagtgac gagttcgatg acgatgagtt tgatgaagat | 2580 |
| gagtttgagg attag | 2595 |

<210> SEQ ID NO 6
<211> LENGTH: 6708
<212> TYPE: DNA
<213> ORGANISM: Artificial Sequence
<220> FEATURE:
<223> OTHER INFORMATION: Codon-optimized S. cerevisiae acetyl Coa
      carboxylase (ACC1)

<400> SEQUENCE: 6

| | |
|---|---|
| atggaattct ccgaggaaag tttgttcgaa agcagtccgc agaaaatgga atatgaaatt | 60 |

```
acgaattatt cggaacgcca cacggagctc cccgggcact tcatcggact caacaccgtg    120
gataagctcg aagaaagtcc cctccgcgat tttgtgaaaa gccacggcgg ccataccgtg    180
atctcgaaga ttctgattgc caataacgga attgccgctg tcaaggagat ccgcagcgtc    240
cggaagtggg cgtacgaaac ttttggcgat gaccgtacag tccagtttgt tgctatggcg    300
actccggaag acttggaggc gaatgcggaa tacattcgaa tggccgatca atacatcgaa    360
gtccccggag gaacgaacaa caacaattat gcgaacgtcg atttgatcgt ggatatcgca    420
gaacgcgcgg acgtggatgc tgtttgggcc ggatggggcc acgcttcgga aaaccctctg    480
ttgccggaaa aactcagcca gtctaaacgg aaagtcattt tcatcggccc tccgggcaac    540
gcaatgcgct cgttgggtga taagatcagc tcgaccattg tggctcagag cgctaaagtc    600
ccatgtattc cctggtcggg taccggcgtg gatacggtcc atgttgatga aaaactggat    660
ctggtcagcg tcgatgatga tatctaccaa aagggctgtt gcaccagccc ggaagatggc    720
ctgcaaaagg cgaagcgcat cgggttccca gtcatgatca aggcatccga aggcggaggc    780
ggtaagggta tccgccaggt tgagcgtgaa gaagatttta tcgcactgta tcatcaagcg    840
gctaacgaaa tcccgggctc gccaattttc attatgaaac tggctggtcg ggcgcgtcat    900
ctcgaagtgc aactcctcgc tgaccagtac ggtacgaaca tctctttgtt cggtcgggat    960
tgttcggtcc agcgtcgtca ccagaagatc attgaagaag ccctgttac catcgcaaag   1020 gccgagacgt tcatgagat ggagaaagcg gccgtccgcc tcggcaagct ggtcggttac   1080
gttagcgcag gcaccgtgga atacctctat tcccacgacg atggtaagtt ttactttctc   1140
gaactgaatc ctcgcctgca ggttgaacac ccgaccacag atggtgtc gggggtcaat   1200 ctgccggctg cgcagttgca gattgcaatg gcattccga tgcatcgaat cagcgacatc   1260
cgaaccctgt acggcatgaa cccgcacagt gcgagcgaaa tcgactttga gttcaagacc   1320
caagacgcca cgaagaaaca gcgacgccca attccgaagg gccattgcac cgcgtgtcgc   1380
attacctcgg aggaccccaa tgatggtttt aagcccctcgg gcggtactct gcacgagctc   1440
aacttccgct cctcctcgaa cgtctgggc tatttcagcg tcggaaataa tggtaacatt   1500
catagttttt ccgattccca atttggccat atcttcgcct ttggcgaaaa ccgacaagct   1560
agccgcaaac acatggtcgt ggcgttgaag gagctgagta tccgagggga ctttcgcacg   1620
acggtggaat atctgatcaa actgctcgaa acggaggact ttgaggataa cacaattacc   1680
accggatggt tggacgacct gattacgcac aaaatgaccg ccgagaaacc cgaccccacc   1740
ttggcagtga tttgtggcgc ggcaacgaag gcctttttgg cctctgaaga ggcacgccac   1800
aagtacattg agagtctcca aaagggtcag gtgctgagta aagatctgct gcaaaccatg   1860
tttcctgtcg actttattca tgaggggaaa cgctacaaat tcacggttgc taagtctggt   1920
aatgatcggt acacattgtt tatcaatgga tcgaagtgcg atattatctt gcgacaactc   1980
tccgacggcg gcctcctgat tgctatcggc gggaaaagtc ataccatcta ttggaaagaa   2040
gaggtcgccg ccaccccgact gagcgttgat tcgatgacta ctctgctcga agttgaaaac   2100
gatccaacgc aactgcgcac tccctctccg ggtaagctcg tgaagtttct cgtcgagaat   2160
ggcgaacaca ttattaaggg ccagccgtat gcggaaatcg aggtgatgaa gatgcagatg   2220
cccctggtca gccaagagaa cggtattgtg caactgctga acagcccgg cagcaccatc   2280 gtcgctggcg atatcatggc tatcatgacc ctcgatgatc cttccaaagt caaacatgcc   2340
ctgcccttcg aaggcatgct cccccgatttt ggctcccccg tgattgaggg caccaaacca   2400
gcttacaagt ttaaatcgct ggtttccacc ctcgagaaca tcttgaaggg ctacgataat   2460
```

```
caggtcatta tgaatgccag cctccagcag ctcattgagg tcctccgtaa ccccaagctg   2520
ccctacagtg aatggaagct ccacatcagt gcgctccact cgcgactgcc cgcgaagctc   2580
gatgagcaga tggaagagct cgtcgctcgc agcctgcgtc gcggcgcagt ctttccggca   2640
cggcaactgt cgaagctcat cgatatggct gtcaaaaacc ccgaatacaa ccccgataaa   2700
ctcttgggtg ctgtcgttga gccgctcgcc gatatcgcgc acaagtacag taatggcctg   2760
gaggcgcacg aacacagtat ctttgttcac ttcctggaag aatactatga ggttgagaaa   2820
ctgttcaatg ggcctaatgt ccgggaagag aatattatcc tgaagctccg tgatgaaaat   2880
ccgaaagatt tggataaagt cgccttgacg gtgctcagtc atagcaaggt gagtgccaag   2940
aacaatctca tcctggcgat cttgaaacac taccaacctt tgtgcaagct gagttccaag   3000
gtgtcggcta tttttagtac gcccctgcag cacatcgtgg aactcgaaag taaagccacc   3060
gccaaggtgg ctctgcaggc ccgggagatt ctgatccagg gtgctctgcc gagcgtgaaa   3120
gagcggacgg aacaaatcga acacatcctg aagagttcgg tcgtgaaggt tgcatatggc   3180
agcagtaacc ctaaacgctc ggaaccggac ctcaatatcc tgaaggatct gatcgatagt   3240
aattatgttg ttttttgatgt cctgctccaa tttctgactc accagatcc ggttgttact   3300 gcggctgccg cgcaagttta cattcgacgc gcctatcgcg cctacacaat cggcgatatt   3360
cgagtccatg agggcgtgac cgttccaatc gttgaatgga aattccagtt gccatcggcg   3420 gcttttcta cattcccaac agtcaagagt aagatgggca tgaatcgtgc cgtttcggtc   3480
agtgatttgt cctatgtcgc aaactcgcaa tctagtcctc tgcgagaggg catcctgatg   3540
gcagtggatc atttggatga tgtcgatgag atcctctcgc aaagtctcga ggtcattcct   3600
cgccaccaat cgtcgtccaa tggcccagct cccgatcgat ccggttcttc cgccagcttg   3660
tcgaatgtcg ccaacgtctg tgtggcgtcg actgaggggt tcgaaagcga agaagaaatt   3720
ttggtccgct tgcgggaaat tttggacctc aacaagcagg aactgattaa tgcctctatt   3780
cgccgcatta cgtttatgtt cggtttcaag gatggctcgt acccaaaata ctatacgttc   3840
aacggcccga actacaatga gaacgagact atccgacata ttgaacctgc cctcgctttc   3900
caactggaac tggggcggct ctcgaatttc aatattaagc ctattttac cgacaaccgt   3960 aacatccacg tttacgaggc tgtcagcaaa acaagcccgc tggataagcg attcttcacc   4020
cggggcatta tccgcacagg ccacatccgt gacgatatca gtatccaaga atacctgact   4080
agcgaagcta accgcttgat gagcgacatt ttggataatc tggaagtgac tgatacttcc   4140
aacagcgact gaatcacat ttttatcaac ttcattgccg tgttcgatat ctcgccggaa   4200
gatgtggaag ccgcgtttgg aggctttctg gaacggtttg gcaaacggct gctgcgcttg   4260
cgggtgtcta gcgcggagat tcggattatc atcaaagatc cgcaaacggg gctcctgtg   4320 ccactgcgcg cgctgattaa taacgtctcg ggttacgtga tcaagaccga gatgtacaca   4380
gaggttaaaa acgctaaagg cgagtgggtc ttcaagagct tgggcaaacc cggcagcatg   4440
catctccgcc ccatcgccac gccgtatccg gtcaaggagt ggctgcagcc caagcgatac   4500
aaggcgcact tgatggggac gacatatgtt tacgattttc ctgaactgtt ccgtcaagca   4560
agcagctccc agtggaaaaa cttttccgca gatgtgaaat tgactgatga tttcttcatc   4620
tcgaatgagc tcatcgaaga tgagaatggc gagctgaccg aagttgagcg agaacctggt   4680
gccaatgcga ttgggatggt cgcctttaaa atcacggtca aaactcccga gtaccctcgg   4740
ggtcgccagt tcgtcgttgt ggctaacgat atcacccttta agattggatc gtttggcccg   4800
```

```
caggaggatg agttctttaa caaggtcact gaatacgccc gaaaacgagg cattccgcgg    4860
atttacttgg cagccaatag cggtgcgcgc atcggcatgg ctgaagaaat cgttccgctg    4920
tttcaggttg cctggaacga cgcggccaac cccgacaagg ggttccagta cttgtatctg    4980
acttccgaag gcatggagac gttgaagaaa tttgataagg agaatagtgt cttgactgag    5040
cggaccgtta ttaacggcga ggagcggttt gtcattaaga ctatcatcgg cagcgaagat    5100
ggcctcggcg tcgaatgttt gcgcgggtcc ggcctgatcg caggggcaac ctcgcgagcc    5160
tatcacgata tctttaccat tactttggtc acgtgtcgtt cggttggcat tggagcatac    5220
ctcgtgcgcc tcggtcagcg cgccatccaa gtggaaggcc aacctatcat tttgactggc    5280
gcgcctgcta tcaataagat gctgggccgt gaagtctaca catcgaacct ccaactgggc    5340
ggtacccaaa ttatgtataa caatggcgtc agccatctga cagccgtcga tgacctggct    5400
ggcgttgaaa agattgttga gtggatgagc tatgtgcccg ccaaacggaa catgccagtc    5460
cccattttgg aaaccaagga tacctgggat cgcccagtgg atttcactcc gactaatgat    5520
gaaacctacg atgtccgctg gatgatcgaa gggcgcgaaa ctgagtcggg cttcgagtac    5580
ggactgtttg ataagggtag tttctttgag actctcagtg gttgggccaa aggcgttgtc    5640
gtcggtcggg cacgtctggg cggcatcccg ctggagttaa ttggtgttga cacgtacg     5700
gtggaaaatc tgatcccggc tgatccggcc aaccccaata gtgcggaaac gctgattcaa    5760
gagcccgggc aagtgtggca cccgaatagt gcctttaaga cggcgcaggc tattaatgat    5820
tttaacaacg gcgaacaact gcctatgatg attctggcga attggcgggg gtttagtggt    5880
gggcagcgcg acatgttcaa cgaagtgctc aagtacggct ccttcatcgt ggacgccctg    5940
gtcgactata acaaccaat tatcatctat attccccccta ccggcgagct gcgaggcggt    6000
agctgggtcg tggtggaccc tactattaat gcagatcaaa tggagatgta cgccgacgtg    6060
aatgctcgag cgggcgtgct ggaaccacaa gggatggttg gcatcaaatt ccgccgcgaa    6120
aaactgttgg atactatgaa tcgactggat gataaatatc gcgagctgcg cagccaactg    6180
tcgaacaagt ctctggcccc ggaagtccat caacagattt ctaaacagct ggcagatcgc    6240
gaacgtgaac tcttgccgat ctacggccaa atcagcctcc aatttgccga cctgcatgat    6300
cgcagcagcc gcatggttgc gaaaggtgtc atcagcaaag agctcgagtg gacggaagct    6360
cggcggtttt tcttttggcg gctgcgccga cgcctgaatg aagaatactt gattaagcgt    6420
ctgagccacc aggtcggcga ggctagtcgg ttggaaaaga tcgcccgcat tcggagttgg    6480
tatccggcat cggttgacca cgaggacgat cgccaggtcg ctacctggat cgaagagaac    6540
tacaaaacct tggatgataa gctgaaagga ctgaagctgg agtctttcgc ccaagatctc    6600
gccaagaaga tccgtagcga tcatgacaat gcaatcgacg gtttgagcga ggttatcaag    6660
atgttgtcta ccgacgacaa ggagaagctg ctcaaaacgc tgaagtag              6708
```

<210> SEQ ID NO 7
<211> LENGTH: 1376
<212> TYPE: DNA
<213> ORGANISM: Acinetobacter sp.

<400> SEQUENCE: 7

```
atgcgcccat acatccgat tgattttata ttcctgtcac tagaaaaaag acaacagcct      60
atgcatgtag gtggtttatt tttgtttcag attcctgata acgccccaga cacctttatt    120
caagatctgg tgaatgatat ccggatatca aaatcaatcc ctgttccacc attcaacaat    180
aaactgaatg ggctttttttg ggatgaagat gaagagtttg atttagatca tcattttcgt    240
```

```
catattgcac tgcctcatcc tggtcgtatt cgtgaattgc ttatttatat ttcacaagag      300
cacagtacgc tgctagatcg ggcaaagccc ttgtggacct gcaatattat tgaaggaatt      360
gaaggcaatc gttttgccat gtacttcaaa attcaccatg cgatggtcga tggcgttgct      420
ggtatgcggt taattgaaaa atcactctcc catgatgtaa cagaaaaaag tatcgtgcca      480
ccttggtgtg ttgagggaaa acgtgcaaag cgcttaagag aacctaaaac aggtaaaatt      540
aagaaaatca tgtctggtat taagagtcag cttcaggcga cacccacagt cattcaagag      600
ctttctcaga cagtatttaa agatattgga cgtaatcctg atcatgtttc aagctttcag      660
gcgccttgtt ctattttgaa tcagcgtgtg agctcatcgc gacgttttgc agcacagtct      720
tttgacctag atcgttttcg taatattgcc aaatcgttga atgtgaccat taatgatgtt      780
gtactagcgg tatgttctgg tgcattacgt gcgtatttga tgagtcataa tagttttgcct     840 tcaaaaccat taattgccat ggttccagcc tctattcgca atgacgattc agatgtcagc      900
aaccgtatta cgatgattct ggcaaatttg gcaacccaca aagatgatcc tttacaacgt      960
cttgaaatta ccgccgtag tgttcaaaac tcaaagcaac gcttcaaacg tatgaccagc     1020
gatcagattc taaattatag tgctgtcgta tatggccctg caggactcaa cataatttct     1080
ggcatgatgc caaaacgcca agccttcaat ctggttattt ccaatgtgcc tggcccaaga     1140
gagccacttt actggaatgg tgccaaactt gatgcactct acccagcttc aattgtatta     1200
gacggtcaag cattgaatat tacaatgacc agttatttag ataaacttga agttggtttg     1260
attgcatgcc gtaatgcatt gccaagaatg cagaatttac tgacacattt agaagaagaa     1320
attcaactat ttgaaggcgt aattgcaaag caggaagata ttaaaacagc caatta         1376

<210> SEQ ID NO 8
<211> LENGTH: 2589
<212> TYPE: DNA
<213> ORGANISM: Artificial Sequence
<220> FEATURE:
<223> OTHER INFORMATION: Synthetic construct Saccharomyces cerevisiae
      clone FLH148377.01X SMP2 gene

<400> SEQUENCE: 8
atgcagtacg taggcagagc tcttgggtct gtgtctaaaa catggtcttc tatcaatccg       60
gctacgctat caggtgctat agatgtcatt gtagtggagc atccagacgg aaggctatca      120
tgttctccct ttcatgtgag gttcggcaaa tttcaaattc taaagccatc tcaaaagaaa      180
gtccaagtgt ttataaatga aaactgagt aatatgccaa tgaaactgag tgattctgga      240
gaagccattt tcgttttcga gatgggtgac caggtcactg atgtccctga cgaattgctt      300
gtgtcgcccg tgatgagcgc cacatcaagc cccctcaat cacctgaaac atccatctta      360
gaaggaggaa ccgagggtga aggtgaaggt gaaatgaaa ataagaagaa ggaaaagaaa      420
gtgctagagg aaccagattt tttagatatc aatgacactg agattcagg cagtaaaaat      480 agtgaaacta cagggtcgct ttctcctact gaatcctcta caacgacacc accagattca      540
gttgaagaga ggaagcttgt tgagcagcgt acaaagaact ttcagcaaaa actaaacaaa      600
aaactcactg aaatccatat acccagtaaa cttgataaca atggcgactt actactagac      660
actgaaggtt acaagccaaa caagaatatg atgcatgaca cagacataca actgaagcag      720
ttgttaaagg acgaattcgg taatgattca gatatttcca gttttatcaa ggaggacaaa      780
aatggcaaca tcaagatcgt aaatccttac gagcacctta ctgatttatc tcctccaggt      840
acgcctccaa caatggccac aagcggatca gttttaggct tagatgcaat ggaatcagga      900
```

```
agtactttga attcgttatc ttcttcacct tctggttccg atactgagga cgaaacatca      960
tttagcaaag aacaaagcag taaaagtgaa aaaactagca agaaaggaac agcagggagc     1020
ggtgagaccg agaaaagata catacgaacg ataagattga ctaatgacca gttaaagtgc     1080
ctaaatttaa cttatggtga aaatgatctg aaattttccg tagatcacgg aaaagctatt     1140
gttacgtcaa aattattcgt ttggaggtgg gatgttccaa ttgttatcag tgatattgat     1200
ggcaccatca caaaatcgga cgctttaggc catgttctgg caatgatagg aaaagactgg     1260
acgcacttgg gtgtagccaa gttatttagc gagatctcca ggaatggcta taatatactc     1320
tatctaactg caagaagtgc tggacaagct gattccacga ggagttattt gcgatcaatt     1380
gaacagaatg gcagcaaact accaaatggg cctgtgattt tatcacccga tagaacgatg     1440
gctgcgttaa ggcgggaagt aatactaaaa aaacctgaag tctttaaaat cgcgtgtcta     1500
aacgacataa gatccttgta ttttgaagac agtgataacg aagtggatac agaggaaaaa     1560
tcaacaccat tttttgccgg ctttggtaat aggattactg atgctttatc ttacagaact     1620
gtggggatac ctagttcaag aattttcaca ataaatacag agggtgaggt tcatatggaa     1680
ttattggagt tagcaggtta cagaagctcc tatattcata tcaatgagct tgtcgatcat     1740
ttctttccac cagtcagcct tgatagtgtc gatctaagaa ctaatacttc catggttcct     1800
ggctcccccc ctaatagaac gttggataac tttgactcag aaattacttc aggtcgcaaa     1860
acgctattta gaggcaatca ggaagagaaa ttcacagacg taaattttg gagagacccg      1920 ttagtcgaca tcgacaactt atcggatatt agcaatgatg attctgataa catcgatgaa     1980
gatactgacg tatcacaaca agcaacatt agtagaaata gggcaaattc agtcaaaacc      2040
gccaaggtca ctaaagcccc gcaaagaaat gtgagcggca gcacaaataa caacgaagtt     2100
ttagccgctt cgtctgatgt agaaaatgcg tctgacctgg tgagttccca tagtagctca     2160
ggatccacgc ccaataaatc tacaatgtcc aaaggggaca ttggaaaaca aatatatttg     2220
gagctaggtt ctccacttgc atcgccaaaa ctaagatatt tagacgatat ggatgatgaa     2280
gactccaatt acaatagaac taaatcaagg agagcatctt ctgcagccgc gactagtatc     2340
gataaagagt tcaaaaagct ctctgtgtca aaggccggcg ctccaacaag aattgtttca     2400
aagatcaacg tttcaaatga cgtacattca cttgggaatt cagataccga atcacgaagg     2460
gagcaaagtg ttaatgaaac agggcgcaat cagctacccc acaactcaat ggacgataaa     2520
gatttggatt caagagtaag cgatgaattc gatgacgatg aattcgacga agatgaattc     2580
gaagattag                                                           2589

<210> SEQ ID NO 9
<211> LENGTH: 6702
<212> TYPE: DNA
<213> ORGANISM: Artificial Sequence
<220> FEATURE:
<223> OTHER INFORMATION: Synthetic construct Saccharomyces cerevisiae
      clone FLH148869.01X ACC1

<400> SEQUENCE: 9
atgagcgaag aaagcttatt cgagtcttct ccacagaaga tggagtacga aattacaaac       60
tactcagaaa gacatacaga acttccaggt catttcattg gcctcaatac agtagataaa      120
ctagaggagt ccccgttaag ggactttgtt aagagtcacg gtggtcacac ggtcatatcc      180
aagatcctga tagcaaataa tggtattgcc gccgtgaaaa aaattagatc cgtcagaaaa      240
tgggcatacg agacgttcgg cgatgacaga accgtccaat tcgtcgccat ggccacccca      300
```

```
gaagatctgg aggccaacgc agaatatatc cgtatggccg atcaatacat tgaagtgcca    360
ggtggtacta ataataacaa ctacgctaac gtagacttga tcgtagacat cgccgaaaga    420
gcagacgtag acgccgtatg ggctggctgg ggtcacgcct ccgagaatcc actattgcct    480
gaaaaattgt cccagtctaa gaggaaagtc atctttattg ggcctccagg taacgccatg    540
aggtctttag gtgataaaat ctcctctacc attgtcgctc aaagtgctaa agtcccatgt    600
attccatggt ctggtaccgg tgttgacacc gttcacgtgg acgagaaaac cggtctggtc    660
tctgtcgacg atgacatcta tcaaagggt tgttgtacct ctcctgaaga tggtttacaa    720
aaggccaagc gtattggttt tcctgtcatg attaaggcat ccgaaggtgg tggtggtaaa    780
ggtatcagac aagttgaacg tgaagaagat ttcatcgctt tataccacca ggcagccaac    840
gaaattccag gctcccccat tttcatcatg aagttggccg gtagagcgcg tcacttggaa    900
gttcaactgc tagcagatca gtacggtaca aatatttcct tgttcggtag agactgttcc    960
gttcagagac gtcatcaaaa aattatcgaa gaagcaccag ttacaattgc caaggctgaa    1020
acatttcacg agatggaaaa ggctgccgtc agactgggga aactagtcgg ttatgtctct    1080
gccggtaccg tggagtatct atattctcat gatgatggaa aattctactt tttagaattg    1140
aacccaagat tacaagtcga gcatccaaca acggaaatgg tctccggtgt taacttacct    1200
gcagctcaat tacaaatcgc tatgggtatc cctatgcata gaataagtga cattagaact    1260
ttatatggta tgaatcctca ttctgcctca gaaatcgatt tcgaattcaa aactcaagat    1320
gccaccaaga aacaagaag acctattcca aagggtcatt gtaccgcttg tcgtatcaca    1380
tcagaagatc caaacgatgg attcaagcca tcgggtggta ctttgcatga actaaacttc    1440
cgttcttcct ctaatgtttg gggttacttc tccgtgggta acaatggtaa tattcactcc    1500
ttttcggact ctcagttcgg ccatattttt gcttttggtg aaaatagaca agcttccagg    1560
aaacacatgg ttgttgccct gaaggaattg tccattaggg gtgatttcag aactactgtg    1620
gaatacttga tcaaacttt ggaaactgaa gatttcgagg ataacactat taccaccggt    1680
tggttggacg atttgattac tcataaaatg accgctgaaa agcctgatcc aactcttgcc    1740
gtcatttgcg gtgccgctac aaaggctttc ttagcatctg aagaagcccg ccacaagtat    1800
atcgaatcct tacaaagggg acaagttcta tctaaagacc tactgcaaac tatgttccct    1860
gtagatttta tccatgaggg taaaagatac aagttcaccg tagctaaatc cggtaatgac    1920
cgttacacat tatttatcaa tggttctaaa tgtgatatca tactgcgtca actatctgat    1980
ggtggtcttt tgattgccat aggcggtaaa tcgcatacca tctattggaa agaagaagtt    2040
gctgctacaa gattatccgt tgactctatg actactttgt ggaagttgaa aaacgatcca    2100
acccagttgc gtactccatc ccctggtaaa ttggttaaat tcttggtgga aaatggtgaa    2160
cacattatca agggccaacc atatgcagaa attgaagtta tgaaaatgca aatgcctttg    2220
gtttctcaag aaaatggtat cgtccagtta ttaaagcaac ctggttctac cattgttgca    2280
ggtgatatca tggctattat gactcttgac gatccatcca aggtcaagca cgctctacca    2340
tttgaaggta tgctgccaga ttttggttct ccagttatcg aaggaaccaa acctgcctat    2400
aaattcaagt cattagtgtc tactttggaa aacatttga agggttatga caaccaagtt    2460
attatgaacg cttccttgca acaattgata gaggttttga gaaatccaaa actgccttac    2520
tcagaatgga aactacacat ctctgcttta cattcaagat tgcctgctaa gctagatgaa    2580
caaatggaag agttagttgc acgttctttg agacgtggtg ctgttttccc agctagacaa    2640
```

```
ttaagtaaat tgattgatat ggccgtgaag aatcctgaat acaacccega caaattgctg   2700
ggcgccgtcg tggaaccatt ggcggatatt gctcataagt actctaacgg gttagaagcc   2760
catgaacatt ctatatttgt ccatttcttg gaagaatatt acgaagttga aaagttattc   2820
aatggtccaa atgttcgtga ggaaaatatc attctgaaat tgcgtgatga aaaccctaaa   2880
gatctagata aagttgcgct aactgttttg tctcattcga aagtttcagc gaagaataac   2940
ctgatcctag ctatcttgaa acattatcaa ccattgtgca agttatcttc taaagttcct   3000
gccattttct ctactcctct acaacatatt gttgaactag aatctaaggc taccgctaag   3060
gtcgctctac aagcaagaga aattttgatt caaggcgctt taccttcggt caaggaaaga   3120
actgaacaaa ttgaacatat cttaaaatcc tctgttgtga aggttgccta tggctcatcc   3180
aatccaaagc gctctgaacc agatttgaat atcttgaagg acttgatcga ttctaattac   3240
gttgtgttcg atgttttact tcaattccta acccatcaag acccagttgt gactgctgca   3300
gctgctcaag tctatattcg tcgtgcttat cgtgcttaca ccataggaga tattagagtt   3360
cacgaaggtg tcacagttcc aattgttgaa tggaaattcc aactaccttc agctgcgttc   3420
tccacctttc caactgttaa atctaaaatg gtatgaaca gggctgtttc tgtttcagat   3480
ttgtcatatg ttgcaaacag tcagtcatct ccgttaagag aaggtatttt gatggctgtg   3540
gatcatttag atgatgttga tgaaattttg tcacaaagtt tggaagttat tcctcgtcac   3600
caatcttctt ctaacggacc tgctcctgat cgttctggta gctccgcatc gttgagtaat   3660
gttgctaatg tttgtgttgc ttctacagaa ggtttcgaat ctgaagagga aattttggta   3720
aggttgagag aaattttgga tttgaataag caggaattaa tcaatgcttc tatccgtcgt   3780
atcacattta tgttcggttt taaagatggg tcttatccaa agtattatac ttttaacggt   3840
ccaaattata acgaaaatga aacaattcgt cacattgagc cggctttggc cttccaactg   3900
gaattaggaa gattgtccaa cttcaacatt aaaccaattt tcactgataa tagaaacatc   3960
catgtctacg aagctgttag taagacttct ccattggata agagattctt tacaagaggt   4020
attattagaa cgggtcatat ccgtgatgac atttctattc aagaatatct gacttctgaa   4080
gctaacagat tgatgagtga tatattggat aatttgaag tcaccgacac ttcaaattct   4140
gatttgaatc atatcttcat caacttcatt gcggtgtttg atatctctcc agaagatgtc   4200
gaagccgcct tcggtggttt cttagaaaga tttggtaaga gattgttgag attgcgtgtt   4260
tcttctgccg aaattagaat catcatcaaa gatcctcaaa caggtgcccc agtaccattg   4320
cgtgccttga tcaataacgt ttctggttat gttatcaaaa cagaaatgta caccgaagtc   4380
aagaacgcaa aaggtgaatg ggtatttaag tctttgggta aacctggatc catgcattta   4440
agacctattg ctactcctta cctgttaag gaatggttgc aaccaaaacg ttataaggca   4500
cacttgatgg gtaccacata tgtctatgac ttcccagaat tattccgcca agcatcgtca   4560
tcccaatgga aaaatttctc tgcagatgtt aagttaacag atgatttctt tatttccaac   4620
gagttgattg aagatgaaaa cggcgaatta actgaggtgg aaagagaacc tggtgccaac   4680
gctattggta tggttgcctt taagattact gtaaagactc ctgaatatcc aagaggccgt   4740
caatttgttg ttgttgctaa cgatatcaca ttcaagatcg gttcctttgg tccacaagaa   4800
gacgaattct tcaataaggt tactgaatat gctagaaagc gtggtatccc aagaatttac   4860
ttggctgcaa actcaggtgc cagaattggt atggctgaag agattgttcc actatttcaa   4920
gttgcatgga atgatgctgc caatccggac aagggcttcc aatacttata cttaacaagt   4980
gaaggtatgg aaactttaaa gaaatttgac aaagaaaatt ctgttctcac tgaacgtact   5040
```

```
gttataaacg gtgaagaaag atttgtcatc aagacaatta ttggttctga agatgggtta    5100
ggtgtcgaat gtctacgtgg atctggttta attgctggtg caacgtcaag ggcttaccac    5160
gatatcttca ctatcacctt agtcacttgt agatccgtcg gtatcggtgc ttatttggtt    5220
cgtttgggtc aaagagctat tcaggtcgaa ggccagccaa ttattttaac tggtgctcct    5280
gcaatcaaca aaatgctggg tagagaagtt tatacttcta acttacaatt gggtggtact    5340
caaatcatgt ataacaacgg tgtttcacat ttgactgctg ttgacgattt agctggtgta    5400
gagaagattg ttgaatggat gtcttatgtt ccagccaagc gtaatatgcc agttcctatc    5460
ttggaaacta aagacacatg ggatagacca gttgatttca ctccaactaa tgatgaaact    5520
tacgatgtaa gatggatgat tgaaggtcgt gagactgaaa gtggatttga atatggtttg    5580
tttgataaag ggtcttttctt tgaaactttg tcaggatggg ccaaaggtgt tgtcgttggt    5640
agagcccgtc ttggtggtat tccactgggt gttattggtg ttgaaacaag aactgtcgag    5700
aacttgattc ctgctgatcc agctaatcca aatagtgctg aaacattaat tcaagaacct    5760
ggtcaagttt ggcatccaaa ctccgccttc aagactgctc aagctatcaa tgactttaac    5820
aacggtgaac aattgccaat gatgattttg gccaactgga gaggtttctc tggtggtcaa    5880
cgtgatatgt tcaacgaagt cttgaagtat ggttcgttta ttgttgacgc attggtggat    5940
tacaaacaac caattattat ctatatccca cctaccggtg aactaagagg tggttcatgg    6000
gttgttgtcg atccaactat caacgctgac caaatggaaa tgtatgccga cgtcaacgct    6060
agagctggtg ttttggaacc acaaggtatg gttggtatca agttccgtag agaaaaattg    6120
ctggacacca tgaacagatt ggatgacaag tacagagaat tgagatctca attatccaac    6180
aagagtttgg ctccagaagt acatcagcaa atatccaagc aattagctga tcgtgagaga    6240
gaactattgc caatttacgg acaaatcagt cttcaatttg ctgatttgca cgataggtct    6300
tcacgtatgg tggccaaggg tgttatttct aaggaactgg aatggaccga ggcacgtcgt    6360
ttcttcttct ggagattgag aagaagattg aacgaagaat atttgattaa aaggttgagc    6420
catcaggtag gcgaagcatc aagattagaa aagatcgcaa gaattagatc gtggtaccct    6480
gcttcagtgg accatgaaga tgataggcaa gtcgcaacat ggattgaaga aaactacaaa    6540
actttggacg ataaactaaa gggttttgaaa ttagagtcat tcgctcaaga cttagctaaa    6600
aagatcagaa gcgaccatga caatgctatt gatggattat ctgaagttat caagatgtta    6660
tctaccgatg ataaagaaaa attgttgaag actttgaaat ag                       6702
```

<210> SEQ ID NO 10
<211> LENGTH: 9
<212> TYPE: PRT
<213> ORGANISM: Artificial Sequence
<220> FEATURE:
<223> OTHER INFORMATION: Domain 1 lipid phosphatase catalytic motif
<220> FEATURE:
<221> NAME/KEY: VARIANT
<222> LOCATION: 2, 3, 4, 5, 6, 7
<223> OTHER INFORMATION: Xaa = Any Amino Acid

<400> SEQUENCE: 10

Lys Xaa Xaa Xaa Xaa Xaa Xaa Arg Pro
1               5

<210> SEQ ID NO 11
<211> LENGTH: 4
<212> TYPE: PRT
<213> ORGANISM: Artificial Sequence

```
<220> FEATURE:
<223> OTHER INFORMATION: Domain 2 lipid phosphatase catalytic motif

<400> SEQUENCE: 11

Pro Ser Gly His
1

<210> SEQ ID NO 12
<211> LENGTH: 12
<212> TYPE: PRT
<213> ORGANISM: Artificial Sequence
<220> FEATURE:
<223> OTHER INFORMATION: Domain 3 lipid phosphatase catalytic motif
<220> FEATURE:
<221> NAME/KEY: VARIANT
<222> LOCATION: 3, 4, 5, 6, 7, 9, 10, 11
<223> OTHER INFORMATION: Xaa = Any Amino Acid

<400> SEQUENCE: 12

Ser Arg Xaa Xaa Xaa Xaa Xaa His Xaa Xaa Xaa Asp
1               5                  10

<210> SEQ ID NO 13
<211> LENGTH: 7
<212> TYPE: PRT
<213> ORGANISM: Artificial Sequence
<220> FEATURE:
<223> OTHER INFORMATION: Heptapeptide retention motif
<220> FEATURE:
<221> NAME/KEY: VARIANT
<222> LOCATION: 3
<223> OTHER INFORMATION: Xaa = Any Amino Acid

<400> SEQUENCE: 13

Phe Tyr Xaa Asp Trp Trp Asn
1               5

<210> SEQ ID NO 14
<211> LENGTH: 446
<212> TYPE: PRT
<213> ORGANISM: Streptomyces coelicolor

<400> SEQUENCE: 14

Met Thr Pro Asp Pro Leu Ala Pro Leu Asp Leu Ala Phe Trp Asn Ile
1               5                  10                  15

Glu Ser Ala Glu His Pro Met His Leu Gly Ala Leu Gly Val Phe Glu
            20                  25                  30

Ala Asp Ser Pro Thr Ala Gly Ala Leu Ala Ala Asp Leu Leu Ala Ala
        35                  40                  45

Arg Ala Pro Ala Val Pro Gly Leu Arg Met Arg Ile Arg Asp Thr Trp
    50                  55                  60

Gln Pro Pro Met Ala Leu Arg Arg Pro Phe Ala Phe Gly Gly Ala Thr
65                  70                  75                  80

Arg Glu Pro Asp Pro Arg Phe Asp Pro Leu Asp His Val Arg Leu His
                85                  90                  95

Ala Pro Ala Thr Asp Phe His Ala Arg Ala Gly Arg Leu Met Glu Arg
            100                 105                 110

Pro Leu Glu Arg Gly Arg Pro Pro Trp Glu Ala His Val Leu Pro Gly
        115                 120                 125

Ala Asp Gly Gly Ser Phe Ala Val Leu Phe Lys Phe His His Ala Leu
    130                 135                 140

Ala Asp Gly Leu Arg Ala Leu Thr Leu Ala Ala Gly Val Leu Asp Pro
145                 150                 155                 160
```

Met Asp Leu Pro Ala Pro Arg Pro Arg Pro Glu Gln Pro Pro Arg Gly
            165                 170                 175

Leu Leu Pro Asp Val Arg Ala Leu Pro Asp Arg Leu Arg Gly Ala Leu
            180                 185                 190

Ser Asp Ala Gly Arg Ala Leu Asp Ile Gly Ala Ala Ala Leu Ser
            195                 200                 205

Thr Leu Asp Val Arg Ser Ser Pro Ala Leu Thr Ala Ala Ser Ser Gly
            210                 215                 220

Thr Arg Arg Thr Ala Gly Val Ser Val Asp Leu Asp Val His His
225                 230                 235                 240

Val Arg Lys Thr Thr Gly Gly Thr Val Asn Asp Val Leu Ile Ala Val
            245                 250                 255

Val Ala Gly Ala Leu Arg Arg Trp Leu Asp Glu Arg Gly Asp Gly Ser
            260                 265                 270

Glu Gly Val Ala Pro Arg Ala Leu Ile Pro Val Ser Arg Arg Pro
            275                 280                 285

Arg Ser Ala His Pro Gln Gly Asn Arg Leu Ser Gly Tyr Leu Met Arg
290                 295                 300

Leu Pro Val Gly Asp Pro Asp Pro Leu Ala Arg Leu Gly Thr Val Arg
305                 310                 315                 320

Ala Ala Met Asp Arg Asn Lys Asp Ala Gly Pro Gly Arg Gly Ala Gly
            325                 330                 335

Ala Val Ala Leu Leu Ala Asp His Val Pro Ala Leu Gly His Arg Leu
            340                 345                 350

Gly Gly Pro Leu Val Ser Gly Ala Ala Arg Leu Trp Phe Asp Leu Leu
            355                 360                 365

Val Thr Ser Val Pro Leu Pro Ser Leu Gly Leu Arg Leu Gly Gly His
            370                 375                 380

Pro Leu Thr Glu Val Tyr Pro Leu Ala Pro Leu Ala Arg Gly His Ser
385                 390                 395                 400

Leu Ala Val Ala Val Ser Thr Tyr Arg Gly Arg Val His Tyr Gly Leu
            405                 410                 415

Leu Ala Asp Ala Lys Ala Val Pro Asp Leu Asp Arg Leu Ala Val Ala
            420                 425                 430

Val Ala Glu Glu Val Glu Thr Leu Leu Thr Ala Cys Arg Pro
            435                 440                 445

<210> SEQ ID NO 15
<211> LENGTH: 457
<212> TYPE: PRT
<213> ORGANISM: Alcanivorax borkumensis

<400> SEQUENCE: 15

Met Lys Ala Leu Ser Pro Val Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Gly Pro Lys Tyr Val Ser Glu Leu Ala Gln Gln Met Arg
            35                  40                  45

Asp Tyr Cys His Pro Val Ala Pro Phe Asn Gln Arg Leu Thr Arg Arg
        50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu

```
                    85                  90                  95
Leu Ser Leu Val Ser Ala Glu His Ser Asn Leu Leu Asp Arg Glu Arg
                100                 105                 110

Pro Met Trp Glu Ala His Leu Ile Glu Gly Ile Arg Gly Arg Gln Phe
            115                 120                 125

Ala Leu Tyr Tyr Lys Ile His His Ser Val Met Asp Gly Ile Ser Ala
        130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
            180                 185                 190

Ser Ile Ser Lys Gln Ala Ala Thr Val Pro Gly Leu Ala Arg Glu Val
        195                 200                 205

Tyr Lys Val Thr Gln Lys Ala Lys Lys Asp Glu Asn Tyr Val Ser Ile
    210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Val Leu Ser Met Cys Gly
            260                 265                 270

His Ala Leu Arg Glu Tyr Leu Ile Ser Gln His Ala Leu Pro Asp Glu
        275                 280                 285

Pro Leu Ile Ala Met Val Pro Met Ser Leu Arg Gln Asp Asp Ser Thr
    290                 295                 300

Gly Gly Asn Gln Ile Gly Met Ile Leu Ala Asn Leu Gly Thr His Ile
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
            340                 345                 350

Thr Ala Leu Thr Met Ala Pro Thr Gly Leu Asn Leu Leu Thr Gly Leu
        355                 360                 365

Ala Pro Lys Trp Arg Ala Phe Asn Val Val Ile Ser Asn Ile Pro Gly
    370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415

Ser Tyr Val Asp Gln Met Glu Phe Gly Leu Ile Ala Cys Arg Arg Thr
            420                 425                 430

Leu Pro Ser Met Gln Arg Leu Leu Asp Tyr Leu Glu Gln Ser Ile Arg
        435                 440                 445

Glu Leu Glu Ile Gly Ala Gly Ile Lys
    450                 455

<210> SEQ ID NO 16
<211> LENGTH: 1341
<212> TYPE: DNA
<213> ORGANISM: Artificial Sequence
<220> FEATURE:
<223> OTHER INFORMATION: Codon-optimized Streptomyces coelicolor DGAT
```

-continued

<400> SEQUENCE: 16
atgacgcctg acccgttggc tcccttggac ttggctttct ggaatatcga aagtgccgag 60
cacccgatgc acttgggggc actgggggtc tttgaggcgg atagtccaac cgctggtgca 120
ctcgccgcgg atctcctggc tgcccgcgct cccgcagtgc ccgggctgcg catgcggatt 180
cgcgatacat ggcagccgcc tatggcgctc cgtcgccctt ttgcttttgg cggtgctaca 240
cgcgagcccg acccgcggtt tgatccactc gatcatgtgc ggctccatgc cccagcgacg 300
gatttccacg cacgcgcagg tcggttgatg gagcgccctc tggaacgagg ccgtcctcct 360
tgggaagccc atgtcctgcc aggggctgac ggtggatcgt ttgcggtctt gtttaagttc 420
catcatgccc tggccgacgg tctgcgggcg ctgacgctgg cggcgggcgt gctcgatccg 480
atggatctcc ccgctccacg gccccgccca gagcagcccc cccgtggtct cctgccggat 540
gtccgcgcgc tgccggatcg gctgcgaggg gctctgtctg acgcgggccg cgcgttggac 600
atcggcgccg ccgcagccct cagcaccctg gatgtgcgga gcagtcccgc tctgactgcg 660
gcgtcctcgg gcacgcgacg taccgccggc gtgtccgtgg atctcgacga cgtgcaccat 720
gttcgcaaaa cgacaggcgg taccgttaac gatgttttga tcgccgttgt tgccggggcc 780
ctgcgacgct ggctggatga acgaggcgat gggtcggaag gcgtcgcccc gcgcgccctc 840
attcccgtca gccggcggcg acctcggagc gcacacccgc aaggcaaccg attgagtggc 900
tacctgatgc gcttgccggt cggcgacccg gaccctctcg cacggttggg aaccgtccgt 960
gccgcgatgg atcgaaataa ggatgcgggg cccggccgcg gagctggcgc agttgctctc 1020
ttggcagacc acgttcctgc cctgggccac cgcctgggtg gacccctcgt ctcgggcgct 1080
gctcgactgt ggttcgatct gttggtcacg agcgtcccgt tgccctcttt gggtttgcgc 1140
ctcggtgggc atccgctgac cgaagtgtac ccactggccc ccctggcccg tggccactcc 1200
ttggcggtgg cggtgagcac ttatcgcggt cgggttcatt acggtctcct cgctgatgct 1260
aaagccgttc ctgatctgga tcgtctggca gtggccgtcg ccgaggaggt tgaaaccttg 1320
ctcactgcgt gccgccccta g 1341

<210> SEQ ID NO 17
<211> LENGTH: 1374
<212> TYPE: DNA
<213> ORGANISM: Artificial Sequence
<220> FEATURE:
<223> OTHER INFORMATION: Codon-optimized Alcanivorax borkumensis DGAT

<400> SEQUENCE: 17
atgaaagctt tgagccccgt tgatcagctg tttctgtggt tggaaaaacg gcagcaaccc 60
atgcatgtgg gtgggttgca gctgttctcc tttcccgaag gcgcggggcc gaaatatgtc 120
tcggaactgg cccaacagat gcgcgattat tgtcaccctg tcgccccgtt caaccaacgt 180
ctgacacggc gcctggggca atactactgg acacgtgata agcaatttga cattgaccat 240
cattttcggc acgaggccct gcccaaaccg ggtcggattc gcgagttgct cagcttggtg 300
agtgcggaac actccaactt gttggatcgt gaacgaccca tgtgggaagc gcacctgatc 360
gaaggaatcc gcgggcgcca atttgccttg tattacaaaa ttcatcactc cgtcatggac 420
ggtatctccg ctatgcggat tgcctctaag accttgtcca cggaccccag tgagcgggag 480
atggcccccg cttgggcgtt taatactaag aagcgatcgc gcagcctgcc aagcaatccc 540
gtggatatgg cgagctcgat ggctcgactc actgcaagta tttcgaaaca agctgccacc 600
gtgcccggcc tggcacgaga ggtctacaag gtgacccaaa aagctaaaaa ggatgaaaat 660

```
tacgttagta ttttccaagc accagacacc atcctcaata atacgattac gggcagtcga    720
cgcttcgccg ctcagtcgtt ccctctcccc cgtctgaagg ttatcgctaa ggcttacaac    780
tgcactatta acacggttgt gctctcgatg tgcggccacg ccctgcgcga atacctcatc    840
agtcaacatg ccctgccgga tgaaccctg atcgcgatgg tccctatgag cctgcgccaa     900
gatgatagca ccggaggcaa ccagatcgga atgattttgg cgaatctggg cacgcatatc    960
tgcgatcctg ccaatcgcct gcgtgtcatc catgatagcg tggaggaggc gaaaagccgt   1020
tttagccaaa tgtctccgga ggagattctg aactttacag cactcactat ggcgccgacc   1080
ggtctgaact tgctcaccgg tttggctccc aaatggcgcg catttaacgt cgttatctct   1140
aacatcccag ggccaaagga accactgtac tggaatgggg cacagctcca gggtgtgtat   1200
ccggtctcca tcgccttgga tcggattgcc ctgaacatta cactgacgtc ttatgttgat   1260
cagatggagt tcggcttgat tgcgtgtcgc cggaccctcc cgtcgatgca acgactcctc   1320
gactatctcg aacagagtat ccgcgaactg gagattggcg cgggcatcaa atag         1374
```

<210> SEQ ID NO 18
<211> LENGTH: 460
<212> TYPE: PRT
<213> ORGANISM: Acinetobacter baylii sp.

<400> SEQUENCE: 18

```
Met Glu Phe Arg Pro Leu His Pro Ile Asp Phe Ile Phe Leu Ser Leu
  1               5                  10                  15

Glu Lys Arg Gln Gln Pro Met His Val Gly Gly Leu Phe Leu Phe Gln
             20                  25                  30

Ile Pro Asp Asn Ala Pro Asp Thr Phe Ile Gln Asp Leu Val Asn Asp
         35                  40                  45

Ile Arg Ile Ser Lys Ser Ile Pro Val Pro Pro Phe Asn Asn Lys Leu
     50                  55                  60

Asn Gly Leu Phe Trp Asp Glu Asp Glu Phe Asp Leu Asp His His
 65                  70                  75                  80

Phe Arg His Ile Ala Leu Pro His Pro Gly Arg Ile Arg Glu Leu Leu
                 85                  90                  95

Ile Tyr Ile Ser Gln Glu His Ser Thr Leu Leu Asp Arg Ala Lys Pro
            100                 105                 110

Leu Trp Thr Cys Asn Ile Ile Glu Gly Ile Glu Gly Asn Arg Phe Ala
        115                 120                 125

Met Tyr Phe Lys Ile His His Ala Met Val Asp Gly Val Ala Gly Met
    130                 135                 140

Arg Leu Ile Glu Lys Ser Leu Ser His Asp Val Thr Glu Lys Ser Ile
145                 150                 155                 160

Val Pro Pro Trp Cys Val Glu Gly Lys Arg Ala Lys Arg Leu Arg Glu
                165                 170                 175

Pro Lys Thr Gly Lys Ile Lys Lys Ile Met Ser Gly Ile Lys Ser Gln
            180                 185                 190

Leu Gln Ala Thr Pro Thr Val Ile Gln Glu Leu Ser Gln Thr Val Phe
        195                 200                 205

Lys Asp Ile Gly Arg Asn Pro Asp His Val Ser Ser Phe Gln Ala Pro
    210                 215                 220

Cys Ser Ile Leu Asn Gln Arg Val Ser Ser Arg Arg Phe Ala Ala
225                 230                 235                 240

Gln Ser Phe Asp Leu Asp Arg Phe Arg Asn Ile Ala Lys Ser Leu Asn
```

```
                  245                 250                 255
Val Thr Ile Asn Asp Val Val Leu Ala Val Cys Ser Gly Ala Leu Arg
            260                 265                 270

Ala Tyr Leu Met Ser His Asn Ser Leu Pro Ser Lys Pro Leu Ile Ala
            275                 280                 285

Met Val Pro Ala Ser Ile Arg Asn Asp Asp Ser Asp Val Ser Asn Arg
            290                 295                 300

Ile Thr Met Ile Leu Ala Asn Leu Ala Thr His Lys Asp Asp Pro Leu
305                 310                 315                 320

Gln Arg Leu Glu Ile Ile Arg Arg Ser Val Gln Asn Ser Lys Gln Arg
                325                 330                 335

Phe Lys Arg Met Thr Ser Asp Gln Ile Leu Asn Tyr Ser Ala Val Val
            340                 345                 350

Tyr Gly Pro Ala Gly Leu Asn Ile Ile Ser Gly Met Met Pro Lys Arg
            355                 360                 365

Gln Ala Phe Asn Leu Val Ile Ser Asn Val Pro Gly Pro Arg Glu Pro
            370                 375                 380

Leu Tyr Trp Asn Gly Ala Lys Leu Asp Ala Leu Tyr Pro Ala Ser Ile
385                 390                 395                 400

Val Leu Asp Gly Gln Ala Leu Asn Ile Thr Met Thr Ser Tyr Leu Asp
                405                 410                 415

Lys Leu Glu Val Gly Leu Ile Ala Cys Arg Asn Ala Leu Pro Arg Met
            420                 425                 430

Gln Asn Leu Leu Thr His Leu Glu Glu Glu Ile Gln Leu Phe Glu Gly
            435                 440                 445

Val Ile Ala Lys Gln Glu Asp Ile Lys Thr Ala Asn
            450                 455                 460

<210> SEQ ID NO 19
<211> LENGTH: 1383
<212> TYPE: DNA
<213> ORGANISM: Artificial Sequence
<220> FEATURE:
<223> OTHER INFORMATION: Codon-optimized Acinetobacter baylii sp. DGATd

<400> SEQUENCE: 19
atggaattcc ggcccttgca ccccattgac ttcatctttc tgagttttgga gaaacggcaa     60 cagcccatgc atgtcggtgg cttgtttctc ttccaaatcc ccgataacgc cccggacacc    120
tttattcagg atctggtcaa tgatatccgg atctcgaaat cgatccccgt gccgccgttt    180
aataataaac tgaacggcct cttttgggac gaagacgagg aatttgatct ggatcaccat    240
tttcggcaca tcgctttgcc ccacccgggt cggattcgcg aactcctgat ctatattagc    300
caagaacaca gcacgttgtt ggaccgggcc aaaccgctct ggacgtgcaa tatcatcgaa    360
ggcatcgaag caaccgcttt gcgatgtac ttcaagattc atcacgcgat ggttgacggt    420
gtcgctggca tgcgcctgat cgaaaaatcg ctgagccatg atgtgaccga aagagtatc    480 gtcccccct ggtgcgtgga aggtaagcgc gccaagcgcc tccgcgaacc gaaaacgggc    540
aagattaaga aaatcatgag cggtatcaag tcgcagctgc aggctacccc gaccgtgatc    600
caggagctgt cgcaaaccgt gtttaaggat attggtcgga accgggatca tgtcagtagt    660
ttccaagctc cctgttcgat cttgaatcag cgcgttagca gcagccgccg gttcgctgct    720
caaagttttg atctcgatcg gtttcggaat attgccaagt cgctgaacgt caccatcaat    780
gatgtggttc tcgcggtttg ttcgggtgcc ctccgcgcgt atctgatgag ccataacagt    840
```

```
ctccccagta agccgctgat tgctatggtt cccgcgtcga ttcggaatga cgacagcgat    900
gtgagcaacc ggattaccat gatcctggct aacctcgcga cccacaaaga tgatccgttg    960
caacgcctgg agattatccg ccgcagtgtg cagaacagta acagcgcttc aaacggatg    1020 accagtgatc aaattctgaa ttacagcgct gtggtctatg gtcccgccgg cttgaatatt   1080
atcagtggta tgatgcccaa cgccaagcg tttaacttgg tgatcagtaa tgtgccgggt    1140
ccgcgcgaac ccttgtattg gaacggtgct aaactcgatg ccctctaccc cgccagtatc   1200
gtgctcgatg ccaggctct caatattacc atgaccagct atctcgataa actcgaggtg    1260
ggtttgattg cgtgccgcaa cgcgctgccc cgcatgcaga acttgctgac ccacctggaa   1320
gaggaaatcc agctcttcga gggcgtgatt gcgaagcagg aagatattaa aacggccaac   1380
tag                                                                 1383
```

<210> SEQ ID NO 20
<211> LENGTH: 325
<212> TYPE: PRT
<213> ORGANISM: Synechococcus sp. PCC7002

<400> SEQUENCE: 20

```
Met Pro Lys Thr Glu Arg Arg Thr Phe Leu Leu Asp Phe Glu Lys Pro
 1               5                   10                  15

Leu Ser Glu Leu Glu Ser Arg Ile His Gln Ile Arg Asp Leu Ala Ala
             20                  25                  30

Glu Asn Asn Val Asp Val Ser Glu Gln Ile Gln Gln Leu Glu Ala Arg
         35                  40                  45

Ala Asp Gln Leu Arg Glu Glu Ile Phe Ser Thr Leu Thr Pro Ala Gln
     50                  55                  60

Arg Leu Gln Leu Ala Arg His Pro Arg Arg Pro Ser Thr Leu Asp Tyr
 65                  70                  75                  80

Val Gln Met Met Ala Asp Glu Trp Phe Glu Leu His Gly Asp Arg Gly
                 85                  90                  95

Gly Ser Asp Asp Pro Ala Leu Ile Gly Gly Val Ala Arg Phe Asp Gly
            100                 105                 110

Gln Pro Val Met Met Leu Gly His Gln Lys Gly Arg Asp Thr Lys Asp
        115                 120                 125

Asn Val Ala Arg Asn Phe Gly Met Pro Ala Pro Gly Gly Tyr Arg Lys
    130                 135                 140

Ala Met Arg Leu Met Asp His Ala Asn Arg Phe Gly Met Pro Ile Leu
145                 150                 155                 160

Thr Phe Ile Asp Thr Pro Gly Ala Trp Ala Gly Leu Glu Ala Glu Lys
                165                 170                 175

Leu Gly Gln Gly Glu Ala Ile Ala Phe Asn Leu Arg Glu Met Phe Ser
            180                 185                 190

Leu Asp Val Pro Ile Ile Cys Thr Val Ile Gly Glu Gly Gly Ser Gly
        195                 200                 205

Gly Ala Leu Gly Ile Gly Val Gly Asp Arg Val Leu Met Leu Lys Asn
    210                 215                 220

Ser Val Tyr Thr Val Ala Thr Pro Glu Ala Cys Ala Ala Ile Leu Trp
225                 230                 235                 240

Lys Asp Ala Gly Lys Ser Glu Gln Ala Ala Ala Leu Lys Ile Thr
                245                 250                 255

Ala Glu Asp Leu Lys Ser Leu Gly Ile Ile Asp Glu Ile Val Pro Glu
            260                 265                 270
```

```
Pro Ala Ser Cys Ala His Ala Asp Pro Ile Gly Ala Ala Gln Leu Leu
            275                 280                 285

Lys Ala Ala Ile Gln Asp Asn Leu Gln Ala Leu Leu Lys Leu Thr Pro
            290                 295                 300

Glu Arg Arg Arg Glu Leu Arg Tyr Gln Arg Phe Arg Lys Ile Gly Val
305                 310                 315                 320

Phe Leu Glu Ser Ser
                325

<210> SEQ ID NO 21
<211> LENGTH: 165
<212> TYPE: PRT
<213> ORGANISM: Synechococcus sp. PCC 7002

<400> SEQUENCE: 21

Met Ala Ile Asn Leu Gln Glu Ile Gln Glu Leu Leu Ser Thr Ile Gly
1               5                   10                  15

Gln Thr Asn Val Thr Glu Phe Glu Leu Lys Thr Asp Asp Phe Glu Leu
            20                  25                  30

Arg Val Ser Lys Gly Thr Val Ala Ala Pro Gln Thr Met Val Met
        35                  40                  45

Ser Glu Ala Ile Ala Gln Pro Ala Met Ser Thr Pro Val Val Ser Gln
    50                  55                  60

Ala Thr Ala Thr Pro Glu Ala Ser Gln Ala Glu Thr Pro Ala Pro Ser
65                  70                  75                  80

Val Ser Ile Asp Asp Lys Trp Val Ala Ile Thr Ser Pro Met Val Gly
                85                  90                  95

Thr Phe Tyr Arg Ala Pro Ala Pro Gly Glu Asp Pro Phe Val Ala Val
            100                 105                 110

Gly Asp Arg Val Gly Asn Gly Gln Thr Val Cys Ile Ile Glu Ala Met
        115                 120                 125

Lys Leu Met Asn Glu Ile Glu Ala Glu Val Ser Gly Glu Val Val Lys
    130                 135                 140

Ile Ala Val Glu Asp Gly Glu Pro Ile Glu Phe Gly Gln Thr Leu Met
145                 150                 155                 160

Trp Val Asn Pro Thr
                165

<210> SEQ ID NO 22
<211> LENGTH: 448
<212> TYPE: PRT
<213> ORGANISM: Synechococcus sp. PCC 7002

<400> SEQUENCE: 22

Met Gln Phe Ser Lys Ile Leu Ile Ala Asn Arg Gly Glu Val Ala Leu
1               5                   10                  15

Arg Ile Ile His Thr Cys Gln Glu Leu Gly Ile Ala Thr Val Ala Val
            20                  25                  30

His Ser Thr Val Asp Arg Gln Ala Leu His Val Gln Leu Ala Asp Glu
        35                  40                  45

Ser Ile Cys Ile Gly Pro Pro Gln Ser Ser Lys Ser Tyr Leu Asn Ile
    50                  55                  60

Pro Asn Ile Ile Ala Ala Leu Ser Ser Asn Ala Asp Ala Ile His
65                  70                  75                  80

Pro Gly Tyr Gly Phe Leu Ala Glu Asn Ala Lys Phe Ala Glu Ile Cys
                85                  90                  95
```

```
Ala Asp His Gln Ile Thr Phe Ile Gly Pro Ser Pro Glu Ala Met Ile
            100                 105                 110

Ala Met Gly Asp Lys Ser Thr Ala Lys Lys Thr Met Gln Ala Ala Lys
        115                 120                 125

Val Pro Thr Val Pro Gly Ser Ala Gly Leu Val Ala Ser Glu Glu Gln
    130                 135                 140

Ala Leu Glu Ile Ala Gln Gln Ile Gly Tyr Pro Val Met Ile Lys Ala
145                 150                 155                 160

Thr Ala Gly Gly Gly Arg Gly Met Arg Leu Val Pro Ser Ala Glu
                165                 170                 175

Glu Leu Pro Arg Leu Tyr Arg Ala Ala Gln Gly Glu Ala Glu Ala Ala
            180                 185                 190

Phe Gly Asn Gly Gly Val Tyr Ile Glu Lys Phe Ile Glu Arg Pro Arg
        195                 200                 205

His Ile Glu Phe Gln Ile Leu Ala Asp Gln Tyr Gly Asn Val Ile His
    210                 215                 220

Leu Gly Glu Arg Asp Cys Ser Ile Gln Arg Arg His Gln Lys Leu Leu
225                 230                 235                 240

Glu Glu Ala Pro Ser Ala Ile Leu Thr Pro Arg Leu Arg Asp Lys Met
                245                 250                 255

Gly Lys Ala Ala Val Lys Ala Ala Lys Ser Ile Asp Tyr Val Gly Ala
            260                 265                 270

Gly Thr Val Glu Phe Leu Val Asp Lys Asn Gly Asp Phe Tyr Phe Met
        275                 280                 285

Glu Met Asn Thr Arg Ile Gln Val Glu His Pro Val Thr Glu Met Val
    290                 295                 300

Thr Gly Leu Asp Leu Ile Ala Glu Gln Ile Lys Val Ala Gln Gly Asp
305                 310                 315                 320

Arg Leu Ser Leu Asn Gln Asn Gln Val Asn Leu Asn Gly His Ala Ile
                325                 330                 335

Glu Cys Arg Ile Asn Ala Glu Asp Pro Asp His Asp Phe Arg Pro Thr
            340                 345                 350

Pro Gly Lys Ile Ser Gly Tyr Leu Pro Pro Gly Gly Pro Gly Val Arg
        355                 360                 365

Met Asp Ser His Val Tyr Thr Asp Tyr Glu Ile Ser Pro Tyr Tyr Asp
    370                 375                 380

Ser Leu Ile Gly Lys Leu Ile Val Trp Gly Pro Asp Arg Asp Thr Ala
385                 390                 395                 400

Ile Arg Arg Met Lys Arg Ala Leu Arg Glu Cys Ala Ile Thr Gly Val
                405                 410                 415

Ser Thr Thr Ile Ser Phe His Gln Lys Ile Leu Asn His Pro Ala Phe
            420                 425                 430

Leu Ala Ala Asp Val Asp Thr Asn Phe Ile Gln Gln His Met Leu Pro
        435                 440                 445

<210> SEQ ID NO 23
<211> LENGTH: 319
<212> TYPE: PRT
<213> ORGANISM: Synechococcus sp. PCC 7002

<400> SEQUENCE: 23

Met Ser Leu Phe Asp Trp Phe Ala Ala Asn Arg Gln Asn Ser Glu Thr
1               5                   10                  15

Gln Leu Gln Pro Gln Gln Glu Arg Glu Ile Ala Asp Gly Leu Trp Thr
            20                  25                  30
```

```
Lys Cys Lys Ser Cys Asp Ala Leu Thr Tyr Thr Lys Asp Leu Arg Asn
            35                  40                  45

Asn Gln Met Val Cys Lys Glu Cys Gly Phe His Asn Arg Val Gly Ser
     50                  55                  60

Arg Glu Arg Val Arg Gln Leu Ile Asp Glu Gly Thr Trp Thr Glu Ile
 65                  70                  75                  80

Ser Gln Asn Val Ala Pro Thr Asp Pro Leu Lys Phe Arg Asp Lys Lys
                85                  90                  95

Ala Tyr Ser Asp Arg Leu Lys Asp Tyr Gln Glu Lys Thr Asn Leu Thr
               100                 105                 110

Asp Ala Val Ile Thr Gly Thr Gly Leu Ile Asp Gly Leu Pro Leu Ala
               115                 120                 125

Leu Ala Val Met Asp Phe Gly Phe Met Gly Gly Ser Met Gly Ser Val
       130                 135                 140

Val Gly Glu Lys Ile Cys Arg Leu Val Glu His Gly Thr Ala Glu Gly
145                 150                 155                 160

Leu Pro Val Val Val Cys Ala Ser Gly Gly Ala Arg Met Gln Glu
               165                 170                 175

Gly Met Leu Ser Leu Met Gln Met Ala Lys Ile Ser Gly Ala Leu Glu
       180                 185                 190

Arg His Arg Thr Lys Lys Leu Leu Tyr Ile Pro Val Leu Thr Asn Pro
       195                 200                 205

Thr Thr Gly Gly Val Thr Ala Ser Phe Ala Met Leu Gly Asp Leu Ile
       210                 215                 220

Leu Ala Glu Pro Lys Ala Thr Ile Gly Phe Ala Gly Arg Arg Val Ile
225                 230                 235                 240

Glu Gln Thr Leu Arg Glu Lys Leu Pro Asp Asp Phe Gln Thr Ser Glu
               245                 250                 255

Tyr Leu Leu Gln His Gly Phe Val Asp Ala Ile Val Pro Arg Thr Glu
               260                 265                 270

Leu Lys Lys Thr Leu Ala Gln Met Ile Ser Leu His Gln Pro Phe His
       275                 280                 285

Pro Ile Leu Pro Glu Leu Gln Leu Ala Pro His Val Glu Lys Glu Lys
       290                 295                 300

Val Tyr Glu Pro Ile Ala Ser Thr Ser Thr Asn Asp Phe Tyr Lys
305                 310                 315

<210> SEQ ID NO 24
<211> LENGTH: 978
<212> TYPE: DNA
<213> ORGANISM: Synechococcus sp. PCC 7002

<400> SEQUENCE: 24
atgccgaaaa cggagcgccg gacgtttctg cttgattttg aaaaacctct ttcggaatta    60
gaatcacgca tccatcaaat tcgtgatctt gctgcggaga ataatgttga tgtttcagaa   120
cagattcagc agctagaggc gcgggcagac cagctccggg aagaaatttt tagtaccctc   180
accccggccc aacggctgca attggcacgg catccccggc gtcccagcac ccttgattat   240
gttcaaatga tggcggacga atggtttgaa ctccatggcg atcgcggtgg atctgatgat   300
ccggctctca ttgcgggggt ggcccgcttc gatggtcaac cggtgatgat gctagggcac   360
caaaaaggac gggatacgaa ggataatgtc gcccgcaatt ttggcatgcc agctcctggg   420
ggctaccgta aggcgatgcg gctgatggac catgccaacc gttttgggat gccgatttta   480
```

```
acgtttattg atactcctgg ggcttgggcg ggtttagaag cggaaaagtt gggccaaggg      540
gaggcgatcg cctttaacct ccgggaaatg tttagcctcg atgtgccgat tatttgcacg      600
gtcattggcg aaggcggttc cggtggggcc ttagggattg gcgtgggcga tcgcgtcttg      660
atgttaaaaa attccgttta cacagtggcg accccagagg cttgtgccgc cattctctgg      720
aaagatgccg ggaaatcaga gcaggccgcc gccgccctca agattacagc agaggatctg      780
aaaagccttg agattatcga tgaaattgtc ccagagccag cctcctgcgc ccacgccgat      840
cccattgggg ccgcccaact cctgaaagca gcgatccaag ataacctcca agccttgctg      900
aagctgacgc cagaacgccg ccgtgaattg cgctaccagc ggttccggaa aattggtgtg      960
tttttagaaa gttcctaa                                                   978

<210> SEQ ID NO 25
<211> LENGTH: 498
<212> TYPE: DNA
<213> ORGANISM: Synechococcus sp. PCC 7002

<400> SEQUENCE: 25
atggctatta atttacaaga gatccaagaa cttctatcca ccatcggcca aaccaatgtc       60
accgagtttg aactcaaaac cgatgatttt gaactccgtg tgagcaaagg tactgttgtg      120
gctgctcccc agacgatggt gatgtccgag gcgatcgccc aaccagcaat gtccactccc      180
gttgtttctc aagcaactgc aaccccagaa gcctcccaag cggaaacccc ggctcccagt      240
gtgagcattg atgataagtg ggtcgccatt accctccccca tggtgggaac gttttaccgc      300
gcgccggccc ctggtgaaga tcccttcgtt gccgttggcg atcgcgttgg caatggtcaa      360
accgtttgca tcatcgaagc gatgaaatta atgaatgaga ttgaggcaga agtcagcggt      420
gaagttgtta aaattgccgt tgaagacggt gaacccattg aatttggtca daccctaatg      480
tgggtcaacc caacctaa                                                   498

<210> SEQ ID NO 26
<211> LENGTH: 1347
<212> TYPE: DNA
<213> ORGANISM: Synechococcus sp. PCC 7002

<400> SEQUENCE: 26
atgcagtttt caaagattct catcgccaat cgcggagaag ttgccctacg cattatccac       60
acctgtcagg agctcggcat tgccacagtt gccgtccact ccaccgtaga tcgccaagcc      120
ctccacgttc agctcgccga tgagagcatt tgcattggcc cgcccagag cagcaaaagc       180 tatctcaaca ttcccaatat tatcgctgcg gccctcagca gtaacgccga cgcaatccac      240
ccaggctacg gttcctcgc tgaaaatgcc aagtttgcag aaatttgtgc cgaccaccaa      300
atcaccttca ttggcccttc cccagaagca atgatcgcca tggggacaa atccaccgcc       360 aaaaaaacga tgcaggcggc aaaagtccct accgtacccg tagtgctgg gttggtggcc      420 tccgaagaac aagccctaga aatcgcccaa caaattggct accctgtgat gatcaaagcc      480
acggcgggtg gtggtggccg ggggatgcgc cttgtgccca cgctgagga gttaccccgt      540 ttgtaccgag cggcccaggg ggaagcagaa gcagcctttg gaatggcgg cgtttacatc       600 gaaaaattta ttgaacggcc ccgtcacatc gaatttcaga tcctgcggga tcagtacggc      660
aatgtaattc acctcggcga acgggattgt tcgatccaac ggcggcacca aaaactcctc      720
gaagaagctc ccagcgcgat cctcacccccc agactgcggg acaaaatggg gaaagcggca      780
gtaaaagcgg cgaaatccat tgattatgtc ggggcgggga cggtggaatt cctcgtggat      840
```

-continued

```
aagaatgggg atttctactt tatggaaatg aataccccgca ttcaggtgga cacccggtc      900 acagagatgg tgacgggact agatctgatc gccgagcaaa ttaaagttgc ccaaggcgat      960
cgcctcagtt tgaatcaaaa tcaagtgaac ttgaatggtc atgccatcga gtgccggatt     1020
aatgccgaag atcccgacca tgatttccga ccgaccccag gcaaaatcag tggctatctt     1080
ccccccggtg gccctggggt acggatggat cccacgtttt acaccgacta tgaaatttct     1140
ccttactacg attctttgat cggtaaaatta atcgtttggg gaccagaccg agacaccgcc    1200
attcgccgca tgaagcgggc actccgagaa tgtgccatta ctggagtatc gaccaccatt    1260
agcttccacc aaaagatttt gaatcatccg gcttttttgg cggccgatgt cgatacaaac    1320
tttatccagc agcacatgtt gccctag                                         1347
```

<210> SEQ ID NO 27
<211> LENGTH: 960
<212> TYPE: DNA
<213> ORGANISM: Synechococcus sp. PCC 7002

<400> SEQUENCE: 27

```
atgtctcttt ttgattggtt tgccgcaaat cgccaaaatt ctgaaaccca gctccagccc      60
caacaggagc gcgagattgc cgatggcctc tggacgaaat gcaaatcctg cgatgctctc     120
acctacacta aagacctccg caacaatcaa atggtctgta aagagtgtgg cttccataac     180
cgggtcggca gtcgggaacg ggtacgccaa ttgattgacg aaggcacctg gacagaaatt     240
agtcagaatg tcgcgccgac cgaccccctg aaattccgcg acaaaaaagc ctatagcgat     300
cgcctcaaag attaccaaga gaaaacgaac ctcaccgatg ctgtaatcac tggcacagga    360
ctgattgacg gtttacccct tgctttggca gtgatggact ttggctttat gggcggcagc    420
atgggatccg ttgtcggcga aaaaatttgt cgcctcgtag aacatggcac cgccgaaggt    480
ttacccgtgg tggttgtttg tgcttctggt ggagcaagaa tgcaagaggg catgctcagt    540
ctgatgcaga tggcgaaaat ctctggtgcc ctcgaacgcc atcgcaccaa aaaattactc    600
tacatccctg ttttgactaa tcccaccacc gggggcgtca ccgctagctt tgcgatgttg    660
ggcgatttga ttcttgccga acccaaagca accatcggtt tgctggacg ccgcgtcatt    720 gaacaaacat tgcgcgaaaa acttcctgac gattttcaga catctgaata tttactccaa    780
catgggtttg tggatgcgat tgtgcccccgc actgaattga aaaaaccct cgcccaaatg    840 attagtctcc atcagcccctt tcacccgatt ctgccagagc tacaattggc tccccatgtg    900
gaaaaagaaa aagtttacga acccattgcc tctacttcaa ccaacgactt ttacaagtag    960
```

<210> SEQ ID NO 28
<211> LENGTH: 2311
<212> TYPE: PRT
<213> ORGANISM: Triticum aestivum

<400> SEQUENCE: 28

```
Met Gly Ser Thr His Leu Pro Ile Val Gly Leu Asn Ala Ser Thr Thr
 1               5                  10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Ser Arg Arg Val
        35                  40                  45

Gln Ser Leu Arg Asp Gly Gly Asp Gly Gly Val Ser Asp Pro Asn Gln
    50                  55                  60
```

```
Ser Ile Arg Gln Gly Leu Ala Gly Ile Ile Asp Leu Pro Lys Glu Gly
 65                  70                  75                  80

Thr Ser Ala Pro Glu Val Asp Ile Ser His Gly Ser Glu Glu Pro Arg
                 85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
        115                 120                 125

Lys Thr Pro Ile His Ser Val Leu Val Ala Asn Asn Gly Arg Ala Ala
130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Tyr Ala Asn Val Gln Leu Ile Val
        195                 200                 205

Glu Ile Ala Val Arg Thr Gly Val Ser Ala Val Trp Pro Gly Trp Gly
210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
                245                 250                 255

Lys Val Gly Ser Ala Leu Ile Ala Gln Ala Ala Gly Val Pro Thr Leu
                260                 265                 270

Pro Trp Gly Gly Ser Gln Val Glu Ile Pro Leu Glu Val Cys Leu Asp
                275                 280                 285

Ser Ile Pro Ala Glu Met Tyr Arg Lys Ala Cys Val Ser Thr Thr Glu
            290                 295                 300

Glu Ala Leu Ala Ser Cys Gln Met Ile Gly Tyr Pro Ala Met Ile Lys
305                 310                 315                 320

Ala Ser Trp Gly Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
370                 375                 380

Arg Asp Cys Ser Val Gln Arg His Gln Lys Ile Ile Glu Glu Gly
385                 390                 395                 400

Pro Val Thr Val Ala Pro Arg Glu Thr Val Lys Glu Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val His Pro Val Thr Glu Trp Ile Ala Glu
450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
```

```
            485                 490                 495
Gly Tyr Asp Ile Trp Arg Glu Thr Ala Ala Leu Ala Thr Pro Phe Asn
            500                 505                 510

Phe Asp Glu Val Asp Ser Gln Trp Pro Lys Gly His Cys Val Ala Val
            515                 520                 525

Arg Ile Thr Ser Glu Asp Pro Asp Asp Gly Phe Lys Pro Thr Gly Gly
            530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
                    565                 570                 575

Phe Gly His Val Phe Ala Tyr Gly Val Ser Arg Ala Ala Ile Thr
                580                 585                 590

Asn Met Ser Leu Ala Leu Lys Glu Ile Gln Ile Arg Gly Glu Ile His
            595                 600                 605

Ser Asn Val Asp Tyr Thr Val Asp Leu Leu Asn Ala Ser Asp Phe Lys
            610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
                    645                 650                 655

Leu Tyr Lys Thr Ile Thr Ser Asn Thr Asp Thr Val Ser Glu Tyr Val
                660                 665                 670

Ser Tyr Leu Val Lys Gly Gln Ile Pro Pro Lys His Ile Ser Leu Val
            675                 680                 685

His Ser Thr Val Ser Leu Asn Ile Glu Glu Ser Lys Tyr Thr Ile Glu
            690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
                    725                 730                 735

Gln Leu Asp Gly Asn Ser His Val Ile Tyr Ala Glu Glu Ala Gly
                740                 745                 750

Gly Thr Arg Leu Leu Ile Asp Gly Lys Thr Tyr Leu Leu Gln Asn Asp
            755                 760                 765

His Asp Pro Ser Arg Leu Leu Ala Glu Thr Pro Cys Lys Leu Leu Arg
            770                 775                 780

Phe Leu Val Ala Asp Gly Ala His Val Glu Ala Asp Val Pro Tyr Ala
785                 790                 795                 800

Glu Val Glu Val Met Lys Met Cys Met Pro Leu Leu Ser Pro Ala Ala
                    805                 810                 815

Gly Val Ile Asn Val Leu Leu Ser Glu Gly Gln Pro Met Gln Ala Gly
                820                 825                 830

Asp Leu Ile Ala Arg Leu Asp Leu Asp Pro Ser Ala Val Lys Arg
            835                 840                 845

Ala Glu Pro Phe Asn Gly Ser Phe Pro Glu Met Ser Leu Pro Ile Ala
850                 855                 860

Ala Ser Gly Gln Val His Lys Arg Cys Ala Thr Ser Leu Asn Ala Ala
865                 870                 875                 880

Arg Met Val Leu Ala Gly Tyr Asp His Pro Ile Asn Lys Val Val Gln
                    885                 890                 895

Asp Leu Val Ser Cys Leu Asp Ala Pro Glu Leu Pro Phe Leu Gln Trp
                900                 905                 910
```

```
Glu Glu Leu Met Ser Val Leu Ala Thr Arg Leu Pro Arg Leu Leu Lys
            915                 920                 925

Ser Glu Leu Glu Gly Lys Tyr Ser Glu Tyr Lys Leu Asn Val Gly His
930                 935                 940

Gly Lys Ser Lys Asp Phe Pro Ser Lys Met Leu Arg Glu Ile Ile Glu
945                 950                 955                 960

Glu Asn Leu Ala His Gly Ser Glu Lys Glu Ile Ala Thr Asn Glu Arg
            965                 970                 975

Leu Val Glu Pro Leu Met Ser Leu Leu Lys Ser Tyr Glu Gly Gly Arg
            980                 985                 990

Glu Ser His Ala His Phe Ile Val Lys Ser Leu Phe Gly Asp Tyr Leu
            995                 1000                1005

Ser Val Glu Glu Leu Phe Ser Asp Gly Ile Gln Ser Asp Val Ile Glu
            1010                1015                1020

Arg Leu Arg Gln Gln His Ser Lys Asp Leu Gln Lys Val Val Asp Ile
1025                1030                1035                1040

Val Leu Ser His Gln Gly Val Arg Asn Lys Thr Lys Leu Ile Leu Thr
            1045                1050                1055

Leu Met Glu Lys Leu Val Tyr Pro Asn Pro Ala Val Tyr Lys Asp Gln
            1060                1065                1070

Leu Thr Arg Phe Ser Ser Leu Asn His Lys Arg Tyr Tyr Lys Leu Ala
            1075                1080                1085

Leu Lys Ala Ser Glu Leu Leu Glu Gln Thr Lys Leu Ser Glu Leu Arg
            1090                1095                1100

Thr Ser Ile Ala Arg Ser Leu Ser Glu Leu Met Phe Thr Glu Glu
1105                1110                1115                1120

Arg Thr Ala Ile Ser Glu Ile Met Gly Asp Leu Val Thr Ala Pro Leu
            1125                1130                1135

Pro Val Glu Asp Ala Leu Val Ser Leu Phe Asp Cys Ser Asp Gln Thr
            1140                1145                1150

Leu Gln Gln Arg Val Ile Glu Thr Tyr Ile Ser Arg Leu Tyr Gln Pro
            1155                1160                1165

His Leu Val Lys Asp Ser Ile Gln Leu Lys Tyr Gln Glu Ser Gly Val
            1170                1175                1180

Ile Ala Leu Trp Glu Phe Ala Glu Ala His Ser Glu Lys Arg Leu Gly
1185                1190                1195                1200

Ala Met Val Ile Val Lys Ser Leu Glu Ser Val Ser Ala Ala Ile Gly
            1205                1210                1215

Ala Ala Leu Lys Gly Thr Ser Arg Tyr Ala Ser Ser Glu Gly Asn Ile
            1220                1225                1230

Met His Ile Ala Leu Leu Gly Ala Asp Asn Gln Met His Gly Thr Glu
            1235                1240                1245

Asp Ser Gly Asp Asn Asp Gln Ala Gln Val Arg Ile Asp Lys Leu Ser
1250                1255                1260

Ala Thr Leu Glu Gln Asn Thr Val Thr Ala Asp Leu Arg Ala Ala Gly
1265                1270                1275                1280

Val Lys Val Ile Ser Cys Ile Val Gln Arg Asp Gly Ala Leu Met Pro
            1285                1290                1295

Met Arg His Thr Phe Leu Leu Ser Asp Glu Lys Leu Cys Tyr Gly Glu
            1300                1305                1310

Glu Pro Val Leu Arg His Val Glu Pro Pro Leu Ser Ala Leu Leu Glu
            1315                1320                1325
```

```
Leu Gly Lys Leu Lys Val Lys Gly Tyr Asn Glu Val Lys Tyr Thr Pro
    1330                1335                1340

Ser Arg Asp Arg Gln Trp Asn Ile Tyr Thr Leu Arg Asn Thr Glu Asn
1345                1350                1355                1360

Pro Lys Met Leu His Arg Val Phe Phe Arg Thr Leu Val Arg Gln Pro
                1365                1370                1375

Gly Ala Ser Asn Lys Phe Thr Ser Gly Asn Ile Ser Asp Val Glu Val
                1380                1385                1390

Gly Gly Ala Glu Glu Ser Leu Ser Phe Thr Ser Ser Ile Leu Arg
            1395                1400                1405

Ser Leu Met Thr Ala Ile Glu Glu Leu Glu Leu His Ala Ile Arg Thr
    1410                1415                1420

Gly His Ser His Met Phe Leu Cys Ile Leu Lys Glu Arg Lys Leu Leu
1425                1430                1435                1440

Asp Leu Val Pro Val Ser Gly Asn Lys Val Val Asp Ile Gly Gln Asp
                1445                1450                1455

Glu Ala Thr Ala Cys Leu Leu Leu Lys Glu Met Ala Leu Gln Ile His
            1460                1465                1470

Glu Leu Val Gly Ala Arg Met His His Leu Ser Val Cys Gln Trp Glu
    1475                1480                1485

Val Lys Leu Lys Leu Asp Ser Asp Gly Pro Ala Ser Gly Thr Trp Arg
            1490                1495                1500

Val Val Thr Thr Asn Val Thr Ser His Thr Cys Thr Val Asp Ile Tyr
1505                1510                1515                1520

Arg Glu Val Glu Asp Thr Glu Ser Gln Lys Leu Val Tyr His Ser Ala
            1525                1530                1535

Pro Ser Ser Ser Gly Pro Leu His Gly Val Ala Leu Asn Thr Pro Tyr
                1540                1545                1550

Gln Pro Leu Ser Val Ile Asp Leu Lys Arg Cys Ser Ala Arg Asn Asn
            1555                1560                1565

Arg Thr Thr Tyr Cys Tyr Asp Phe Pro Leu Ala Phe Glu Thr Ala Val
    1570                1575                1580

Gln Lys Ser Trp Ser Asn Ile Ser Ser Asp Asn Asn Arg Cys Tyr Val
1585                1590                1595                1600

Lys Ala Thr Glu Leu Val Phe Ala His Lys Asn Gly Ser Trp Gly Thr
            1605                1610                1615

Pro Val Ile Pro Met Glu Arg Pro Ala Gly Leu Asn Asp Ile Gly Met
                1620                1625                1630

Val Ala Trp Ile Leu Asp Met Ser Thr Pro Glu Tyr Pro Asn Gly Arg
            1635                1640                1645

Gln Ile Val Val Ile Ala Asn Asp Ile Thr Phe Arg Ala Gly Ser Phe
    1650                1655                1660

Gly Pro Arg Glu Asp Ala Phe Phe Glu Thr Val Thr Asn Leu Ala Cys
1665                1670                1675                1680

Glu Arg Arg Leu Pro Leu Ile Tyr Leu Ala Ala Asn Ser Gly Ala Arg
            1685                1690                1695

Ile Gly Ile Ala Asp Glu Val Lys Ser Cys Phe Arg Val Gly Trp Ser
            1700                1705                1710

Asp Asp Gly Ser Pro Glu Arg Gly Phe Gln Tyr Ile Tyr Leu Thr Glu
            1715                1720                1725

Glu Asp His Ala Arg Ile Ser Ala Ser Val Ile Ala His Lys Met Gln
    1730                1735                1740

Leu Asp Asn Gly Glu Ile Arg Trp Val Ile Asp Ser Val Val Gly Lys
```

-continued

```
            1745                1750                1755                1760
        Glu Asp Gly Leu Gly Val Glu Asn Ile His Gly Ser Ala Ala Ile Ala
                        1765                1770                1775
        Ser Ala Tyr Ser Arg Ala Tyr Glu Glu Thr Phe Thr Leu Thr Phe Val
                        1780                1785                1790
        Thr Gly Arg Thr Val Gly Ile Gly Ala Tyr Leu Ala Arg Leu Gly Ile
                        1795                1800                1805
        Arg Cys Ile Gln Arg Thr Asp Gln Pro Ile Ile Leu Thr Gly Phe Ser
                1810                1815                1820
        Ala Leu Asn Lys Leu Leu Gly Arg Glu Val Tyr Ser Ser His Met Gln
                1825                1830                1835                1840
        Leu Gly Gly Pro Lys Ile Met Ala Thr Asn Gly Val Val His Leu Thr
                        1845                1850                1855
        Val Ser Asp Asp Leu Glu Gly Val Ser Asn Ile Leu Arg Trp Leu Ser
                        1860                1865                1870
        Tyr Val Pro Ala Asn Ile Gly Gly Pro Leu Pro Ile Thr Lys Ser Leu
                        1875                1880                1885
        Asp Pro Pro Asp Arg Pro Val Ala Tyr Ile Pro Glu Asn Thr Cys Asp
                1890                1895                1900
        Pro Arg Ala Ala Ile Ser Gly Ile Asp Asp Ser Gln Gly Lys Trp Leu
        1905                1910                1915                1920
        Gly Gly Met Phe Asp Lys Asp Ser Phe Val Glu Thr Phe Glu Gly Trp
                        1925                1930                1935
        Ala Lys Ser Val Val Thr Gly Arg Ala Lys Leu Gly Gly Ile Pro Val
                        1940                1945                1950
        Gly Val Ile Ala Val Glu Thr Gln Thr Met Met Gln Leu Ile Pro Ala
                        1955                1960                1965
        Asp Pro Gly Gln Leu Asp Ser His Glu Arg Ser Val Pro Arg Ala Gly
                1970                1975                1980
        Gln Val Trp Phe Pro Asp Ser Ala Thr Lys Thr Ala Gln Ala Met Leu
        1985                1990                1995                2000
        Asp Phe Asn Arg Glu Gly Leu Pro Leu Phe Ile Leu Ala Asn Trp Arg
                        2005                2010                2015
        Gly Phe Ser Gly Gly Gln Arg Asp Leu Phe Glu Gly Ile Leu Gln Ala
                        2020                2025                2030
        Gly Ser Thr Ile Val Glu Asn Leu Arg Ala Tyr Asn Gln Pro Ala Phe
                        2035                2040                2045
        Val Tyr Ile Pro Lys Ala Ala Glu Leu Arg Gly Gly Ala Trp Val Val
                2050                2055                2060
        Ile Asp Ser Lys Ile Asn Pro Asp Arg Ile Glu Phe Tyr Ala Glu Arg
        2065                2070                2075                2080
        Thr Ala Lys Gly Asn Val Leu Glu Pro Gln Gly Leu Ile Glu Ile Lys
                        2085                2090                2095
        Phe Arg Ser Glu Glu Leu Gln Glu Cys Met Gly Arg Leu Asp Pro Glu
                        2100                2105                2110
        Leu Ile Asn Leu Lys Ala Lys Leu Gln Gly Val Lys His Glu Asn Gly
                2115                2120                2125
        Ser Leu Pro Glu Ser Glu Ser Leu Gln Lys Ser Ile Glu Ala Arg Lys
                2130                2135                2140
        Lys Gln Leu Leu Pro Leu Tyr Thr Gln Ile Ala Val Arg Phe Ala Glu
        2145                2150                2155                2160
        Leu His Asp Thr Ser Leu Arg Met Ala Ala Lys Gly Val Ile Lys Lys
                        2165                2170                2175
```

```
Val Val Asp Trp Glu Asp Ser Arg Ser Phe Phe Tyr Lys Arg Leu Arg
            2180                2185                2190
Arg Arg Ile Ser Glu Asp Val Leu Ala Lys Glu Ile Arg Gly Val Ser
            2195                2200                2205
Gly Lys Gln Phe Ser His Gln Ser Ala Ile Glu Leu Ile Gln Lys Trp
            2210                2215                2220
Tyr Leu Ala Ser Lys Gly Ala Glu Thr Gly Ser Thr Glu Trp Asp Asp
2225                2230                2235                2240
Asp Asp Ala Phe Val Ala Trp Arg Glu Asn Pro Glu Asn Tyr Gln Glu
            2245                2250                2255
Tyr Ile Lys Glu Pro Arg Ala Gln Arg Val Ser Gln Leu Leu Ser Asp
            2260                2265                2270
Val Ala Asp Ser Ser Pro Asp Leu Glu Ala Leu Pro Gln Gly Leu Ser
            2275                2280                2285
Met Leu Leu Glu Lys Met Asp Pro Ala Lys Arg Glu Ile Val Glu Asp
            2290                2295                2300
Phe Glu Ile Asn Leu Val Lys
2305                2310

<210> SEQ ID NO 29
<211> LENGTH: 6936
<212> TYPE: DNA
<213> ORGANISM: Triticum aestivum

<400> SEQUENCE: 29
```

| | | | | | |
|---|---|---|---|---|---|
| atgggatcca | cacatttgcc | cattgtcggc | cttaatgcct | cgacaacacc | atcgctatcc | 60 |
| actattcgcc | cggtaaattc | agccggtgct | gcattccaac | catctgcccc | ttctagaacc | 120 |
| tccaagaaga | aaagtcgtcg | tgttcagtca | ttaaggatg | gaggcgatgg | aggcgtgtca | 180 |
| gaccctaacc | agtctattcg | ccaaggtctt | gccggcatca | ttgacctccc | aaaggagggc | 240 |
| acatcagctc | cggaagtgga | tatttcacat | gggtccgaag | aacccagggg | ctcctaccaa | 300 |
| atgaatggga | tactgaatga | agcacataat | gggaggcatg | cttcgctgtc | taaggttgtc | 360 |
| gaattttgta | tggcattggg | cggcaaaaca | ccaattcaca | gtgtattagt | tgcgaacaat | 420 |
| ggaagggcag | cagctaagtt | catgcggagt | gtccgaacat | gggctaatga | acatttggg | 480 |
| tcagagaagg | caattcagtt | gatagctatg | gctactccag | aagacatgag | gataaatgca | 540 |
| gagcacatta | gaattgctga | tcaatttgtt | gaagtacccg | gtgaacaaa | caataacaac | 600 |
| tatgcaaatg | tccaactcat | agtggagata | gcagtgagaa | ccgtgtgttc | tgctgtttgg | 660 |
| cctggttggg | gccatgcatc | tgagaatcct | gaacttccag | atgcactaaa | tgcaaacgga | 720 |
| attgttttc | ttgggccacc | atcatcatca | atgaacgcac | taggtgacaa | ggttggttca | 780 |
| gctctcattg | ctcaagcagc | aggggttccg | actcttcctt | ggggtggatc | acaggtggaa | 840 |
| attccattag | aagtttgttt | ggactcgata | cctgcggaga | tgtataggaa | gcttgtgtt | 900 |
| agtactacgg | aggaagcact | tgcgagttgt | cagatgattg | ggtatccagc | catgattaaa | 960 |
| gcatcatggg | gtggtggtgg | taaagggatc | cgaaaggtta | taacgacga | tgatgtcaga | 1020 |
| gcactgttta | agcaagtgca | aggtgaagtt | cctggctccc | caatatttat | catgagactt | 1080 |
| gcatctcaga | gtcgacatct | tgaagttcag | ttgctttgtg | atcaatatgg | caatgtagct | 1140 |
| gcgcttcaca | gtcgtgactg | cagtgtgcaa | cggcgacacc | aaaagattat | tgaggaagga | 1200 |
| ccagttactg | ttgctcctcg | cgagacagtg | aaagagctag | agcaagcagc | aaggaggctt | 1260 |
| gctaaggctg | tgggttatgt | tggtgctgct | actgttgaat | atctctacag | catggagact | 1320 |

```
ggtgaatact attttctgga acttaatcca cggttgcagg ttgagcatcc agtcaccgag   1380
tggatagctg aagtaaactt gcctgcagct caagttgcag ttggaatggg tataccccctt  1440 tggcaggttc cagagatcag acgtttctat ggaatggaca atggaggagg ctatgacatt   1500
tggagggaaa cagcagctct tgctactcca tttaacttcg atgaagtgga ttctcaatgg   1560
ccaaagggtc attgtgtagc agttaggata accagtgagg atccagatga cggattcaag   1620
cctaccggtg aaaagtaaa ggagatcagt tttaaaagca agccaaatgt ttgggcctat    1680
ttctctgtta agtccggtgg aggcattcat gaatttgctg attctcagtt tggacatgtt   1740
tttgcatatg gagtgtctag agcagcagca ataaccaaca tgtctcttgc gctaaaagag   1800
attcaaattc gtggagaaat tcattcaaat gttgattaca cagttgatct cttgaatgcc   1860
tcagacttca agaaaaacag gattcatact ggctggctgg ataacagaat agcaatgcga   1920
gtccaagctg agagacctcc gtggtatatt tcagtggttg gaggagctct atataaaaca   1980
ataacgagca cacagacac tgtttctgaa tatgttagct atctcgtcaa gggtcagatt    2040
ccaccgaagc atatatccct tgtccattca actgtttctt tgaatataga ggaaagcaaa   2100
tatacaattg aaactataag gagcggacag ggtagctaca gattgcgaat gaatggatca   2160
gttattgaag caaatgtcca acattatgt gatggtggac ttttaatgca gttggatgga    2220
aacagccatg taatttatgc tgaagaagag gccggtggta cacggcttct aattgatgga   2280
aagacatact tgttacagaa tgatcacgat ccttcaaggt tattagctga gacaccctgc   2340
aaacttcttc gtttcttggt tgccgatggt gctcatgttg aagctgatgt accatatgcg   2400
gaagttgagg ttatgaagat gtgcatgccc ctcttgtcac ctgctgctgg tgtcattaat   2460
gttttgttgt ctgagggcca gcctatgcag gctggtgatc ttatagcaag acttgatctt   2520 gatgacccctt ctgctgtgaa gagagctgag ccatttaacg gatctttccc agaaatgagc  2580
cttcctattg ctgcttctgg ccaagttcac aaaagatgtg ccacaagctt gaatgctgct   2640
cggatggtcc ttgcaggata tgatcacccg atcaacaaag ttgtacaaga tctggtatcc   2700
tgtctagatg ctcctgagct tcctttccta caatgggaag agcttatgtc tgttttagca   2760
actagacttc caaggcttct taagagcgag ttggagggta aatacagtga atataagtta   2820
aatgttggcc atgggaagag caaggatttc ccttccaaga tgctaagaga gataatcgag   2880
gaaaatcttg cacatggttc tgagaaggaa attgctacaa atgagaggct tgttgagcct   2940
cttatgagcc tactgaagtc atatgagggt ggcagagaaa gccatgcaca ctttattgtg   3000
aagtcccttt tcgaggacta tctctcggtt gaggaactat tcagtgatgg cattcagtct   3060
gatgtgattg aacgcctgcg ccaacaacat agtaaagatc tccagaaggt tgtagacatt   3120
gtgttgtctc accagggtgt gagaaacaaa actaagctga tactaacact catggagaaa   3180
ctggtctatc caaaccctgc tgtctacaag gatcagttga ctcgcttttc ctccctcaat   3240
cacaaaagat attataagtt ggcccttaaa gctagcgagc ttcttgaaca aaccaagctt   3300
agtgagctcc gcacaagcat tgcaaggagc ctttcagaac ttgagatgtt tactgaagaa   3360
aggacggcca ttagtgagat catgggagat ttagtgactg ccccactgcc agttgaagat   3420
gcactggttt ctttgtttga ttgtagtgat caaactcttc agcagagggt gatcgagacg   3480
tacatatctc gattataccca gcctcatctt gtcaaggata gtatccagct gaaatatcag   3540
gaatctggtg ttattgcttt atgggaattc gctgaagcgc attcagagaa agattgggt    3600 gctatggtta ttgtgaagtc gttagaatct gtatcagcag caattggagc tgcactaaag   3660
```

```
ggtacatcac gctatgcaag ctctgagggt aacataatgc atattgcttt attgggtgct   3720
gataatcaaa tgcatggaac tgaagacagt ggtgataacg atcaagctca agtcaggata   3780
gacaaacttt ctgcgacact ggaacaaaat actgtcacag ctgatctccg tgctgctggt   3840
gtgaaggtta ttagttgcat tgttcaaagg gatggagcac tcatgcctat gcgccatacc   3900
ttcctcttgt cggatgaaaa gctttgttat ggggaagagc cggttctccg gcatgtggag   3960
cctcctcttt ctgctcttct tgagttgggt aagttgaaag tgaaaggata caatgaggtg   4020
aagtatacac cgtcacgtga tcgtcagtgg aacatataca cacttagaaa tacagagaac   4080
cccaaaatgt tgcacagggt gttttttccga actcttgtca ggcaacccgg tgcttccaac   4140
aaattcacat caggcaacat cagtgatgtt gaagtgggag gagctgagga atctctttca   4200
tttacatcga gcagcatatt aagatcgctg atgactgcta tagaagagtt ggagcttcac   4260
gcgattagga caggtcactc tcatatgttt ttgtgcatat tgaaagagcg aaagcttctt   4320
gatcttgttc ccgtttcagg gaacaaagtt gtggatattg ccaagatgaa agctactgca   4380
tgcttgcttc tgaaagaaat ggctctacag atacatgaac ttgtgggtgc aaggatgcat   4440
catctttctg tatgccaatg ggaggtgaaa cttaagttgg acagcgatgg gcctgccagt   4500
ggtacctgga gagttgtaac aaccaatgtt actagtcaca cctgcactgt ggatatctac   4560
cgtgaggttg aagatacaga atcacagaaa ctagtatacc actctgctcc atcgtcatct   4620
ggtcctttgc atggcgttgc actgaatact ccatatcagc ctttgagtgt tattgatctg   4680
aaacgttgct ccgctagaaa caacagaact acatactgct atgattttcc gttggcattt   4740
gaaactgcag tgcagaagtc atggtctaac atttctagtg acaataaccg atgttatgtt   4800
aaagcaacgg agctggtgtt tgctcacaag aatgggtcat ggggcactcc tgtaattcct   4860
atggagcgtc ctgctgggct caatgacatt ggtatggtag cttggatctt ggacatgtcc   4920
actcctgaat atcccaatgg caggcagatt gttgtcatcg caaatgatat tacttttaga   4980
gctggatcgt ttggtccaag ggaagatgca ttttttgaaa ctgttaccaa cctagcttgt   5040
gagaggaggc ttcctctcat ctacttggca gcaaactctg gtgctcggat cggcatagca   5100
gatgaagtaa aatcttgctt ccgtgttgga tggtctgatg atggcagccc tgaacgtggg   5160
tttcaatata tttatctgac tgaagaagac catgctcgta ttagcgcttc tgttatagcg   5220
cacaagatgc agcttgataa tggtgaaatt aggtgggtta ttgattctgt tgtagggaag   5280
gaggatgggc taggtgtgga aacatacat ggaagtgctg ctattgccag tgcctattct   5340
agggcctatg aggagacatt tacgcttaca tttgtgactg gaaggactgt tggaatagga   5400
gcatatcttg ctcgacttgg catacggtgc attcagcgta ctgaccagcc cattatccta   5460
actgggtttt ctgccttgaa caagcttctt ggccgggaag tgtacagctc ccacatgcag   5520
ttgggtggcc ccaaaattat ggcgacaaac ggtgttgtcc atctgacagt ttcagatgac   5580
cttgaaggtg tatctaatat attgaggtgg ctcagctatg ttcctgccaa cattggtgga   5640
cctcttccta ttacaaaatc tttggaccca cctgacagac ccgttgctta catccctgag   5700
aatacatgcg atcctcgtgc tgccatcagt ggcattgatg atagccaagg gaaatggttg   5760
gggggcatgt tcgacaaaga cagttttgtg gagacatttg aaggatgggc gaagtcagtt   5820
gttactggca gagcgaaact cggagggatt ccggtgggtg ttatagctgt ggagacacag   5880
actatgatgc agctcatccc tgctgatcca ggccagcttg attcccatga gcgatctgtt   5940
cctcgtgctg ggcaagtctg gtttccagat tcagctacta agacagcgca ggcaatgctg   6000
gacttcaacc gtgaaggatt acctctgttc atccttgcta actggagagg cttctctggt   6060
```

```
ggacaaagag atcttttga aggaatcctt caggctgggt caacaattgt tgagaacctt    6120
agggcataca atcagcctgc ctttgtatat atccccaagg ctgcagagct acgtggaggg    6180
gcttgggtcg tgattgatag caagataaat ccagatcgca ttgagttcta tgctgagagg    6240
actgcaaagg gcaatgttct cgaacctcaa gggttgatcg agatcaagtt caggtcagag    6300
gaactccaag agtgcatggg taggcttgat ccagaattga taaatctgaa ggcaaagctc    6360
cagggagtaa agcatgaaaa tggaagtcta cctgagtcag aatcccttca gaagagcata    6420
gaagcccgga agaaacagtt gttgcctttg tatactcaaa ttgcggtacg gttcgctgaa    6480
ttgcatgaca cttcccttag aatggctgct aagggtgtga ttaagaaggt tgtagactgg    6540
gaagattcta ggtcgttctt ctacaagaga ttacggagga ggatatccga ggatgttctt    6600
gcgaaggaaa ttagaggtgt aagtggcaag cagttttctc accaatcggc aatcgagctg    6660
atccagaaat ggtacttggc ctctaaggga gctgaaacag gaagcactga atgggatgat    6720
gacgatgctt ttgttgcctg gagggaaaac cctgaaaact accaggagta tatcaaagaa    6780
cccagggctc aaagggtatc tcagttgctc tcagatgttg cagactccag tccagatcta    6840
gaagccttgc cacagggtct ttctatgcta ctagagaaga tggatcctgc aaagagggaa    6900
attgttgaag actttgaaat aaaccttgta aagtaa                              6936

<210> SEQ ID NO 30
<211> LENGTH: 5
<212> TYPE: PRT
<213> ORGANISM: Artificial Sequence
<220> FEATURE:
<223> OTHER INFORMATION: PAP1 enzyme catalytic motif
<220> FEATURE:
<221> NAME/KEY: VARIANT
<222> LOCATION: 2, 4
<223> OTHER INFORMATION: Xaa = Any Amino Acid

<400> SEQUENCE: 30

Asp Xaa Asp Xaa Thr
1               5

<210> SEQ ID NO 31
<211> LENGTH: 2535
<212> TYPE: DNA
<213> ORGANISM: Synechococcus elongatus PCC 7942

<400> SEQUENCE: 31
atgagtgatt ccaccgccca actcagctac gaccccacca cgagctacct cgagcccagt     60
ggcttggtct gtgaggatga acggacttct gtgactcccg agaccttgaa acgggcttac    120
gaggcccatc tctactacag ccagggcaaa acctcagcga tcgccaccct gcgtgatcac    180
tacatggcac tggcctacat ggtccgcgat cgcctcctgc aacggtggct agcttcactg    240
tcgacctatc aacaacagca cgtcaaagtg gtctgttacc tgtccgctga gttttttgatg    300 ggtcggcacc tcgaaaactg cctgatcaac ctgcatcttc acgaccgcgt tcagcaagtt    360
ttggatgaac tgggtctcga ttttgagcaa ctgctagaga agaggaagaa acccgggcta    420
ggcaacggtg gcctcggtcg cctcgcagct tgtttcctcg actccatggc tacccctcgac    480 attcctgccg tcggctatgg cattcgctat gagttcggta tcttccacca agaactccac    540
aacggctggc agatcgaaat ccccgataac tggctgcgct ttggcaaccc ttgggagcta    600
gagcggcgcg aacaggccgt ggaaattaag ttgggcggcc acacggaggc ctaccacgat    660
gcgcgaggcc gctactgcgt ctcttggatc cccgatcgcg tcattcgcgc catcccctac    720
```

```
gacacccccg taccgggcta cgacaccaat aacgtcagca tgttgcggct ctggaaggct     780
gagggcacca cggaactcaa ccttgaggct ttcaactcag gcaactacga cgatgcggtt     840
gccgacaaaa tgtcgtcgga aacgatctcg aaggtgctct atcccaacga caacaccccc     900
caagggcggg aactgcggct ggagcagcag tatttcttcg tctcggcttc gctccaagac     960
atcatccgtc gccacttgat gaaccacggt catcttgagc ggctgcatga ggcgatcgca    1020
gtccagctta cgacaccca tcccagcgtg gcggtgccgg agttgatgcg cctcctgatc    1080
gatgagcatc acctgacttg gacaatgct tggacgatta cacagcgcac cttcgcctac     1140
accaaccaca cgctgctacc tgaagccttg aacgctggc ccgtgggcat gttccagcgc     1200
actttaccgc gcttgatgga gattatctac gaaatcaact ggcgcttctt ggccaatgtg    1260
cgggcctggt atcccggtga cgacacgaga gctcgccgcc tctccctgat tgaggaagga    1320
gctgagcccc aggtgcgcat ggctcacctc gcctgcgtgg gcagtcatgc catcaacggt    1380
gtggcagccc tgcatacgca actgctcaag caagaaaccc tgcgagattt ctacgagctt    1440
tggcccgaga aattcttcaa catgaccaac ggtgtgacgc ccgccgctg gctgctgcaa      1500 agtaatcctc gcctagccaa cctgatcagc gatcgcattg gcaatgactg gattcatgat    1560
ctcaggcaac tgcgacggct ggaagacagc gtgaacgatc gcgagttttt acagcgctgg    1620
gcagaggtca agcaccaaaa taaggtcgat ctgagccgct acatctacca gcagactcgc    1680
atagaagtcg atccgcactc tctctttgat gtgcaagtca acggattca cgaatacaaa     1740 cgccagctcc tcgctgtcat gcatatcgtg acgctctaca actggctgaa gcacaatccc    1800
cagctcaacc tggtgccgcg cacttttatc tttgcgggca agcggcccc gggttactac     1860 cgtgccaagc aaatcgtcaa actgatcaat gcggtcggga gcatcatcaa ccatgatccc    1920
gatgtccaag gcgactgaa ggtcgtcttc ctacctaact tcaacgtttc cttggggcag     1980
cgcatttatc cagctgccga tttgtcggag caaatctcaa ctgcagggaa agaagcgtcc    2040
ggcaccggca acatgaagtt caccatgaat ggcgcgctga caatcggaac ctacgatggt    2100
gccaacatcg agatccgcga ggaagtcggc cccgaaaact tcttcctgtt tggcctgcga    2160
gccgaagata tcgcccgacg ccaaagtcgg ggctatcgac ctgtggagtt ctggagcagc    2220
aatgcggaac tgcgggcagt cctcgatcgc tttagcagtg gtcacttcac accggatcag    2280
cccaacctct tccaagactt ggtcagcgat ctgctgcagc gggatgagta catgttgatg    2340
gcggactatc agtcctacat cgactgccag cgcgaagctg ctgctgccta ccgcgattcc    2400
gatcgctggt ggcggatgtc gctactcaac accgcgagat cgggcaagtt ctcctccgat    2460
cgcacgatcg ctgactacag cgaacagatc tgggaggtca aaccagtccc cgtcagccta    2520
agcactagct tttag                                                    2535
```

<210> SEQ ID NO 32
<211> LENGTH: 844
<212> TYPE: PRT
<213> ORGANISM: Synechococcus elongatus PCC 7942

<400> SEQUENCE: 32

Met Ser Asp Ser Thr Ala Gln Leu Ser Tyr Asp Pro Thr Thr Ser Tyr
1               5                   10                  15

Leu Glu Pro Ser Gly Leu Val Cys Glu Asp Glu Arg Thr Ser Val Thr
            20                  25                  30

Pro Glu Thr Leu Lys Arg Ala Tyr Glu Ala His Leu Tyr Tyr Ser Gln
        35                  40                  45

```
Gly Lys Thr Ser Ala Ile Ala Thr Leu Arg Asp His Tyr Met Ala Leu
 50                  55                  60

Ala Tyr Met Val Arg Asp Arg Leu Leu Gln Arg Trp Leu Ala Ser Leu
 65                  70                  75                  80

Ser Thr Tyr Gln Gln Gln His Val Lys Val Cys Tyr Leu Ser Ala
                 85                  90                  95

Glu Phe Leu Met Gly Arg His Leu Glu Asn Cys Leu Ile Asn Leu His
                100                 105                 110

Leu His Asp Arg Val Gln Gln Val Leu Asp Glu Leu Gly Leu Asp Phe
            115                 120                 125

Glu Gln Leu Leu Glu Lys Glu Glu Pro Gly Leu Gly Asn Gly Gly
            130                 135                 140

Leu Gly Arg Leu Ala Ala Cys Phe Leu Asp Ser Met Ala Thr Leu Asp
145                 150                 155                 160

Ile Pro Ala Val Gly Tyr Gly Ile Arg Tyr Glu Phe Gly Ile Phe His
                165                 170                 175

Gln Glu Leu His Asn Gly Trp Gln Ile Glu Ile Pro Asp Asn Trp Leu
                180                 185                 190

Arg Phe Gly Asn Pro Trp Glu Leu Glu Arg Arg Glu Gln Ala Val Glu
                195                 200                 205

Ile Lys Leu Gly Gly His Thr Glu Ala Tyr His Asp Ala Arg Gly Arg
            210                 215                 220

Tyr Cys Val Ser Trp Ile Pro Asp Arg Val Ile Arg Ala Ile Pro Tyr
225                 230                 235                 240

Asp Thr Pro Val Pro Gly Tyr Asp Thr Asn Asn Val Ser Met Leu Arg
                245                 250                 255

Leu Trp Lys Ala Glu Gly Thr Thr Glu Leu Asn Leu Glu Ala Phe Asn
                260                 265                 270

Ser Gly Asn Tyr Asp Asp Ala Val Ala Asp Lys Met Ser Ser Glu Thr
            275                 280                 285

Ile Ser Lys Val Leu Tyr Pro Asn Asp Asn Thr Pro Gln Gly Arg Glu
            290                 295                 300

Leu Arg Leu Glu Gln Gln Tyr Phe Phe Val Ser Ala Ser Leu Gln Asp
305                 310                 315                 320

Ile Ile Arg Arg His Leu Met Asn His Gly His Leu Glu Arg Leu His
                325                 330                 335

Glu Ala Ile Ala Val Gln Leu Asn Asp Thr His Pro Ser Val Ala Val
            340                 345                 350

Pro Glu Leu Met Arg Leu Leu Ile Asp Glu His His Leu Thr Trp Asp
            355                 360                 365

Asn Ala Trp Thr Ile Thr Gln Arg Thr Phe Ala Tyr Thr Asn His Thr
370                 375                 380

Leu Leu Pro Glu Ala Leu Glu Arg Trp Pro Val Gly Met Phe Gln Arg
385                 390                 395                 400

Thr Leu Pro Arg Leu Met Glu Ile Ile Tyr Glu Ile Asn Trp Arg Phe
                405                 410                 415

Leu Ala Asn Val Arg Ala Trp Tyr Pro Gly Asp Asp Thr Arg Ala Arg
                420                 425                 430

Arg Leu Ser Leu Ile Glu Glu Gly Ala Glu Pro Gln Val Arg Met Ala
            435                 440                 445

His Leu Ala Cys Val Gly Ser His Ala Ile Asn Gly Val Ala Ala Leu
450                 455                 460
```

His Thr Gln Leu Leu Lys Gln Glu Thr Leu Arg Asp Phe Tyr Glu Leu
465                 470                 475                 480

Trp Pro Glu Lys Phe Phe Asn Met Thr Asn Gly Val Thr Pro Arg Arg
            485                 490                 495

Trp Leu Leu Gln Ser Asn Pro Arg Leu Ala Asn Leu Ile Ser Asp Arg
        500                 505                 510

Ile Gly Asn Asp Trp Ile His Asp Leu Arg Gln Leu Arg Arg Leu Glu
    515                 520                 525

Asp Ser Val Asn Asp Arg Glu Phe Leu Gln Arg Trp Ala Glu Val Lys
530                 535                 540

His Gln Asn Lys Val Asp Leu Ser Arg Tyr Ile Tyr Gln Gln Thr Arg
545                 550                 555                 560

Ile Glu Val Asp Pro His Ser Leu Phe Asp Val Gln Val Lys Arg Ile
                565                 570                 575

His Glu Tyr Lys Arg Gln Leu Leu Ala Val Met His Ile Val Thr Leu
            580                 585                 590

Tyr Asn Trp Leu Lys His Asn Pro Gln Leu Asn Leu Val Pro Arg Thr
        595                 600                 605

Phe Ile Phe Ala Gly Lys Ala Ala Pro Gly Tyr Tyr Arg Ala Lys Gln
    610                 615                 620

Ile Val Lys Leu Ile Asn Ala Val Gly Ser Ile Ile Asn His Asp Pro
625                 630                 635                 640

Asp Val Gln Gly Arg Leu Lys Val Val Phe Leu Pro Asn Phe Asn Val
                645                 650                 655

Ser Leu Gly Gln Arg Ile Tyr Pro Ala Ala Asp Leu Ser Glu Gln Ile
            660                 665                 670

Ser Thr Ala Gly Lys Glu Ala Ser Gly Thr Gly Asn Met Lys Phe Thr
        675                 680                 685

Met Asn Gly Ala Leu Thr Ile Gly Thr Tyr Asp Gly Ala Asn Ile Glu
    690                 695                 700

Ile Arg Glu Glu Val Gly Pro Glu Asn Phe Phe Leu Phe Gly Leu Arg
705                 710                 715                 720

Ala Glu Asp Ile Ala Arg Arg Gln Ser Arg Gly Tyr Arg Pro Val Glu
                725                 730                 735

Phe Trp Ser Ser Asn Ala Glu Leu Arg Ala Val Leu Asp Arg Phe Ser
            740                 745                 750

Ser Gly His Phe Thr Pro Asp Gln Pro Asn Leu Phe Gln Asp Leu Val
        755                 760                 765

Ser Asp Leu Leu Gln Arg Asp Glu Tyr Met Leu Met Ala Asp Tyr Gln
770                 775                 780

Ser Tyr Ile Asp Cys Gln Arg Glu Ala Ala Ala Tyr Arg Asp Ser
785                 790                 795                 800

Asp Arg Trp Trp Arg Met Ser Leu Leu Asn Thr Ala Arg Ser Gly Lys
            805                 810                 815

Phe Ser Ser Asp Arg Thr Ile Ala Asp Tyr Ser Glu Gln Ile Trp Glu
        820                 825                 830

Val Lys Pro Val Pro Val Ser Leu Ser Thr Ser Phe
        835                 840

<210> SEQ ID NO 33
<211> LENGTH: 2085
<212> TYPE: DNA
<213> ORGANISM: Synechococcus elongatus PCC 7942

<400> SEQUENCE: 33

```
atgactgttt catcccgtcg ccctgaatcg accgtggctg ttgacccgg ccaaagctat      60
ccctcgggg caaccgtcta tcccaccggc gtcaacttct cgctctacac caagtacgcg     120
acgggcgttg aattactgct gtttgatgac cctgagggtg cccagcctca acggacagtg    180
cgcctcgatc cgcacctcaa tcgcacctct ttctactggc atgtttttat tccgggcatt    240
cgctccggtc aggtttatgc ttaccgcgtc tttggcccct acgcacctga tcgcggcctc    300
tgttttaacc ccaacaaagt gctgctggat ccctacgctc gcggggttgt cggctggcag    360
cactacagtc gcgaagcggc tattaaaccc agtaataact gcgttcaagc cctgcgtagc    420
gtggttgttg accccagcga ctacgactgg aaggcgatc gccatccacg cacacccta    480
gctcgcacag taatctatga gctgcatgtt ggcggcttca ccaagcatcc caattccggc    540
gtcgcccctg aaaaacgtgg cacctacgct ggtctaatcg aaaaaattcc ctacctgcaa    600
tccctcggcg tcacggccgt tgagttgctg ccggtgcacc agttcgatcg ccaagatgcc    660
cccttaggac gcgagaacta ctggggctac agcaccatgg cttttttgc gccccacgca    720
gcctacagct ctcgccatga tccacttggt ccagttgatg agttccgcga cctcgtcaag    780
gcgctccacc aagcagggat tgaggtgatt ctcgacgtgg tgttcaacca cactgctgaa    840
gggaatgaag acgtccaac gctgtctttc aaaggtctag cgaattcaac ctactatctg    900
ctggatgaac aggcgggcta tcgcaactac accggctgcg gcaacaccgt caaagctaac    960
aattcgatcg tgcgatcgct gattctcgat tgcctgcgtt attgggtctc ggaaatgcac   1020
gtcgatggct tccgctttga ccttgcgtcg gtgctgagtc gtgatgccaa tggcaacccc   1080
ctatcggatc cgcccttgct ttgggcgatt gattccgatc cggttttggc cggtacgaag   1140
ctcattgctg aagcttggga cgcagccggc ttatatcagg ttggtaccttc tattggcgat   1200
cgctttggga cttggaacgg tcccttccgg gacgatattc ggcgttttg gcgtggagat   1260
cagggctgta cttacgccct cagtcaacgc ctgctgggta gccccgatgt ctacagcaca   1320
gaccaatggt atgccggacg caccattaac ttcatcacct gccatgacgg ctttacgctg   1380
cgagatctag tcagctatag ccagaagcac aactttgcca atggagagaa caatcgggac   1440
gggaccaatg acaactacag ctggaactac ggcattgaag gcgagaccga tgaccccacg   1500
attctgagct acgggaacg gcagcagcgc aatttgctcg ccacgttatt cctcgcccag   1560
ggcacaccga tgctgacgat gggcgatgag gtcaaacgca gtcagcaggg taacaataac   1620
gcctactgcc aagacaatga gatcagctgg tttgattggt cgctgtgcga tcgccatgcc   1680
gatttcttgg tgttcagtcg ccgcctgatt gaactttccc agtcgctggt gatgttccaa   1740
cagaacgaac tgctgcagaa cgaaccccat ccgcgtcgtc cctatgccat ctggcatggc   1800
gtcaaactca acaacccga ttgggcgctg tggtcccaca gtctggccgt cagtctctgc   1860
catcctcgcc agcaggaatg gctttaccta gcctttaatg cttactggga agacctgcgc   1920
ttccagttgc cgaggcctcc tcgcggccgc gtttggtatc gcttgctcga tacttcactg   1980
ccgaatcttg aagcttgtca tctgccggat gaggcaaaac cctgcctacg gcgcgattac   2040
atcgtcccag cgcgatcgct cttactgttg atggctcgtg cttaa                   2085
```

<210> SEQ ID NO 34
<211> LENGTH: 694
<212> TYPE: PRT
<213> ORGANISM: Synechococcus elongatus PCC 7942

<400> SEQUENCE: 34

```
Met Thr Val Ser Ser Arg Arg Pro Glu Ser Thr Val Ala Val Asp Pro
1               5                   10                  15

Gly Gln Ser Tyr Pro Leu Gly Ala Thr Val Tyr Pro Thr Gly Val Asn
            20                  25                  30

Phe Ser Leu Tyr Thr Lys Tyr Ala Thr Gly Val Glu Leu Leu Leu Phe
        35                  40                  45

Asp Pro Glu Gly Ala Gln Pro Gln Arg Thr Val Arg Leu Asp Pro
50                  55                  60

His Leu Asn Arg Thr Ser Phe Tyr Trp His Val Phe Ile Pro Gly Ile
65                  70                  75                  80

Arg Ser Gly Gln Val Tyr Ala Tyr Arg Val Phe Gly Pro Tyr Ala Pro
                85                  90                  95

Asp Arg Gly Leu Cys Phe Asn Pro Asn Lys Val Leu Leu Asp Pro Tyr
                100                 105                 110

Ala Arg Gly Val Val Gly Trp Gln His Tyr Ser Arg Glu Ala Ala Ile
                115                 120                 125

Lys Pro Ser Asn Asn Cys Val Gln Ala Leu Arg Ser Val Val Val Asp
            130                 135                 140

Pro Ser Asp Tyr Asp Trp Glu Gly Asp Arg His Pro Arg Thr Pro Tyr
145                 150                 155                 160

Ala Arg Thr Val Ile Tyr Glu Leu His Val Gly Gly Phe Thr Lys His
                165                 170                 175

Pro Asn Ser Gly Val Ala Pro Glu Lys Arg Gly Thr Tyr Ala Gly Leu
                180                 185                 190

Ile Glu Lys Ile Pro Tyr Leu Gln Ser Leu Gly Val Thr Ala Val Glu
            195                 200                 205

Leu Leu Pro Val His Gln Phe Asp Arg Gln Asp Ala Pro Leu Gly Arg
210                 215                 220

Glu Asn Tyr Trp Gly Tyr Ser Thr Met Ala Phe Phe Ala Pro His Ala
225                 230                 235                 240

Ala Tyr Ser Ser Arg His Asp Pro Leu Gly Pro Val Asp Glu Phe Arg
                245                 250                 255

Asp Leu Val Lys Ala Leu His Gln Ala Gly Ile Glu Val Ile Leu Asp
                260                 265                 270

Val Val Phe Asn His Thr Ala Glu Gly Asn Glu Asp Gly Pro Thr Leu
            275                 280                 285

Ser Phe Lys Gly Leu Ala Asn Ser Thr Tyr Tyr Leu Leu Asp Glu Gln
290                 295                 300

Ala Gly Tyr Arg Asn Tyr Thr Gly Cys Gly Asn Thr Val Lys Ala Asn
305                 310                 315                 320

Asn Ser Ile Val Arg Ser Leu Ile Leu Asp Cys Leu Arg Tyr Trp Val
                325                 330                 335

Ser Glu Met His Val Asp Gly Phe Arg Phe Asp Leu Ala Ser Val Leu
                340                 345                 350

Ser Arg Asp Ala Asn Gly Asn Pro Leu Ser Asp Pro Pro Leu Leu Trp
            355                 360                 365

Ala Ile Asp Ser Asp Pro Val Leu Ala Gly Thr Lys Leu Ile Ala Glu
        370                 375                 380

Ala Trp Asp Ala Ala Gly Leu Tyr Gln Val Gly Thr Phe Ile Gly Asp
385                 390                 395                 400

Arg Phe Gly Thr Trp Asn Gly Pro Phe Arg Asp Asp Ile Arg Arg Phe
                405                 410                 415

Trp Arg Gly Asp Gln Gly Cys Thr Tyr Ala Leu Ser Gln Arg Leu Leu
```

```
                     420                 425                 430
Gly Ser Pro Asp Val Tyr Ser Thr Asp Gln Trp Tyr Ala Gly Arg Thr
            435                 440                 445
Ile Asn Phe Ile Thr Cys His Asp Gly Phe Thr Leu Arg Asp Leu Val
            450                 455                 460
Ser Tyr Ser Gln Lys His Asn Phe Ala Asn Gly Glu Asn Asn Arg Asp
465                 470                 475                 480
Gly Thr Asn Asp Asn Tyr Ser Trp Asn Tyr Gly Ile Glu Gly Glu Thr
                485                 490                 495
Asp Asp Pro Thr Ile Leu Ser Leu Arg Glu Arg Gln Arg Asn Leu
            500                 505                 510
Leu Ala Thr Leu Phe Leu Ala Gln Gly Thr Pro Met Leu Thr Met Gly
            515                 520                 525
Asp Glu Val Lys Arg Ser Gln Gln Gly Asn Asn Asn Ala Tyr Cys Gln
            530                 535                 540
Asp Asn Glu Ile Ser Trp Phe Asp Trp Ser Leu Cys Asp Arg His Ala
545                 550                 555                 560
Asp Phe Leu Val Phe Ser Arg Arg Leu Ile Glu Leu Ser Gln Ser Leu
                565                 570                 575
Val Met Phe Gln Gln Asn Glu Leu Leu Gln Asn Glu Pro His Pro Arg
            580                 585                 590
Arg Pro Tyr Ala Ile Trp His Gly Val Lys Leu Lys Gln Pro Asp Trp
            595                 600                 605
Ala Leu Trp Ser His Ser Leu Ala Val Ser Leu Cys His Pro Arg Gln
            610                 615                 620
Gln Glu Trp Leu Tyr Leu Ala Phe Asn Ala Tyr Trp Glu Asp Leu Arg
625                 630                 635                 640
Phe Gln Leu Pro Arg Pro Pro Arg Gly Arg Val Trp Tyr Arg Leu Leu
                645                 650                 655
Asp Thr Ser Leu Pro Asn Leu Glu Ala Cys His Leu Pro Asp Glu Ala
            660                 665                 670
Lys Pro Cys Leu Arg Arg Asp Tyr Ile Val Pro Ala Arg Ser Leu Leu
            675                 680                 685
Leu Leu Met Ala Arg Ala
    690

<210> SEQ ID NO 35
<211> LENGTH: 1500
<212> TYPE: DNA
<213> ORGANISM: Synechococcus elongatus PCC 7942

<400> SEQUENCE: 35
gtgtttacac gagccgccgg cattttgtta catcccactt cgttgccggg gccattcggc    60
agcggcgacc ttggtccggc ctcgcggcag tttcttgact ggttggcaac ggcgggacaa   120
caactgtggc aagtgttgcc ccttgggccg acaggctatg ctattcgcc ttacctctgc    180
tattccgcct ggctggcaa tcccgctctg atcagccctg aactcttggc agaagatggc   240
tggctccaag aatcggactg gcagactgt cctgcttttc cgagcgatcg cgtcgatttt   300
gccagcgtct tgccctatcg cgatcaactg ctgcgccgtg cctacagcca attcctgcaa   360
agagcggctt ccagcgatcg ccaactcttt caagctttct gtgaacagga agcccattgg   420
ctggatgact acgccctgtt catggcgatt aagctggcta gccaaggtca gccttggaca   480
gaatggccgg aagcgctgcg tcagcggcaa cctcaagcct ggctaaagc ccgcgatcgc    540
```

```
tggggcggcg aaattggctt ccagcagttt ctgcagtggc aatttcgcga gcagtggttg    600
gccctgcggg aagaagccca agcccgccat atttcgctga ttggcgatat tccgatctac    660
gtcgctcatg acagtgcgga cgtttgggcc aatcctcagt tctttgccct cgatcctgaa    720
acgggcgcag ttgatcagca ggccggtgtg ccgcctgact atttctccga aaccggccaa    780
ctctggggca atcccgtcta caactgggct gcgctgcagg cggatggcta tcgctggtgg    840
ttgcaacggc tgcaacagct cctcagctta gtggactaca ttcgcatcga ccacttccgc    900
ggtttagagg cgttttggtc ggttcccgct ggtgaagaaa cggcgatcga cggagagtgg    960
gtcaaagccc aggcgctga tctgctgagc acgattcgcc aaaaactggg agcgctaccg   1020
attctggcag aggatctcgg tgtgattacg ccggaggtgg aagcgctgcg cgatcgcttt   1080
gagctgccgg gcatgaagat tctgcagttc gcctttgact ctggggccgg caatgcctat   1140
ctaccgcaca actactgggg tcgtcgctgg gtggcttaca ccggcaccca cgacaatgac   1200
acgaccgtcg gctggttcct gtcccgcaat gacagcgatc gccaaacggt gctggattat   1260
ctgggcgcag agtcgggctg ggaaattgag tggaagctga tccgcttggc ttggagctcg   1320
acggcagatt gggcgatcgc accgctccaa gatgtcttcg gctggatag cagcgcccgc   1380
atgaatcgac cggggcaagc caccggcaac tgggactggc gcttcagtgc cgactggctg   1440
acgggcgatc gtgcccaacg cctgcggcga ctctcgcagc tctatggacg ctgtagatga   1500
```

<210> SEQ ID NO 36
<211> LENGTH: 499
<212> TYPE: PRT
<213> ORGANISM: Synechococcus elongatus PCC 7942

<400> SEQUENCE: 36

Met Phe Thr Arg Ala Ala Gly Ile Leu Leu His Pro Thr Ser Leu Pro
1               5                   10                  15

Gly Pro Phe Gly Ser Gly Asp Leu Gly Pro Ala Ser Arg Gln Phe Leu
            20                  25                  30

Asp Trp Leu Ala Thr Ala Gly Gln Gln Leu Trp Gln Val Leu Pro Leu
        35                  40                  45

Gly Pro Thr Gly Tyr Gly Tyr Ser Pro Tyr Leu Cys Tyr Ser Ala Leu
    50                  55                  60

Ala Gly Asn Pro Ala Leu Ile Ser Pro Glu Leu Leu Ala Glu Asp Gly
65                  70                  75                  80

Trp Leu Gln Glu Ser Asp Trp Ala Asp Cys Pro Ala Phe Pro Ser Asp
                85                  90                  95

Arg Val Asp Phe Ala Ser Val Leu Pro Tyr Arg Asp Gln Leu Leu Arg
            100                 105                 110

Arg Ala Tyr Ser Gln Phe Leu Gln Arg Ala Ala Ser Ser Asp Arg Gln
        115                 120                 125

Leu Phe Gln Ala Phe Cys Glu Gln Glu Ala His Trp Leu Asp Asp Tyr
    130                 135                 140

Ala Leu Phe Met Ala Ile Lys Leu Ala Ser Gln Gly Gln Pro Trp Thr
145                 150                 155                 160

Glu Trp Pro Glu Ala Leu Arg Gln Arg Gln Pro Gln Ala Leu Ala Lys
                165                 170                 175

Ala Arg Asp Arg Trp Gly Gly Glu Ile Gly Phe Gln Gln Phe Leu Gln
            180                 185                 190

Trp Gln Phe Arg Glu Gln Trp Leu Ala Leu Arg Glu Glu Ala Gln Ala
        195                 200                 205

```
Arg His Ile Ser Leu Ile Gly Asp Ile Pro Ile Tyr Val Ala His Asp
    210                 215                 220
Ser Ala Asp Val Trp Ala Asn Pro Gln Phe Phe Ala Leu Asp Pro Glu
225                 230                 235                 240
Thr Gly Ala Val Asp Gln Gln Ala Gly Val Pro Pro Asp Tyr Phe Ser
                245                 250                 255
Glu Thr Gly Gln Leu Trp Gly Asn Pro Val Tyr Asn Trp Ala Ala Leu
            260                 265                 270
Gln Ala Asp Gly Tyr Arg Trp Trp Leu Gln Arg Leu Gln Gln Leu Leu
        275                 280                 285
Ser Leu Val Asp Tyr Ile Arg Ile Asp His Phe Arg Gly Leu Glu Ala
    290                 295                 300
Phe Trp Ser Val Pro Ala Gly Glu Thr Ala Ile Asp Gly Glu Trp
305                 310                 315                 320
Val Lys Ala Pro Gly Ala Asp Leu Leu Ser Thr Ile Arg Gln Lys Leu
                325                 330                 335
Gly Ala Leu Pro Ile Leu Ala Glu Asp Leu Gly Val Ile Thr Pro Glu
            340                 345                 350
Val Glu Ala Leu Arg Asp Arg Phe Glu Leu Pro Gly Met Lys Ile Leu
        355                 360                 365
Gln Phe Ala Phe Asp Ser Gly Ala Gly Asn Ala Tyr Leu Pro His Asn
    370                 375                 380
Tyr Trp Gly Arg Arg Trp Val Ala Tyr Thr Gly Thr His Asp Asn Asp
385                 390                 395                 400
Thr Thr Val Gly Trp Phe Leu Ser Arg Asn Asp Ser Asp Arg Gln Thr
                405                 410                 415
Val Leu Asp Tyr Leu Gly Ala Glu Ser Gly Trp Glu Ile Glu Trp Lys
            420                 425                 430
Leu Ile Arg Leu Ala Trp Ser Ser Thr Ala Asp Trp Ala Ile Ala Pro
        435                 440                 445
Leu Gln Asp Val Phe Gly Leu Asp Ser Ser Ala Arg Met Asn Arg Pro
    450                 455                 460
Gly Gln Ala Thr Gly Asn Trp Asp Trp Arg Phe Ser Ala Asp Trp Leu
465                 470                 475                 480
Thr Gly Asp Arg Ala Gln Arg Leu Arg Arg Leu Ser Gln Leu Tyr Gly
                485                 490                 495
Arg Cys Arg

<210> SEQ ID NO 37
<211> LENGTH: 1632
<212> TYPE: DNA
<213> ORGANISM: Synechococcus elongatus PCC 7942

<400> SEQUENCE: 37
atgaatatcc acactgtcgc gacgcaagcc tttagcgacc aaaagcccgg tacctccggc      60
ctgcgcaagc aagttcctgt cttccaaaaa cggcactatc tcgaaaactt tgtccagtcg     120
atcttcgata gccttgaggg ttatcagggc cagacgttag tgctgggggg tgatggccgc     180
tactacaatc gcacagccat ccaaaccatt ctgaaaatgg cggcggccaa tggttggggc     240
cgcgttttag ttggacaagg cggtattctc tccacgccag cagtctccaa cctaatccgc     300
cagaacggag ccttcggcgg catcatcctc tcggctagcc acaacccagg gggccctgag     360
ggcgatttcg gcatcaagta caacatcagc aacggtggcc ctgcacccga aaaagtcacc     420
gatgccatct atgcctgcag cctcaaaatt gaggcctacc gcattctcga agccggtgac     480
```

```
gttgacctcg atcgactcgg tagtcaacaa ctgggcgaga tgaccgttga ggtgatcgac    540
tcggtcgccg actacagccg cttgatgcaa tccctgtttg acttcgatcg cattcgcgat    600
cgcctgaggg gggggctacg gattgcgatc gactcgatgc atgccgtcac cggtccctac    660
gccaccacga ttttgagaa ggagctaggc gcggcggcag gcactgtttt taatggcaag    720
ccgctggaag actttggcgg gggtcaccca gacccgaatt tggtctacgc ccacgacttg    780
gttgaactgt tgtttggcga tcgcgcccca gattttggcg cggcctccga tggcgatggc    840
gatcgcaaca tgatcttggg caatcacttt tttgtgaccc ctagcgacag cttggcgatt    900
ctcgcagcca atgccagcct agtgccggcc taccgcaatg actgtctgg gattgcgcga    960 tccatgccca ccagtgcggc ggccgatcgc gtcgcccaag ccctcaacct gccctgctac   1020
gaaaccccaa cggggttggaa gttttttcggc aatctgctcg atgccgatcg cgtcaccctc   1080
tgcggcgaag aaagctttgg cacaggctcc aaccatgtgc gcgagaagga tggcctgtgg   1140
gccgtgctgt tctggctgaa tattctggcg gtgcgcgagc aatccgtggc cgaaattgtc   1200
caagaacact ggcgcaccta cggccgcaac tactactctc gccacgacta cgaaggggtg   1260
gagagcgatc gagccagtac gctggtggac aaactgcgat cgcagctacc cagcctgacc   1320
ggacagaaac tgggagccta caccgttgcc tacgccgacg acttccgcta cgaagatccg   1380
gtcgatggca gcatcagcga acagcagggc attcgtattg ctttgaaga cggctcacgt   1440 atggtcttcc gcttgtctgg tactggtacg gcaggagcca ccctgcgcct ctacctcgag   1500
cgcttcgaag gggacaccac caaacagggt ctcgatcccc aagttgccct ggcagatttg   1560
attgcaatcg ccgatgaagt cgcccagatc acaaccttga cgggcttcga tcaaccgaca   1620
gtgatcacct ga                                                       1632
```

<210> SEQ ID NO 38
<211> LENGTH: 543
<212> TYPE: PRT
<213> ORGANISM: Synechococcus elongatus PCC 7942

<400> SEQUENCE: 38

```
Met Asn Ile His Thr Val Ala Thr Gln Ala Phe Ser Asp Gln Lys Pro
  1               5                  10                  15

Gly Thr Ser Gly Leu Arg Lys Gln Val Pro Val Phe Gln Lys Arg His
             20                  25                  30

Tyr Leu Glu Asn Phe Val Gln Ser Ile Phe Asp Ser Leu Glu Gly Tyr
         35                  40                  45

Gln Gly Gln Thr Leu Val Leu Gly Gly Asp Gly Arg Tyr Tyr Asn Arg
     50                  55                  60

Thr Ala Ile Gln Thr Ile Leu Lys Met Ala Ala Ala Asn Gly Trp Gly
 65                  70                  75                  80

Arg Val Leu Val Gly Gln Gly Gly Ile Leu Ser Thr Pro Ala Val Ser
                 85                  90                  95

Asn Leu Ile Arg Gln Asn Gly Ala Phe Gly Gly Ile Ile Leu Ser Ala
            100                 105                 110

Ser His Asn Pro Gly Gly Pro Glu Gly Asp Phe Gly Ile Lys Tyr Asn
        115                 120                 125

Ile Ser Asn Gly Gly Pro Ala Pro Glu Lys Val Thr Asp Ala Ile Tyr
    130                 135                 140

Ala Cys Ser Leu Lys Ile Glu Ala Tyr Arg Ile Leu Glu Ala Gly Asp
145                 150                 155                 160
```

Val Asp Leu Asp Arg Leu Gly Ser Gln Gln Leu Gly Glu Met Thr Val
                165                 170                 175

Glu Val Ile Asp Ser Val Ala Asp Tyr Ser Arg Leu Met Gln Ser Leu
            180                 185                 190

Phe Asp Phe Asp Arg Ile Arg Asp Arg Leu Arg Gly Gly Leu Arg Ile
        195                 200                 205

Ala Ile Asp Ser Met His Ala Val Thr Gly Pro Tyr Ala Thr Thr Ile
    210                 215                 220

Phe Glu Lys Glu Leu Gly Ala Ala Gly Thr Val Phe Asn Gly Lys
225                 230                 235                 240

Pro Leu Glu Asp Phe Gly Gly His Pro Asp Pro Asn Leu Val Tyr
            245                 250                 255

Ala His Asp Leu Val Glu Leu Leu Phe Gly Asp Arg Ala Pro Asp Phe
        260                 265                 270

Gly Ala Ala Ser Asp Gly Asp Gly Asp Arg Asn Met Ile Leu Gly Asn
    275                 280                 285

His Phe Phe Val Thr Pro Ser Asp Ser Leu Ala Ile Leu Ala Ala Asn
290                 295                 300

Ala Ser Leu Val Pro Ala Tyr Arg Asn Gly Leu Ser Gly Ile Ala Arg
305                 310                 315                 320

Ser Met Pro Thr Ser Ala Ala Ala Asp Arg Val Ala Gln Ala Leu Asn
            325                 330                 335

Leu Pro Cys Tyr Glu Thr Pro Thr Gly Trp Lys Phe Phe Gly Asn Leu
        340                 345                 350

Leu Asp Ala Asp Arg Val Thr Leu Cys Gly Glu Glu Ser Phe Gly Thr
    355                 360                 365

Gly Ser Asn His Val Arg Glu Lys Asp Gly Leu Trp Ala Val Leu Phe
370                 375                 380

Trp Leu Asn Ile Leu Ala Val Arg Glu Gln Ser Val Ala Glu Ile Val
385                 390                 395                 400

Gln Glu His Trp Arg Thr Tyr Gly Arg Asn Tyr Tyr Ser Arg His Asp
            405                 410                 415

Tyr Glu Gly Val Glu Ser Asp Arg Ala Ser Thr Leu Val Asp Lys Leu
        420                 425                 430

Arg Ser Gln Leu Pro Ser Leu Thr Gly Gln Lys Leu Gly Ala Tyr Thr
    435                 440                 445

Val Ala Tyr Ala Asp Asp Phe Arg Tyr Glu Asp Pro Val Asp Gly Ser
450                 455                 460

Ile Ser Glu Gln Gln Gly Ile Arg Ile Gly Phe Glu Asp Gly Ser Arg
465                 470                 475                 480

Met Val Phe Arg Leu Ser Gly Thr Gly Thr Ala Gly Ala Thr Leu Arg
            485                 490                 495

Leu Tyr Leu Glu Arg Phe Glu Gly Asp Thr Thr Lys Gln Gly Leu Asp
        500                 505                 510

Pro Gln Val Ala Leu Ala Asp Leu Ile Ala Ile Ala Asp Glu Val Ala
    515                 520                 525

Gln Ile Thr Thr Leu Thr Gly Phe Asp Gln Pro Thr Val Ile Thr
530                 535                 540

<210> SEQ ID NO 39
<211> LENGTH: 1038
<212> TYPE: DNA
<213> ORGANISM: Synechococcus elongatus PCC 7942

<400> SEQUENCE: 39

-continued

```
atgaccttgc tattggccgg ggatatcggc ggaaccaaaa cgaatttaat gttggcgatc     60
gcctctgatt gcgatcgttt agaaccgctc atcaggcca gttttgccag tgcggcctac    120
cctgatttag tgccgatggt gcaggagttt ttggctgccg cacctccgc cgaggtgcga    180
tcgccagttg tggcttgttt tggcattgcc ggccccgttg tccatggaac cgcgaagctg    240
acgaacctgc cttggcagct ctctgaagcg cggctggcga aggaattggg cattgcgcag    300
gtggcgttga tcaatgattt tgctgcgatc gcctacggcc tacccggctt gaccgccgaa    360
gatcaagtcg ttgtgcaagt cggtgaagcc gatccggcgg ctccgatcgc cattctgggg    420
gcaggaactg gcttgggcga aggcttcatc attcccacag cccaaggccg ccaagtgttt    480
ggcagcgaag ttctcacgc tgactttgcg ccgcaaaccg aactggagtc cgagttactg    540
catttttctac gcaattttta cgcaatcgag catatctcgg tcgagcgagt ggtctccggc    600
caagggattg cagccatcta cgccttcctg cgcgatcgcc atcccgacca agaaaatcca    660
gcccttgggg cgattgcctc ggcttggcaa acgggcggcg accaagcccc tgatctggca    720
gcagccgtat cccaagcagc cttgagcgat cgcgatccgc tggccctaca agccatgcag    780
atatttgtca gtgcttacgg ggcggaagcc ggcaacctcg cgttgaaatt gctctcctac    840
ggcggggtct acgtcgccgg cgggattgcg ggcaaaatcc tgccgctctt gactgatggc    900
acttttctgc aagccttcca agccaaggga cgggtgaagg ggctgctgac gcggatgcct    960
atcacgatcg tcacgaacca cgaagtcggg ctgatcgggg ctggactgcg ggcggctgcg   1020
atcgctactc aaccatga                                                 1038
```

<210> SEQ ID NO 40
<211> LENGTH: 345
<212> TYPE: PRT
<213> ORGANISM: Synechococcus elongatus PCC 7942

<400> SEQUENCE: 40

```
Met Thr Leu Leu Leu Ala Gly Asp Ile Gly Gly Thr Lys Thr Asn Leu
  1               5                  10                  15

Met Leu Ala Ile Ala Ser Asp Cys Asp Arg Leu Glu Pro Leu His Gln
             20                  25                  30

Ala Ser Phe Ala Ser Ala Ala Tyr Pro Asp Leu Val Pro Met Val Gln
         35                  40                  45

Glu Phe Leu Ala Ala Ala Pro Ser Ala Glu Val Arg Ser Pro Val Val
     50                  55                  60

Ala Cys Phe Gly Ile Ala Gly Pro Val His Gly Thr Ala Lys Leu
 65                  70                  75                  80

Thr Asn Leu Pro Trp Gln Leu Ser Glu Ala Arg Leu Ala Lys Glu Leu
                 85                  90                  95

Gly Ile Ala Gln Val Ala Leu Ile Asn Asp Phe Ala Ala Ile Ala Tyr
            100                 105                 110

Gly Leu Pro Gly Leu Thr Ala Glu Asp Gln Val Val Gln Val Gly
        115                 120                 125

Glu Ala Asp Pro Ala Ala Pro Ile Ala Ile Leu Gly Ala Gly Thr Gly
    130                 135                 140

Leu Gly Glu Gly Phe Ile Ile Pro Thr Ala Gln Gly Arg Gln Val Phe
145                 150                 155                 160

Gly Ser Glu Gly Ser His Ala Asp Phe Ala Pro Gln Thr Glu Leu Glu
                165                 170                 175

Ser Glu Leu Leu His Phe Leu Arg Asn Phe Tyr Ala Ile Glu His Ile
```

|      |      | 180  |      |      |      | 185  |      |      |      | 190  |      |
|------|------|------|------|------|------|------|------|------|------|------|------|
| Ser  | Val  | Glu  | Arg  | Val  | Ser  | Gly  | Gln  | Gly  | Ile  | Ala  | Ala  | Ile Tyr Ala |

Ser Val Glu Arg Val Ser Gly Gln Gly Ile Ala Ala Ile Tyr Ala
            195                   200                 205

Phe Leu Arg Asp Arg His Pro Asp Gln Glu Asn Pro Ala Leu Gly Ala
    210                   215                 220

Ile Ala Ser Ala Trp Gln Thr Gly Gly Asp Gln Ala Pro Asp Leu Ala
225                 230                 235             240

Ala Ala Val Ser Gln Ala Ala Leu Ser Asp Arg Asp Pro Leu Ala Leu
         245                 250               255

Gln Ala Met Gln Ile Phe Val Ser Ala Tyr Gly Ala Glu Ala Gly Asn
    260                 265               270

Leu Ala Leu Lys Leu Leu Ser Tyr Gly Gly Val Tyr Val Ala Gly Gly
         275               280             285

Ile Ala Gly Lys Ile Leu Pro Leu Leu Thr Asp Gly Thr Phe Leu Gln
    290                 295               300

Ala Phe Gln Ala Lys Gly Arg Val Lys Gly Leu Leu Thr Arg Met Pro
305                 310                 315             320

Ile Thr Ile Val Thr Asn His Glu Val Gly Leu Ile Gly Ala Gly Leu
         325                 330               335

Arg Ala Ala Ala Ile Ala Thr Gln Pro
    340                 345

<210> SEQ ID NO 41
<211> LENGTH: 1587
<212> TYPE: DNA
<213> ORGANISM: Synechococcus elongatus PCC 7942

<400> SEQUENCE: 41

```
atgaccgccc agcagctctg caacgctac ctcgattggc tctactacga tccctcgctg      60
gagttttacc tcgacatcag ccgcatggga ttcgatgacg ctttcgttac tagcatgcag     120
cccaagttcc agcacgcctt tgcggcgatg cagagctcg aggccggagc gatcgccaac     180
cccgatgaac agcggatggt cggccactac tggctgcgcg atcctgagct ggcacccaca     240
ccggagctgc agacccaaat tcgcgacacg ctggccgcga tccaagactt cgccctcaaa     300
gtacacagtg gcgtgttgcg gccacccacc ggctcccgct tcaccgacat tctctcaatt     360
ggcattggcg gtcggccct agggccgcag tttgtctcag aagccctccg gcctcaagcg     420
gcactgctcc agattcactt ctttgacaac accgatccag ctggcttcga tcgcgttta      480
gctgatctcg cgatcgcct tgcttccacc ttagtaatcg ttatttccaa atctggcggc     540
actcccgaaa cccgcaacgg catgctggag gttcagtccg cctttgccca gcgagggatt     600
gcctttgcgc ccaagctgt cgccgtcaca ggggtgggga ccatctcga tcatgtagcg      660
atcacagaaa gatggctggc ccgtttcccc atggaagact gggtgggcgg ccgcacctct     720
gaactatctg cagtcggtct actctcggca gccctactgg gatcgacat caccgccatg     780
ctggccgggg cgcggcaaat ggacgccctg acccgccatt ccgatttgcg acaaaatccg     840
gcagcgctct tggctttgag ctggtactgg gccggcaatg ggcaaggcaa aaaagacatg     900
gtcatcctgc cctacaagga cagcctgctg ctgtttagcc gctatctgca gcagttgatc     960
atggagtcac tgggcaagga gcgcgatctg ctcggcaagg tagttcacca aggcatcgcc    1020
gtttacggca acaaaggctc gaccgatcaa catgcctacg tccagcaact gcgcgagggc    1080
attcctaact tctttgccac gtttatcgag gtgctcgaag accgacaggg gccgtcgcca    1140
gtcgtggagc ctggcatcac cagtggcgac tatctcagcg ggctgcttca aggcacccgc    1200
```

-continued

```
gcggcgcttt acgaaaatgg gcgtgagtcg atcacgatta cggtgccgcg cgttgatgca      1260
caacaggtgg gggccttgat cgcgctgtat gaacgggcgg tgggactcta tgccagcttg      1320
gttggcatca atgcctatca ccagccgggg gtggaagccg gcaaaaaggc tgctgccggt      1380
gttctcgaga tccagcgcca gattgtggag ttgctccaac agggacaacc actctcgatc      1440
gcagcgatcg cagacgattt aggtcagagt gagcagattg aaacgatcta caaaatcctg      1500
cgccatctcg aagccaatca acgcggcgtt cagttaaccg cgatcgcca taatcccctc      1560 agtctgattg cgagttggca acgataa                                         1587
```

<210> SEQ ID NO 42
<211> LENGTH: 528
<212> TYPE: PRT
<213> ORGANISM: Synechococcus elongatus PCC 7942

<400> SEQUENCE: 42

```
Met Thr Ala Gln Gln Leu Trp Gln Arg Tyr Leu Asp Trp Leu Tyr Tyr
  1               5                  10                  15

Asp Pro Ser Leu Glu Phe Tyr Leu Asp Ile Ser Arg Met Gly Phe Asp
             20                  25                  30

Asp Ala Phe Val Thr Ser Met Gln Pro Lys Phe Gln His Ala Phe Ala
         35                  40                  45

Ala Met Ala Glu Leu Glu Ala Gly Ala Ile Ala Asn Pro Asp Glu Gln
     50                  55                  60

Arg Met Val Gly His Tyr Trp Leu Arg Asp Pro Glu Leu Ala Pro Thr
 65                  70                  75                  80

Pro Glu Leu Gln Thr Gln Ile Arg Asp Thr Leu Ala Ala Ile Gln Asp
                 85                  90                  95

Phe Ala Leu Lys Val His Ser Gly Val Leu Arg Pro Pro Thr Gly Ser
            100                 105                 110

Arg Phe Thr Asp Ile Leu Ser Ile Gly Ile Gly Gly Ser Ala Leu Gly
        115                 120                 125

Pro Gln Phe Val Ser Glu Ala Leu Arg Pro Gln Ala Ala Leu Leu Gln
    130                 135                 140

Ile His Phe Phe Asp Asn Thr Asp Pro Ala Gly Phe Asp Arg Val Leu
145                 150                 155                 160

Ala Asp Leu Gly Asp Arg Leu Ala Ser Thr Leu Val Ile Val Ile Ser
                165                 170                 175

Lys Ser Gly Gly Thr Pro Glu Thr Arg Asn Gly Met Leu Glu Val Gln
            180                 185                 190

Ser Ala Phe Ala Gln Arg Gly Ile Ala Phe Ala Pro Gln Ala Val Ala
        195                 200                 205

Val Thr Gly Val Gly Ser His Leu Asp His Val Ala Ile Thr Glu Arg
    210                 215                 220

Trp Leu Ala Arg Phe Pro Met Glu Asp Trp Val Gly Gly Arg Thr Ser
225                 230                 235                 240

Glu Leu Ser Ala Val Gly Leu Leu Ser Ala Ala Leu Leu Gly Ile Asp
                245                 250                 255

Ile Thr Ala Met Leu Ala Gly Ala Arg Gln Met Asp Ala Leu Thr Arg
            260                 265                 270

His Ser Asp Leu Arg Gln Asn Pro Ala Ala Leu Leu Ala Leu Ser Trp
        275                 280                 285

Tyr Trp Ala Gly Asn Gly Gln Gly Lys Lys Asp Met Val Ile Leu Pro
    290                 295                 300
```

```
Tyr Lys Asp Ser Leu Leu Leu Phe Ser Arg Tyr Leu Gln Gln Leu Ile
305                 310                 315                 320

Met Glu Ser Leu Gly Lys Glu Arg Asp Leu Leu Gly Lys Val Val His
            325                 330                 335

Gln Gly Ile Ala Val Tyr Gly Asn Lys Gly Ser Thr Asp Gln His Ala
        340                 345                 350

Tyr Val Gln Gln Leu Arg Glu Gly Ile Pro Asn Phe Phe Ala Thr Phe
    355                 360                 365

Ile Glu Val Leu Glu Asp Arg Gln Gly Pro Ser Pro Val Val Glu Pro
370                 375                 380

Gly Ile Thr Ser Gly Asp Tyr Leu Ser Gly Leu Leu Gln Gly Thr Arg
385                 390                 395                 400

Ala Ala Leu Tyr Glu Asn Gly Arg Glu Ser Ile Thr Ile Thr Val Pro
            405                 410                 415

Arg Val Asp Ala Gln Gln Val Gly Ala Leu Ile Ala Leu Tyr Glu Arg
        420                 425                 430

Ala Val Gly Leu Tyr Ala Ser Leu Val Gly Ile Asn Ala Tyr His Gln
    435                 440                 445

Pro Gly Val Glu Ala Gly Lys Lys Ala Ala Ala Gly Val Leu Glu Ile
450                 455                 460

Gln Arg Gln Ile Val Glu Leu Leu Gln Gln Gly Gln Pro Leu Ser Ile
465                 470                 475                 480

Ala Ala Ile Ala Asp Asp Leu Gly Gln Ser Glu Gln Ile Glu Thr Ile
            485                 490                 495

Tyr Lys Ile Leu Arg His Leu Glu Ala Asn Gln Arg Gly Val Gln Leu
        500                 505                 510

Thr Gly Asp Arg His Asn Pro Leu Ser Leu Ile Ala Ser Trp Gln Arg
    515                 520                 525

<210> SEQ ID NO 43
<211> LENGTH: 1434
<212> TYPE: DNA
<213> ORGANISM: Synechocystis sp. PCC 6803

<400> SEQUENCE: 43
atgaagattt tatttgtggc ggcggaagta tccccctag caaaggtagg tggcatgggg      60
gatgtggtgg gttccctgcc taaagttctg catcagttgg ccatgatgt ccgtgtcttc     120 atgcccctact acggtttcat cggcgacaag attgatgtgc caaggagcc ggtctggaaa    180 ggggaagcca tgttccagca gtttgctgtt taccagtcct atctaccgga caccaaaatt    240
cctctctact tgttcggcca tccagctttc gactcccgaa ggatctatgg cggagatgac    300
gaggcgtggc ggttcacttt ttttctaac ggggcagctg aatttgcctg gaaccattgg    360
aagccggaaa ttatccattg ccatgattgg cacactggca tgatccctgt ttggatgcat    420
cagtccccag acatcgccac cgttttcacc atccataatc ttgcttacca agggccctgg    480
cggggcttgc ttgaaactat gacttggtgt ccttggtaca tgcagggaga caatgtgatg    540
gcggcggcga ttcaatttgc caatcgggtg actaccgttt ctcccaccta tgcccaacag    600
atccaaaccc cggcctatgg ggaaaagctg aagggttat tgtcctacct gagtggtaat    660
ttagtcggta ttctcaacgg tattgatacg agatttaca acccggcgga agaccgcttt    720
atcagcaatg tttcgatgc ggacagtttg acaagcggg tgaaaaataa aattgccatc    780
caggaggaaa cggggttaga aattaatcgt aatgccatgg tggtgggtat agtggctcgc    840
```

-continued

```
ttggtggaac aaaaggggat tgatttggtg attcagatcc ttgaccgctt catgtcctac    900
accgattccc agttaattat cctcggcact ggcgatcgcc attacgaaac ccaactttgg    960
cagatggctt cccgatttcc tgggcggatg gcggtgcaat tactccacaa cgatgccctt   1020
tcccgtcgag tctatgccgg ggcggatgtg tttttaatgc cttctcgctt tgagccctgt   1080
gggctgagtc aattgatggc catgcgttat ggctgtatcc ccattgtgcg gcggacaggg   1140
ggtttggtgg atacggtatc cttctacgat cctatcaatg aagccggcac cggctattgc   1200
tttgaccgtt atgaaccoct ggattgcttt acggccatgg tgcgggcctg ggagggtttc   1260
cgtttcaagg cagattggca aaaattacag caacgggcca tgcgggcaga ctttagttgg   1320
taccgttccg ccggggaata tatcaaagtt tataagggcg tggtggggaa accggaggaa   1380
ttaagcccca tggaagagga aaaaatcgct gagttaactg cttcctatcg ctaa         1434
```

<210> SEQ ID NO 44
<211> LENGTH: 477
<212> TYPE: PRT
<213> ORGANISM: Synechocystis sp. PCC 6803

<400> SEQUENCE: 44

```
Met Lys Ile Leu Phe Val Ala Ala Glu Val Ser Pro Leu Ala Lys Val
 1               5                  10                  15
Gly Gly Met Gly Asp Val Val Gly Ser Leu Pro Lys Val Leu His Gln
                20                  25                  30
Leu Gly His Asp Val Arg Val Phe Met Pro Tyr Tyr Gly Phe Ile Gly
            35                  40                  45
Asp Lys Ile Asp Val Pro Lys Glu Pro Val Trp Lys Gly Glu Ala Met
    50                  55                  60
Phe Gln Gln Phe Ala Val Tyr Gln Ser Tyr Leu Pro Asp Thr Lys Ile
65                  70                  75                  80
Pro Leu Tyr Leu Phe Gly His Pro Ala Phe Asp Ser Arg Arg Ile Tyr
                85                  90                  95
Gly Gly Asp Asp Glu Ala Trp Arg Phe Thr Phe Ser Asn Gly Ala
                100                 105                 110
Ala Glu Phe Ala Trp Asn His Trp Lys Pro Glu Ile Ile His Cys His
            115                 120                 125
Asp Trp His Thr Gly Met Ile Pro Val Trp Met His Gln Ser Pro Asp
    130                 135                 140
Ile Ala Thr Val Phe Thr Ile His Asn Leu Ala Tyr Gln Gly Pro Trp
145                 150                 155                 160
Arg Gly Leu Leu Glu Thr Met Thr Trp Cys Pro Trp Tyr Met Gln Gly
                165                 170                 175
Asp Asn Val Met Ala Ala Ala Ile Gln Phe Ala Asn Arg Val Thr Thr
            180                 185                 190
Val Ser Pro Thr Tyr Ala Gln Gln Ile Gln Thr Pro Ala Tyr Gly Glu
        195                 200                 205
Lys Leu Glu Gly Leu Leu Ser Tyr Leu Ser Gly Asn Leu Val Gly Ile
    210                 215                 220
Leu Asn Gly Ile Asp Thr Glu Ile Tyr Asn Pro Ala Glu Asp Arg Phe
225                 230                 235                 240
Ile Ser Asn Val Phe Asp Ala Asp Ser Leu Asp Lys Arg Val Lys Asn
                245                 250                 255
Lys Ile Ala Ile Gln Glu Glu Thr Gly Leu Glu Ile Asn Arg Asn Ala
            260                 265                 270
```

```
Met Val Val Gly Ile Val Ala Arg Leu Val Glu Gln Lys Gly Ile Asp
            275                 280                 285
Leu Val Ile Gln Ile Leu Asp Arg Phe Met Ser Tyr Thr Asp Ser Gln
            290                 295                 300
Leu Ile Ile Leu Gly Thr Gly Asp Arg His Tyr Glu Thr Gln Leu Trp
305                 310                 315                 320
Gln Met Ala Ser Arg Phe Pro Gly Arg Met Ala Val Gln Leu Leu His
                325                 330                 335
Asn Asp Ala Leu Ser Arg Arg Val Tyr Ala Gly Ala Asp Val Phe Leu
            340                 345                 350
Met Pro Ser Arg Phe Glu Pro Cys Gly Leu Ser Gln Leu Met Ala Met
            355                 360                 365
Arg Tyr Gly Cys Ile Pro Ile Val Arg Arg Thr Gly Gly Leu Val Asp
            370                 375                 380
Thr Val Ser Phe Tyr Asp Pro Ile Asn Glu Ala Gly Thr Gly Tyr Cys
385                 390                 395                 400
Phe Asp Arg Tyr Glu Pro Leu Asp Cys Phe Thr Ala Met Val Arg Ala
                405                 410                 415
Trp Glu Gly Phe Arg Phe Lys Ala Asp Trp Gln Lys Leu Gln Gln Arg
            420                 425                 430
Ala Met Arg Ala Asp Phe Ser Trp Tyr Arg Ser Ala Gly Glu Tyr Ile
            435                 440                 445
Lys Val Tyr Lys Gly Val Val Gly Lys Pro Glu Glu Leu Ser Pro Met
            450                 455                 460
Glu Glu Glu Lys Ile Ala Glu Leu Thr Ala Ser Tyr Arg
465                 470                 475

<210> SEQ ID NO 45
<211> LENGTH: 1419
<212> TYPE: DNA
<213> ORGANISM: Nostoc sp. PCC 7120

<400> SEQUENCE: 45
atgcggattc tatttgtggc agcagaagca gcacccattg caaaagtagg agggatgggt      60
gatgttgtcg gtgcattacc taaggtcttg agaaaaatgg ggcatgatgt acgtatcttc     120
ttgccctatt acggcttttt gccagacaaa atggagattc ccaaagatcc aatatggaag     180
ggatacgcca tgtttcagga ctttacagtt cacgaagcag ttctgcctgg tactgatgtt     240
cccttgtatt tatttggaca tccagccttt acccccggc ggattattc gggagatgat      300 gaagactggc gcttcaccct tgttttccaa tggtgcggctg agttttgctg gaattactgg     360
aaacccgaca ttattcactg tcatgattgg cacacgggca tgattcctgt gtggatgaac     420
caatcaccag atatccacca gtcttcact atccacaatc tggcttacca agggccttgg      480
cgttggtatt tagataaaat tacttggtgt ccttggtata tgcagggaca caacacaatg     540
gcggcggctg tccagtttgc ggacagggta aatacagttt ctcccacata cgccgagcaa     600
atcaagaccc cggcttacgg tgagaaaata gaaggtttgc tgtctttcat cagtggtaaa     660
ttatctggga ttgttaacgg tatagatacg gaagtttacg acccagctaa tgataaatat     720
attgctcaaa cgttcactgc cgatacttta gataaacgca agccaacaa aattgcttta      780 caagaagaag taggattaga agttaacagc aatgcctttt taattggcat ggtgacaagg     840
ttagtcgagc agaagggctt agatttagtc atccaaatgc tcgatcgctt tatggcttat     900
actgatgctc agttcgtctt gttgggaaca ggcgatcgct actacgaaac ccaaatgtgg     960
```

-continued

```
caattagcat cccgctaccc cggtcgtatg gctacttacc tcctgtataa cgatgcccta   1020
tctcgccgca tctacgctgg tactgatgcc tttttgatgc ccagtcgctt tgaaccatgc   1080
ggtattagtc aaatgatggc tttacgctac ggttccattc ccatcgtccg ccgcactgga   1140
ggcttggttg acaccgtatc ccaccacgac cccatcaacg aagcaggtac aggctactgc   1200
ttcgaccgct acgaacccct cgacttattt acctgcatga ttcgcgcctg ggaaggcttc   1260
cgctacaaac cacaatggca agaactacaa aaacgcggta tgagtcaaga cttcagctgg   1320
tacaaatccg ctaaggaata cgacaaactc tatcgctcaa tgtacggttt gccagaccca   1380
gaagagacac agccggagtt aattctgaca aatcagtag                          1419
```

```
<210> SEQ ID NO 46
<211> LENGTH: 472
<212> TYPE: PRT
<213> ORGANISM: Nostoc sp. PCC 7120

<400> SEQUENCE: 46

Met Arg Ile Leu Phe Val Ala Ala Glu Ala Ala Pro Ile Ala Lys Val
1               5                   10                  15

Gly Gly Met Gly Asp Val Val Gly Ala Leu Pro Lys Val Leu Arg Lys
            20                  25                  30

Met Gly His Asp Val Arg Ile Phe Leu Pro Tyr Tyr Gly Phe Leu Pro
        35                  40                  45

Asp Lys Met Glu Ile Pro Lys Asp Pro Ile Trp Lys Gly Tyr Ala Met
    50                  55                  60

Phe Gln Asp Phe Thr Val His Glu Ala Val Leu Pro Gly Thr Asp Val
65                  70                  75                  80

Pro Leu Tyr Leu Phe Gly His Pro Ala Phe Thr Pro Arg Arg Ile Tyr
                85                  90                  95

Ser Gly Asp Asp Glu Asp Trp Arg Phe Thr Leu Phe Ser Asn Gly Ala
            100                 105                 110

Ala Glu Phe Cys Trp Asn Tyr Trp Lys Pro Asp Ile Ile His Cys His
        115                 120                 125

Asp Trp His Thr Gly Met Ile Pro Val Trp Met Asn Gln Ser Pro Asp
    130                 135                 140

Ile Thr Thr Val Phe Thr Ile His Asn Leu Ala Tyr Gln Gly Pro Trp
145                 150                 155                 160

Arg Trp Tyr Leu Asp Lys Ile Thr Trp Cys Pro Trp Tyr Met Gln Gly
                165                 170                 175

His Asn Thr Met Ala Ala Ala Val Gln Phe Ala Asp Arg Val Asn Thr
            180                 185                 190

Val Ser Pro Thr Tyr Ala Glu Gln Ile Lys Thr Pro Ala Tyr Gly Glu
        195                 200                 205

Lys Ile Glu Gly Leu Leu Ser Phe Ile Ser Gly Lys Leu Ser Gly Ile
    210                 215                 220

Val Asn Gly Ile Asp Thr Glu Val Tyr Asp Pro Ala Asn Asp Lys Tyr
225                 230                 235                 240

Ile Ala Gln Thr Phe Thr Ala Asp Thr Leu Asp Lys Arg Lys Ala Asn
                245                 250                 255

Lys Ile Ala Leu Gln Glu Glu Val Gly Leu Glu Val Asn Ser Asn Ala
            260                 265                 270

Phe Leu Ile Gly Met Val Thr Arg Leu Val Glu Gln Lys Gly Leu Asp
        275                 280                 285

Leu Val Ile Gln Met Leu Asp Arg Phe Met Ala Tyr Thr Asp Ala Gln
```

```
                290                 295                 300
Phe Val Leu Leu Gly Thr Gly Asp Arg Tyr Tyr Glu Thr Gln Met Trp
305                 310                 315                 320

Gln Leu Ala Ser Arg Tyr Pro Gly Arg Met Ala Thr Tyr Leu Leu Tyr
                325                 330                 335

Asn Asp Ala Leu Ser Arg Arg Ile Tyr Ala Gly Thr Asp Ala Phe Leu
            340                 345                 350

Met Pro Ser Arg Phe Glu Pro Cys Gly Ile Ser Gln Met Met Ala Leu
        355                 360                 365

Arg Tyr Gly Ser Ile Pro Ile Val Arg Arg Thr Gly Gly Leu Val Asp
    370                 375                 380

Thr Val Ser His His Asp Pro Ile Asn Glu Ala Gly Thr Gly Tyr Cys
385                 390                 395                 400

Phe Asp Arg Tyr Glu Pro Leu Asp Leu Phe Thr Cys Met Ile Arg Ala
                405                 410                 415

Trp Glu Gly Phe Arg Tyr Lys Pro Gln Trp Gln Glu Leu Gln Lys Arg
            420                 425                 430

Gly Met Ser Gln Asp Phe Ser Trp Tyr Lys Ser Ala Lys Glu Tyr Asp
        435                 440                 445

Lys Leu Tyr Arg Ser Met Tyr Gly Leu Pro Asp Pro Glu Glu Thr Gln
    450                 455                 460

Pro Glu Leu Ile Leu Thr Asn Gln
465                 470

<210> SEQ ID NO 47
<211> LENGTH: 1419
<212> TYPE: DNA
<213> ORGANISM: Anabaena variabilis

<400> SEQUENCE: 47
atgcggattc tatttgtggc agcagaagca gcacccatcg caaaagtagg agggatgggt      60
gatgttgtcg gtgcattacc taaggtcttg agaaaaatgg ggcatgatgt gcgtatcttc     120
ttgccctatt acggcttttt gccagacaaa atggaaattc ccaaagatcc aatctggaag     180
ggatacgcca tgtttcagga ctttacagtt cacgaagcag ttctgcctgg tactgatgtt     240
cccttgtatt tatttggaca tccagccttc aaccccggc gaattttatt gggagatgat     300
gaagactggc ggttcacctt gttttccaat ggtgcgcgg aattttgttg gaattactgg     360
aaaccagaaa ttattcactg tcacgattgg cacacaggca tgattcctgt gtggatgaac     420
caatcaccag atatccacca gtcttcact atccacaacc tagcttacca agggccttgg     480
cgttggtatc tagataaaat tacttggtgt ccttggtata tgcagggaca caacacaatg     540
gcggcggctg tccagtttgc tgacagagta aataccgttt ctcctacata cgccgagcaa     600
atcaagaccc cggcttacgg tgagaaaata gaaggcttgc tgtctttcat cagtggtaaa     660
ttatctggga ttgttaacgg tatagatacg gaagtttatg acccagctaa tgataaattt     720
attgctcaaa cttttactgc tgatacttta gataaacgca agccaacaa aattgcttta     780 caagaagaag tagggttaga agttaacagc aatgcctttt taattggcat ggtgacaagg     840
ttagtcgagc agaagggttt agatttagtc atccaaatgc tcgatcgctt atggcttat     900 actgatgctc agttcgtctt gttaggaaca ggcgatcgct actacgaaac tcaaatgtgg     960
caattagcat cccgctaccc cggacgtatg gccacctatc tcctatacaa tgatgcccta    1020
tcccgccgca tctacgccgg ttctgatgcc tttttaatgc ccagccgctt tgaaccatgc    1080
```

```
ggtattagcc agatgatggc tttacgctac ggttccatcc ccatcgttcg ccgcactggg    1140
ggtttagttg acaccgtatc ccaccacgac cccgtaaacg aagccggtac aggctactgc    1200
tttgaccgct acgaacccct agacttattc acctgcatga ttcgcgcctg ggaaggcttc    1260
cgctacaaac cccaatggca agaactacaa aagcgtggta tgagtcaaga cttcagctgg    1320
tacaaatccg ctaaggaata cgacagactc tatcgctcaa tatacggttt gccagaagca    1380
gaagagacac agccagagtt aattctggca aatcagtag                           1419
```

<210> SEQ ID NO 48
<211> LENGTH: 472
<212> TYPE: PRT
<213> ORGANISM: Anabaena variabilis

<400> SEQUENCE: 48

```
Met Arg Ile Leu Phe Val Ala Ala Glu Ala Ala Pro Ile Ala Lys Val
1               5                   10                  15

Gly Gly Met Gly Asp Val Val Gly Ala Leu Pro Lys Val Leu Arg Lys
            20                  25                  30

Met Gly His Asp Val Arg Ile Phe Leu Pro Tyr Tyr Gly Phe Leu Pro
        35                  40                  45

Asp Lys Met Glu Ile Pro Lys Asp Pro Ile Trp Lys Gly Tyr Ala Met
    50                  55                  60

Phe Gln Asp Phe Thr Val His Glu Ala Val Leu Pro Gly Thr Asp Val
65                  70                  75                  80

Pro Leu Tyr Leu Phe Gly His Pro Ala Phe Asn Pro Arg Arg Ile Tyr
                85                  90                  95

Ser Gly Asp Asp Glu Asp Trp Arg Phe Thr Leu Phe Ser Asn Gly Ala
            100                 105                 110

Ala Glu Phe Cys Trp Asn Tyr Trp Lys Pro Glu Ile Ile His Cys His
        115                 120                 125

Asp Trp His Thr Gly Met Ile Pro Val Trp Met Asn Gln Ser Pro Asp
    130                 135                 140

Ile Thr Thr Val Phe Thr Ile His Asn Leu Ala Tyr Gln Gly Pro Trp
145                 150                 155                 160

Arg Trp Tyr Leu Asp Lys Ile Thr Trp Cys Pro Trp Tyr Met Gln Gly
                165                 170                 175

His Asn Thr Met Ala Ala Ala Val Gln Phe Ala Asp Arg Val Asn Thr
            180                 185                 190

Val Ser Pro Thr Tyr Ala Glu Gln Ile Lys Thr Pro Ala Tyr Gly Glu
        195                 200                 205

Lys Ile Glu Gly Leu Leu Ser Phe Ile Ser Gly Lys Leu Ser Gly Ile
    210                 215                 220

Val Asn Gly Ile Asp Thr Glu Val Tyr Asp Pro Ala Asn Asp Lys Phe
225                 230                 235                 240

Ile Ala Gln Thr Phe Thr Ala Asp Thr Leu Asp Lys Arg Lys Ala Asn
                245                 250                 255

Lys Ile Ala Leu Gln Glu Glu Val Gly Leu Glu Val Asn Ser Asn Ala
            260                 265                 270

Phe Leu Ile Gly Met Val Thr Arg Leu Val Glu Gln Lys Gly Leu Asp
        275                 280                 285

Leu Val Ile Gln Met Leu Asp Arg Phe Met Ala Tyr Thr Asp Ala Gln
    290                 295                 300

Phe Val Leu Leu Gly Thr Gly Asp Arg Tyr Tyr Glu Thr Gln Met Trp
305                 310                 315                 320
```

```
Gln Leu Ala Ser Arg Tyr Pro Gly Arg Met Ala Thr Tyr Leu Leu Tyr
            325                 330                 335

Asn Asp Ala Leu Ser Arg Arg Ile Tyr Ala Gly Ser Asp Ala Phe Leu
            340                 345                 350

Met Pro Ser Arg Phe Glu Pro Cys Gly Ile Ser Gln Met Met Ala Leu
            355                 360                 365

Arg Tyr Gly Ser Ile Pro Ile Val Arg Arg Thr Gly Gly Leu Val Asp
            370                 375                 380

Thr Val Ser His His Asp Pro Val Asn Glu Ala Gly Thr Gly Tyr Cys
385                 390                 395                 400

Phe Asp Arg Tyr Glu Pro Leu Asp Leu Phe Thr Cys Met Ile Arg Ala
                405                 410                 415

Trp Glu Gly Phe Arg Tyr Lys Pro Gln Trp Gln Glu Leu Gln Lys Arg
            420                 425                 430

Gly Met Ser Gln Asp Phe Ser Trp Tyr Lys Ser Ala Lys Glu Tyr Asp
            435                 440                 445

Arg Leu Tyr Arg Ser Ile Tyr Gly Leu Pro Glu Ala Glu Glu Thr Gln
            450                 455                 460

Pro Glu Leu Ile Leu Ala Asn Gln
465                 470
```

<210> SEQ ID NO 49
<211> LENGTH: 1383
<212> TYPE: DNA
<213> ORGANISM: Trichodesmium erythraeum IMS 101

<400> SEQUENCE: 49

```
atgcgaattt tatttgtgtc tgctgaagcg actcctttag caaaagttgg tggtatggca      60
gatgtagtgg gtgccttacc caaagtacta cggaaaatgg gtcacgatgt tcgtatcttc     120
atgccttatt atggcttttt aggcgacaag atggaagttc ctgaggaacc tatctgggaa     180
ggaacggcca tgtatcaaaa ctttaagatt tatgagacgg tactaccaaa aagtgacgtg     240
ccattgtacc tatttggtca cccggctttt tggccacgtc atatttacta tggagatgat     300
gaggactgga gattcactct atttgctaat ggggcggccg agttttgctg aatggctgg      360
aaaccagaga tagttcattg taatgactgg cacactggca tgattccagt ttggatgcac     420
gaaactccag acattaaaac cgtatttact attcataacc tagcttatca aggaccttgg     480
cgctggtact tggaaagaat tacttggtgt ccttggtaca tggaagggca taatacaatg     540
gcagcagcag ttcagtttgc agatcgggta actactgttt ctccaaccta tgctagtcag     600
atccaaacac ctgcctacgg agaaaatcta gatggtttaa tgtctttat tacggggaaa     660
ctacacggta tcctcaatgg tattgatatg aactttata atccagctaa tgacagatat     720
attcctcaaa cttatgatgt caataccctg gaaaacgggt tgacaataa aattgctctt     780
caagaagaag taggttttga agttaacaaa aatagcttc tcatgggaat ggtctcccga     840
ctggtagaac aaaaaggact tgatttaatg ctgcaagtct agatcggtt tatggcttat     900
actgatactc agtttatttt gttgggtaca ggcgatcgct tctatgaaac ccaaatgtgg     960
caaatagcaa gtcgttatcc tggtcggatg agtgtccaac ttttacataa tgatgcccctt   1020
tcccgacgaa tatatgcagg tactgatgct tccttaatgc ccagtcgatt tgagccttgt    1080
ggtattagtc agttattggc aatgcgttat ggtagtatac ctattgtccg tcgcacaggt    1140
gggttagttg atactgtctc tttctatgat cctattaata tgtaggtac tggctattct    1200
```

```
tttgatcgct atgaaccact agacctgctt actgcaatgg tccgagccta tgaaggtttc    1260
cggttcaaag atcaatggca ggagttacag aagcgtggca tgagagagaa ctttagctgg    1320
gataagtcag ctcaaggtta tatcaaaatg tacaaatcaa tgctcggatt acctgaagaa    1380
taa                                                                  1383
```

<210> SEQ ID NO 50
<211> LENGTH: 460
<212> TYPE: PRT
<213> ORGANISM: Trichodesmium erythraeum IMS 101

<400> SEQUENCE: 50

```
Met Arg Ile Leu Phe Val Ser Ala Glu Ala Thr Pro Leu Ala Lys Val
 1               5                  10                  15

Gly Gly Met Ala Asp Val Val Gly Ala Leu Pro Lys Val Leu Arg Lys
            20                  25                  30

Met Gly His Asp Val Arg Ile Phe Met Pro Tyr Tyr Gly Phe Leu Gly
        35                  40                  45

Asp Lys Met Glu Val Pro Glu Glu Pro Ile Trp Glu Gly Thr Ala Met
    50                  55                  60

Tyr Gln Asn Phe Lys Ile Tyr Glu Thr Val Leu Pro Lys Ser Asp Val
65                  70                  75                  80

Pro Leu Tyr Leu Phe Gly His Pro Ala Phe Trp Pro Arg His Ile Tyr
                85                  90                  95

Tyr Gly Asp Asp Glu Asp Trp Arg Phe Thr Leu Phe Ala Asn Gly Ala
            100                 105                 110

Ala Glu Phe Cys Trp Asn Gly Trp Lys Pro Glu Ile Val His Cys Asn
        115                 120                 125

Asp Trp His Thr Gly Met Ile Pro Val Trp Met His Glu Thr Pro Asp
    130                 135                 140

Ile Lys Thr Val Phe Thr Ile His Asn Leu Ala Tyr Gln Gly Pro Trp
145                 150                 155                 160

Arg Trp Tyr Leu Glu Arg Ile Thr Trp Cys Pro Trp Tyr Met Glu Gly
                165                 170                 175

His Asn Thr Met Ala Ala Ala Val Gln Phe Ala Asp Arg Val Thr Thr
            180                 185                 190

Val Ser Pro Thr Tyr Ala Ser Gln Ile Gln Thr Pro Ala Tyr Gly Glu
        195                 200                 205

Asn Leu Asp Gly Leu Met Ser Phe Ile Thr Gly Lys Leu His Gly Ile
    210                 215                 220

Leu Asn Gly Ile Asp Met Asn Phe Asn Pro Ala Asn Asp Arg Tyr
225                 230                 235                 240

Ile Pro Gln Thr Tyr Asp Val Asn Thr Leu Glu Lys Arg Val Asp Asn
                245                 250                 255

Lys Ile Ala Leu Gln Glu Glu Val Gly Phe Glu Val Asn Lys Asn Ser
            260                 265                 270

Phe Leu Met Gly Met Val Ser Arg Leu Val Glu Gln Lys Gly Leu Asp
        275                 280                 285

Leu Met Leu Gln Val Leu Asp Arg Phe Met Ala Tyr Thr Asp Thr Gln
    290                 295                 300

Phe Ile Leu Leu Gly Thr Gly Asp Arg Phe Tyr Glu Thr Gln Met Trp
305                 310                 315                 320

Gln Ile Ala Ser Arg Tyr Pro Gly Arg Met Ser Val Gln Leu Leu His
                325                 330                 335
```

Asn Asp Ala Leu Ser Arg Arg Ile Tyr Ala Gly Thr Asp Ala Phe Leu
                340                 345                 350

Met Pro Ser Arg Phe Glu Pro Cys Gly Ile Ser Gln Leu Leu Ala Met
            355                 360                 365

Arg Tyr Gly Ser Ile Pro Ile Val Arg Arg Thr Gly Gly Leu Val Asp
        370                 375                 380

Thr Val Ser Phe Tyr Asp Pro Ile Asn Asn Val Gly Thr Gly Tyr Ser
385                 390                 395                 400

Phe Asp Arg Tyr Glu Pro Leu Asp Leu Leu Thr Ala Met Val Arg Ala
                405                 410                 415

Tyr Glu Gly Phe Arg Phe Lys Asp Gln Trp Gln Glu Leu Gln Lys Arg
            420                 425                 430

Gly Met Arg Glu Asn Phe Ser Trp Asp Lys Ser Ala Gln Gly Tyr Ile
        435                 440                 445

Lys Met Tyr Lys Ser Met Leu Gly Leu Pro Glu Glu
450                 455                 460

<210> SEQ ID NO 51
<211> LENGTH: 1398
<212> TYPE: DNA
<213> ORGANISM: Synechococcus elongatus PCC 7942

<400> SEQUENCE: 51

```
atgcggattc tgttcgtggc tgccgaatgt gctcccttcg ccaaagtggg aggcatggga      60
gatgtggttg gttccctgcc caaagtgctg aaagctctgg ccatgatgt ccgaatcttc     120
atgccgtact acggctttct gaacagtaag ctcgatattc cgctgaacc gatctggtgg     180
ggctacgcga tgtttaatca cttcgcggtt tacgaaacgc agctgcccgg ttcagatgtg     240
ccgctctact aatggggca tccagctttt gatccgcatc gcatctactc aggagaagac     300
gaagactggc gcttcacgtt ttttgccaat ggggctgctg aattttcttg gaactactgg     360
aaaccacaag tcattcactg ccacgattgg cacactggga tgattccggt ttggatgcac     420
cagtccccgg atatctcgac tgtcttcacc attcataact tggcctacca gggccgtgg     480
cgctggaagc tcgagaaaat cacctggtgc ccttggtaca tgcagggcga cagcaccatg     540
gcggcggcct tgctctatgc cgatcgcgtc aacacggtat cgcccaccta tgcccagcag     600
attcaaacac cgacctacgg tgaaaagctg gaggtcttc tctcatttat cagtggcaag     660
ctaagcggca tccttaacgg gattgatgtt gatagctaca ccctgcaac ggatacgcgg     720
attgtggcca actacgatcg cgacactctt gataaacgac tgaacaataa gctggcgctc     780
caaaaggaga tggggcttga ggtcaatccc gatcgcttcc tgattggctt tgtggctcgt     840
ctagtcgagc agaagggcat tgacttgctg ctgcaaattc ttgatcgctt tctgtcttac     900
agcgatgccc aatttgttgt cttaggaacg ggcgagcgct actacgaaac ccagctctgg     960
gagttggcga cccgctatcc gggccggatg tccacttatc tgatgtacga cgaggggctg    1020
tcgcgacgca tttatgccgg tagcgacgcc ttcttggtgc cctctcgttt tgaaccttgc    1080
ggtatcacgc aaatgctggc actgcgctac ggcagtgtgc cgattgtgcg ccgtacgggg    1140
gggttggtcg atacggtctt ccaccacgat ccgcgtcatg ccgagggcaa tggctattgc    1200
ttcgatcgct acgagccgct ggacctctat acctgtctgg tgcgggcttg ggagagttac    1260
cagtaccagc cccaatggca aaagctacag caacggggta tggccgttga tctgagctgg    1320
aaacaatcgg cgatcgccta cgaacagctc tacgctgaag cgattgggct accgatcgat    1380
gtcttacagg aggcctag                                                 1398
```

<210> SEQ ID NO 52
<211> LENGTH: 465
<212> TYPE: PRT
<213> ORGANISM: Synechococcus elongatus PCC 7942

<400> SEQUENCE: 52

| Met | Arg | Ile | Leu | Phe | Val | Ala | Ala | Glu | Cys | Ala | Pro | Phe | Ala | Lys | Val |
|---|---|---|---|---|---|---|---|---|---|---|---|---|---|---|---|
| 1 | | | | 5 | | | | | 10 | | | | | 15 | |

| Gly | Gly | Met | Gly | Asp | Val | Val | Gly | Ser | Leu | Pro | Lys | Val | Leu | Lys | Ala |
| | | | 20 | | | | | 25 | | | | | 30 | | |

| Leu | Gly | His | Asp | Val | Arg | Ile | Phe | Met | Pro | Tyr | Tyr | Gly | Phe | Leu | Asn |
| | | 35 | | | | | 40 | | | | | 45 | | | |

| Ser | Lys | Leu | Asp | Ile | Pro | Ala | Glu | Pro | Ile | Trp | Trp | Gly | Tyr | Ala | Met |
| | 50 | | | | | 55 | | | | | 60 | | | | |

| Phe | Asn | His | Phe | Ala | Val | Tyr | Glu | Thr | Gln | Leu | Pro | Gly | Ser | Asp | Val |
| 65 | | | | | 70 | | | | | 75 | | | | | 80 |

| Pro | Leu | Tyr | Leu | Met | Gly | His | Pro | Ala | Phe | Asp | Pro | His | Arg | Ile | Tyr |
| | | | | 85 | | | | | 90 | | | | | 95 | |

| Ser | Gly | Glu | Asp | Glu | Asp | Trp | Arg | Phe | Thr | Phe | Phe | Ala | Asn | Gly | Ala |
| | | | 100 | | | | | 105 | | | | | 110 | | |

| Ala | Glu | Phe | Ser | Trp | Asn | Tyr | Trp | Lys | Pro | Gln | Val | Ile | His | Cys | His |
| | | 115 | | | | | 120 | | | | | 125 | | | |

| Asp | Trp | His | Thr | Gly | Met | Ile | Pro | Val | Trp | Met | His | Gln | Ser | Pro | Asp |
| | 130 | | | | | 135 | | | | | 140 | | | | |

| Ile | Ser | Thr | Val | Phe | Thr | Ile | His | Asn | Leu | Ala | Tyr | Gln | Gly | Pro | Trp |
| 145 | | | | | 150 | | | | | 155 | | | | | 160 |

| Arg | Trp | Lys | Leu | Glu | Lys | Ile | Thr | Trp | Cys | Pro | Trp | Tyr | Met | Gln | Gly |
| | | | | 165 | | | | | 170 | | | | | 175 | |

| Asp | Ser | Thr | Met | Ala | Ala | Ala | Leu | Leu | Tyr | Ala | Asp | Arg | Val | Asn | Thr |
| | | | 180 | | | | | 185 | | | | | 190 | | |

| Val | Ser | Pro | Thr | Tyr | Ala | Gln | Gln | Ile | Gln | Thr | Pro | Thr | Tyr | Gly | Glu |
| | | 195 | | | | | 200 | | | | | 205 | | | |

| Lys | Leu | Glu | Gly | Leu | Leu | Ser | Phe | Ile | Ser | Gly | Lys | Leu | Ser | Gly | Ile |
| | 210 | | | | | 215 | | | | | 220 | | | | |

| Leu | Asn | Gly | Ile | Asp | Val | Asp | Ser | Tyr | Asn | Pro | Ala | Thr | Asp | Thr | Arg |
| 225 | | | | | 230 | | | | | 235 | | | | | 240 |

| Ile | Val | Ala | Asn | Tyr | Asp | Arg | Asp | Thr | Leu | Asp | Lys | Arg | Leu | Asn | Asn |
| | | | | 245 | | | | | 250 | | | | | 255 | |

| Lys | Leu | Ala | Leu | Gln | Lys | Glu | Met | Gly | Leu | Glu | Val | Asn | Pro | Asp | Arg |
| | | | 260 | | | | | 265 | | | | | 270 | | |

| Phe | Leu | Ile | Gly | Phe | Val | Ala | Arg | Leu | Val | Glu | Gln | Lys | Gly | Ile | Asp |
| | | 275 | | | | | 280 | | | | | 285 | | | |

| Leu | Leu | Leu | Gln | Ile | Leu | Asp | Arg | Phe | Leu | Ser | Tyr | Ser | Asp | Ala | Gln |
| | 290 | | | | | 295 | | | | | 300 | | | | |

| Phe | Val | Val | Leu | Gly | Thr | Gly | Glu | Arg | Tyr | Tyr | Glu | Thr | Gln | Leu | Trp |
| 305 | | | | | 310 | | | | | 315 | | | | | 320 |

| Glu | Leu | Ala | Thr | Arg | Tyr | Pro | Gly | Arg | Met | Ser | Thr | Tyr | Leu | Met | Tyr |
| | | | | 325 | | | | | 330 | | | | | 335 | |

| Asp | Glu | Gly | Leu | Ser | Arg | Arg | Ile | Tyr | Ala | Gly | Ser | Asp | Ala | Phe | Leu |
| | | | 340 | | | | | 345 | | | | | 350 | | |

| Val | Pro | Ser | Arg | Phe | Glu | Pro | Cys | Gly | Ile | Thr | Gln | Met | Leu | Ala | Leu |
| | | 355 | | | | | 360 | | | | | 365 | | | |

| Arg | Tyr | Gly | Ser | Val | Pro | Ile | Val | Arg | Arg | Thr | Gly | Gly | Leu | Val | Asp |

```
                370             375             380
Thr Val Phe His His Asp Pro Arg His Ala Glu Gly Asn Gly Tyr Cys
385             390             395             400

Phe Asp Arg Tyr Glu Pro Leu Asp Leu Tyr Thr Cys Leu Val Arg Ala
            405             410             415

Trp Glu Ser Tyr Gln Tyr Gln Pro Gln Trp Gln Lys Leu Gln Gln Arg
            420             425             430

Gly Met Ala Val Asp Leu Ser Trp Lys Gln Ser Ala Ile Ala Tyr Glu
            435             440             445

Gln Leu Tyr Ala Glu Ala Ile Gly Leu Pro Ile Asp Val Leu Gln Glu
            450             455             460

Ala
465

<210> SEQ ID NO 53
<211> LENGTH: 1542
<212> TYPE: DNA
<213> ORGANISM: Synechococcus sp. WH8102

<400> SEQUENCE: 53
atgcgcatcc tcttcgctgc cgcggaatgc gccccgatga tcaaggtcgg tggcatgggg     60
gatgtggtgg gatcgctgcc tccggctctg gccaagcttg ccacgacgt gcggctgatc     120 atgccgggct actccaagct ctggaccaag ctgacgatct cggacgaacc catctggcgc     180
gcccagacga tgggtacgga attcgcggtt tacgagacga agcatccagg caatgggatg     240
accatctacc tggtgggaca tccggtgttc gatcccgagc ggatctatgg cggtgaagat     300
gaggactggc gcttcacctt ctttgccagt gccgccgctg aattcgcctg gaatgtctgg     360
aagccgaatg ttcttcactg ccacgactgg cacaccggca tgattccggt ctggatgcac     420
caggacccgg agatcagcac ggtcttcacc atccacaacc tcaagtacca gggcccctgg     480
cgttggaagc tggatcgcat cacctggtgc ccctggtaca tgcagggaga tcacaccatg     540
gcggcggcac ttctgtacgc cgaccgggtc aacgccgtct cccccaccta cgccgaggaa     600
atccgtacgg cggagtacgg cgaaaagctg atggttttgc tcaatttcgt ctccggcaag     660
ctgcgcggca tcctcaatgg cattgacctc gaggcctgga ccccagac cgatggggct      720 ctgccggcca ccttcagcgc cgacgacctc tccggtaaag cggtctgcaa gcgggtgttg     780
caggagcgca tgggtcttga ggtgcgtgac gacgcctttg tcctcggcat ggtcagccga     840
ctcgtcgatc agaagggcgt cgatctgctt ctgcaggtgg cggaccgttt gctcgcctac     900
accgacacgc agatcgtggt gctcggcacc ggtgaccgtg gcctggaatc cggcctgtgg     960
cagctggcct cccgccatgc cggccgttgc gccgtcttcc tcacctacga cgacgacctc    1020
tcccgactga tctatgccgg cagtgacgcc ttcctgatgc ccagtcgctt cgagccctgc    1080
ggcatcagcc agctgtacgc catgcgttac ggctccgttc ctgtggtgcg caaggtgggc    1140
ggcctggtgg acaccgttcc tccccacagt ccagctgatg ccagcgggac cggcttctgc    1200
ttcgatcgtt ttgagccggt cgacttctac accgcattgg tgcgtgcctg ggaggcctac    1260
cgccatcgcg acagctggca ggagttgcag aagcgcggca tgcagcagga ctacagctgg    1320
gaccgttcgg ccatcgatta cgacgtcatg taccgcgatg tctgcggtct gaaggaaccc    1380 accctgatg ccgcgatggt ggaacagttc tcccagggac aggctgcgga tccctcccgc    1440
ccagaggatg atgcgatcaa tgctgctccc gagcgggtca ccgcgccgtc ggccccagcc    1500
cgcaaccccc ttaatcgtct cttcggccgc agggccgact ga                      1542
```

<210> SEQ ID NO 54
<211> LENGTH: 513
<212> TYPE: PRT
<213> ORGANISM: Synechococcus sp. WH8102

<400> SEQUENCE: 54

```
Met Arg Ile Leu Phe Ala Ala Glu Cys Ala Pro Met Ile Lys Val
 1               5                  10                  15

Gly Gly Met Gly Asp Val Val Gly Ser Leu Pro Pro Ala Leu Ala Lys
             20                  25                  30

Leu Gly His Asp Val Arg Leu Ile Met Pro Gly Tyr Ser Lys Leu Trp
             35                  40                  45

Thr Lys Leu Thr Ile Ser Asp Glu Pro Ile Trp Arg Ala Gln Thr Met
 50                  55                  60

Gly Thr Glu Phe Ala Val Tyr Glu Thr Lys His Pro Gly Asn Gly Met
 65                  70                  75                  80

Thr Ile Tyr Leu Val Gly His Pro Val Phe Asp Pro Glu Arg Ile Tyr
                 85                  90                  95

Gly Gly Glu Asp Glu Asp Trp Arg Phe Thr Phe Phe Ala Ser Ala Ala
             100                 105                 110

Ala Glu Phe Ala Trp Asn Val Trp Lys Pro Asn Val Leu His Cys His
         115                 120                 125

Asp Trp His Thr Gly Met Ile Pro Val Trp Met His Gln Asp Pro Glu
130                 135                 140

Ile Ser Thr Val Phe Thr Ile His Asn Leu Lys Tyr Gln Gly Pro Trp
145                 150                 155                 160

Arg Trp Lys Leu Asp Arg Ile Thr Trp Cys Pro Trp Tyr Met Gln Gly
                165                 170                 175

Asp His Thr Met Ala Ala Ala Leu Leu Tyr Ala Asp Arg Val Asn Ala
            180                 185                 190

Val Ser Pro Thr Tyr Ala Glu Glu Ile Arg Thr Ala Glu Tyr Gly Glu
        195                 200                 205

Lys Leu Asp Gly Leu Leu Asn Phe Val Ser Gly Lys Leu Arg Gly Ile
    210                 215                 220

Leu Asn Gly Ile Asp Leu Glu Ala Trp Asn Pro Gln Thr Asp Gly Ala
225                 230                 235                 240

Leu Pro Ala Thr Phe Ser Ala Asp Asp Leu Ser Gly Lys Ala Val Cys
                245                 250                 255

Lys Arg Val Leu Gln Glu Arg Met Gly Leu Glu Val Arg Asp Asp Ala
            260                 265                 270

Phe Val Leu Gly Met Val Ser Arg Leu Val Asp Gln Lys Gly Val Asp
        275                 280                 285

Leu Leu Leu Gln Val Ala Asp Arg Leu Leu Ala Tyr Thr Asp Thr Gln
    290                 295                 300

Ile Val Val Leu Gly Thr Gly Asp Arg Gly Leu Glu Ser Gly Leu Trp
305                 310                 315                 320

Gln Leu Ala Ser Arg His Ala Gly Arg Cys Ala Val Phe Leu Thr Tyr
                325                 330                 335

Asp Asp Asp Leu Ser Arg Leu Ile Tyr Ala Gly Ser Asp Ala Phe Leu
            340                 345                 350

Met Pro Ser Arg Phe Glu Pro Cys Gly Ile Ser Gln Leu Tyr Ala Met
        355                 360                 365

Arg Tyr Gly Ser Val Pro Val Val Arg Lys Val Gly Gly Leu Val Asp
```

```
         370              375              380
Thr Val Pro Pro His Ser Pro Ala Asp Ala Ser Gly Thr Gly Phe Cys
385              390              395              400

Phe Asp Arg Phe Glu Pro Val Asp Phe Tyr Thr Ala Leu Val Arg Ala
             405              410              415

Trp Glu Ala Tyr Arg His Arg Asp Ser Trp Gln Glu Leu Gln Lys Arg
             420              425              430

Gly Met Gln Gln Asp Tyr Ser Trp Asp Arg Ser Ala Ile Asp Tyr Asp
         435              440              445

Val Met Tyr Arg Asp Val Cys Gly Leu Lys Glu Pro Thr Pro Asp Ala
         450              455              460

Ala Met Val Glu Gln Phe Ser Gln Gly Gln Ala Ala Asp Pro Ser Arg
465              470              475              480

Pro Glu Asp Asp Ala Ile Asn Ala Ala Pro Glu Ala Val Thr Ala Pro
             485              490              495

Ser Gly Pro Ser Arg Asn Pro Leu Asn Arg Leu Phe Gly Arg Arg Ala
             500              505              510

Asp

<210> SEQ ID NO 55
<211> LENGTH: 1524
<212> TYPE: DNA
<213> ORGANISM: Synechococcus sp RCC 307

<400> SEQUENCE: 55
atgcgcatcc tctttgctgc ggccgaatgc gcaccgatgg tgaaagtcgg cggcatggga      60
gatgtggtgg gatctctgcc tccagccctc gctgagttgg tcacgacgt gcgcgtgatc      120
atgcccggct acggcaagct ctggtcccag cttgatgtgc ccagcgagcc gatctggcgt      180
gcccaaacca tgggcaccga ttttgctgtc tatgagaccc gtcaccccaa gaccgggctc      240
acgatctatt tggtgggcca tccggttttt gatggtgagc gcatctatgg aggtgaagac      300
gaggactggc gcttcaccct cttcgctagc gccacctccg aatttgcctg gaacgcttgg      360
aagccccagg tgctgcattg ccatgactgg cacaccggca tgattccggt gtggatgcac      420
caagacccccg agatcagcac ggtcttcacc atccacaacc tcaaatatca aggtccctgg      480
cgctggaagc tcgagcgcat gacctggtgc cctggtaca tgcagggcga ccacaccatg      540
gcggcagcct tgctgtatgc cgaccgcgtc aatgcggttt cacccaccta cgcccaagag      600
atccgcacgc cggaatacgg cgaacaactg gaggggttgc tgaactacat cagcggcaag      660
ctgcgaggca tcctcaatgg catcgatgtg gaggcttgga atcccgccac tgattcgcgg      720
attccggcca cctacagcac tgctgacctc agtggcaaag ccgtctgcaa gcgggctctg      780
caagagcgca tggggcttca ggtgaacccc gacacctttg tgatcggttt ggtgagccgt      840
ttggtggacc aaaaaggcgt cgacctgctg ctgcaggttg ccgaacgctt ccttgcctac      900
accgatacgc agatcgttgt gttgggcacc ggggatcgcc atttggaatc gggcctgtgg      960
caaatggcga gtcagcacag cggccgcttc gcttccttcc tcacctacga cgatgatctc      1020
tcccggctga tctacgccgg cagtgatgcc ttcttgatgc cctcgcgctt tgagccctgc      1080
ggcatcagcc agttgctctc gatgcgctac ggcaccatcc cggtggtgcg ccgcgtcggt      1140
ggactggtcg acaccgtgcc tccctatgtt cccgccaccc aagagggcaa tggcttctgc      1200
ttcgaccgct atgaagcgat cgacctttac accgccttgg tgcgcgcctg ggaggcctac      1260
cgccatcaag acagctggca gcaattgatg aagcgggtga tgcaggttga tttcagctgg      1320
```

```
gctcgttccg ccttggaata cgaccgcatg tatcgcgatg tttgcggaat gaaggagccc    1380
acgccggaag ccgatgcggt ggcggccttc tccattcccc agccgcctga acagcaggcc    1440
gcacgtgctg ccgctgaagc cgctgacccc aaccccccaac ggcgctttaa tccccttgga    1500
ttgctgcgcc gaaacggcgg ttga                                           1524
```

<210> SEQ ID NO 56
<211> LENGTH: 507
<212> TYPE: PRT
<213> ORGANISM: Synechococcus sp RCC 307

<400> SEQUENCE: 56

```
Met Arg Ile Leu Phe Ala Ala Glu Cys Ala Pro Met Val Lys Val
 1               5                  10                  15

Gly Gly Met Gly Asp Val Val Gly Ser Leu Pro Pro Ala Leu Ala Glu
            20                  25                  30

Leu Gly His Asp Val Arg Val Ile Met Pro Gly Tyr Gly Lys Leu Trp
        35                  40                  45

Ser Gln Leu Asp Val Pro Ser Glu Pro Ile Trp Arg Ala Gln Thr Met
 50                  55                  60

Gly Thr Asp Phe Ala Val Tyr Glu Thr Arg His Pro Lys Thr Gly Leu
 65                  70                  75                  80

Thr Ile Tyr Leu Val Gly His Pro Val Phe Asp Gly Glu Arg Ile Tyr
                85                  90                  95

Gly Gly Glu Asp Glu Asp Trp Arg Phe Thr Phe Phe Ala Ser Ala Thr
            100                 105                 110

Ser Glu Phe Ala Trp Asn Ala Trp Lys Pro Gln Val Leu His Cys His
        115                 120                 125

Asp Trp His Thr Gly Met Ile Pro Val Trp Met His Gln Asp Pro Glu
130                 135                 140

Ile Ser Thr Val Phe Thr Ile His Asn Leu Lys Tyr Gln Gly Pro Trp
145                 150                 155                 160

Arg Trp Lys Leu Glu Arg Met Thr Trp Cys Pro Trp Tyr Met Gln Gly
                165                 170                 175

Asp His Thr Met Ala Ala Ala Leu Leu Tyr Ala Asp Arg Val Asn Ala
            180                 185                 190

Val Ser Pro Thr Tyr Ala Gln Glu Ile Arg Thr Pro Glu Tyr Gly Glu
        195                 200                 205

Gln Leu Glu Gly Leu Leu Asn Tyr Ile Ser Gly Lys Leu Arg Gly Ile
    210                 215                 220

Leu Asn Gly Ile Asp Val Glu Ala Trp Asn Pro Ala Thr Asp Ser Arg
225                 230                 235                 240

Ile Pro Ala Thr Tyr Ser Thr Ala Asp Leu Ser Gly Lys Ala Val Cys
                245                 250                 255

Lys Arg Ala Leu Gln Glu Arg Met Gly Leu Gln Val Asn Pro Asp Thr
            260                 265                 270

Phe Val Ile Gly Leu Val Ser Arg Leu Val Asp Gln Lys Gly Val Asp
        275                 280                 285

Leu Leu Leu Gln Val Ala Glu Arg Phe Leu Ala Tyr Thr Asp Thr Gln
    290                 295                 300

Ile Val Val Leu Gly Thr Gly Asp Arg His Leu Glu Ser Gly Leu Trp
305                 310                 315                 320

Gln Met Ala Ser Gln His Ser Gly Arg Phe Ala Ser Phe Leu Thr Tyr
                325                 330                 335
```

Asp Asp Asp Leu Ser Arg Leu Ile Tyr Ala Gly Ser Asp Ala Phe Leu
            340                 345                 350

Met Pro Ser Arg Phe Glu Pro Cys Gly Ile Ser Gln Leu Leu Ser Met
        355                 360                 365

Arg Tyr Gly Thr Ile Pro Val Val Arg Arg Val Gly Gly Leu Val Asp
    370                 375                 380

Thr Val Pro Pro Tyr Val Pro Ala Thr Gln Glu Gly Asn Gly Phe Cys
385                 390                 395                 400

Phe Asp Arg Tyr Glu Ala Ile Asp Leu Tyr Thr Ala Leu Val Arg Ala
                405                 410                 415

Trp Glu Ala Tyr Arg His Gln Asp Ser Trp Gln Leu Met Lys Arg
            420                 425                 430

Val Met Gln Val Asp Phe Ser Trp Ala Arg Ser Ala Leu Glu Tyr Asp
        435                 440                 445

Arg Met Tyr Arg Asp Val Cys Gly Met Lys Glu Pro Thr Pro Glu Ala
    450                 455                 460

Asp Ala Val Ala Ala Phe Ser Ile Pro Gln Pro Glu Gln Gln Ala
465                 470                 475                 480

Ala Arg Ala Ala Ala Glu Ala Ala Asp Pro Asn Pro Gln Arg Arg Phe
                485                 490                 495

Asn Pro Leu Gly Leu Leu Arg Arg Asn Gly Gly
            500                 505

<210> SEQ ID NO 57
<211> LENGTH: 1437
<212> TYPE: DNA
<213> ORGANISM: Synechococcus sp. PCC 7002

<400> SEQUENCE: 57
atgcgtattt tgtttgtttc tgccgaggct gctcccatcg ctaaagctgg aggcatggga      60
gatgtggtgg atcactgcc taaagtttta cggcagttag acatgacgc gagaattttc      120 ttaccctatt acggctttct caacgacaaa ctcgacatcc ctgcagaacc cgtttggtgg      180
ggcagtgcga tgttcaatac ttttgccgtt tatgaaactg tgttgcccaa caccgatgtc      240 ccccttatc tgtttggcca tccgcccttt gatggacggc atatttatgg tgggcaggat      300
gaattttggc gctttacctt ttttgccaat ggggccgctg aatttatgtg gaaccactgg      360
aaaccccaga tcgcccactg tcacgactgg cacacgggca tgattccggt atggatgcac      420
caatcgccgg atatcagtac ggtgtttacg atccacaact tagcctacca agggccttgg      480
cggggtttcc tggagcgcaa tacttggtgt ccctggtata tggatggtga taacgtgatg      540
gcttcggcgc tgatgtttgc cgatcaggtg aacaccgtat ctcccaccta tgcccaacaa      600
atccaaacca aagtctatgg tgaaaaatta gagggtttgt tgtcttggat cagtggcaaa      660
agtcgcggca tcgtgaatgg tattgacgta gaactttata atccttctaa cgatcaagcc      720
ctggtgaagc aattttctac gactaatctt gaggatcggg ccgccaacaa agtgattatc      780
caagaagaaa cggggctaga ggtcaactcc aaggcttttt tgatggcgat ggtcacccgc      840
ttagtggaac aaaagggcat tgatctgctg ctaaatatcc tggagcagtt tatggcatac      900
actgacgccc agctcattat cctcggcact ggcgatcgcc actacgaaac ccaactctgg      960
cagactgcct accgctttaa ggggcggatg tccgtgcaac tgctctataa tgatgccctc      1020
tcccgccgga tttacgctgg atccgatgtc ttttgatgc cgtcacgctt tgagccctgt      1080
ggcattagtc aaatgatggc gatgcgctac ggttctgtac cgattgtgcg gcgcaccggg      1140

-continued

```
ggtttggtgg atacggtctc tttccatgat ccgattcacc aaaccgggac aggctttagt    1200
tttgaccgct acgaaccgct ggatatgtac acctgcatgg tgcgggcttg ggaaagtttc    1260
cgctacaaaa aagactgggc tgaactacaa agacgaggca tgagccatga ctttagttgg    1320
tacaaatctg ccggggaata tctcaagatg taccgccaaa gcattaaaga agctccggaa    1380
ttaacgaccg atgaagccga aaaaatcacc tatttagtga aaaaacacgc catttaa       1437
```

<210> SEQ ID NO 58
<211> LENGTH: 478
<212> TYPE: PRT
<213> ORGANISM: Synechococcus sp. PCC 7002

<400> SEQUENCE: 58

| Met | Arg | Ile | Leu | Phe | Val | Ser | Ala | Glu | Ala | Pro | Ile | Ala | Lys | Ala |
|---|---|---|---|---|---|---|---|---|---|---|---|---|---|---|
| 1 | | | | 5 | | | | | 10 | | | | | 15 |

| Gly | Gly | Met | Gly | Asp | Val | Val | Gly | Ser | Leu | Pro | Lys | Val | Leu | Arg | Gln |
|---|---|---|---|---|---|---|---|---|---|---|---|---|---|---|---|
| | | | 20 | | | | | 25 | | | | | 30 | | |

| Leu | Gly | His | Asp | Ala | Arg | Ile | Phe | Leu | Pro | Tyr | Tyr | Gly | Phe | Leu | Asn |
|---|---|---|---|---|---|---|---|---|---|---|---|---|---|---|---|
| | | 35 | | | | | 40 | | | | | 45 | | | |

| Asp | Lys | Leu | Asp | Ile | Pro | Ala | Glu | Pro | Val | Trp | Trp | Gly | Ser | Ala | Met |
|---|---|---|---|---|---|---|---|---|---|---|---|---|---|---|---|
| 50 | | | | | 55 | | | | | 60 | | | | | |

| Phe | Asn | Thr | Phe | Ala | Val | Tyr | Glu | Thr | Val | Leu | Pro | Asn | Thr | Asp | Val |
|---|---|---|---|---|---|---|---|---|---|---|---|---|---|---|---|
| 65 | | | | | 70 | | | | | 75 | | | | | 80 |

| Pro | Leu | Tyr | Leu | Phe | Gly | His | Pro | Ala | Phe | Asp | Gly | Arg | His | Ile | Tyr |
|---|---|---|---|---|---|---|---|---|---|---|---|---|---|---|---|
| | | | | 85 | | | | | 90 | | | | | 95 | |

| Gly | Gly | Gln | Asp | Glu | Phe | Trp | Arg | Phe | Thr | Phe | Ala | Asn | Gly | Ala |
|---|---|---|---|---|---|---|---|---|---|---|---|---|---|---|
| | | | 100 | | | | | 105 | | | | | 110 | |

| Ala | Glu | Phe | Met | Trp | Asn | His | Trp | Lys | Pro | Gln | Ile | Ala | His | Cys | His |
|---|---|---|---|---|---|---|---|---|---|---|---|---|---|---|---|
| | | 115 | | | | | 120 | | | | | 125 | | | |

| Asp | Trp | His | Thr | Gly | Met | Ile | Pro | Val | Trp | Met | His | Gln | Ser | Pro | Asp |
|---|---|---|---|---|---|---|---|---|---|---|---|---|---|---|---|
| | 130 | | | | | 135 | | | | | 140 | | | | |

| Ile | Ser | Thr | Val | Phe | Thr | Ile | His | Asn | Leu | Ala | Tyr | Gln | Gly | Pro | Trp |
|---|---|---|---|---|---|---|---|---|---|---|---|---|---|---|---|
| 145 | | | | | 150 | | | | | 155 | | | | | 160 |

| Arg | Gly | Phe | Leu | Glu | Arg | Asn | Thr | Trp | Cys | Pro | Trp | Tyr | Met | Asp | Gly |
|---|---|---|---|---|---|---|---|---|---|---|---|---|---|---|---|
| | | | | 165 | | | | | 170 | | | | | 175 | |

| Asp | Asn | Val | Met | Ala | Ser | Ala | Leu | Met | Phe | Ala | Asp | Gln | Val | Asn | Thr |
|---|---|---|---|---|---|---|---|---|---|---|---|---|---|---|---|
| | | | 180 | | | | | 185 | | | | | 190 | | |

| Val | Ser | Pro | Thr | Tyr | Ala | Gln | Gln | Ile | Gln | Thr | Lys | Val | Tyr | Gly | Glu |
|---|---|---|---|---|---|---|---|---|---|---|---|---|---|---|---|
| | | 195 | | | | | 200 | | | | | 205 | | | |

| Lys | Leu | Glu | Gly | Leu | Leu | Ser | Trp | Ile | Ser | Gly | Lys | Ser | Arg | Gly | Ile |
|---|---|---|---|---|---|---|---|---|---|---|---|---|---|---|---|
| | 210 | | | | | 215 | | | | | 220 | | | | |

| Val | Asn | Gly | Ile | Asp | Val | Glu | Leu | Tyr | Asn | Pro | Ser | Asn | Asp | Gln | Ala |
|---|---|---|---|---|---|---|---|---|---|---|---|---|---|---|---|
| 225 | | | | | 230 | | | | | 235 | | | | | 240 |

| Leu | Val | Lys | Gln | Phe | Ser | Thr | Thr | Asn | Leu | Glu | Asp | Arg | Ala | Ala | Asn |
|---|---|---|---|---|---|---|---|---|---|---|---|---|---|---|---|
| | | | | 245 | | | | | 250 | | | | | 255 | |

| Lys | Val | Ile | Ile | Gln | Glu | Glu | Thr | Gly | Leu | Glu | Val | Asn | Ser | Lys | Ala |
|---|---|---|---|---|---|---|---|---|---|---|---|---|---|---|---|
| | | | 260 | | | | | 265 | | | | | 270 | | |

| Phe | Leu | Met | Ala | Met | Val | Thr | Arg | Leu | Val | Glu | Gln | Lys | Gly | Ile | Asp |
|---|---|---|---|---|---|---|---|---|---|---|---|---|---|---|---|
| | | 275 | | | | | 280 | | | | | 285 | | | |

| Leu | Leu | Leu | Asn | Ile | Leu | Glu | Gln | Phe | Met | Ala | Tyr | Thr | Asp | Ala | Gln |
|---|---|---|---|---|---|---|---|---|---|---|---|---|---|---|---|
| | 290 | | | | | 295 | | | | | 300 | | | | |

| Leu | Ile | Ile | Leu | Gly | Thr | Gly | Asp | Arg | His | Tyr | Glu | Thr | Gln | Leu | Trp |
|---|---|---|---|---|---|---|---|---|---|---|---|---|---|---|---|
| 305 | | | | | 310 | | | | | 315 | | | | | 320 |

Gln Thr Ala Tyr Arg Phe Lys Gly Arg Met Ser Val Gln Leu Leu Tyr
            325                 330                 335

Asn Asp Ala Leu Ser Arg Arg Ile Tyr Ala Gly Ser Asp Val Phe Leu
        340                 345                 350

Met Pro Ser Arg Phe Glu Pro Cys Gly Ile Ser Gln Met Met Ala Met
        355                 360                 365

Arg Tyr Gly Ser Val Pro Ile Val Arg Arg Thr Gly Gly Leu Val Asp
    370                 375                 380

Thr Val Ser Phe His Asp Pro Ile His Gln Thr Gly Thr Gly Phe Ser
385                 390                 395                 400

Phe Asp Arg Tyr Glu Pro Leu Asp Met Tyr Thr Cys Met Val Arg Ala
                405                 410                 415

Trp Glu Ser Phe Arg Tyr Lys Lys Asp Trp Ala Glu Leu Gln Arg Arg
            420                 425                 430

Gly Met Ser His Asp Phe Ser Trp Tyr Lys Ser Ala Gly Glu Tyr Leu
        435                 440                 445

Lys Met Tyr Arg Gln Ser Ile Lys Glu Ala Pro Glu Leu Thr Thr Asp
        450                 455                 460

Glu Ala Glu Lys Ile Thr Tyr Leu Val Lys Lys His Ala Ile
465                 470                 475

<210> SEQ ID NO 59
<211> LENGTH: 1320
<212> TYPE: DNA
<213> ORGANISM: Synechocystis sp. PCC 6803

<400> SEQUENCE: 59
gtgtgttgtt ggcaatcgag aggtctgctt gtgaaacgtg tcttagcgat tatcctgggc      60
ggtggggccg ggacccgcct ctatccttta accaaactca gagccaaacc cgcagttccc     120
ttggccggaa agtatcgcct catcgatatt cccgtcagta attgcatcaa ctcagaaatc     180
gttaaaattt acgtccttac ccagtttaat tccgcctccc ttaaccgtca catcagccgg     240
gcctataatt tttccggctt ccaagaagga tttgtggaag tcctcgccgc caacaaaacc     300
aaagataatc ctgattggtt tcagggcact gctgatgcgg tacggcaata cctctggttg     360
tttagggaat gggacgtaga tgaatatctt attctgtccg gcgaccatct ctaccgcatg     420
gattacgccc aatttgttaa agacaccgg gaaaccaatg ccgacataac cctttccgtt     480
gtgcccgtgg atgacagaaa ggcacccgag ctgggcttaa tgaaaatcga cgcccagggc     540
agaattactg actttctga aaagcccag ggggaagccc tccgggccat gcaggtggac     600
accagcgttt tgggcctaag tgcggagaag gctaagctta atccttacat tgcctccatg     660
ggcatttacg ttttcaagaa ggaagtattg cacaacctcc tggaaaaata tgaaggggca     720
acggactttg gcaaagaaat cattcctgat tcagccagtg atcacaatct gcaagcctat     780
ctctttgatg actattggga agacattggt accattgaag ccttctatga ggctaattta     840
gccctgacca acaacctag tcccgacttt agtttttata cgaaaaagc ccccatctat     900
accaggggtc gttatcttcc ccccaccaaa atgttgaatt ccaccgtgac ggaatccatg     960
atcggggaag gttgcatgat taagcaatgt cgcatccacc actcagtttt aggcattcgc    1020
agtcgcattg aatctgattg caccattgag gatactttgg tgatgggcaa tgatttctac    1080
gaatcttcat cagaacgaga cacccctcaaa gcccggggg aaattgccgc tggcataggt    1140
tccggcacca ctatccgccg agccatcatc gacaaaaatg cccgcatcgg caaaaacgtc    1200
atgattgtca caaggaaaa tgtccaggag gctaaccggg aagagttagg ttttttacatc    1260 cgcaatggca tcgtagtagt gattaaaaat gtcacgatcg ccgacggcac ggtaatctag      1320

<210> SEQ ID NO 60
<211> LENGTH: 439
<212> TYPE: PRT
<213> ORGANISM: Synechocystis sp. PCC 6803

<400> SEQUENCE: 60

Met Cys Cys Trp Gln Ser Arg Gly Leu Leu Val Lys Arg Val Leu Ala
1               5                   10                  15

Ile Ile Leu Gly Gly Gly Ala Gly Thr Arg Leu Tyr Pro Leu Thr Lys
            20                  25                  30

Leu Arg Ala Lys Pro Ala Val Pro Leu Ala Gly Lys Tyr Arg Leu Ile
        35                  40                  45

Asp Ile Pro Val Ser Asn Cys Ile Asn Ser Glu Ile Val Lys Ile Tyr
    50                  55                  60

Val Leu Thr Gln Phe Asn Ser Ala Ser Leu Asn Arg His Ile Ser Arg
65                  70                  75                  80

Ala Tyr Asn Phe Ser Gly Phe Gln Glu Gly Phe Val Glu Val Leu Ala
                85                  90                  95

Ala Gln Gln Thr Lys Asp Asn Pro Asp Trp Phe Gln Gly Thr Ala Asp
            100                 105                 110

Ala Val Arg Gln Tyr Leu Trp Leu Phe Arg Glu Trp Asp Val Asp Glu
        115                 120                 125

Tyr Leu Ile Leu Ser Gly Asp His Leu Tyr Arg Met Asp Tyr Ala Gln
    130                 135                 140

Phe Val Lys Arg His Arg Glu Thr Asn Ala Asp Ile Thr Leu Ser Val
145                 150                 155                 160

Val Pro Val Asp Asp Arg Lys Ala Pro Glu Leu Gly Leu Met Lys Ile
                165                 170                 175

Asp Ala Gln Gly Arg Ile Thr Asp Phe Ser Glu Lys Pro Gln Gly Glu
            180                 185                 190

Ala Leu Arg Ala Met Gln Val Asp Thr Ser Val Leu Gly Leu Ser Ala
        195                 200                 205

Glu Lys Ala Lys Leu Asn Pro Tyr Ile Ala Ser Met Gly Ile Tyr Val
    210                 215                 220

Phe Lys Lys Glu Val Leu His Asn Leu Leu Glu Lys Tyr Glu Gly Ala
225                 230                 235                 240

Thr Asp Phe Gly Lys Glu Ile Ile Pro Asp Ser Ala Ser Asp His Asn
                245                 250                 255

Leu Gln Ala Tyr Leu Phe Asp Asp Tyr Trp Glu Asp Ile Gly Thr Ile
            260                 265                 270

Glu Ala Phe Tyr Glu Ala Asn Leu Ala Leu Thr Lys Gln Pro Ser Pro
        275                 280                 285

Asp Phe Ser Phe Tyr Asn Glu Lys Ala Pro Ile Tyr Thr Arg Gly Arg
    290                 295                 300

Tyr Leu Pro Pro Thr Lys Met Leu Asn Ser Thr Val Thr Glu Ser Met
305                 310                 315                 320

Ile Gly Glu Gly Cys Met Ile Lys Gln Cys Arg Ile His His Ser Val
                325                 330                 335

Leu Gly Ile Arg Ser Arg Ile Glu Ser Asp Cys Thr Ile Glu Asp Thr
            340                 345                 350

Leu Val Met Gly Asn Asp Phe Tyr Glu Ser Ser Ser Glu Arg Asp Thr
        355                 360                 365

Leu Lys Ala Arg Gly Glu Ile Ala Ala Gly Ile Gly Ser Gly Thr Thr
        370                 375                 380

Ile Arg Arg Ala Ile Ile Asp Lys Asn Ala Arg Ile Gly Lys Asn Val
385                 390                 395                 400

Met Ile Val Asn Lys Glu Asn Val Gln Glu Ala Asn Arg Glu Glu Leu
                405                 410                 415

Gly Phe Tyr Ile Arg Asn Gly Ile Val Val Ile Lys Asn Val Thr
            420                 425                 430

Ile Ala Asp Gly Thr Val Ile
        435

<210> SEQ ID NO 61
<211> LENGTH: 1290
<212> TYPE: DNA
<213> ORGANISM: Nostoc sp. PCC 7120

<400> SEQUENCE: 61
gtgaaaaaag tcttagcaat tattcttggt ggtggtgcgg gtactcgcct ttacccacta      60
accaaactcc gcgctaaacc ggcagtacca gtggcaggga ataccgcct aatagatatc     120 cctgtcagta actgcattaa ttcggaaatt tttaaaatct acgtattaac acaatttaac     180
tcagcttctc tcaatcgcca cattgcccgt acctacaact ttagtggttt tagcgagggt     240
tttgtggaag tgctggccgc ccagcagaca ccagagaacc ctaactggtt ccaaggtaca     300
gccgatgctg tacgtcagta tctctggatg ttacaagagt gggacgtaga tgaattttg     360 atcctgtcgg gggatcacct gtaccggatg gactatcgcc tatttatcca gcgccatcga     420
gaaaccaatg cggatatcac actttccgta attcccattg atgatcgccg cgcctcggat     480
tttggtttaa tgaaaatcga taactctgga cgagtcattg atttcagtga aaacccaag     540 ggcgaagcct taaccaaaat gcgtgttgat accacggttt taggcttgac accagaacag     600
gcggcatcac agccttacat tgcctcgatg gggatttacg tatttaaaaa agacgttttg     660
atcaagctgt tgaaggaagc tttagaacgt actgatttcg gcaaagaaat tattcctgat     720
gccgccaaag atcacaacgt tcaagcttac ctattcgatg actactggga agatattggg     780
acaatcgaag cttttttataa cgccaattta gcgttaactc agcagcccat gccgcccttt     840
agcttctacg atgaagaagc acctatttat acccgcgctc gttacttacc acccacaaaa     900
ctattagatt gccacgttac agaatcaatc attggcgaag gctgtattct gaaaaactgt     960
cgcattcaac actcagtatt gggagtgcga tcgcgtattg aaactggctg catgatcgaa    1020
gaatctttac tcatgggtgc cgacttctac caagcttcag tggaacgcca gtgcagcatc    1080
gataaaggag acatccctgt aggcatcggt ccagatacaa tcattcgccg tgccatcatc    1140
gataaaaatg cccgcatcgg tcacgatgtc aaaattatca ataaagacaa cgtgcaagaa    1200
gccgaccgcg aaagtcaagg attttacatc cgcagtggca ttgtcgtcgt cctcaaaaat    1260
gccgttatta cagatggcac aatcattag                                      1290

<210> SEQ ID NO 62
<211> LENGTH: 429
<212> TYPE: PRT
<213> ORGANISM: Nostoc sp. PCC 7120

<400> SEQUENCE: 62

Met Lys Lys Val Leu Ala Ile Ile Leu Gly Gly Gly Ala Gly Thr Arg
1               5                   10                  15

```
Leu Tyr Pro Leu Thr Lys Leu Arg Ala Lys Pro Ala Val Pro Val Ala
             20                  25                  30

Gly Lys Tyr Arg Leu Ile Asp Ile Pro Val Ser Asn Cys Ile Asn Ser
             35                  40                  45

Glu Ile Phe Lys Ile Tyr Val Leu Thr Gln Phe Asn Ser Ala Ser Leu
 50                  55                  60

Asn Arg His Ile Ala Arg Thr Tyr Asn Phe Ser Gly Phe Ser Glu Gly
 65                  70                  75                  80

Phe Val Glu Val Leu Ala Ala Gln Gln Thr Pro Glu Asn Pro Asn Trp
                 85                  90                  95

Phe Gln Gly Thr Ala Asp Ala Val Arg Gln Tyr Leu Trp Met Leu Gln
                100                 105                 110

Glu Trp Asp Val Asp Glu Phe Leu Ile Leu Ser Gly Asp His Leu Tyr
            115                 120                 125

Arg Met Asp Tyr Arg Leu Phe Ile Gln Arg His Arg Glu Thr Asn Ala
            130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
            195                 200                 205

Ser Met Gly Ile Tyr Val Phe Lys Lys Asp Val Leu Ile Lys Leu Leu
210                 215                 220

Lys Glu Ala Leu Glu Arg Thr Asp Phe Gly Lys Glu Ile Ile Pro Asp
225                 230                 235                 240

Ala Ala Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
            275                 280                 285

Ile Tyr Thr Arg Ala Arg Tyr Leu Pro Pro Thr Lys Leu Leu Asp Cys
290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335

Cys Met Ile Glu Glu Ser Leu Leu Met Gly Ala Asp Phe Tyr Gln Ala
            340                 345                 350

Ser Val Glu Arg Gln Cys Ser Ile Asp Lys Gly Asp Ile Pro Val Gly
            355                 360                 365

Ile Gly Pro Asp Thr Ile Ile Arg Arg Ala Ile Ile Asp Lys Asn Ala
            370                 375                 380

Arg Ile Gly His Asp Val Lys Ile Ile Asn Lys Asp Asn Val Gln Glu
385                 390                 395                 400

Ala Asp Arg Glu Ser Gln Gly Phe Tyr Ile Arg Ser Gly Ile Val Val
                405                 410                 415

Val Leu Lys Asn Ala Val Ile Thr Asp Gly Thr Ile Ile
                420                 425
```

<210> SEQ ID NO 63
<211> LENGTH: 1290
<212> TYPE: DNA
<213> ORGANISM: Anabaena variabilis

<400> SEQUENCE: 63

```
gtgaaaaaag tcttagcaat tattcttggt ggtggtgcgg gtactcgcct ttacccacta    60
accaaactcc gcgctaaacc ggcagtacca gtggcaggga ataccgcct aatagatatc    120
cctgtcagta actgcattaa ttcggaaatt tttaaaatct acgtattaac acaatttaac   180
tcagcttctc tcaatcgcca cattgcccgt acctacaact ttagtggttt tagcgagggt   240
tttgtggaag tgctggccgc ccagcagaca ccagagaacc ctaactggtt ccaaggtaca   300
gccgatgctg tacgtcagta tctctggatg ttacaagagt gggacgtaga tgaattttg    360
atcctgtcag gagatcacct gtaccggatg gattatcgcc tatttatcca gcgccatcga   420
gaaaccaatg cggatatcac actttccgta attcccattg acgatcgccg cgcctcggat   480
tttggtttaa tgaagatcga taactctgga cgagtcatcg attttagcga aaaacccaaa   540
ggcgaagcct taaccaaaat gcgtgttgat accaccgttt taggcttgac accagaacag   600
gcagcatcac agccttacat cgcctcgatg gggatttacg tatttaaaaa agatgttttg   660
atcaaactgt tgaaggaatc tttagaacgt actgatttcg gcaaagaaat tattcctgat   720
gcctccaaag atcacaacgt tcaagcttac ttattcgatg actactggga agatattggg   780
acaatcgaag cttttatat gctaattta gcattgactc agcagcccat gccgcccttt   840
agcttctacg acgaagaagc accaatttat acccgcgcac gttacttacc acccacaaaa   900
ctattagatt gccacgttac agaatcaatc attggcgaag gctgtattct gaaaaactgt   960
cgcattcaac actcagtatt gggagtgcga tcgcgtattg aaaccggctg cgtcatcgaa  1020
gaatctttac tcatgggtgc cgacttctac caagcttcag tggaacgcca gtgcagcatt  1080
gacaaaggag acatccccgt aggcatcggc ccagatacca ttattcgccg tgccatcatc  1140
gataaaaatg cccgcatcgg tcacgatgtc aaaattatca ataaagacaa cgtgcaggaa  1200
gccgaccgcg aaagtcaagg atttttacatc cgcagtggca ttgtcgtcgt tctcaaaaat  1260
gccgtcatta ccgatggcac aataatttag                                   1290
```

<210> SEQ ID NO 64
<211> LENGTH: 429
<212> TYPE: PRT
<213> ORGANISM: Anabaena variabilis

<400> SEQUENCE: 64

```
Met Lys Lys Val Leu Ala Ile Ile Leu Gly Gly Gly Ala Gly Thr Arg
1               5                   10                  15

Leu Tyr Pro Leu Thr Lys Leu Arg Ala Lys Pro Ala Val Pro Val Ala
                20                  25                  30

Gly Lys Tyr Arg Leu Ile Asp Ile Pro Val Ser Asn Cys Ile Asn Ser
            35                  40                  45

Glu Ile Phe Lys Ile Tyr Val Leu Thr Gln Phe Asn Ser Ala Ser Leu
        50                  55                  60

Asn Arg His Ile Ala Arg Thr Tyr Asn Phe Ser Gly Phe Ser Glu Gly
65                  70                  75                  80

Phe Val Glu Val Leu Ala Ala Gln Gln Thr Pro Glu Asn Pro Asn Trp
                85                  90                  95

Phe Gln Gly Thr Ala Asp Ala Val Arg Gln Tyr Leu Trp Met Leu Gln
            100                 105                 110
```

Glu Trp Asp Val Asp Glu Phe Leu Ile Leu Ser Gly Asp His Leu Tyr
            115                 120                 125

Arg Met Asp Tyr Arg Leu Phe Ile Gln Arg His Arg Glu Thr Asn Ala
    130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
        195                 200                 205

Ser Met Gly Ile Tyr Val Phe Lys Lys Asp Val Leu Ile Lys Leu Leu
    210                 215                 220

Lys Glu Ser Leu Glu Arg Thr Asp Phe Gly Lys Glu Ile Ile Pro Asp
225                 230                 235                 240

Ala Ser Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
        275                 280                 285

Ile Tyr Thr Arg Ala Arg Tyr Leu Pro Pro Thr Lys Leu Leu Asp Cys
    290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335

Cys Val Ile Glu Glu Ser Leu Leu Met Gly Ala Asp Phe Tyr Gln Ala
            340                 345                 350

Ser Val Glu Arg Gln Cys Ser Ile Asp Lys Gly Asp Ile Pro Val Gly
        355                 360                 365

Ile Gly Pro Asp Thr Ile Ile Arg Arg Ala Ile Ile Asp Lys Asn Ala
    370                 375                 380

Arg Ile Gly His Asp Val Lys Ile Ile Asn Lys Asp Asn Val Gln Glu
385                 390                 395                 400

Ala Asp Arg Glu Ser Gln Gly Phe Tyr Ile Arg Ser Gly Ile Val Val
                405                 410                 415

Val Leu Lys Asn Ala Val Ile Thr Asp Gly Thr Ile Ile
            420                 425

<210> SEQ ID NO 65
<211> LENGTH: 1287
<212> TYPE: DNA
<213> ORGANISM: Trichodesmium erythraeum IMS 101

<400> SEQUENCE: 65
gtgaaaaacg tactaagtat aattctaggc ggtggcgcag gtacccgttt atatccctta      60
acaaaactac gggccaagcc tgcagtgccc ctagcaggaa aatatcgttt aatagatatt     120
cctataagta attgcataaa ctcagaaatc cagaaaattt atgttttgac ccaatttaac     180
tcagcttctc taaaccgcca tatcactcgt acctataact tctcaggttt cagtgatggt     240
tttgtcgaag ttctagcagc tcaacaaact aaagataatc cagagtggtt tcaaggaaca     300

-continued

```
gcagatgctg tccgtaaata tatatggtta ttcaaagagt gggatattga ttattatcta    360
attctctctg gagaccatct ctaccgtatg gactaccgag actttgtcca acgccatatc    420
gacaccaagg cagatatcac cctttctgtc ttgcctattg atgaagcacg ggcctccgag    480
tttggcgtca tgaaaattga taactcaggt cgaattgttg aatttagtga aaaaccgaaa    540
ggtaatgccc ttaaagctat ggcagttgat acttctattt taggagtcag tccagaaata    600
gctacaaaac aaccttatat tgcttctatg ggaatttatg tatttaataa agatgcaatg    660
atcaaactta tagaagattc agaggataca gattttggta aggaaatttt acccaagtcg    720
gctcaatctt ataatcttca agcctaccca ttccaaggtt actgggaaga catcggaacc    780
atcaaatcat tttatgaagc taatttggct ttgactcaac agcctcagcc acccttagc    840
ttttatgatg aacaagcccc tatctatacc cgctctcgtt atttacctcc gagcaaactt    900
ttggactgtg agattacaga gtcaattgtg ggagaaggtt gtattcttaa aaaatgtcgg    960
attgaccatt gtgtcttagg agtgcgatcg cgtatagaag ctaattgtat aattcaagat   1020
tctctgctaa tgggttcaga tttctatgaa tctcctacag aacgtcgata tggcctaaaa   1080
aaaggttctg tacctttggg tattggtgct gaaacgaaaa ttcgtggagc aattattgac   1140
aaaaatgccc gcattggttg taatgtccaa ataatcaata aggacaatgt agaagaagcc   1200
caacgtgagg aggaagggtt tatcattcgc agtggtattg ttgttgtttt gaaaaatgct   1260
actattcccg atggtacagt gatttag                                      1287
```

<210> SEQ ID NO 66
<211> LENGTH: 428
<212> TYPE: PRT
<213> ORGANISM: Trichodesmium erythraeum IMS 101

<400> SEQUENCE: 66

```
Met Lys Asn Val Leu Ser Ile Ile Leu Gly Gly Gly Ala Gly Thr Arg
 1               5                  10                  15

Leu Tyr Pro Leu Thr Lys Leu Arg Ala Lys Pro Ala Val Pro Leu Ala
            20                  25                  30

Gly Lys Tyr Arg Leu Ile Asp Ile Pro Ile Ser Asn Cys Ile Asn Ser
        35                  40                  45

Glu Ile Gln Lys Ile Tyr Val Leu Thr Gln Phe Asn Ser Ala Ser Leu
    50                  55                  60

Asn Arg His Ile Thr Arg Thr Tyr Asn Phe Ser Gly Phe Ser Asp Gly
65                  70                  75                  80

Phe Val Glu Val Leu Ala Ala Gln Gln Thr Lys Asp Asn Pro Glu Trp
                85                  90                  95

Phe Gln Gly Thr Ala Asp Ala Val Arg Lys Tyr Ile Trp Leu Phe Lys
            100                 105                 110

Glu Trp Asp Ile Asp Tyr Tyr Leu Ile Leu Ser Gly Asp His Leu Tyr
        115                 120                 125

Arg Met Asp Tyr Arg Asp Phe Val Gln Arg His Ile Thr Lys Ala
    130                 135                 140

Asp Ile Thr Leu Ser Val Leu Pro Ile Asp Glu Ala Arg Ala Ser Glu
145                 150                 155                 160

Phe Gly Val Met Lys Ile Asp Asn Ser Gly Arg Ile Val Glu Phe Ser
                165                 170                 175

Glu Lys Pro Lys Gly Asn Ala Leu Lys Ala Met Ala Val Asp Thr Ser
            180                 185                 190

Ile Leu Gly Val Ser Pro Glu Ile Ala Thr Lys Gln Pro Tyr Ile Ala
```

|  |  |  |  |  | 195 |  |  |  |  | 200 |  |  |  |  | 205 |  |
|---|---|---|---|---|---|---|---|---|---|---|---|---|---|---|---|---|

Ser Met Gly Ile Tyr Val Phe Asn Lys Asp Ala Met Ile Lys Leu Ile
210                     215                     220

Glu Asp Ser Glu Asp Thr Asp Phe Gly Lys Glu Ile Leu Pro Lys Ser
225                     230                     235                 240

Ala Gln Ser Tyr Asn Leu Gln Ala Tyr Pro Phe Gln Gly Tyr Trp Glu
            245                     250                     255

Asp Ile Gly Thr Ile Lys Ser Phe Tyr Glu Ala Asn Leu Ala Leu Thr
            260                     265                     270

Gln Gln Pro Gln Pro Pro Phe Ser Phe Tyr Asp Glu Gln Ala Pro Ile
            275                     280                     285

Tyr Thr Arg Ser Arg Tyr Leu Pro Pro Ser Lys Leu Leu Asp Cys Glu
290                     295                     300

Ile Thr Glu Ser Ile Val Gly Glu Gly Cys Ile Leu Lys Lys Cys Arg
305                     310                     315                 320

Ile Asp His Cys Val Leu Gly Val Arg Ser Arg Ile Glu Ala Asn Cys
                325                     330                     335

Ile Ile Gln Asp Ser Leu Leu Met Gly Ser Asp Phe Tyr Glu Ser Pro
            340                     345                     350

Thr Glu Arg Arg Tyr Gly Leu Lys Lys Gly Ser Val Pro Leu Gly Ile
            355                     360                     365

Gly Ala Glu Thr Lys Ile Arg Gly Ala Ile Ile Asp Lys Asn Ala Arg
370                     375                     380

Ile Gly Cys Asn Val Gln Ile Ile Asn Lys Asp Asn Val Glu Glu Ala
385                     390                     395                 400

Gln Arg Glu Glu Glu Gly Phe Ile Ile Arg Ser Gly Ile Val Val Val
                405                     410                     415

Leu Lys Asn Ala Thr Ile Pro Asp Gly Thr Val Ile
            420                     425

<210> SEQ ID NO 67
<211> LENGTH: 1293
<212> TYPE: DNA
<213> ORGANISM: Synechococcus elongatus PCC 7942

<400> SEQUENCE: 67

```
gtgaaaaacg tgctggcgat cattctcggt ggaggcgcag gcagtcgtct ctatccacta      60
accaaacagc gcgccaaacc agcggtcccc ctggcgggca ataccgcttt gatcgatatt     120
cccgtcagca attgcatcaa cgctgacatc aacaaaatct atgtgctgac gcagtttaac     180
tctgcctcgc tcaaccgcca cctcagtcag acctacaacc tctccagcgg ctttggcaat     240
ggctttgttg aggtgctagc agctcagatt acgccgagag accccaactg gttccaaggc     300
accgccgatg cggttcgcca gtatctctgg ctaatcaaag agtgggatgt ggatgagtac     360
ctgatcctgt cggggatca tctctaccgc atggactata gccagttcat tcagcggcac     420
cgagacacca atgccgacat cacactctcg gtcttgccga tcgatgaaaa gcgcgcctct     480
gattttggcc tgatgaagct agatggcagc ggccgggtgg tcgagttcag cgaaaagccc     540
aaagggatg aactcaggc gatgcaagtc gataccacga tcctcgggct tgaccctgtc     600
gctgctgctg cccagcccctt cattgcctcg atgggcatct acgtcttcaa gcgggatgtt     660
ctgatcgatt tgctcagcca tcatcccgag caaaccgact tggcaagga agtgattccc     720
gctgcagcca cccgctacaa cacccaagcc tttctgttca cgactactg ggaagacatc     780
ggcacgatcg cctcattcta cgaggccaat ctggcgctga ctcagcaacc tagcccaccc     840
```

```
ttcagcttct acgacgagca ggcgccgatt tacacccgcg ctcgctacct gccgccaacc    900
aagctgctcg attgccaggt gacccagtcg atcattggcg agggctgcat tctcaagcaa    960
tgcaccgttc agaattccgt cttagggatt cgctcccgca ttgaggccga ctgcgtgatc   1020
caggacgcct tgttgatggg cgctgacttc tacgaaacct cggagctacg caccagaat    1080 cgggccaatg caaagtgcc gatgggaatc ggcagtggca gcaccatccg tcgcgccatc    1140
gtcgacaaaa atgcccacat tggccagaac gttcagatcg tcaacaaaga ccatgtggaa    1200
gaggccgatc gcgaagatct gggctttatg atccgcagcg gcattgtcgt tgtggtcaaa    1260
ggggcggtta ttcccgacaa cacggtgatc taa                                 1293
```

<210> SEQ ID NO 68
<211> LENGTH: 430
<212> TYPE: PRT
<213> ORGANISM: Synechococcus elongatus PCC 7942

<400> SEQUENCE: 68

```
Met Lys Asn Val Leu Ala Ile Ile Leu Gly Gly Gly Ala Gly Ser Arg
 1               5                  10                  15

Leu Tyr Pro Leu Thr Lys Gln Arg Ala Lys Pro Ala Val Pro Leu Ala
             20                  25                  30

Gly Lys Tyr Arg Leu Ile Asp Ile Pro Val Ser Asn Cys Ile Asn Ala
         35                  40                  45

Asp Ile Asn Lys Ile Tyr Val Leu Thr Gln Phe Asn Ser Ala Ser Leu
     50                  55                  60

Asn Arg His Leu Ser Gln Thr Tyr Asn Leu Ser Ser Gly Phe Gly Asn
 65                  70                  75                  80

Gly Phe Val Glu Val Leu Ala Ala Gln Ile Thr Pro Glu Asn Pro Asn
                 85                  90                  95

Trp Phe Gln Gly Thr Ala Asp Ala Val Arg Gln Tyr Leu Trp Leu Ile
            100                 105                 110

Lys Glu Trp Asp Val Asp Glu Tyr Leu Ile Leu Ser Gly Asp His Leu
        115                 120                 125

Tyr Arg Met Asp Tyr Ser Gln Phe Ile Gln Arg His Arg Asp Thr Asn
    130                 135                 140

Ala Asp Ile Thr Leu Ser Val Leu Pro Ile Asp Glu Lys Arg Ala Ser
145                 150                 155                 160

Asp Phe Gly Leu Met Lys Leu Asp Gly Ser Gly Arg Val Val Glu Phe
                165                 170                 175

Ser Glu Lys Pro Lys Gly Asp Glu Leu Arg Ala Met Gln Val Asp Thr
            180                 185                 190

Thr Ile Leu Gly Leu Asp Pro Val Ala Ala Ala Gln Pro Phe Ile
        195                 200                 205

Ala Ser Met Gly Ile Tyr Val Phe Lys Arg Asp Val Leu Ile Asp Leu
    210                 215                 220

Leu Ser His His Pro Glu Gln Thr Asp Phe Gly Lys Glu Val Ile Pro
225                 230                 235                 240

Ala Ala Ala Thr Arg Tyr Asn Thr Gln Ala Phe Leu Phe Asn Asp Tyr
                245                 250                 255

Trp Glu Asp Ile Gly Thr Ile Ala Ser Phe Tyr Glu Ala Asn Leu Ala
            260                 265                 270

Leu Thr Gln Gln Pro Ser Pro Pro Phe Ser Phe Tyr Asp Glu Gln Ala
        275                 280                 285
```

```
Pro Ile Tyr Thr Arg Ala Arg Tyr Leu Pro Pro Thr Lys Leu Leu Asp
    290                 295                 300

Cys Gln Val Thr Gln Ser Ile Ile Gly Glu Gly Cys Ile Leu Lys Gln
305                 310                 315                 320

Cys Thr Val Gln Asn Ser Val Leu Gly Ile Arg Ser Arg Ile Glu Ala
                325                 330                 335

Asp Cys Val Ile Gln Asp Ala Leu Leu Met Gly Ala Asp Phe Tyr Glu
            340                 345                 350

Thr Ser Glu Leu Arg His Gln Asn Arg Ala Asn Gly Lys Val Pro Met
        355                 360                 365

Gly Ile Gly Ser Gly Ser Thr Ile Arg Arg Ala Ile Val Asp Lys Asn
    370                 375                 380

Ala His Ile Gly Gln Asn Val Gln Ile Val Asn Lys Asp His Val Glu
385                 390                 395                 400

Glu Ala Asp Arg Glu Asp Leu Gly Phe Met Ile Arg Ser Gly Ile Val
                405                 410                 415

Val Val Val Lys Gly Ala Val Ile Pro Asp Asn Thr Val Ile
            420                 425                 430
```

<210> SEQ ID NO 69
<211> LENGTH: 1296
<212> TYPE: DNA
<213> ORGANISM: Synechococcus sp. WH8102

<400> SEQUENCE: 69

```
atgaagcggg ttttggccat cattctcggc ggcggtgccg ggactcgtct ctacccgctc      60
accaagatgc gcgccaagcc ggccgtcccc ttggccggta agtatcgact gattgatatc     120
cccatcagca actgcatcaa ctcgaacatc aacaagatgt acgtgatgac gcagttcaac     180
agtgcgtctc tcaatcgtca cctcagccag acgttcaacc tgagcgcatc cttcggtcag     240
ggattcgtcg aggtgcttgc tgcccagcag acgcctgaca gtccatcctg gtttgaaggc     300
actgccgacg ctgtgcggaa gtaccagtgg ctgttccagg aatgggatgt cgatgaatac     360
ctgatcctgt ccggtgacca gctgtaccgg atggattaca gcctgttcgt tgaacatcac     420
cgcagcactg gtgctgacct caccgttgca gcccttcctg tggacccgaa acaggccgag     480
gcgttcggct tgatgcgcac ggatggtgac ggagacatca aggagttccg cgaaaagccc     540
aagggtgatt ctttgcttga tggcggtt gacaccagcc gatttggact cagtgcgaat     600
tcggccaagg agcgtcccta cctggcgtcg atggggattt atgtcttcag cagagacact     660
ctgttcgacc tgctcgattc caatcctggt tataaggact cggcaagga agtcattcct     720
gaggccctca gcgtggcga caagctgaag agctatgtct tgacgatta ttgggaagat     780
atcggaacga tcggagcgtt ctacgaggcc aacctggcgc tcacccagca cccacaccc     840
cccttcagct tctacgacga gaagttcccg atctacactc gtccccgcta tttaccccg     900
agcaaactgg ttgatgctca gatcaccaat tcgatcgttg gcgaaggctc aattttgaag     960
tcatgcagca ttcatcactg cgttttgggt gttcgcagtc gcattgaaac cgatgtggtg    1020
ctgcaagaca ccttggtgat gggcgctgac ttcttttgaat ccagtgatga gcgtgccgtg    1080
cttcgcgagc gtggtggtat tccggtcggg gtgggccaag gtacgactgt gaagcgcgcc    1140
atcctcgata aaacgctcg catcggatcc aacgtcacca tcgtcaacaa ggatcacgtc    1200
gaggaagctg atcgttccga tcagggcttc tatattcgta atggcattgt tgttgttgtc    1260
aagaacgcca ccatccagga cggaactgtg atctga                              1296
```

<210> SEQ ID NO 70
<211> LENGTH: 431
<212> TYPE: PRT
<213> ORGANISM: Synechococcus sp. WH8102

<400> SEQUENCE: 70

| | | | | | | | | | | | | | | |
|---|---|---|---|---|---|---|---|---|---|---|---|---|---|---|
| Met | Lys | Arg | Val | Leu | Ala | Ile | Ile | Leu | Gly | Gly | Ala | Gly | Thr | Arg |
| 1 | | | | 5 | | | | | 10 | | | | | 15 |
| Leu | Tyr | Pro | Leu | Thr | Lys | Met | Arg | Ala | Lys | Pro | Ala | Val | Pro | Leu | Ala |
| | | | 20 | | | | | 25 | | | | | 30 | | |
| Gly | Lys | Tyr | Arg | Leu | Ile | Asp | Ile | Pro | Ile | Ser | Asn | Cys | Ile | Asn | Ser |
| | | | 35 | | | | | 40 | | | | | 45 | | |
| Asn | Ile | Asn | Lys | Met | Tyr | Val | Met | Thr | Gln | Phe | Asn | Ser | Ala | Ser | Leu |
| 50 | | | | | 55 | | | | | 60 | | | | | |
| Asn | Arg | His | Leu | Ser | Gln | Thr | Phe | Asn | Leu | Ser | Ala | Ser | Phe | Gly | Gln |
| 65 | | | | | 70 | | | | | 75 | | | | | 80 |
| Gly | Phe | Val | Glu | Val | Leu | Ala | Ala | Gln | Gln | Thr | Pro | Asp | Ser | Pro | Ser |
| | | | | 85 | | | | | 90 | | | | | 95 | |
| Trp | Phe | Glu | Gly | Thr | Ala | Asp | Ala | Val | Arg | Lys | Tyr | Gln | Trp | Leu | Phe |
| | | | 100 | | | | | 105 | | | | | 110 | | |
| Gln | Glu | Trp | Asp | Val | Asp | Glu | Tyr | Leu | Ile | Leu | Ser | Gly | Asp | Gln | Leu |
| | | | 115 | | | | | 120 | | | | | 125 | | |
| Tyr | Arg | Met | Asp | Tyr | Ser | Leu | Phe | Val | Glu | His | His | Arg | Ser | Thr | Gly |
| | 130 | | | | | 135 | | | | | 140 | | | | |
| Ala | Asp | Leu | Thr | Val | Ala | Ala | Leu | Pro | Val | Asp | Pro | Lys | Gln | Ala | Glu |
| 145 | | | | | 150 | | | | | 155 | | | | | 160 |
| Ala | Phe | Gly | Leu | Met | Arg | Thr | Asp | Gly | Asp | Gly | Asp | Ile | Lys | Glu | Phe |
| | | | | 165 | | | | | 170 | | | | | 175 | |
| Arg | Glu | Lys | Pro | Lys | Gly | Asp | Ser | Leu | Leu | Glu | Met | Ala | Val | Asp | Thr |
| | | | 180 | | | | | 185 | | | | | 190 | | |
| Ser | Arg | Phe | Gly | Leu | Ser | Ala | Asn | Ser | Ala | Lys | Glu | Arg | Pro | Tyr | Leu |
| | | | 195 | | | | | 200 | | | | | 205 | | |
| Ala | Ser | Met | Gly | Ile | Tyr | Val | Phe | Ser | Arg | Asp | Thr | Leu | Phe | Asp | Leu |
| | 210 | | | | | 215 | | | | | 220 | | | | |
| Leu | Asp | Ser | Asn | Pro | Gly | Tyr | Lys | Asp | Phe | Gly | Lys | Glu | Val | Ile | Pro |
| 225 | | | | | 230 | | | | | 235 | | | | | 240 |
| Glu | Ala | Leu | Lys | Arg | Gly | Asp | Lys | Leu | Lys | Ser | Tyr | Val | Phe | Asp | Asp |
| | | | | 245 | | | | | 250 | | | | | 255 | |
| Tyr | Trp | Glu | Asp | Ile | Gly | Thr | Ile | Gly | Ala | Phe | Tyr | Glu | Ala | Asn | Leu |
| | | | 260 | | | | | 265 | | | | | 270 | | |
| Ala | Leu | Thr | Gln | Gln | Pro | Thr | Pro | Pro | Phe | Ser | Phe | Tyr | Asp | Glu | Lys |
| | | | 275 | | | | | 280 | | | | | 285 | | |
| Phe | Pro | Ile | Tyr | Thr | Arg | Pro | Arg | Tyr | Leu | Pro | Pro | Ser | Lys | Leu | Val |
| | | | | 290 | | | | | 295 | | | | | 300 | |
| Asp | Ala | Gln | Ile | Thr | Asn | Ser | Ile | Val | Gly | Glu | Gly | Ser | Ile | Leu | Lys |
| 305 | | | | | 310 | | | | | 315 | | | | | 320 |
| Ser | Cys | Ser | Ile | His | His | Cys | Val | Leu | Gly | Val | Arg | Ser | Arg | Ile | Glu |
| | | | | 325 | | | | | 330 | | | | | 335 | |
| Thr | Asp | Val | Val | Leu | Gln | Asp | Thr | Leu | Val | Met | Gly | Ala | Asp | Phe | Phe |
| | | | 340 | | | | | 345 | | | | | 350 | | |
| Glu | Ser | Ser | Asp | Glu | Arg | Ala | Val | Leu | Arg | Glu | Arg | Gly | Gly | Ile | Pro |
| | | | 355 | | | | | 360 | | | | | 365 | | |
| Val | Gly | Val | Gly | Gln | Gly | Thr | Thr | Val | Lys | Arg | Ala | Ile | Leu | Asp | Lys |
| | 370 | | | | | 375 | | | | | 380 | | | | |

Asn Ala Arg Ile Gly Ser Asn Val Thr Ile Val Asn Lys Asp His Val
385                 390                 395                 400

Glu Glu Ala Asp Arg Ser Asp Gln Gly Phe Tyr Ile Arg Asn Gly Ile
                405                 410                 415

Val Val Val Val Lys Asn Ala Thr Ile Gln Asp Gly Thr Val Ile
        420                 425                 430

<210> SEQ ID NO 71
<211> LENGTH: 1296
<212> TYPE: DNA
<213> ORGANISM: Synechococcus sp. RCC 307

<400> SEQUENCE: 71

```
atgaaacggg ttctcgcaat cattctcggt ggcggtgcgg gtacgcggct ctatccgctg      60
accaaaatgc gggccaaacc agccgtgccg ctggcgggta agtaccgcct catcgacatc    120
cccgttagca actgcatcaa cagcgggatc aacaagatct atgtgctgac gcagttcaac    180
agcgcatcac tgaatcgcca catcgctcaa accttcaacc tctcctcggg gtttgatcaa    240
gggtttgttg aagttctggc ggcccagcag accccagata gccccagttg gtttgaagga    300
acagccgatg ctgttcgtaa atacgaatgg ctgctgcagg agtgggacat cgacgaagtg    360
ctgatccttt cgggtgacca gctctaccgg atggactatg cccattttgt ggctcagcac    420
cgcgccagcg cgctgaccct caccgtggcc gccctcccgg ttgatcgcga gcaagcccag    480
agctttggct tgatgcacac cggtgcagaa gcctccatca ccaagttccg gaaaagccc     540
aaaggcgagg cactcgatga tgtcctgc gataccgcca gcatgggctt gagcgctgag     600
gaagcccatc gccggccgtt cctggcttcc atgggcatct acgtgttcaa gcgggacgtg    660
ctcttccgct tactggctga aaaccccggt gccactgact tcggtaagga gatcatcccc    720
aaggcactcg acgatggctt caaactccgc tcctatctct tcgacgatta ctgggaagac    780
atcggaacca tccgtgcttt ctatgaagcg aatctggcgc tgacgaccca gccgcgtccg    840
cccttctctt tctacgacaa gcgtttcccg atctacacac gtcatcgcta cctgccgccc    900
tccaagcttc aagatgcgca ggtcaccgac tccattgttg gtgagggggtc cattttgaag    960
gcttgcagta ttcaccactg cgtcttgggt gtgcgcagcc gcattgaaga cgaggttgcc   1020
ttgcaagaca ccctggtgat gggcaacgac ttctatgagt ccggcgaaga gcgggccatc   1080
ctgcgggaac gtggtggcat ccccatgggt gtgggccgag aaccacggt gaaaaaggcc   1140
atcctcgata gaacgtccg catcggcagc aacgtcagca tcatcaacaa agacaacgtt   1200
gaggaagccg accgcgctga gcagggcttc tacatccgtg gcgggattgt ggtgatcacc   1260
aaaaacgctt cgattcccga cgggatggtg atctga                            1296
```

<210> SEQ ID NO 72
<211> LENGTH: 431
<212> TYPE: PRT
<213> ORGANISM: Synechococcus sp. RCC 307

<400> SEQUENCE: 72

Met Lys Arg Val Leu Ala Ile Ile Leu Gly Gly Gly Ala Gly Thr Arg
1               5                   10                  15

Leu Tyr Pro Leu Thr Lys Met Arg Ala Lys Pro Ala Val Pro Leu Ala
                20                  25                  30

Gly Lys Tyr Arg Leu Ile Asp Ile Pro Val Ser Asn Cys Ile Asn Ser
            35                  40                  45

Gly Ile Asn Lys Ile Tyr Val Leu Thr Gln Phe Asn Ser Ala Ser Leu
            50                  55                  60

Asn Arg His Ile Ala Gln Thr Phe Asn Leu Ser Ser Gly Phe Asp Gln
 65                  70                  75                  80

Gly Phe Val Glu Val Leu Ala Ala Gln Gln Thr Pro Asp Ser Pro Ser
                 85                  90                  95

Trp Phe Glu Gly Thr Ala Asp Ala Val Arg Lys Tyr Glu Trp Leu Leu
                100                 105                 110

Gln Glu Trp Asp Ile Asp Glu Val Leu Ile Leu Ser Gly Asp Gln Leu
            115                 120                 125

Tyr Arg Met Asp Tyr Ala His Phe Val Ala Gln His Arg Ala Ser Gly
130                 135                 140

Ala Asp Leu Thr Val Ala Ala Leu Pro Val Asp Arg Glu Gln Ala Gln
145                 150                 155                 160

Ser Phe Gly Leu Met His Thr Gly Ala Glu Ala Ser Ile Thr Lys Phe
                165                 170                 175

Arg Glu Lys Pro Lys Gly Glu Ala Leu Asp Glu Met Ser Cys Asp Thr
            180                 185                 190

Ala Ser Met Gly Leu Ser Ala Glu Glu Ala His Arg Arg Pro Phe Leu
            195                 200                 205

Ala Ser Met Gly Ile Tyr Val Phe Lys Arg Asp Val Leu Phe Arg Leu
210                 215                 220

Leu Ala Glu Asn Pro Gly Ala Thr Asp Phe Gly Lys Glu Ile Ile Pro
225                 230                 235                 240

Lys Ala Leu Asp Asp Gly Phe Lys Leu Arg Ser Tyr Leu Phe Asp Asp
                245                 250                 255

Tyr Trp Glu Asp Ile Gly Thr Ile Arg Ala Phe Tyr Glu Ala Asn Leu
            260                 265                 270

Ala Leu Thr Thr Gln Pro Arg Pro Phe Ser Phe Tyr Asp Lys Arg
            275                 280                 285

Phe Pro Ile Tyr Thr Arg His Arg Tyr Leu Pro Pro Ser Lys Leu Gln
            290                 295                 300

Asp Ala Gln Val Thr Asp Ser Ile Val Gly Glu Gly Ser Ile Leu Lys
305                 310                 315                 320

Ala Cys Ser Ile His His Cys Val Leu Gly Val Arg Ser Arg Ile Glu
                325                 330                 335

Asp Glu Val Ala Leu Gln Asp Thr Leu Val Met Gly Asn Asp Phe Tyr
            340                 345                 350

Glu Ser Gly Glu Glu Arg Ala Ile Leu Arg Glu Arg Gly Gly Ile Pro
            355                 360                 365

Met Gly Val Gly Arg Gly Thr Thr Val Lys Lys Ala Ile Leu Asp Lys
370                 375                 380

Asn Val Arg Ile Gly Ser Asn Val Ser Ile Ile Asn Lys Asp Asn Val
385                 390                 395                 400

Glu Glu Ala Asp Arg Ala Glu Gln Gly Phe Tyr Ile Arg Gly Gly Ile
                405                 410                 415

Val Val Ile Thr Lys Asn Ala Ser Ile Pro Asp Gly Met Val Ile
            420                 425                 430

<210> SEQ ID NO 73
<211> LENGTH: 1290
<212> TYPE: DNA
<213> ORGANISM: Synechococcus sp. PCC 7002

<400> SEQUENCE: 73

-continued

```
gtgaaacgag tcctaggaat catacttggc ggcggcgcag gtactcgcct atatccgcta    60
acaaaactca gagctaagcc cgcagtacct ctagcaggca aatatcgtct cattgatatt   120
cctgttagca attgcattaa ttctgaaatt cataaaatct acattttaac ccaatttaat   180
tcagcatctt taaatcgtca cattagtcga acctacaact ttaccggctt caccgaaggc   240
tttaccgaag tactcgcagc ccaacaaact aaagaaaatc ccgattggtt ccaaggcacc   300
gccgacgctg tccgacagta cagttggctt ctagaagact gggatgtcga tgaatacatc   360
attctctccg gtgatcacct ctaccgtatg gattaccgtg aatttatcca gcgccaccgt   420
gacactgggg cagacatcac cctgtctgtg gttcccgtgg gcgaaaaagt agcccccgcc   480
tttgggttga tgaaaattga tgccaatggt cgtgtcgtgg actttagtga aaagcccact   540
ggtgaagccc ttaaggcgat gcaggtggat acccagtcct gggtctcga tccagagcag   600
gcgaaagaaa agccctacat tgcgtcgatg gggatctacg tctttaagaa caagtactc   660
ctcgatctac tcaaagaagg caaagataaa accgatttcg ggaaagaaat tattcctgat   720
gcggccaagg actacaacgt tcaggcctat ctctttgatg attattgggc tgacattggg   780
accatcgaag cgttctatga agcaaaacctt ggcttgacga agcagccgat cccacccttt   840
agtttctatg acgaaaaggc tcccatctac acccgggcgc gctacttacc gccgacgaag   900
gtgctcaacg ctgacgtgac agaatcgatg atcagcgaag gttgcatcat aaaaaactgc   960
cgcattcacc actcagttct tggcattcgc acccgtgtcg aagcggactg cactatcgaa  1020
gatacgatga tcatgggcgc agattattat cagccctatg agaagcgcca ggattgtctc  1080
cgtcgtggca agcctcccat tgggattggt gaagggacaa cgattcgccg ggcgatcatc  1140
gataaaaatg cacgcatcgg taaaaacgtg atgatcgtca ataaggaaaa tgtggaggag  1200
tcaaaccgtg aggagcttgg ctactacatt cgcagcggca ttacagtggt gctaaagaac  1260
gccgttattc ccgacggtac ggtcatttaa                                    1290
```

<210> SEQ ID NO 74
<211> LENGTH: 429
<212> TYPE: PRT
<213> ORGANISM: Synechococcus sp. PCC 7002

<400> SEQUENCE: 74

```
Met Lys Arg Val Leu Gly Ile Ile Leu Gly Gly Gly Ala Gly Thr Arg
  1               5                  10                  15

Leu Tyr Pro Leu Thr Lys Leu Arg Ala Lys Pro Ala Val Pro Leu Ala
             20                  25                  30

Gly Lys Tyr Arg Leu Ile Asp Ile Pro Val Ser Asn Cys Ile Asn Ser
         35                  40                  45

Glu Ile His Lys Ile Tyr Ile Leu Thr Gln Phe Asn Ser Ala Ser Leu
     50                  55                  60

Asn Arg His Ile Ser Arg Thr Tyr Asn Phe Thr Gly Phe Thr Glu Gly
 65                  70                  75                  80

Phe Thr Glu Val Leu Ala Ala Gln Gln Thr Lys Glu Asn Pro Asp Trp
                 85                  90                  95

Phe Gln Gly Thr Ala Asp Ala Val Arg Gln Tyr Ser Trp Leu Leu Glu
            100                 105                 110

Asp Trp Asp Val Asp Glu Tyr Ile Ile Leu Ser Gly Asp His Leu Tyr
        115                 120                 125

Arg Met Asp Tyr Arg Glu Phe Ile Gln Arg His Arg Asp Thr Gly Ala
    130                 135                 140
```

```
Asp Ile Thr Leu Ser Val Val Pro Val Gly Glu Lys Val Ala Pro Ala
145                 150                 155                 160

Phe Gly Leu Met Lys Ile Asp Ala Asn Gly Arg Val Val Asp Phe Ser
            165                 170                 175

Glu Lys Pro Thr Gly Glu Ala Leu Lys Ala Met Gln Val Asp Thr Gln
            180                 185                 190

Ser Leu Gly Leu Asp Pro Glu Gln Ala Lys Glu Lys Pro Tyr Ile Ala
            195                 200                 205

Ser Met Gly Ile Tyr Val Phe Lys Lys Gln Val Leu Leu Asp Leu Leu
210                 215                 220

Lys Glu Gly Lys Asp Lys Thr Asp Phe Gly Lys Glu Ile Ile Pro Asp
225                 230                 235                 240

Ala Ala Lys Asp Tyr Asn Val Gln Ala Tyr Leu Phe Asp Asp Tyr Trp
            245                 250                 255

Ala Asp Ile Gly Thr Ile Glu Ala Phe Tyr Glu Ala Asn Leu Gly Leu
            260                 265                 270

Thr Lys Gln Pro Ile Pro Pro Phe Ser Phe Tyr Asp Glu Lys Ala Pro
            275                 280                 285

Ile Tyr Thr Arg Ala Arg Tyr Leu Pro Pro Thr Lys Val Leu Asn Ala
290                 295                 300

Asp Val Thr Glu Ser Met Ile Ser Glu Gly Cys Ile Ile Lys Asn Cys
305                 310                 315                 320

Arg Ile His His Ser Val Leu Gly Ile Arg Thr Arg Val Glu Ala Asp
            325                 330                 335

Cys Thr Ile Glu Asp Thr Met Ile Met Gly Ala Asp Tyr Tyr Gln Pro
            340                 345                 350

Tyr Glu Lys Arg Gln Asp Cys Leu Arg Arg Gly Lys Pro Pro Ile Gly
            355                 360                 365

Ile Gly Glu Gly Thr Thr Ile Arg Arg Ala Ile Ile Asp Lys Asn Ala
            370                 375                 380

Arg Ile Gly Lys Asn Val Met Ile Val Asn Lys Glu Asn Val Glu Glu
385                 390                 395                 400

Ser Asn Arg Glu Glu Leu Gly Tyr Tyr Ile Arg Ser Gly Ile Thr Val
            405                 410                 415

Val Leu Lys Asn Ala Val Ile Pro Asp Gly Thr Val Ile
            420                 425

<210> SEQ ID NO 75
<211> LENGTH: 1704
<212> TYPE: DNA
<213> ORGANISM: Synechocystis sp. PCC 6803

<400> SEQUENCE: 75
gtgtctaagc ccctgatcgc cgccctccat tttttacaat ttttgtatat gacaagcaga     60
attaatcccc tcgccggcca gcatccccccc gccgacagcc ttttggatgt ggccaaactt    120
ttagacgact attaccgtca gcaaccggac ccggaaaatc ccgcccagtt agtgagcttt    180
ggtacctctg gccatcgggg ttctgccctc aacggtactt ttaatgaagc ccatattttg    240
gcggtgaccc aggcagtggt ggactatcgc caagcccagg cattacgggc cccctttat     300 atggggatgg atagccatgc tctgtcggaa ccagcccaga aaacggcgtt ggaagtgttg    360
gccgctaacc aagtagaaac ttttttaacc accgccacgg atttaacccg tttcaccccc    420
actccggcgg tatcctacgc cattttgacc cacaaccagg acgtaaaaga aggtttagcg    480
```

-continued

```
gacggcatta ttattacccc ttcccacaat cccccactg atggaggctt taaatataat      540 ccccctccg gtggcccggc ggaaccggaa gcgacccaat ggattcagaa ccgggccaat      600
gagttgctga aaaatggcaa taaaacagtt aaacggctgg attacgagca ggcattaaaa      660
gccaccacca cccatgccca tgattttgtc actccctatg tggccggtct ggcggacatc      720
attgacttgg atgtaattcg ttcagcgggc ttgcgcttgg gagttgaccc cctgggggga      780
gccaatgtgg gctattggga acccattgcc gctaaataca atttgaacat cagcttggtt      840
aatcccgggg tagatcccac gtttaaattt atgaccctgg attgggacgg caaaatccgc      900
atggattgtt cttcccccta cgccatggcc agtttggtga aaatcaaaga ccattacgac      960
attgcctttg caacgacac cgacggcgat cgccatggca ttgtcacccc cagcgtgggt     1020
ttgatgaatc ccaatcattt tctttccgtg gccatttggt atttgtttag tcagcggcaa     1080
cagtggtcag ggctgtcggc gatcggcaaa accctagtca gcagcagcat gattgaccgg     1140 gtggggcca tgattaatcg ccaagtttac gaagtgcccg tgggctttaa atggtttgtc      1200
agcggtttgc tagatggttc ctttggcttt ggggtgaag aaagtgccgg ggcttcgttt      1260
ttgaaaaaaa atggcaccgt ttggaccacc gacaaagatg gcaccattat ggatttattg     1320
gcggcggaaa tcaccgctaa aaccggcaaa gatcccggcc tccattacca ggatttgacc     1380
gctaagttag gtaatcccat ttaccaacgc attgatgccc cgccactcc ggcccaaaaa     1440 gaccgcttga aaaaactgtc ccccgatgac gttacagcta cctccttagc tggggatgcc     1500
attactgcta aattaaccaa agcccctggc aaccaagcgg cgatcggtgg gttgaaggtg     1560
accactgcga aaggttggtt tgcggcccgg ccctccggca cggaaaatgt ttacaaaatc     1620
tatgccgaaa gtttcaaaga cgaagcccat ctccaggcta ttttcacgga ggcggaagcc     1680
attgttacct cggctttggg ctaa                                            1704
```

<210> SEQ ID NO 76
<211> LENGTH: 567
<212> TYPE: PRT
<213> ORGANISM: Synechocystis sp. PCC 6803

<400> SEQUENCE: 76

```
Met Ser Lys Pro Leu Ile Ala Ala Leu His Phe Leu Gln Phe Leu Tyr
  1               5                  10                  15

Met Thr Ser Arg Ile Asn Pro Leu Ala Gly Gln His Pro Pro Ala Asp
             20                  25                  30

Ser Leu Leu Asp Val Ala Lys Leu Leu Asp Asp Tyr Tyr Arg Gln Gln
         35                  40                  45

Pro Asp Pro Glu Asn Pro Ala Gln Leu Val Ser Phe Gly Thr Ser Gly
     50                  55                  60

His Arg Gly Ser Ala Leu Asn Gly Thr Phe Asn Glu Ala His Ile Leu
 65                  70                  75                  80

Ala Val Thr Gln Ala Val Val Asp Tyr Arg Gln Ala Gln Gly Ile Thr
                 85                  90                  95

Gly Pro Leu Tyr Met Gly Met Asp Ser His Ala Leu Ser Glu Pro Ala
            100                 105                 110

Gln Lys Thr Ala Leu Glu Val Leu Ala Ala Asn Gln Val Glu Thr Phe
        115                 120                 125

Leu Thr Thr Ala Thr Asp Leu Thr Arg Phe Thr Pro Thr Pro Ala Val
    130                 135                 140

Ser Tyr Ala Ile Leu Thr His Asn Gln Gly Arg Lys Glu Gly Leu Ala
145                 150                 155                 160
```

-continued

```
Asp Gly Ile Ile Ile Thr Pro Ser His Asn Pro Pro Thr Asp Gly Gly
                165                 170                 175

Phe Lys Tyr Asn Pro Pro Ser Gly Gly Pro Ala Glu Pro Glu Ala Thr
            180                 185                 190

Gln Trp Ile Gln Asn Arg Ala Asn Glu Leu Leu Lys Asn Gly Asn Lys
        195                 200                 205

Thr Val Lys Arg Leu Asp Tyr Glu Gln Ala Leu Lys Ala Thr Thr Thr
    210                 215                 220

His Ala His Asp Phe Val Thr Pro Tyr Val Ala Gly Leu Ala Asp Ile
225                 230                 235                 240

Ile Asp Leu Asp Val Ile Arg Ser Ala Gly Leu Arg Leu Gly Val Asp
                245                 250                 255

Pro Leu Gly Gly Ala Asn Val Gly Tyr Trp Glu Pro Ile Ala Ala Lys
            260                 265                 270

Tyr Asn Leu Asn Ile Ser Leu Val Asn Pro Gly Val Asp Pro Thr Phe
        275                 280                 285

Lys Phe Met Thr Leu Asp Trp Asp Gly Lys Ile Arg Met Asp Cys Ser
    290                 295                 300

Ser Pro Tyr Ala Met Ala Ser Leu Val Lys Ile Lys Asp His Tyr Asp
305                 310                 315                 320

Ile Ala Phe Gly Asn Asp Thr Asp Gly Asp Arg His Gly Ile Val Thr
                325                 330                 335

Pro Ser Val Gly Leu Met Asn Pro Asn His Phe Leu Ser Val Ala Ile
            340                 345                 350

Trp Tyr Leu Phe Ser Gln Arg Gln Gln Trp Ser Gly Leu Ser Ala Ile
        355                 360                 365

Gly Lys Thr Leu Val Ser Ser Ser Met Ile Asp Arg Val Gly Ala Met
    370                 375                 380

Ile Asn Arg Gln Val Tyr Glu Val Pro Val Gly Phe Lys Trp Phe Val
385                 390                 395                 400

Ser Gly Leu Leu Asp Gly Ser Phe Gly Phe Gly Gly Glu Glu Ser Ala
                405                 410                 415

Gly Ala Ser Phe Leu Lys Lys Asn Gly Thr Val Trp Thr Thr Asp Lys
            420                 425                 430

Asp Gly Thr Ile Met Asp Leu Leu Ala Ala Glu Ile Thr Ala Lys Thr
        435                 440                 445

Gly Lys Asp Pro Gly Leu His Tyr Gln Asp Leu Thr Ala Lys Leu Gly
    450                 455                 460

Asn Pro Ile Tyr Gln Arg Ile Asp Ala Pro Thr Pro Ala Gln Lys
465                 470                 475                 480

Asp Arg Leu Lys Lys Leu Ser Pro Asp Val Thr Ala Thr Ser Leu
                485                 490                 495

Ala Gly Asp Ala Ile Thr Ala Lys Leu Thr Lys Ala Pro Gly Asn Gln
            500                 505                 510

Ala Ala Ile Gly Gly Leu Lys Val Thr Thr Ala Glu Gly Trp Phe Ala
        515                 520                 525

Ala Arg Pro Ser Gly Thr Glu Asn Val Tyr Lys Ile Tyr Ala Glu Ser
    530                 535                 540

Phe Lys Asp Glu Ala His Leu Gln Ala Ile Phe Thr Glu Ala Glu Ala
545                 550                 555                 560

Ile Val Thr Ser Ala Leu Gly
                565
```

<210> SEQ ID NO 77
<211> LENGTH: 1632
<212> TYPE: DNA
<213> ORGANISM: Synechococcus elongatus PCC 7942

<400> SEQUENCE: 77

```
atgaatatcc acactgtcgc gacgcaagcc tttagcgacc aaaagcccgg tacctccggc      60
ctgcgcaagc aagttcctgt cttccaaaaa cggcactatc tcgaaaactt tgtccagtcg     120
atcttcgata gccttgaggg ttatcagggc cagacgttag tgctgggggg tgatggccgc     180
tactacaatc gcacagccat ccaaaccatt ctgaaaatgg cggcggccaa tggttggggc     240
cgcgttttag ttggacaagg cggtattctc tccacgccag cagtctccaa cctaatccgc     300
cagaacggag ccttcggcgg catcatcctc tcggctagcc acaacccagg ggccctgag      360
ggcgatttcg gcatcaagta caacatcagc aacggtggcc ctgcacccga aaaagtcacc     420
gatgccatct atgcctgcag cctcaaaatt gaggcctacc gcattctcga agccggtgac     480
gttgacctcg atcgactcgg tagtcaacaa ctgggcgaga tgaccgttga ggtgatcgac     540
tcggtcgccg actacagccg cttgatgcaa tccctgtttg acttcgatcg cattcgcgat     600
cgcctgaggg gggggctacg gattgcgatc gactcgatgc atgccgtcac cggtccctac     660
gccaccacga tttttgagaa ggagctaggc gcggcggcag gcactgtttt taatggcaag     720
ccgctggaag actttggcgg gggtcacccaa gacccgaatt tggtctacgc ccacgacttg     780
gttgaactgt tgtttggcga tcgcgcccca gattttggcg cggcctccga tggcgatggc     840
gatcgcaaca tgatcttggg caatcacttt tttgtgaccc ctagcgacag cttggcgatt     900
ctcgcagcca atgccagcct agtgccggcc taccgcaatg gactgtctgg gattgcgcga     960
tccatgccca ccagtgcggc ggccgatcgc gtcgcccaag ccctcaacct gccctgctac    1020
gaaaccccaa cgggttggaa gttttcggc aatctgctcg atgccgatcg cgtcacccctc    1080
tgcggcgaag aaagctttgg cacaggctcc aaccatgtgc gcgagaagga tggcctgtgg    1140
gccgtgctgt tctggctgaa tattctggcg gtgcgcgagc aatccgtggc cgaaattgtc    1200
caagaacact ggcgcaccta cggccgcaac tactactctc gccacgacta cgaaggggtg    1260
gagagcgatc gagccagtac gctggtggac aaactgcgat cgcagctacc cagcctgacc    1320
ggacagaaac tgggagccta caccgttgcc tacgccgacg acttccgcta cgaagatccg    1380
gtcgatggca gcatcagcga acagcagggc attcgtattg ctttgaaga cggctcacgt    1440
atggtcttcc gcttgtctgg tactggtacg gcaggagcca ccctgcgcct ctacctcgag    1500
cgcttcgaag gggacaccac caaacagggt ctcgatcccc aagttgccct ggcagatttg    1560
attgcaatcg ccgatgaagt cgcccagatc acaaccttga cgggcttcga tcaaccgaca    1620
gtgatcacct ga                                                        1632
```

<210> SEQ ID NO 78
<211> LENGTH: 543
<212> TYPE: PRT
<213> ORGANISM: Synechococcus elongatus PCC 7942

<400> SEQUENCE: 78

Met Asn Ile His Thr Val Ala Thr Gln Ala Phe Ser Asp Gln Lys Pro
1               5                   10                  15

Gly Thr Ser Gly Leu Arg Lys Gln Val Pro Val Phe Gln Lys Arg His
            20                  25                  30

Tyr Leu Glu Asn Phe Val Gln Ser Ile Phe Asp Ser Leu Glu Gly Tyr

-continued

```
             35                  40                  45
Gln Gly Gln Thr Leu Val Leu Gly Gly Asp Gly Arg Tyr Tyr Asn Arg
             50                  55                  60
Thr Ala Ile Gln Thr Ile Leu Lys Met Ala Ala Asn Gly Trp Gly
 65                  70                  75                  80
Arg Val Leu Val Gly Gln Gly Gly Ile Leu Ser Thr Pro Ala Val Ser
                 85                  90                  95
Asn Leu Ile Arg Gln Asn Gly Ala Phe Gly Gly Ile Ile Leu Ser Ala
                100                 105                 110
Ser His Asn Pro Gly Gly Pro Glu Gly Asp Phe Gly Ile Lys Tyr Asn
                115                 120                 125
Ile Ser Asn Gly Gly Pro Ala Pro Glu Lys Val Thr Asp Ala Ile Tyr
            130                 135                 140
Ala Cys Ser Leu Lys Ile Glu Ala Tyr Arg Ile Leu Glu Ala Gly Asp
145                 150                 155                 160
Val Asp Leu Asp Arg Leu Gly Ser Gln Gln Leu Gly Glu Met Thr Val
                165                 170                 175
Glu Val Ile Asp Ser Val Ala Asp Tyr Ser Arg Leu Met Gln Ser Leu
                180                 185                 190
Phe Asp Phe Asp Arg Ile Arg Asp Arg Leu Arg Gly Gly Leu Arg Ile
                195                 200                 205
Ala Ile Asp Ser Met His Ala Val Thr Gly Pro Tyr Ala Thr Thr Ile
            210                 215                 220
Phe Glu Lys Glu Leu Gly Ala Ala Gly Thr Val Phe Asn Gly Lys
225                 230                 235                 240
Pro Leu Glu Asp Phe Gly Gly His Pro Asp Pro Asn Leu Val Tyr
                245                 250                 255
Ala His Asp Leu Val Glu Leu Leu Phe Gly Asp Arg Ala Pro Asp Phe
            260                 265                 270
Gly Ala Ala Ser Asp Gly Asp Gly Asp Arg Asn Met Ile Leu Gly Asn
            275                 280                 285
His Phe Phe Val Thr Pro Ser Asp Ser Leu Ala Ile Leu Ala Ala Asn
        290                 295                 300
Ala Ser Leu Val Pro Ala Tyr Arg Asn Gly Leu Ser Gly Ile Ala Arg
305                 310                 315                 320
Ser Met Pro Thr Ser Ala Ala Asp Arg Val Ala Gln Ala Leu Asn
                325                 330                 335
Leu Pro Cys Tyr Glu Thr Pro Thr Gly Trp Lys Phe Phe Gly Asn Leu
            340                 345                 350
Leu Asp Ala Asp Arg Val Thr Leu Cys Gly Glu Glu Ser Phe Gly Thr
            355                 360                 365
Gly Ser Asn His Val Arg Glu Lys Asp Gly Leu Trp Ala Val Leu Phe
            370                 375                 380
Trp Leu Asn Ile Leu Ala Val Arg Glu Gln Ser Val Ala Glu Ile Val
385                 390                 395                 400
Gln Glu His Trp Arg Thr Tyr Gly Arg Asn Tyr Tyr Ser Arg His Asp
                405                 410                 415
Tyr Glu Gly Val Glu Ser Asp Arg Ala Ser Thr Leu Val Asp Lys Leu
                420                 425                 430
Arg Ser Gln Leu Pro Ser Leu Thr Gly Gln Lys Leu Gly Ala Tyr Thr
            435                 440                 445
Val Ala Tyr Ala Asp Asp Phe Arg Tyr Glu Asp Pro Val Asp Gly Ser
        450                 455                 460
```

```
Ile Ser Glu Gln Gln Gly Ile Arg Ile Gly Phe Asp Gly Ser Arg
465                 470                 475                 480

Met Val Phe Arg Leu Ser Gly Thr Gly Thr Ala Gly Ala Thr Leu Arg
            485                 490                 495

Leu Tyr Leu Glu Arg Phe Glu Gly Asp Thr Thr Lys Gln Gly Leu Asp
                500                 505                 510

Pro Gln Val Ala Leu Ala Asp Leu Ile Ala Ile Ala Asp Glu Val Ala
            515                 520                 525

Gln Ile Thr Thr Leu Thr Gly Phe Asp Gln Pro Thr Val Ile Thr
        530                 535                 540
```

<210> SEQ ID NO 79
<211> LENGTH: 1659
<212> TYPE: DNA
<213> ORGANISM: Synechococcus sp. WH8102

<400> SEQUENCE: 79

| | |
|---|---:|
| atgaccacct cggcccccgc ggaaccgacc ctgcgcctgg tgcgcctgga cgcacctttc | 60 |
| acggatcaga aacccggcac atccggtttg cgcaaaagca gccagcagtt cgagcaagcg | 120 |
| aactatctgg agagctttgt ggaagccgta ttccgcacct gcccggtgt tcaaggggc | 180 |
| acgctggtgt tgggaggtga cggccgttac ggcaaccgcc gtgccatcga cgtgatcctg | 240 |
| cgcatgggcg cggcccacgg cctcagcaag gtgatcgtca ccaccggcgg catcctctcc | 300 |
| accccggcgg cctcgaacct gattcgccag cgtcaggcca tcggcggcat catcctctcg | 360 |
| gcaagccaca accctggcgg ccccaatgga gacttcggcg tcaaggtgaa tggcgccaac | 420 |
| ggtggcccga ccccggcctc gttcaccgat gcggtgttcg agtgcaccaa gaccttggag | 480 |
| caatacacga tcgttgatgc cgcggccatc gccatcgata cccccggcag ctacagcatc | 540 |
| ggcgccatgc aggtggaggt gatcgacggc gtcgacgact tcgtggctct gatgcaacag | 600 |
| ctgttcgact tgatcggat ccgggagctg atccgcagcg acttcccgct ggcgtttgat | 660 |
| gcgatgcatg cggtcactgg cccctacgcc actcgcctgt tggaagagat cctcggcgct | 720 |
| cctgccggca gcgtccgcaa cggcgttcct ctggaggact cggcggcgg ccaccccgac | 780 |
| cccaacctca cctacgccca cgagctggcc gaacttctgc tcgacgggga ggagttccgc | 840 |
| ttcggggccg cctgcgacgg cgatggtgac cgcaacatga tcctggggca gcactgcttc | 900 |
| gtaaacccca gcgacagcct ggcggtgctc acagccaacg ccacggtggc accggcctat | 960 |
| gccgatggtt tggctggcgt ggcccgctcg atgcccacca gctctgccgt ggatgtggtg | 1020 |
| gccaaggaac tgggcatcga ctgctacgag accccaccg gctggaagtt cttcggcaat | 1080 |
| ctgctggatg ccggcaaaat cacgctctgc ggtgaagaga gcttcggcac ggcagcaac | 1140 |
| cacgtgcgtg aaaaggatgg cctctgggct gttctgttct ggctgcagat cctggccgag | 1200 |
| cgccgctgca gcgtcgccga gatcatggct gagcattgga agcgcttcgg ccgccactac | 1260 |
| tactctcgcc acgactacga agccgtcgcc agcgacgcag cccatgggct gttccaccgc | 1320 |
| ctcgagggca tgctccctgg tctggtgggg cagagcttcg ctggccgcag cgtcagcgca | 1380 |
| gccgacaact tcagctacac cgatcccgtt gatggtctg tgaccaaggg ccagggcctg | 1440 |
| cgcatcctgc tggaggatgg cagccgcgtg atggtgcgcc tctcgggcac cggcaccaag | 1500 |
| ggcgccacga tccgcgtcta tctggagagt tatgtaccga gcagcggtga tctcaaccag | 1560 |
| gatcccccagg tcgctctggc cgacatgatc agcgccatca atgaactggc ggagatcaag | 1620 |
| cagcgcaccg gcatggatcg gcccaccgtg atcacctga | 1659 |

<210> SEQ ID NO 80
<211> LENGTH: 552
<212> TYPE: PRT
<213> ORGANISM: Synechococcus sp. WH8102

<400> SEQUENCE: 80

```
Met Thr Thr Ser Ala Pro Ala Glu Pro Thr Leu Arg Leu Val Arg Leu
 1               5                  10                  15

Asp Ala Pro Phe Thr Asp Gln Lys Pro Gly Thr Ser Gly Leu Arg Lys
             20                  25                  30

Ser Ser Gln Gln Phe Glu Gln Ala Asn Tyr Leu Glu Ser Phe Val Glu
         35                  40                  45

Ala Val Phe Arg Thr Leu Pro Gly Val Gln Gly Thr Leu Val Leu
     50                  55                  60

Gly Gly Asp Gly Arg Tyr Gly Asn Arg Arg Ala Ile Asp Val Ile Leu
65                  70                  75                  80

Arg Met Gly Ala Ala His Gly Leu Ser Lys Val Ile Val Thr Thr Gly
                 85                  90                  95

Gly Ile Leu Ser Thr Pro Ala Ala Ser Asn Leu Ile Arg Gln Arg Gln
            100                 105                 110

Ala Ile Gly Gly Ile Ile Leu Ser Ala Ser His Asn Pro Gly Gly Pro
        115                 120                 125

Asn Gly Asp Phe Gly Val Lys Val Asn Gly Ala Asn Gly Gly Pro Thr
    130                 135                 140

Pro Ala Ser Phe Thr Asp Ala Val Phe Glu Cys Thr Lys Thr Leu Glu
145                 150                 155                 160

Gln Tyr Thr Ile Val Asp Ala Ala Ala Ile Ala Ile Asp Thr Pro Gly
                165                 170                 175

Ser Tyr Ser Ile Gly Ala Met Gln Val Glu Val Ile Asp Gly Val Asp
            180                 185                 190

Asp Phe Val Ala Leu Met Gln Gln Leu Phe Asp Phe Asp Arg Ile Arg
        195                 200                 205

Glu Leu Ile Arg Ser Asp Phe Pro Leu Ala Phe Asp Ala Met His Ala
    210                 215                 220

Val Thr Gly Pro Tyr Ala Thr Arg Leu Leu Glu Glu Ile Leu Gly Ala
225                 230                 235                 240

Pro Ala Gly Ser Val Arg Asn Gly Val Pro Leu Glu Asp Phe Gly Gly
                245                 250                 255

Gly His Pro Asp Pro Asn Leu Thr Tyr Ala His Glu Leu Ala Glu Leu
            260                 265                 270

Leu Leu Asp Gly Glu Glu Phe Arg Phe Gly Ala Ala Cys Asp Gly Asp
        275                 280                 285

Gly Asp Arg Asn Met Ile Leu Gly Gln His Cys Phe Val Asn Pro Ser
    290                 295                 300

Asp Ser Leu Ala Val Leu Thr Ala Asn Ala Thr Val Ala Pro Ala Tyr
305                 310                 315                 320

Ala Asp Gly Leu Ala Gly Val Ala Arg Ser Met Pro Thr Ser Ser Ala
                325                 330                 335

Val Asp Val Val Ala Lys Glu Leu Gly Ile Asp Cys Tyr Glu Thr Pro
            340                 345                 350

Thr Gly Trp Lys Phe Phe Gly Asn Leu Leu Asp Ala Gly Lys Ile Thr
        355                 360                 365

Leu Cys Gly Glu Glu Ser Phe Gly Thr Gly Ser Asn His Val Arg Glu
```

```
                 370                 375                 380
Lys Asp Gly Leu Trp Ala Val Leu Phe Trp Leu Gln Ile Leu Ala Glu
385                 390                 395                 400

Arg Arg Cys Ser Val Ala Glu Ile Met Ala Glu His Trp Lys Arg Phe
                405                 410                 415

Gly Arg His Tyr Tyr Ser Arg His Asp Tyr Glu Ala Val Ala Ser Asp
            420                 425                 430

Ala Ala His Gly Leu Phe His Arg Leu Glu Gly Met Leu Pro Gly Leu
        435                 440                 445

Val Gly Gln Ser Phe Ala Gly Arg Ser Val Ser Ala Ala Asp Asn Phe
    450                 455                 460

Ser Tyr Thr Asp Pro Val Asp Gly Ser Val Thr Lys Gly Gln Gly Leu
465                 470                 475                 480

Arg Ile Leu Leu Glu Asp Gly Ser Arg Val Met Val Arg Leu Ser Gly
                485                 490                 495

Thr Gly Thr Lys Gly Ala Thr Ile Arg Val Tyr Leu Glu Ser Tyr Val
            500                 505                 510

Pro Ser Ser Gly Asp Leu Asn Gln Asp Pro Gln Val Ala Leu Ala Asp
        515                 520                 525

Met Ile Ser Ala Ile Asn Glu Leu Ala Glu Ile Lys Gln Arg Thr Gly
    530                 535                 540

Met Asp Arg Pro Thr Val Ile Thr
545                 550

<210> SEQ ID NO 81
<211> LENGTH: 1662
<212> TYPE: DNA
<213> ORGANISM: Synechococcus sp. RCC 307

<400> SEQUENCE: 81
gtgacgcttt cctcacccag cactgagttc tccgtgcagc agatcaagct gccagaagcg     60
tttcaagacc agaagcctgg cacctcggga ctgcgcaaga gcacccaaca atttgaacag    120
cctcattacc tcgaaagttt tatcgaggcg atcttccgca ccctccctgg tgtgcaaggc    180
gggaccttgg tggtgggcgg tgatggccgc tacggcaacc gccgcgccat cgatgtcatc    240
acccggatgg cggcagccca tggactgggg cggattgtgc tgaccaccgg cggcatcctc    300
tccacccctg ccgcttccaa cttgatccgc aacgccaggc cattggcgg catcatcctc    360
tcggccagcc acaaccctgg agggcccaaa ggcgactttg cgtcaaggt caatggcgcc    420
aacggcggcc tgcccctga atctcttacc gatgccatct acgcctgcag ccagcagctc    480
gatggctacc gcatcgcaag tggaaccgca ctgcccctcg acgccccagc cgagcatcaa    540
atcggtgcgt tgaacgtgga ggtgatcgac ggcgtcgacg actacctgca actgatgcag    600
cacttgttcg acttcgatct gatcagcgat ttgctcaagg gctcatggcc aatggccttt    660
gacgccatgc atgccgtcac tggtccctac gccagcaaac tctttgagca gctcctagga    720
gccccaagcg ggaccgtgcg caacgggcgc tgcctcgaag actttggtgg cggccatccc    780
gatcccaacc tcacctacgc caaagagctg gcgacgctgc tgctggatgg tgatgactat    840
cgctttggcg cggcctgtga tggcgatggc gaccgcaaca tgattttggg gcagcgctgc    900
tttgtgaacc ccagcgacag cctcgctgtc ttaacggcga acgccacctt ggtgaagggc    960
tatgcctccg gctggccgg cgttgctcgc tcgatgccca ccagtgccgc agtggatgtg   1020
gtggccaagc agctggggat caattgcttt gagaccccca ccggttggaa attttcggc   1080
```

```
aacctgctcg atgccggacg catcacccett tgcggggaag agagctttgg aacaggcagt    1140
gatcacatcc gcgaaaaaga tggcctctgg gctgtgttgt tttggctctc gatcctggcc    1200
aagcgccaat gctctgttgc ggaggtgatg cagcagcact ggagcaccta cgggcgtcat    1260
tactactcgc gccatgacta cgaaggtgtc gaaaccgatc gggcccatgg gctctacaac    1320
ggcctgcgcg atcggcttgg cgagctgact ggaaccagct ttgccgatag ccgcatcgcc    1380
aatgctgacg acttcgccta cagcgacccc gtcgatggct cactgaccca gaagcaaggc    1440
ctacgtctgc tcctggagga cggcagccgc atcatcctgc ggctctcggg aaccggcacc    1500
aaaggagcca cgctgcggct ctatctcgag cgctatgtcg ccactggcgg caacctcgat    1560
caaaatcccc agcaagcctt agccggcatg attgcggccg ccgatgccct cgccggcatc    1620
cggtcaacca ccggcatgga tgtccccacg gtgatcacct ga                        1662
```

<210> SEQ ID NO 82
<211> LENGTH: 553
<212> TYPE: PRT
<213> ORGANISM: Synechococcus sp. RCC 307

<400> SEQUENCE: 82

```
Met Thr Leu Ser Ser Pro Ser Thr Glu Phe Ser Val Gln Gln Ile Lys
 1               5                  10                  15

Leu Pro Glu Ala Phe Gln Asp Gln Lys Pro Gly Thr Ser Gly Leu Arg
                20                  25                  30

Lys Ser Thr Gln Gln Phe Glu Gln Pro His Tyr Leu Glu Ser Phe Ile
            35                  40                  45

Glu Ala Ile Phe Arg Thr Leu Pro Gly Val Gln Gly Gly Thr Leu Val
        50                  55                  60

Val Gly Gly Asp Gly Arg Tyr Gly Asn Arg Arg Ala Ile Asp Val Ile
 65                  70                  75                  80

Thr Arg Met Ala Ala Ala His Gly Leu Gly Arg Ile Val Leu Thr Thr
                85                  90                  95

Gly Gly Ile Leu Ser Thr Pro Ala Ala Ser Asn Leu Ile Arg Gln Arg
                100                 105                 110

Gln Ala Ile Gly Gly Ile Ile Leu Ser Ala Ser His Asn Pro Gly Gly
            115                 120                 125

Pro Lys Gly Asp Phe Gly Val Lys Val Asn Gly Ala Asn Gly Gly Pro
        130                 135                 140

Ala Pro Glu Ser Leu Thr Asp Ala Ile Tyr Ala Cys Ser Gln Gln Leu
145                 150                 155                 160

Asp Gly Tyr Arg Ile Ala Ser Gly Thr Ala Leu Pro Leu Asp Ala Pro
                165                 170                 175

Ala Glu His Gln Ile Gly Ala Leu Asn Val Glu Val Ile Asp Gly Val
            180                 185                 190

Asp Asp Tyr Leu Gln Leu Met Gln His Leu Phe Asp Phe Asp Leu Ile
        195                 200                 205

Ser Asp Leu Leu Lys Gly Ser Trp Pro Met Ala Phe Asp Ala Met His
    210                 215                 220

Ala Val Thr Gly Pro Tyr Ala Ser Lys Leu Phe Glu Gln Leu Leu Gly
225                 230                 235                 240

Ala Pro Ser Gly Thr Val Arg Asn Gly Arg Cys Leu Glu Asp Phe Gly
                245                 250                 255

Gly Gly His Pro Asp Pro Asn Leu Thr Tyr Ala Lys Glu Leu Ala Thr
            260                 265                 270
```

Leu Leu Leu Asp Gly Asp Asp Tyr Arg Phe Gly Ala Ala Cys Asp Gly
            275                 280                 285

Asp Gly Asp Arg Asn Met Ile Leu Gly Gln Arg Cys Phe Val Asn Pro
        290                 295                 300

Ser Asp Ser Leu Ala Val Leu Thr Ala Asn Ala Thr Leu Val Lys Gly
305                 310                 315                 320

Tyr Ala Ser Gly Leu Ala Gly Val Ala Arg Ser Met Pro Thr Ser Ala
                325                 330                 335

Ala Val Asp Val Val Ala Lys Gln Leu Gly Ile Asn Cys Phe Glu Thr
            340                 345                 350

Pro Thr Gly Trp Lys Phe Phe Gly Asn Leu Leu Asp Ala Gly Arg Ile
        355                 360                 365

Thr Leu Cys Gly Glu Glu Ser Phe Gly Thr Gly Ser Asp His Ile Arg
370                 375                 380

Glu Lys Asp Gly Leu Trp Ala Val Leu Phe Trp Leu Ser Ile Leu Ala
385                 390                 395                 400

Lys Arg Gln Cys Ser Val Ala Glu Val Met Gln Gln His Trp Ser Thr
                405                 410                 415

Tyr Gly Arg His Tyr Tyr Ser Arg His Asp Tyr Glu Gly Val Glu Thr
            420                 425                 430

Asp Arg Ala His Gly Leu Tyr Asn Gly Leu Arg Asp Arg Leu Gly Glu
        435                 440                 445

Leu Thr Gly Thr Ser Phe Ala Asp Ser Arg Ile Ala Asn Ala Asp Asp
    450                 455                 460

Phe Ala Tyr Ser Asp Pro Val Asp Gly Ser Leu Thr Gln Lys Gln Gly
465                 470                 475                 480

Leu Arg Leu Leu Leu Glu Asp Gly Ser Arg Ile Ile Leu Arg Leu Ser
                485                 490                 495

Gly Thr Gly Thr Lys Gly Ala Thr Leu Arg Leu Tyr Leu Glu Arg Tyr
            500                 505                 510

Val Ala Thr Gly Gly Asn Leu Asp Gln Asn Pro Gln Gln Ala Leu Ala
        515                 520                 525

Gly Met Ile Ala Ala Ala Asp Ala Leu Ala Gly Ile Arg Ser Thr Thr
    530                 535                 540

Gly Met Asp Val Pro Thr Val Ile Thr
545                 550

<210> SEQ ID NO 83
<211> LENGTH: 1467
<212> TYPE: DNA
<213> ORGANISM: Synechococcus sp PCC 7002

<400> SEQUENCE: 83
gtgttggcgt ttgggaatca acagccgatt cggttcggca cagacggttg gcgtggcatt      60
attgcggcgg attttacctt tgaacgggtg caacgggtgg cgatcgccac agcccatgtt     120
ttaaaagaaa atttcgcaaa ccaagccatt gataacacga taatcgtcgg ctacgaccgg     180
cggtttctcg cagatgaatt tgcccttgct gccgccgaag cgatccaggg ggaaggattt     240
cacgtacttc tagccaatag ttttgcgcca accccagccc tgagctatgc cgcccaccac     300
cacaaggctc tgggggcgat cgccttaacg gccagccata atccagcggg ttatttagga     360
ttaaaagtga aggggctttt cggcggctcg gtttccgaag aaattacggc tcagattgaa     420
gcgcgactgg aagccgggat tgatcctcaa cattcaacga cgggccgttt agattatttt     480
gatccctggc aggactattg cgccggatta cagcaactgg ttgatttaga aaaaattcgc     540

-continued

```
caggcgatcg ccgctggtcg tctccaggtc tttgccgatg taatgtatgg cgcagcggcg      600
ggcggtttga cccaactgct caatgcggcg atccaagaaa tccattgtga accagatcct      660
ttgttcggcg ccgcccacc agagccttta gaaaaacatt tgtctcaact gcaacgcacc       720
attcgcgccg cccataatca agatttagag gcaattcagg tgggatttgt ctttgatggt      780
gatggcgatc gcattgctgc tgtggctggg gatggtgagt ttctcagttc ccaaaagcta      840
atcccgattt tgctggccca tttgtcccaa aatcgccaat atcaagggga agtggtaaaa      900
actgtcagcg gctctgattt aatccccgt tgagcgaat actacggttt gccagtcttt        960
gaaacaccca tcggctacaa atacattgcc gaacgaatgc aacagaccca ggtgcttctt     1020
ggtggcgaag aatccggcgg cattggctac ggccaccaca ttcccgaacg ggatgcgctg     1080
ctggcggcat tgtatctcct agaggcgatc gccattttg atcaagacct cggcgagatt      1140
taccagagtc ttcaaagcaa agctaattt tatggcgcct acgaccgcat tgatttacat      1200
ttgcgggatt tctccagccg cgatcgccta ttaaaaatcc tcgcgacaaa tcccccaag     1260 gcgatctcca accatgacgt aattcacagc gaccccaaag atggctataa attccgcctt     1320
gctgatcaaa gttggttgct gattcgcttc agtggtaccg agcctgtact gcggttatat     1380
agtgaagcgg tcaatcctaa agccgtacaa gaaatcctcg cctgggcgca aacctgggct    1440
gaggctgccg accaagccga aggttag                                        1467
```

<210> SEQ ID NO 84
<211> LENGTH: 488
<212> TYPE: PRT
<213> ORGANISM: Synechococcus sp PCC 7002

<400> SEQUENCE: 84

```
Met Leu Ala Phe Gly Asn Gln Gln Pro Ile Arg Phe Gly Thr Asp Gly
  1               5                  10                  15

Trp Arg Gly Ile Ile Ala Ala Asp Phe Thr Phe Glu Arg Val Gln Arg
             20                  25                  30

Val Ala Ile Ala Thr Ala His Val Leu Lys Glu Asn Phe Ala Asn Gln
         35                  40                  45

Ala Ile Asp Asn Thr Ile Ile Val Gly Tyr Asp Arg Arg Phe Leu Ala
     50                  55                  60

Asp Glu Phe Ala Leu Ala Ala Ala Glu Ala Ile Gln Gly Glu Gly Phe
 65                  70                  75                  80

His Val Leu Leu Ala Asn Ser Phe Ala Pro Thr Pro Ala Leu Ser Tyr
                 85                  90                  95

Ala Ala His His His Lys Ala Leu Gly Ala Ile Ala Leu Thr Ala Ser
            100                 105                 110

His Asn Pro Ala Gly Tyr Leu Gly Leu Lys Val Lys Gly Ala Phe Gly
        115                 120                 125

Gly Ser Val Ser Glu Glu Ile Thr Ala Gln Ile Glu Ala Arg Leu Glu
    130                 135                 140

Ala Gly Ile Asp Pro Gln His Ser Thr Thr Gly Arg Leu Asp Tyr Phe
145                 150                 155                 160

Asp Pro Trp Gln Asp Tyr Cys Ala Gly Leu Gln Gln Leu Val Asp Leu
                165                 170                 175

Glu Lys Ile Arg Gln Ala Ile Ala Ala Gly Arg Leu Gln Val Phe Ala
            180                 185                 190

Asp Val Met Tyr Gly Ala Ala Ala Gly Gly Leu Thr Gln Leu Leu Asn
        195                 200                 205
```

```
Ala Ala Ile Gln Glu Ile His Cys Glu Pro Asp Pro Leu Phe Gly Gly
        210                 215                 220
Arg Pro Pro Glu Pro Leu Glu Lys His Leu Ser Gln Leu Gln Arg Thr
225                 230                 235                 240
Ile Arg Ala Ala His Asn Gln Asp Leu Glu Ala Ile Gln Val Gly Phe
                245                 250                 255
Val Phe Asp Gly Asp Gly Asp Arg Ile Ala Ala Val Ala Gly Asp Gly
                260                 265                 270
Glu Phe Leu Ser Ser Gln Lys Leu Ile Pro Ile Leu Leu Ala His Leu
            275                 280                 285
Ser Gln Asn Arg Gln Tyr Gln Gly Glu Val Val Lys Thr Val Ser Gly
        290                 295                 300
Ser Asp Leu Ile Pro Arg Leu Ser Glu Tyr Tyr Gly Leu Pro Val Phe
305                 310                 315                 320
Glu Thr Pro Ile Gly Tyr Lys Tyr Ile Ala Glu Arg Met Gln Gln Thr
                325                 330                 335
Gln Val Leu Leu Gly Gly Glu Ser Gly Gly Ile Gly Tyr Gly His
            340                 345                 350
His Ile Pro Glu Arg Asp Ala Leu Leu Ala Ala Leu Tyr Leu Leu Glu
        355                 360                 365
Ala Ile Ala Ile Phe Asp Gln Asp Leu Gly Glu Ile Tyr Gln Ser Leu
370                 375                 380
Gln Ser Lys Ala Asn Phe Tyr Gly Ala Tyr Asp Arg Ile Asp Leu His
385                 390                 395                 400
Leu Arg Asp Phe Ser Ser Arg Asp Arg Leu Leu Lys Ile Leu Ala Thr
                405                 410                 415
Asn Pro Pro Lys Ala Ile Ser Asn His Asp Val Ile His Ser Asp Pro
            420                 425                 430
Lys Asp Gly Tyr Lys Phe Arg Leu Ala Asp Gln Ser Trp Leu Leu Ile
        435                 440                 445
Arg Phe Ser Gly Thr Glu Pro Val Leu Arg Leu Tyr Ser Glu Ala Val
450                 455                 460
Asn Pro Lys Ala Val Gln Glu Ile Leu Ala Trp Ala Gln Thr Trp Ala
465                 470                 475                 480
Glu Ala Ala Asp Gln Ala Glu Gly
                485

<210> SEQ ID NO 85
<211> LENGTH: 627
<212> TYPE: DNA
<213> ORGANISM: Escherichia coli

<400> SEQUENCE: 85
atgatgaact tcaacaatgt tttccgctgg catttgccct tcctgttcct ggtcctgtta    60
accttccgtg ccgccgcagc ggacacgtta ttgattctgg gtgatagcct gagcgccggg   120
tatcgaatgt ctgccagcgc ggcctggcct gccttgttga atgataagtg gcagagtaaa   180
acgtcggtag ttaatgccag catcagcggc gacacctcgc aacaaggact ggcgcgcctt   240
ccggctctgc tgaaacagca tcagccgcgt tgggtgctgg ttgaactggg cggcaatgac   300
ggtttgcgtg gttttcagcc acagcaaacc gagcaaacgc tgcgccagat tttgcaggat   360
gtcaaagccg ccaacgctga accattgtta atgcaaatac gtctgcctgc aaactatggt   420
cgccgttata atgaagcctt tagcgccatt taccccaaac tcgccaaaga gtttgatgtt    480
```

```
ccgctgctgc ccttttttat ggaagaggtc tacctcaagc cacaatggat gcaggatgac      540
ggtattcatc ccaaccgcga cgcccagccg tttattgccg actggatggc gaagcagttg      600
cagcctttag taaatcatga ctcataa                                          627
```

<210> SEQ ID NO 86
<211> LENGTH: 208
<212> TYPE: PRT
<213> ORGANISM: Escherichia coli

<400> SEQUENCE: 86

```
Met Met Asn Phe Asn Val Phe Arg Trp His Leu Pro Phe Leu Phe
  1               5                  10                  15

Leu Val Leu Leu Thr Phe Arg Ala Ala Ala Ala Asp Thr Leu Leu Ile
             20                  25                  30

Leu Gly Asp Ser Leu Ser Ala Gly Tyr Arg Met Ser Ala Ser Ala Ala
         35                  40                  45

Trp Pro Ala Leu Leu Asn Asp Lys Trp Gln Ser Lys Thr Ser Val Val
     50                  55                  60

Asn Ala Ser Ile Ser Gly Asp Thr Ser Gln Gln Gly Leu Ala Arg Leu
 65                  70                  75                  80

Pro Ala Leu Leu Lys Gln His Gln Pro Arg Trp Val Leu Val Glu Leu
                 85                  90                  95

Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
    130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Lys Gln Leu Gln Pro Leu Val Asn His Asp Ser
        195                 200                 205
```

<210> SEQ ID NO 87
<211> LENGTH: 1023
<212> TYPE: DNA
<213> ORGANISM: Escherichia coli

<400> SEQUENCE: 87

```
atgtttcagc agcaaaaaga ctgggaaaca agagaaaacg cgtttgctgc ttttaccatg       60
ggaccgctga ctgatttctg gcgtcagcgt gatgaagcag agtttactgg tgtggatgac      120
attccggtgc gctttgtccg ttttcgcgca cagcaccatg accgggtggt agtcatctgc      180
ccggggcgta ttgagagcta cgtaaaatat gcggaactgg cctatgacct gttccatttg      240
gggtttgatg tcttaatcat cgaccatcgc gggcagggac gttccggtcg cctgttagcc      300
gatccgcatc tcgggcatgt taatcgcttt aatgattatg ttgatgatct ggcggcattc      360
tggcagcagg aggttcagcc cggtccgtgg cgtaaacgct atatactggc acattcgatg      420
ggcggtgcga tctccacatt atttctgcaa cgccatccag gtgtatgtga cgccattgcg      480
ctaactgcgc caatgtttgg gatcgtgatt cgtatgccgt catttatggc acggcagatc      540
```

```
ctcaactggg ccgaagcgca tccacgtttc cgtgatggct atgcaatagg caccgggcgc    600
tggcgcgcgt tgccgtttgc tatcaacgta ctgacccaca gcagacagcg atatcgacgt    660
aacttacgct tctatgctga tgacccaacg attcgcgtcg gtgggccgac ctaccattgg    720
gtacgcgaaa gtattctggc tggcgaacag gtgttagccg gtgcgggtga tgacgccacg    780
ccaacgcttc tcttgcaggc tgaagaggaa cgcgtggtgg ataaccgcat gcatgaccgt    840
ttttgtgaac tccgcaccgc cgcgggccat cctgtcgaag gaggacggcc gttggtaatt    900
aaaggtgctt accatgagat cctttttgaa aaggacgcaa tggcctcagt cgcgctccac    960
gccatcgttg attttttcaa caggcataac tcacccagcg aaaccgctc tacagaggtt   1020 taa                                                                  1023
```

<210> SEQ ID NO 88
<211> LENGTH: 340
<212> TYPE: PRT
<213> ORGANISM: Escherichia coli

<400> SEQUENCE: 88

```
Met Phe Gln Gln Gln Lys Asp Trp Glu Thr Arg Glu Asn Ala Phe Ala
 1               5                   10                  15

Ala Phe Thr Met Gly Pro Leu Thr Asp Phe Trp Arg Gln Arg Asp Glu
                20                  25                  30

Ala Glu Phe Thr Gly Val Asp Asp Ile Pro Val Arg Phe Val Arg Phe
            35                  40                  45

Arg Ala Gln His His Asp Arg Val Val Ile Cys Pro Gly Arg Ile
        50                  55                  60

Glu Ser Tyr Val Lys Tyr Ala Glu Leu Ala Tyr Asp Leu Phe His Leu
65                  70                  75                  80

Gly Phe Asp Val Leu Ile Ile Asp His Arg Gly Gln Gly Arg Ser Gly
                85                  90                  95

Arg Leu Leu Ala Asp Pro His Leu Gly His Val Asn Arg Phe Asn Asp
            100                 105                 110

Tyr Val Asp Asp Leu Ala Ala Phe Trp Gln Gln Glu Val Gln Pro Gly
        115                 120                 125

Pro Trp Arg Lys Arg Tyr Ile Leu Ala His Ser Met Gly Gly Ala Ile
    130                 135                 140

Ser Thr Leu Phe Leu Gln Arg His Pro Gly Val Cys Asp Ala Ile Ala
145                 150                 155                 160

Leu Thr Ala Pro Met Phe Gly Ile Val Ile Arg Met Pro Ser Phe Met
                165                 170                 175

Ala Arg Gln Ile Leu Asn Trp Ala Glu Ala His Pro Arg Phe Arg Asp
            180                 185                 190

Gly Tyr Ala Ile Gly Thr Gly Arg Trp Arg Ala Leu Pro Phe Ala Ile
        195                 200                 205

Asn Val Leu Thr His Ser Arg Gln Arg Tyr Arg Asn Leu Arg Phe
    210                 215                 220

Tyr Ala Asp Asp Pro Thr Ile Arg Val Gly Gly Pro Thr Tyr His Trp
225                 230                 235                 240

Val Arg Glu Ser Ile Leu Ala Gly Glu Gln Val Leu Ala Gly Ala Gly
                245                 250                 255

Asp Asp Ala Thr Pro Thr Leu Leu Leu Gln Ala Glu Glu Arg Val
            260                 265                 270

Val Asp Asn Arg Met His Asp Arg Phe Cys Glu Leu Arg Thr Ala Ala
        275                 280                 285
```

Gly His Pro Val Glu Gly Gly Arg Pro Leu Val Ile Lys Gly Ala Tyr
    290             295                 300

His Glu Ile Leu Phe Glu Lys Asp Ala Met Ala Ser Val Ala Leu His
305                 310                 315                 320

Ala Ile Val Asp Phe Phe Asn Arg His Asn Ser Pro Ser Gly Asn Arg
                325                 330                 335

Ser Thr Glu Val
        340

<210> SEQ ID NO 89
<211> LENGTH: 1203
<212> TYPE: DNA
<213> ORGANISM: Artificial Sequence
<220> FEATURE:
<223> OTHER INFORMATION: Vupat1 - nucleotide sequence codon optimized
      for S. elongatus 7942.

<400> SEQUENCE: 89

```
atggccgcca cacagacccc tagtaaagtt gacgatggtg cactgattac ggtgctctcg      60
attgacgggg ggggtatccg cgggatcatc cctgggattc ttctcgcgtt cctcgagagc     120
gaattgcaaa aactggatgg tgctgatgcc cgtctcgccg actactttga tgtcatcgca     180
ggcacttcta ccggaggctt ggttactgct atgctgaccg cgccaaatga aataatcgc      240 cccctctacg ctgctaaaga tattaaagat ttctatctcg aacacacccc aaaaatctt     300 ccgcagtcgt cgagctggaa cctgattgcc accgcgatga agaagggccg cagcctgatg     360
gggccacagt acgacggcaa atacctgcat aaattggtcc gtgaaaaact gggcaatacg     420
aagctcgagc acactctgac caacgtggtc atcccggcgt cgacatcaa aaatctgcaa     480 cccgccattt tcagtagctt ccaagttaag aaacgcccct acctcaatgc agccctcagc     540
gacatttgta tctcgaccag cgctgcaccc acgtatctgc cagcgcactg ctttgaaaca     600
aagacttcga cggccagttt caagtttgac ttggtggatg ggggcgtcgc tgcgaataac     660
cctgcgttgg tcgccatggc cgaggtctcg aacgaaatcc gcaacgaggg ttcgtgcgct     720
tccctgaagg tgaaaccgct gcagtacaaa aagtttctgg tcatttctct gggaaccggc     780
tcccagcaac acgaaatgcg atattccgca gataaggcca gcacgtgggg cttggtcgga     840
tggctcagct cgtccggtgg cacccgctg attgacgtct tctctcatgc gagctccgat     900
atggttgatt tcatattag tagtgtgttt caagcccgcc acgcagaaca aaactacctg     960
cggattcaag acgatacct gacgggtgat ctgggctccg tcgatgttgc cacagagaag    1020
aatttgaacg gtctcgtgca ggtggccgaa gcgttgctga agaagcccgt tagcaaaatc    1080
aatttgcgta cgggtatcca cgaaccggtt gaatctaacg aaacgaatgc tgaagcgttg    1140
aagcggtttg cagcacggtt gtctaaccag cggcgatttc gcaaaagtca gactttcgct    1200
tag                                                                 1203
```

<210> SEQ ID NO 90
<211> LENGTH: 400
<212> TYPE: PRT
<213> ORGANISM: Synechococcus elongatus PCC 7942

<400> SEQUENCE: 90

Met Ala Ala Thr Gln Thr Pro Ser Lys Val Asp Asp Gly Ala Leu Ile
1               5                   10                  15

Thr Val Leu Ser Ile Asp Gly Gly Gly Ile Arg Gly Ile Ile Pro Gly
            20                  25                  30

Ile Leu Leu Ala Phe Leu Glu Ser Glu Leu Gln Lys Leu Asp Gly Ala
            35                  40                  45

Asp Ala Arg Leu Ala Asp Tyr Phe Asp Val Ile Ala Gly Thr Ser Thr
 50                  55                  60

Gly Gly Leu Val Thr Ala Met Leu Thr Ala Pro Asn Glu Asn Asn Arg
 65                  70                  75                  80

Pro Leu Tyr Ala Ala Lys Asp Ile Lys Asp Phe Tyr Leu Glu His Thr
                85                  90                  95

Pro Lys Ile Phe Pro Gln Ser Ser Trp Asn Leu Ile Ala Thr Ala
               100                 105                 110

Met Lys Lys Gly Arg Ser Leu Met Gly Pro Gln Tyr Asp Gly Lys Tyr
               115                 120                 125

Leu His Lys Leu Val Arg Glu Lys Leu Gly Asn Thr Lys Leu Glu His
       130                 135                 140

Thr Leu Thr Asn Val Val Ile Pro Ala Phe Asp Ile Lys Asn Leu Gln
145                 150                 155                 160

Pro Ala Ile Phe Ser Ser Phe Gln Val Lys Lys Arg Pro Tyr Leu Asn
                165                 170                 175

Ala Ala Leu Ser Asp Ile Cys Ile Ser Thr Ser Ala Ala Pro Thr Tyr
                180                 185                 190

Leu Pro Ala His Cys Phe Glu Thr Lys Thr Ser Thr Ala Ser Phe Lys
                195                 200                 205

Phe Asp Leu Val Asp Gly Gly Val Ala Ala Asn Asn Pro Ala Leu Val
210                 215                 220

Ala Met Ala Glu Val Ser Asn Glu Ile Arg Asn Glu Gly Ser Cys Ala
225                 230                 235                 240

Ser Leu Lys Val Lys Pro Leu Gln Tyr Lys Lys Phe Leu Val Ile Ser
                245                 250                 255

Leu Gly Thr Gly Ser Gln Gln His Glu Met Arg Tyr Ser Ala Asp Lys
                260                 265                 270

Ala Ser Thr Trp Gly Leu Val Gly Trp Leu Ser Ser Ser Gly Gly Thr
                275                 280                 285

Pro Leu Ile Asp Val Phe Ser His Ala Ser Ser Asp Met Val Asp Phe
                290                 295                 300

His Ile Ser Ser Val Phe Gln Ala Arg His Ala Glu Gln Asn Tyr Leu
305                 310                 315                 320

Arg Ile Gln Asp Asp Thr Leu Thr Gly Asp Leu Gly Ser Val Asp Val
                325                 330                 335

Ala Thr Glu Lys Asn Leu Asn Gly Leu Val Gln Val Ala Glu Ala Leu
                340                 345                 350

Leu Lys Lys Pro Val Ser Lys Ile Asn Leu Arg Thr Gly Ile His Glu
                355                 360                 365

Pro Val Glu Ser Asn Glu Thr Asn Ala Glu Ala Leu Lys Arg Phe Ala
                370                 375                 380

Ala Arg Leu Ser Asn Gln Arg Arg Phe Arg Lys Ser Gln Thr Phe Ala
385                 390                 395                 400

<210> SEQ ID NO 91
<211> LENGTH: 861
<212> TYPE: DNA
<213> ORGANISM: Escherichia coli

<400> SEQUENCE: 91
atgagtcagg cgctaaaaaa tttactgaca ttgttaaatc tggaaaaaat tgaggaagga      60

```
ctctttcgcg gccagagtga agatttaggt ttacgccagg tgtttggcgg ccaggtcgtg      120
ggtcaggcct tgtatgctgc aaaagagacc gtccctgaag agcggctggt acattcgttt      180
cacagctact tcttcgccc tggcgatagt aagaagccga ttatttatga tgtcgaaacg       240
ctgcgtgacg gtaacagctt cagcgcccgc cgggttgctg ctattcaaaa cggcaaaccg      300
attttttata tgactgcctc tttccaggca ccagaagcgg gtttcgaaca tcaaaaaaca      360
atgccgtccg cgccagcgcc tgatggcctc ccttcggaaa cgcaaatcgc caatcgctg      420 gcgcacctgc tgccgccagt gctgaaagat aaattcatct gcgatcgtcc gctggaagtc     480
cgtccggtgg agtttcataa cccactgaaa ggtcacgtcg cagaaccaca tcgtcaggtg     540
tggatccgcg caaatggtag cgtgccggat gacctgcgcg ttcatcagta tctgctcggt     600
tacgcttctg atcttaactt cctgccggta gctctacagc cgcacggcat cggttttctc     660
gaaccgggga ttcagattgc caccattgac cattccatgt ggttccatcg cccgtttaat     720
ttgaatgaat ggctgctgta tagcgtggag agcacctcgg cgtccagcgc acgtggcttt     780
gtgcgcggtg agtttatac ccaagacggc gtactggttg cctcgaccgt tcaggaaggg      840
gtgatgcgta atcacaatta a                                                861
```

<210> SEQ ID NO 92
<211> LENGTH: 286
<212> TYPE: PRT
<213> ORGANISM: Escherichia coli

<400> SEQUENCE: 92

```
Met Ser Gln Ala Leu Lys Asn Leu Leu Thr Leu Leu Asn Leu Glu Lys
  1               5                  10                  15

Ile Glu Glu Gly Leu Phe Arg Gly Gln Ser Glu Asp Leu Gly Leu Arg
             20                  25                  30

Gln Val Phe Gly Gly Gln Val Val Gly Gln Ala Leu Tyr Ala Ala Lys
         35                  40                  45

Glu Thr Val Pro Glu Glu Arg Leu Val His Ser Phe His Ser Tyr Phe
     50                  55                  60

Leu Arg Pro Gly Asp Ser Lys Lys Pro Ile Ile Tyr Asp Val Glu Thr
 65                  70                  75                  80

Leu Arg Asp Gly Asn Ser Phe Ser Ala Arg Arg Val Ala Ala Ile Gln
                 85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220
```

| Gln | Ile | Ala | Thr | Ile | Asp | His | Ser | Met | Trp | Phe | His | Arg | Pro | Phe | Asn |
| --- | --- | --- | --- | --- | --- | --- | --- | --- | --- | --- | --- | --- | --- | --- | --- |
| 225 | | | | 230 | | | | | 235 | | | | | 240 | |

Leu Asn Glu Trp Leu Leu Tyr Ser Val Glu Ser Thr Ser Ala Ser Ser
                245                  250                  255

Ala Arg Gly Phe Val Arg Gly Glu Phe Tyr Thr Gln Asp Gly Val Leu
              260                  265                  270

Val Ala Ser Thr Val Gln Glu Gly Val Met Arg Asn His Asn
      275              280                  285

<210> SEQ ID NO 93
<211> LENGTH: 552
<212> TYPE: DNA
<213> ORGANISM: Escherichia coli

<400> SEQUENCE: 93

```
atggctgata cattgctgat tttgggtgat agtttgtctg cgggttaccg catgagcgcc      60
agcgccgcct ggccagccct cctgaatgat aaatggcagt ccaaaacgag cgttgtcaat     120
gcgtctatta gtggcgatac cagtcaacag ggactggctc gcctcccggc cttgctgaaa     180
cagcatcaac gcgctgggt gctggtcgaa ctcggaggga tgatggtct gcgcggtttt       240
caacctcagc aaaccgagca acgctccgt caaattctgc aggacgttaa ggcggcgaac      300
gctgagcccc tgctgatgca gattcgcctc cccgccaatt acgggcgtcg ctataacgaa     360
gcgttttcgg cgatttaccc gaagctcgcc aaagaatttg atgtcccact gctccccttt     420
ttcatggaag aagtctatct caaaccacaa tggatgcagg atgatggcat tcatcccaac     480
cgcgacgcgc aacccttttat tgcggattgg atggcgaaac aactccaacc actcgtgaac   540
cacgattcgt ag                                                         552
```

<210> SEQ ID NO 94
<211> LENGTH: 183
<212> TYPE: PRT
<213> ORGANISM: Escherichia coli

<400> SEQUENCE: 94

Met Ala Asp Thr Leu Leu Ile Leu Gly Asp Ser Leu Ser Ala Gly Tyr
1               5                  10                 15

Arg Met Ser Ala Ser Ala Ala Trp Pro Ala Leu Leu Asn Asp Lys Trp
              20                  25                  30

Gln Ser Lys Thr Ser Val Val Asn Ala Ser Ile Ser Gly Asp Thr Ser
              35                  40                  45

Gln Gln Gly Leu Ala Arg Leu Pro Ala Leu Leu Lys Gln His Gln Pro
    50                  55                  60

Arg Trp Val Leu Val Glu Leu Gly Gly Asn Asp Gly Leu Arg Gly Phe
65              70                  75                  80

Gln Pro Gln Gln Thr Glu Gln Thr Leu Arg Gln Ile Leu Gln Asp Val
              85                  90                  95

Lys Ala Ala Asn Ala Glu Pro Leu Leu Met Gln Ile Arg Leu Pro Ala
              100                105              110

Asn Tyr Gly Arg Arg Tyr Asn Glu Ala Phe Ser Ala Ile Tyr Pro Lys
              115                120              125

Leu Ala Lys Glu Phe Asp Val Pro Leu Leu Pro Phe Phe Met Glu Glu
    130                135              140

Val Tyr Leu Lys Pro Gln Trp Met Gln Asp Asp Gly Ile His Pro Asn
145            150                155              160

Arg Asp Ala Gln Pro Phe Ile Ala Asp Trp Met Ala Lys Gln Leu Gln

Pro Leu Val Asn His Asp Ser
        180

<210> SEQ ID NO 95
<211> LENGTH: 1023
<212> TYPE: DNA
<213> ORGANISM: Artificial Sequence
<220> FEATURE:
<223> OTHER INFORMATION: pldB from E. coli - codon optimized for S.
      elongatus.

<400> SEQUENCE: 95

```
atgttccagc agcagaagga ctgggagacg cgggagaatg catttgcagc gtttaccatg    60
ggtcctctga ccgatttctg gcgtcaacgc gacgaagctg agtttacggg cgtcgatgat   120
attccggtgc gctttgtccg ctttcgagca caacatcacg atcgcgtggt cgttatttgc   180
cccggtcgta tcgaaagcta tgtgaaatat gcagaattgg cgtatgacct gttccatctc   240
gggtttgatg tgctcattat tgaccaccgg gccaaggtc ggtcgggtcg tctgttggca   300
gatccgcatt tggggcatgt caaccggttt aatgattatg ttgatgacct cgctgctttc   360
tggcaacagg aggttcagcc cggtccatgg cgtaaacgct atatcctggc acattccatg   420
ggcggcgcca ttagtactct gttcctccaa cgccacccgg cgtctgtga tgctattgct   480
ctcaccgccc aatgttcgg catcgttatc cgcatgccga gtttcatggc ccgacagatt   540
ttgaattggg cggaagcgca cccgcggttt cgtgacggat acgccatcgg tacgggccgt   600
tggcgagcac tgccttttgc catcaacgtc ttgactcaca gccgacagcg ataccggcga   660
aacctgcgct tctacgctga tgacccgacc atccggggttg ggcccccac gtatcactgg   720
gtgcgggaat ctattttggc cggggaacag gtgctggcgg gggccggaga cgatgctacc   780
ccaaccctcc tgctgcaagc cgaggaggag cgcgtcgttg ataaccgcat gcatgatcgc   840
ttctgcgagc tccgcacagc agccggccat ccgtggagg gaggccgccc tttggtgatc   900
aagggggctt accacgaaat cctgttcgaa aaagatgcga tggcttcggt ggccctgcac   960
gcaattgtcg atttttttaa tcgccacaat tctcccagcg gcaaccgttc cacagaagtt  1020
tag                                                               1023
```

<210> SEQ ID NO 96
<211> LENGTH: 1474
<212> TYPE: DNA
<213> ORGANISM: Cuphea hookeriana

<400> SEQUENCE: 96

```
ctggatacca tttcccctgc gaaaaaacat ggtggctgct gcagcaagtt ccgcattctt    60
ccctgttcca gccccgggag cctcccctaa acccgggaag ttcggaaatt ggccctcgag   120
cttgagcccct tccttcaagc ccaagtcaat ccccaatggc ggatttcagg ttaaggcaaa   180
tgacagcgcc atccaaaagg ctaacggttc tgcagttagt ctaaagtctg gcagcctcaa   240
cactcaggag gacacttcgt cgtcccctcc tcctcggact ttccttcacc agttgcctga   300
ttggagtagg cttctgactg caatcacgac cgtgttcgtg aaatctaaga ggcctgacat   360
gcatgatcgg aaatccaaga ggcctgacat gctggtggac tcgtttgggt tggagagtac   420
tgttcaggat gggctcgtgt tccgacagag ttttttcgatt aggtcttatg aaataggcac   480
tgatcgaacg gcctctatag agacacttat gaaccacttg caggaaacat ctctcaatca   540
ttgtaagagt accggtattc tccttgacgg cttcggtcgt actcttgaga tgtgtaaaag   600
```

```
ggacctcatt tgggtggtaa taaaaatgca gatcaaggtg aatcgctatc cagcttgggg      660
cgatactgtc gagatcaata cccggttctc ccggttgggg aaaatcggta tgggtcgcga      720
ttggctaata agtgattgca acacaggaga aattcttgta agagctacga gcgcgtatgc      780
catgatgaat caaaagacga gaagactctc aaaacttcca tacgaggttc accaggagat      840
agtgcctctt tttgtcgact ctcctgtcat tgaagacagt gatctgaaag tgcataagtt      900
taaagtgaag actggtgatt ccattcaaaa gggtctaact ccggggtgga atgacttgga      960
tgtcaatcag cacgtaagca acgtgaagta cattgggtgg attctcgaga gtatgccaac     1020
agaagttttg gagacccagg agctatgctc tctcgccctt gaatataggc gggaatgcgg     1080
aagggacagt gtgctggagt ccgtgaccgc tatggatccc tcaaaagttg gagtccgttc     1140
tcagtaccag caccttctgc ggcttgagga tgggactgct atcgtgaacg gtgcaactga     1200
gtggcggccg aagaatgcag gagctaacgg ggcgatatca acgggaaaga cttcaaatgg     1260
aaactcggtc tcttagaagt gtctcggaac ccttccgaga tgtgcatttc tttctccttt     1320 ttcatttttgt ggtgagctga agaagagca tgtcgttgca atcagtaaat tgtgtagttc     1380 gttttttcgct ttgcttcgct cctttgtata ataatatggt cagtcgtctt tgtatcattt     1440
catgttttca gtttatttac gccatataat tttt                                 1474
```

<210> SEQ ID NO 97
<211> LENGTH: 987
<212> TYPE: DNA
<213> ORGANISM: Artificial Sequence
<220> FEATURE:
<223> OTHER INFORMATION: Codon optimized polynucleotide encoding mature
      form of C8/C10FatB

<400> SEQUENCE: 97

```
atgctgccag attggagccg actcttgacc gccatcacca cagtctttgt taagtctaaa       60 cggccccgaca tgcacgatcg aaaaagcaag cgccccgata tgctggtgga cagctttggc     120
ttggaatcta ccgtgcagga tgggttggtc tttcgacaga gtttctcgat tcgcagttat      180
gaaattggca ctgatcgtac ggcaagcatt gagactctga tgaaccactt gcaagagaca      240
agcttgaacc attgcaaatc gacagggatt ctcctcgatg gcttcggtcg tacgctggaa      300
atgtgcaagc gcgatctgat ttgggttgtg atcaaaatgc agattaaggt taaccgttat      360
cccgcatggg gtgatacggt ggaaattaac acgcggttct cccgcctggg aaaaatcggc      420
atgggacgcg attggctgat ctccgattgc aacacgggcg agatcctcgt gcgcgctact      480
tcggcctacg ccatgatgaa tcaaaaaacc cggcgcctca gtaagctgcc ctacgaggtg      540
caccaagaaa ttgttccgtt gtttgtggat agccctgtca tcgaggattc ggatctgaag      600
gtccataaat tcaaagttaa aacgggagac tcgatccaaa agggcttgac gccgggttgg      660
aatgacctgg acgtcaatca gcatgtttcg aacgtgaaat acatcggctg gattctggag      720
tccatgccaa ccgaagtgtt ggaaacccag gagttgtgtt cgctcgctct cgaataccgg      780
cgcgaatgtg gccgtgatag tgttctcgag agtgtcaccg ccatggaccc tagcaaagtc      840
ggggtgcgct ctcagtatca acacctgttg cgcttggaag acggcacagc gatcgtgaat      900
ggtgcgaccg agtggcgtcc gaagaacgcc ggtgcgaatg gtgcaatttc gactgggaag      960
accagcaatg gtaatagtgt cagttag                                         987
```

<210> SEQ ID NO 98
<211> LENGTH: 415

<212> TYPE: PRT
<213> ORGANISM: Cuphea hookeriana

<400> SEQUENCE: 98

```
Met Val Ala Ala Ala Ser Ala Phe Phe Pro Val Pro Ala Pro
 1               5                  10                  15

Gly Ala Ser Pro Lys Pro Gly Lys Phe Gly Asn Trp Pro Ser Ser Leu
                20                  25                  30

Ser Pro Ser Phe Lys Pro Lys Ser Ile Pro Asn Gly Gly Phe Gln Val
            35                  40                  45

Lys Ala Asn Asp Ser Ala His Pro Lys Ala Asn Gly Ser Ala Val Ser
50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Val Asp Ser Phe Gly Leu
        115                 120                 125

Glu Ser Thr Val Gln Asp Gly Leu Val Phe Arg Gln Ser Phe Ser Ile
130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
        195                 200                 205

Ala Trp Gly Asp Thr Val Glu Ile Asn Thr Arg Phe Ser Arg Leu Gly
210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
370                 375                 380

Ile Val Asn Gly Ala Thr Glu Trp Arg Pro Lys Asn Ala Gly Ala Asn
385                 390                 395                 400
```

```
Gly Ala Ile Ser Thr Gly Lys Thr Ser Asn Gly Asn Ser Val Ser
            405                 410                 415

<210> SEQ ID NO 99
<211> LENGTH: 328
<212> TYPE: PRT
<213> ORGANISM: Cuphea hookeriana

<400> SEQUENCE: 99

Met Leu Pro Asp Trp Ser Arg Leu Leu Thr Ala Ile Thr Thr Val Phe
  1               5                  10                  15

Val Lys Ser Lys Arg Pro Asp Met His Asp Arg Lys Ser Lys Arg Pro
             20                  25                  30

Asp Met Leu Val Asp Ser Phe Gly Leu Glu Ser Thr Val Gln Asp Gly
         35                  40                  45

Leu Val Phe Arg Gln Ser Phe Ser Ile Arg Ser Tyr Glu Ile Gly Thr
     50                  55                  60

Asp Arg Thr Ala Ser Ile Glu Thr Leu Met Asn His Leu Gln Glu Thr
 65                  70                  75                  80

Ser Leu Asn His Cys Lys Ser Thr Gly Ile Leu Leu Asp Gly Phe Gly
                 85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Val Pro Leu Phe Val Asp Ser Pro
            180                 185                 190

Val Ile Glu Asp Ser Asp Leu Lys Val His Lys Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 100
<211> LENGTH: 1561
<212> TYPE: DNA
```

<213> ORGANISM: Umbellularia californica

<400> SEQUENCE: 100

```
agagagagag agagagagag agctaaatta aaaaaaaaac ccagaagtgg gaaatcttcc      60
ccatgaaata acggatcctc ttgctactgc tactactact actacaaact gtagccattt     120
atataattct atataatttt caacatggcc accacctctt tagcttccgc tttctgctcg     180
atgaaagctg taatgttggc tcgtgatggc cggggcatga aacccaggag cagtgatttg     240
cagctgaggg cggaaaatgc gccaacctct ttgaagatga tcaatgggac caagttcagt     300
tacacggaga gcttgaaaag gttgcctgac tggagcatgc tctttgcagt gatcacaacc     360
atcttttcgg ctgctgagaa gcagtggacc aatctagagt ggaagccgaa gccgaagcta     420
ccccagttgc ttgatgacca ttttggactg catgggttag ttttcaggcg caccttttgcc    480
atcagatctt atgaggtggg acctgaccgc tccacatcta tactggctgt tatgaatcac     540
atgcaggagg ctacacttaa tcatgcgaag agtgtgggaa ttctaggaga tggattcggg     600
acgacgctag agatgagtaa gagagatctg atgtgggttg tgagacgcac gcatgttgct     660
gtggaacggt acccctacttg gggtgatact gtagaagtag agtgctggat tggtgcatct     720
ggaaataatg gcatgcgacg tgatttcctt gtccgggact gcaaaacagg cgaaattctt     780
acaagatgta ccagcctttc ggtgctgatg aatacaagga caaggaggtt gtccacaatc     840
cctgacgaag ttagaggga gatagggcct gcattcattg ataatgtggc tgtcaaggac     900
gatgaaatta gaaaactaca gaagctcaat gacagcactg cagattacat ccaaggaggt     960
ttgactcctc gatggaatga tttggatgtc aatcagcatg tgaacaacct caaatacgtt    1020
gcctgggttt ttgagaccgt cccagactcc atctttgaga gtcatcatat ttccagcttc    1080
actcttgaat acaggagaga gtgcacgagg atagcgtgc tgcggtccct gaccactgtc    1140
tctggtggct cgtcggaggc tgggttagtg tgcgatcact tgctccagct tgaaggtggg    1200
tctgaggtat tgagggcaag aacagagtgg aggcctaagc ttaccgatag tttcagaggg   1260
attagtgtga tacccgcaga accgagggtg taactaatga agaagcatc tgttgaagtt    1320
tctcccatgc tgttcgtgag gatacttttt agaagctgca gtttgcattg cttgtgcaga   1380
atcatggtct gtggttttag atgtatataa aaaatagtcc tgtagtcatg aaacttaata   1440
tcagaaaaat aactcaatgg gtcaaggtta tcgaagtagt catttaagct ttgaaatatg   1500
ttttgtattc ctcggcttaa tctgtaagct ctttctcttg caataaagtt cgcctttcaa   1560
t                                                                     1561
```

<210> SEQ ID NO 101
<211> LENGTH: 975
<212> TYPE: DNA
<213> ORGANISM: Artificial Sequence
<220> FEATURE:
<223> OTHER INFORMATION: Codon optimized polynucleotide encoding mature form of C12FatB1 from Umbellularia californica

<400> SEQUENCE: 101

```
atgctgccgg attggagtat gttgttcgcg gtcattacca ccatcttctc ggccgcggaa      60
aagcagtgga ctaatctcga atggaagccc aagcctaaat tgccgcaact gttggatgat    120
cactttggtc tgcatggcct ggtcttccga cgaactttcg ccatccgctc ttacgaggtc    180
ggtccagatc gatcgacgtc cattctgcgc gtgatgaacc acatgcagga agctacactg    240
aatcacgcca agagtgtcgg catcctgggc gatggttttg gtacgacgct cgagatgagt    300
```

-continued

```
aagcgcgatt tgatgtgggt ggtccgccgc acacatgtgg ccgtcgaacg ctatcctacg    360
tggggtgaca cggtcgaagt cgagtgttgg atcggagcca gcggcaataa tgggatgcgg    420
cgcgattttc tcgtgcggga ttgtaagacc ggtgaaattc tgacacgttg caccagcctc    480
tccgtcctga tgaacacgcg gactcgccgc ctgtcgacta tcccggatga agtgcgcggc    540
gaaattgggc ccgcatttat cgacaatgtt gctgtcaagg atgacgagat taaaaaactg    600
caaaaactca acgatagcac tgccgattac attcaaggcg gactcacgcc gcgttggaac    660
gacctcgacg ttaaccagca cgtgaacaac ctcaaatacg tggcatgggt cttcgaaacc    720
gttccagaca gcatcttcga atctcatcat atcagctcgt tcacgttgga gtatcgtcgt    780
gagtgcaccc gggattccgt gttgcgatct ctgaccaccg tttccggggg cagcagcgag    840
gctggactcg tttgcgacca cctgctgcaa ttggaaggcg gctcggaggt gctgcgagca    900
cggaccgaat ggcgcccgaa attgacggat agctttcggg gcattagtgt tatccccgcc    960
gagccccgcg tttag                                                    975
```

<210> SEQ ID NO 102
<211> LENGTH: 382
<212> TYPE: PRT
<213> ORGANISM: Umbellularia californica

<400> SEQUENCE: 102

```
Met Ala Thr Thr Ser Leu Ala Ser Ala Phe Cys Ser Met Lys Ala Val
  1               5                  10                  15

Met Leu Ala Arg Asp Gly Arg Gly Met Lys Pro Arg Ser Ser Asp Leu
             20                  25                  30

Gln Leu Arg Ala Gly Asn Ala Pro Thr Ser Leu Lys Met Ile Asn Gly
         35                  40                  45

Thr Lys Phe Ser Tyr Thr Glu Ser Leu Lys Arg Leu Pro Asp Trp Ser
     50                  55                  60

Met Leu Phe Ala Val Ile Thr Thr Ile Phe Ser Ala Ala Glu Lys Gln
 65                  70                  75                  80

Trp Thr Asn Leu Glu Trp Lys Pro Lys Pro Lys Leu Pro Gln Leu Leu
                 85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255
```

```
Lys Leu Gln Lys Leu Asn Asp Ser Thr Ala Asp Tyr Ile Gln Gly Gly
        260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
        290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
        370                 375                 380

<210> SEQ ID NO 103
<211> LENGTH: 324
<212> TYPE: PRT
<213> ORGANISM: Umbellularia californica

<400> SEQUENCE: 103

Met Leu Pro Asp Trp Ser Met Leu Phe Ala Val Ile Thr Thr Ile Phe
1               5                   10                  15

Ser Ala Ala Glu Lys Gln Trp Thr Asn Leu Glu Trp Lys Pro Lys Pro
            20                  25                  30

Lys Leu Pro Gln Leu Leu Asp Asp His Phe Gly Leu His Gly Leu Val
        35                  40                  45

Phe Arg Arg Thr Phe Ala Ile Arg Ser Tyr Glu Val Gly Pro Asp Arg
    50                  55                  60

Ser Thr Ser Ile Leu Ala Val Met Asn His Met Gln Glu Ala Thr Leu
65                  70                  75                  80

Asn His Ala Lys Ser Val Gly Ile Leu Gly Asp Gly Phe Gly Thr Thr
                85                  90                  95

Leu Glu Met Ser Lys Arg Asp Leu Met Trp Val Val Arg Arg Thr His
            100                 105                 110

Val Ala Val Glu Arg Tyr Pro Thr Trp Gly Asp Thr Val Glu Val Glu
        115                 120                 125

Cys Trp Ile Gly Ala Ser Gly Asn Asn Gly Met Arg Arg Asp Phe Leu
    130                 135                 140

Val Arg Asp Cys Lys Thr Gly Glu Ile Leu Thr Arg Cys Thr Ser Leu
145                 150                 155                 160

Ser Val Leu Met Asn Thr Arg Thr Arg Arg Leu Ser Thr Ile Pro Asp
                165                 170                 175

Glu Val Arg Gly Glu Ile Gly Pro Ala Phe Ile Asp Asn Val Ala Val
            180                 185                 190

Lys Asp Asp Glu Ile Lys Lys Leu Gln Lys Leu Asn Asp Ser Thr Ala
        195                 200                 205

Asp Tyr Ile Gln Gly Gly Leu Thr Pro Arg Trp Asn Asp Leu Asp Val
    210                 215                 220

Asn Gln His Val Asn Asn Leu Lys Tyr Val Ala Trp Val Phe Glu Thr
225                 230                 235                 240

Val Pro Asp Ser Ile Phe Glu Ser His His Ile Ser Ser Phe Thr Leu
```

```
            245                 250                 255
Glu Tyr Arg Arg Glu Cys Thr Arg Asp Ser Val Leu Arg Ser Leu Thr
        260                 265                 270

Thr Val Ser Gly Gly Ser Glu Ala Gly Leu Val Cys Asp His Leu
    275                 280                 285

Leu Gln Leu Glu Gly Gly Ser Glu Val Leu Arg Ala Arg Thr Glu Trp
290                 295                 300

Arg Pro Lys Leu Thr Asp Ser Phe Arg Gly Ile Ser Val Ile Pro Ala
305                 310                 315                 320

Glu Pro Arg Val

<210> SEQ ID NO 104
<211> LENGTH: 1430
<212> TYPE: DNA
<213> ORGANISM: Cinnamomum camphora

<400> SEQUENCE: 104
tcaacatggc caccacctct ttagcttctg ctttctgctc gatgaaagct gtaatgttgg      60
ctcgtgatgg caggggcatg aaacccagga gcagtgattt gcagctgagg gcgggaaatg     120
cacaaacctc tttgaagatg atcaatggga ccaagttcag ttacacagag agcttgaaaa     180
agttgcctga ctggagcatg ctctttgcag tgatcacgac catcttttcg gctgctgaga     240
agcagtggac caatctagag tggaagccga agccgaatcc accccagttg cttgatgacc     300
attttgggcc gcatgggtta gttttcaggc gcacctttgc catcagatcg tatgaggtgg     360
gacctgaccg ctccacatct atagtggctg ttatgaatca cttgcaggag ctgcactta      420 atcatgcgaa gagtgtggga attctaggag atggattcgg tacgacgcta gagatgagta     480
agagagatct gatatgggtt gtgaaacgca cgcatgttgc tgtggaacgg tacctgctt     540 ggggtgatac tgttgaagta gagtgctggg ttggtgcatc gggaaataat ggcaggcgcc     600
atgatttcct tgtccgggac tgcaaaacag gcgaaattct acaagatgt accagtcttt     660 cggtgatgat gaatacaagg acaaggaggt tgtccaaaat ccctgaagaa gttagagggg     720
agatagggcc tgcattcatt gataatgtgg ctgtcaagga cgaggaaatt aagaaaccac     780
agaagctcaa tgacagcact gcagattaca tccaaggagg attgactcct cgatggaatg     840
atttggatat caatcagcac gttaacaaca tcaaatacgt tgactggatt cttgagactg     900
tcccagactc aatctttgag agtcatcata tttccagctt cactattgaa tacaggagag     960
agtgcacgat ggatagcgtg ctgcagtccc tgaccactgt ctccggtggc tcgtcggaag    1020
ctgggttagt gtgcgagcac ttgctccagc ttgaaggtgg gtctgaggta ttgagggcaa    1080
aaacagagtg gaggcctaag cttaccgata gtttcagagg gattagtgtg atacccgcag    1140
aatcgagtgt ctaactaacg aaagaagcat ctgatgaagt ttctcctgtg ctgttgttcg    1200
tgaggatgct ttttagaagc tgcagtttgc attgcttgtg cagaatcatg gcctgtggtt    1260
ttagatatat atccaaaatt gtcctatagt caagaaactt aatatcagaa aaataactca    1320
atgagtcaag gttatcgaag tagtcatgta agctttgaaa tatgttgtgt attcctcggc    1380
tttatgtaat ctgtaagctc tttctcttgc aataaatttc gcctttcaat               1430

<210> SEQ ID NO 105
<211> LENGTH: 975
<212> TYPE: DNA
<213> ORGANISM: Artificial Sequence
<220> FEATURE:
<223> OTHER INFORMATION: Codon optimized polynucleotide encoding mature
``` form of C14FatB1 from Cinnamomum camphora

<400> SEQUENCE: 105

```
atgttgcccg attggagcat gttgttcgca gtcatcacca ccatttttcag cgcagcggag      60
aagcaatgga ccaatttgga gtggaaacca aagccgaatc cccctcagct gctggatgat     120
cattttggac cccacggggtt ggtctttcgc cgaacgtttg ccatccgcag ctatgaagtg     180
ggcccggatc gctcgacgag cattgttgct gttatgaatc acctgcaaga agcggctctg     240
aatcatgcta agagcgtggg tatcttgggc gacggtttcg ggacaactct ggagatgtcg     300
aagcgcgatc tgatctgggt ggtcaaacgt acccatgtgg ctgttgaacg gtacccggcc     360
tggggagata ctgtggaggt tgagtgctgg gttggcgcaa gcggcaataa cggccgccga     420
catgatttcc tcgtgcgcga ctgtaaaacc ggcgaaattt tgacccgatg cacctcgctc     480
agtgtcatga tgaacacgcg cactcgtcgg ctgtccaaaa tccccgagga agtccgtggc     540
gagatcggac cggcgttcat tgacaacgtg gcagtgaagg acgaagaaat taaaaagccg     600
cagaagctga acgattccac agcggattac atccagggtg gtctgacgcc ccggtggaac     660
gacctcgaca ttaaccagca cgtcaataac attaagtacg tggattggat cttggaaaca     720
gtgccggatt cgattttttga gtcgcatcat atcagcagtt ttacgatcga atatcgccgc     780
gaatgtacga tggatagcgt gttgcagagc ctcacgacag tctctggggg gagtagtgag     840
gccggtctgg tctgcgaaca cctgctccaa ctcgaaggcg ttctgaagt gctccgtgcc     900
aaaactgagt ggcgcccctaa actcactgac tcgttttcggg gtatttccgt cattccagcc     960
gagtccagtg tttag                                                       975
```

<210> SEQ ID NO 106
<211> LENGTH: 382
<212> TYPE: PRT
<213> ORGANISM: Cinnamomum camphora

<400> SEQUENCE: 106

```
Met Ala Thr Thr Ser Leu Ala Ser Ala Phe Cys Ser Met Lys Ala Val
  1               5                  10                  15

Met Leu Ala Arg Asp Gly Arg Gly Met Lys Pro Arg Ser Ser Asp Leu
             20                  25                  30

Gln Leu Arg Ala Gly Asn Ala Gln Thr Ser Leu Lys Met Ile Asn Gly
         35                  40                  45

Thr Lys Phe Ser Tyr Thr Glu Ser Leu Lys Lys Leu Pro Asp Trp Ser
     50                  55                  60

Met Leu Phe Ala Val Ile Thr Thr Ile Phe Ser Ala Ala Glu Lys Gln
 65                  70                  75                  80

Trp Thr Asn Leu Glu Trp Lys Pro Lys Pro Asn Pro Pro Gln Leu Leu
                 85                  90                  95

Asp Asp His Phe Gly Pro His Gly Leu Val Phe Arg Arg Thr Phe Ala
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175
```

```
Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Met Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Thr Asp
        355                 360                 365

Ser Phe Arg Gly Ile Ser Val Ile Pro Ala Glu Ser Ser Val
    370                 375                 380

<210> SEQ ID NO 107
<211> LENGTH: 324
<212> TYPE: PRT
<213> ORGANISM: Cinnamomum camphora

<400> SEQUENCE: 107

Met Leu Pro Asp Trp Ser Met Leu Phe Ala Val Ile Thr Thr Ile Phe
1               5                   10                  15

Ser Ala Ala Glu Lys Gln Trp Thr Asn Leu Glu Trp Lys Pro Lys Pro
            20                  25                  30

Asn Pro Pro Gln Leu Leu Asp Asp His Phe Gly Pro His Gly Leu Val
        35                  40                  45

Phe Arg Arg Thr Phe Ala Ile Arg Ser Tyr Glu Val Gly Pro Asp Arg
    50                  55                  60

Ser Thr Ser Ile Val Ala Val Met Asn His Leu Gln Glu Ala Ala Leu
65                  70                  75                  80

Asn His Ala Lys Ser Val Gly Ile Leu Gly Asp Gly Phe Gly Thr Thr
                85                  90                  95

Leu Glu Met Ser Lys Arg Asp Leu Ile Trp Val Val Lys Arg Thr His
            100                 105                 110

Val Ala Val Glu Arg Tyr Pro Ala Trp Gly Asp Thr Val Glu Val Glu
        115                 120                 125

Cys Trp Val Gly Ala Ser Gly Asn Asn Gly Arg Arg His Asp Phe Leu
    130                 135                 140

Val Arg Asp Cys Lys Thr Gly Glu Ile Leu Thr Arg Cys Thr Ser Leu
145                 150                 155                 160

Ser Val Met Met Asn Thr Arg Thr Arg Arg Leu Ser Lys Ile Pro Glu
                165                 170                 175
```

```
Glu Val Arg Gly Glu Ile Gly Pro Ala Phe Ile Asp Asn Val Ala Val
            180                 185                 190
Lys Asp Glu Glu Ile Lys Lys Pro Gln Lys Leu Asn Asp Ser Thr Ala
        195                 200                 205
Asp Tyr Ile Gln Gly Gly Leu Thr Pro Arg Trp Asn Asp Leu Asp Ile
    210                 215                 220
Asn Gln His Val Asn Asn Ile Lys Tyr Val Asp Trp Ile Leu Glu Thr
225                 230                 235                 240
Val Pro Asp Ser Ile Phe Glu Ser His His Ile Ser Ser Phe Thr Ile
                245                 250                 255
Glu Tyr Arg Arg Glu Cys Thr Met Asp Ser Val Leu Gln Ser Leu Thr
            260                 265                 270
Thr Val Ser Gly Gly Ser Ser Glu Ala Gly Leu Val Cys Glu His Leu
        275                 280                 285
Leu Gln Leu Glu Gly Gly Ser Glu Val Leu Arg Ala Lys Thr Glu Trp
    290                 295                 300
Arg Pro Lys Leu Thr Asp Ser Phe Arg Gly Ile Ser Val Ile Pro Ala
305                 310                 315                 320
Glu Ser Ser Val

<210> SEQ ID NO 108
<211> LENGTH: 1744
<212> TYPE: DNA
<213> ORGANISM: Cuphea hookeriana

<400> SEQUENCE: 108
ctttgatcgg tcgatccttt cctctcgctc ataatttacc cattagtccc ctttgccttc      60
tttaaaccct cctttccttt ctcttccctt cttcctctct gggaagttta aagcttttgc     120
ctttctcccc cccacaacct ctttcccgca tttgttgagc tgttttttg tcgccattcg      180
tcctctcctc ttcagttcaa cagaaatggt ggctaccgct gcaagttctg cattcttccc     240
cctcccatcc gccgacacct catcgagacc cggaaagctc ggcaataagc catcgagctt     300
gagccccctc aagcccaaat cgaccccaa tggcggtttg caggttaagg caaatgccag     360
tgcccctcct aagatcaatg gttccccggt cggtctaaag tcgggcggtc tcaagactca     420
ggaagacgct cattcggccc ctcctccgcg aacttttatc aaccagttgc ctgattggag     480
tatgcttctt gctgcaatca cgactgtctt cttggctgca gagaagcaat ggatgatgct     540
tgattggaaa cctaagaggc ctgacatgct tgtggacccg tttggattgg aagtattgt      600
tcaggatggg cttgtgttca ggcagaattt ttcgattagg tcctatgaaa taggcgccga     660
tcgcactgcg tctatagaga cggtgatgaa ccatttgcag gaaacagctc tcaatcatgt     720
taagattgct gggctttcta tgacggcttg gtcgtactc ctgagatgt ataaaaggga       780
ccttatttgg gttgttgcga aaatgcaagt catggttaac cgctatccta cttggggtga    840
cacggttgaa gtgaatactt gggttgccaa gtcagggaaa aatggtatgc gtcgtgactg    900
gctcataagt gattgcaata ctggagagat tcttacaaga gcatcaagcg tgtgggtcat    960
gatgaatcaa aagacaagaa gattgtcaaa aattccagat gaggttcgaa atgagataga    1020
gcctcatttt gtggactctc ctcccgtcat tgaagacgat gaccggaaac ttcccaagct    1080
ggatgagaag actgctgact ccatccgcaa gggtctaact ccgaggtgga atgacttgga    1140
tgtcaatcaa cacgtcaaca cgtgaagta catcgggtgg attcttgaga gtactccacc    1200
agaagttctg gagacccagg agttatgttc ccttactctg gaatacaggc gggaatgtgg    1260
```

```
aagggagagc gtgctggagt ccctcactgc tatggatccc tctggagggg gttatgggtc    1320
ccagtttcag caccttctgc ggcttgagga tggaggtgag atcgtgaagg ggagaactga    1380
gtggcggccc aagaatggtg taatcaatgg ggtggtacca accggggagt cctcacctgg    1440
agactactct tagaagggag ccctgacccc tttggagttg tgatttcttt attgtcggac    1500
gagctaagtg aagggcaggt aagatagtag caatcggtag attgtgtagt ttgtttgctg    1560 cttttttcacg atggctctcg tgtataatat catggtctgt cttctttgta tcctcttctt    1620
cgcatgttcc gggttgattc atacattata ttctttctat ttgtttgaag gcgagtagcg    1680
ggttgtaatt atttattttg tcattacaat gtcgtttaac ttttcaaatg aaactactta    1740
tgtg                                                                 1744
```

<210> SEQ ID NO 109
<211> LENGTH: 990
<212> TYPE: DNA
<213> ORGANISM: Artificial Sequence
<220> FEATURE:
<223> OTHER INFORMATION: Codon optimized polynucleotide encoding mature
      form of C16FatB1 from Cuphea hookeriana

<400> SEQUENCE: 109

```
atgctgcctg actggtcgat gctgttggct gcaattacta ccgtcttcct ggcggctgaa     60
aaacaatgga tgatgttgga ctggaagccc aaacgacccg atatgctcgt cgatccgttc    120
gggttgggca gcatcgttca agacggtctg gtgtttcgcc aaaatttttc cattcgatct    180
tatgaaatcg gcgctgaccg gacagcatcc atcgaaacgg tcatgaacca tctccaagag    240
accgccctga tcacgtgaa gattgccgga ctctccaatg atggattcgg ccggaccccg    300
gaaatgtaca acgcgatct gatctgggtg gtcgccaaga tgcaggtcat ggtcaatcgg    360 taccccgacct ggggggacac ggttgaggtc aacacttggg tggcgaaatc gggtaagaac    420
ggcatgcgcc gcgactggct cattagcgac tgcaatacgg gcgagatcct cacgcgtgcc    480
agttctgtgt gggtcatgat gaaccagaaa actcgacgct tgagcaagat tccagatgaa    540
gttcgtaatg agattgaacc tcattttgtt gactcgcccc ccgtgatcga ggatgatgat    600
cggaagctcc ccaagctgga cgaaaaaacg gcggatagca tccgcaaagg cctgacacca    660
cggtggaacg atctggatgt caatcaacac gtgaacaacg tgaaatacat cgggtggatt    720
ctcgaatcta cccccccaga agttctcgag actcaggagc tgtgcagctt gacgttggag    780
taccgccgag aatgtggccg tgagtcggtc ctggagagtc tgaccgcaat ggacccgtcg    840 gcggtggtt atggcagtca gtttcagcat ttgctgcgct tggaggatgg tgggaaatt    900 gtgaaggtc ggactgaatg cgcccccaag aatggagtga ttaatggtgt tgtccctaca    960
ggcgaaagta gccccgggga ttatagttag                                    990
```

<210> SEQ ID NO 110
<211> LENGTH: 415
<212> TYPE: PRT
<213> ORGANISM: Cuphea hookeriana

<400> SEQUENCE: 110

```
Met Val Ala Thr Ala Ala Ser Ser Ala Phe Phe Pro Leu Pro Ser Ala
  1               5                  10                  15

Asp Thr Ser Ser Arg Pro Gly Lys Leu Gly Asn Lys Pro Ser Ser Leu
             20                  25                  30

Ser Pro Leu Lys Pro Lys Ser Thr Pro Asn Gly Gly Leu Gln Val Lys
```

```
            35                  40                  45
Ala Asn Ala Ser Ala Pro Pro Lys Ile Asn Gly Ser Pro Val Gly Leu
 50                  55                  60

Lys Ser Gly Gly Leu Lys Thr Gln Glu Asp Ala His Ser Ala Pro Pro
 65                  70                  75                  80

Pro Arg Thr Phe Ile Asn Gln Leu Pro Asp Trp Ser Met Leu Leu Ala
                 85                  90                  95

Ala Ile Thr Thr Val Phe Leu Ala Ala Glu Lys Gln Trp Met Met Leu
                100                 105                 110

Asp Trp Lys Pro Lys Arg Pro Asp Met Leu Val Asp Pro Phe Gly Leu
            115                 120                 125

Gly Ser Ile Val Gln Asp Gly Leu Val Phe Arg Gln Asn Phe Ser Ile
130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ile Ala Gly
                165                 170                 175

Leu Ser Asn Asp Gly Phe Gly Arg Thr Pro Glu Met Tyr Lys Arg Asp
                180                 185                 190

Leu Ile Trp Val Val Ala Lys Met Gln Val Met Val Asn Arg Tyr Pro
            195                 200                 205

Thr Trp Gly Asp Thr Val Glu Val Asn Thr Trp Val Ala Lys Ser Gly
210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg Asn Glu Ile Glu
            260                 265                 270

Pro His Phe Val Asp Ser Pro Val Ile Glu Asp Asp Arg Lys
            275                 280                 285

Leu Pro Lys Leu Asp Glu Lys Thr Ala Asp Ser Ile Arg Lys Gly Leu
            290                 295                 300

Thr Pro Arg Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Met Asp Pro Ser Gly Gly
            355                 360                 365

Gly Tyr Gly Ser Gln Phe Gln His Leu Leu Arg Leu Glu Asp Gly Gly
            370                 375                 380

Glu Ile Val Lys Gly Arg Thr Glu Trp Arg Pro Lys Asn Gly Val Ile
385                 390                 395                 400

Asn Gly Val Val Pro Thr Gly Glu Ser Ser Pro Gly Asp Tyr Ser
                405                 410                 415
```

<210> SEQ ID NO 111
<211> LENGTH: 329
<212> TYPE: PRT
<213> ORGANISM: Cuphea hookeriana

<400> SEQUENCE: 111

-continued

```
Met Leu Pro Asp Trp Ser Met Leu Leu Ala Ile Thr Thr Val Phe
 1               5                  10                  15

Leu Ala Ala Glu Lys Gln Trp Met Met Leu Asp Trp Lys Pro Lys Arg
             20                  25                  30

Pro Asp Met Leu Val Asp Pro Phe Gly Leu Gly Ser Ile Val Gln Asp
             35                  40                  45

Gly Leu Val Phe Arg Gln Asn Phe Ser Ile Arg Ser Tyr Glu Ile Gly
     50                  55                  60

Ala Asp Arg Thr Ala Ser Ile Glu Thr Val Met Asn His Leu Gln Glu
 65                  70                  75                  80

Thr Ala Leu Asn His Val Lys Ile Ala Gly Leu Ser Asn Asp Gly Phe
                 85                  90                  95

Gly Arg Thr Pro Glu Met Tyr Lys Arg Asp Leu Ile Trp Val Val Ala
             100                 105                 110

Lys Met Gln Val Met Val Asn Arg Tyr Pro Thr Trp Gly Asp Thr Val
             115                 120                 125

Glu Val Asn Thr Trp Val Ala Lys Ser Gly Lys Asn Gly Met Arg Arg
     130                 135                 140

Asp Trp Leu Ile Ser Asp Cys Asn Thr Gly Glu Ile Leu Thr Arg Ala
145                 150                 155                 160

Ser Ser Val Trp Val Met Met Asn Gln Lys Thr Arg Arg Leu Ser Lys
                 165                 170                 175

Ile Pro Asp Glu Val Arg Asn Glu Ile Glu Pro His Phe Val Asp Ser
             180                 185                 190

Pro Pro Val Ile Glu Asp Asp Arg Lys Leu Pro Lys Leu Asp Glu
             195                 200                 205

Lys Thr Ala Asp Ser Ile Arg Lys Gly Leu Thr Pro Arg Trp Asn Asp
    210                 215                 220

Leu Asp Val Asn Gln His Val Asn Asn Val Lys Tyr Ile Gly Trp Ile
225                 230                 235                 240

Leu Glu Ser Thr Pro Pro Glu Val Leu Glu Thr Gln Glu Leu Cys Ser
                245                 250                 255

Leu Thr Leu Glu Tyr Arg Arg Glu Cys Gly Arg Glu Ser Val Leu Glu
            260                 265                 270

Ser Leu Thr Ala Met Asp Pro Ser Gly Gly Tyr Gly Ser Gln Phe
    275                 280                 285

Gln His Leu Leu Arg Leu Glu Asp Gly Gly Glu Ile Val Lys Gly Arg
    290                 295                 300

Thr Glu Trp Arg Pro Lys Asn Gly Val Ile Asn Gly Val Pro Thr
305                 310                 315                 320

Gly Glu Ser Ser Pro Gly Asp Tyr Ser
                325
```